United States Patent
Lee et al.

(10) Patent No.: US 10,981,917 B2
(45) Date of Patent: Apr. 20, 2021

(54) HETEROCYCLIC COMPOUND, ITS PREPARATION METHOD, AND PHARMACEUTICAL COMPOSITION COMPRISING THE SAME

(71) Applicant: Daewoong Pharmaceutical Co., Ltd., Gyeonggi-do (KR)

(72) Inventors: Bong-Yong Lee, Seoul (KR); Min-Jae Cho, Gyeonggi-do (KR); Hyung-Geun Lee, Gyeonggi-do (KR); Myung-gi Jung, Gyeonggi-do (KR); Yunju Oh, Gyeonggi-do (KR)

(73) Assignee: Daewoong Pharmaceutical Co., Ltd., Gyeonggi-do (KR)

( * ) Notice: Subject to any disclaimer, the term of this patent is extended or adjusted under 35 U.S.C. 154(b) by 0 days.

(21) Appl. No.: 16/477,575

(22) PCT Filed: Feb. 7, 2018

(86) PCT No.: PCT/KR2018/001625
§ 371 (c)(1),
(2) Date: Jul. 12, 2019

(87) PCT Pub. No.: WO2018/147626
PCT Pub. Date: Aug. 16, 2018

(65) Prior Publication Data
US 2019/0359617 A1   Nov. 28, 2019

(30) Foreign Application Priority Data
Feb. 7, 2017   (KR) .................. 10-2017-0016971

(51) Int. Cl.
| C07D 487/04 | (2006.01) |
| C07D 401/04 | (2006.01) |
| C07D 401/06 | (2006.01) |
| C07D 471/04 | (2006.01) |
| C07D 473/12 | (2006.01) |

(52) U.S. Cl.
CPC ......... *C07D 487/04* (2013.01); *C07D 401/04* (2013.01); *C07D 401/06* (2013.01); *C07D 471/04* (2013.01); *C07D 473/12* (2013.01)

(58) Field of Classification Search
CPC .. C07D 487/04; C07D 401/04; C07D 401/06; C07D 471/04; C07D 473/12
See application file for complete search history.

(56) References Cited

U.S. PATENT DOCUMENTS

| 5,348,954 A | 9/1994 | Almen et al. |
| 5,698,553 A | 12/1997 | Prucher et al. |
| 6,051,577 A | 4/2000 | Altmann |
| 7,951,940 B2 | 5/2011 | Maddaford et al. |
| 10,011,586 B2 | 7/2018 | Park et al. |
| 10,081,634 B2 | 9/2018 | Park et al. |
| 2004/0147573 A1 | 7/2004 | Eriksson et al. |
| 2008/0269240 A1 | 10/2008 | Hashimoto et al. |
| 2009/0131458 A1 | 5/2009 | Lazarides et al. |
| 2010/0120799 A1 | 5/2010 | Lazarides et al. |
| 2011/0263532 A1 | 10/2011 | Keller et al. |
| 2011/0269781 A1 | 11/2011 | Lazarides et al. |
| 2012/0283438 A1 | 11/2012 | Lazarides et al. |
| 2013/0338201 A1 | 12/2013 | Song |
| 2016/0002252 A1 | 1/2016 | Schiltz et al. |
| 2017/0088551 A1 | 3/2017 | Park et al. |

FOREIGN PATENT DOCUMENTS

| EP | 2830628 | 2/2015 | |
| ES | 2231824 T3 | 5/2005 | |
| KR | 2015-0146462 A | 12/2015 | |
| KR | 2016-0144213 A | 12/2016 | |
| RU | 2160259 C2 | 12/2000 | |
| WO | WO-2004/005279 A2 | 1/2004 | |
| WO | WO-2007/034882 A1 | 3/2007 | |
| WO | WO-2010/018134 A1 | 2/2010 | |
| WO | WO-2013/149148 A2 | 10/2013 | |
| WO | WO-2015/199418 A2 | 12/2015 | |
| WO | WO-2015199418 A2 * | 12/2015 | ........... C07D 473/40 |
| WO | WO-2016/200116 A1 | 12/2016 | |

OTHER PUBLICATIONS

American Cancer Society, Can Kidney Cancer Be Prevented?, obtained from https://www.cancer.org/cancer/kidney-cancer/causes-risks-prevention/prevention.html on Sep. 13, 2017 (Year: 2017).*
American Cancer Society, Can Lung Cancer Be Prevented?, obtained from https://www.cancer.org/cancer/lung-cancer/prevention-and-early-detection/prevention.html on Sep. 13, 2017 (Year: 2017).*
CDC, Head and Neck Cancers, obtained from https://www.cdc.gov/cancer/headneck/index.htm on Sep. 13, 2017 (Year: 2017).*
Weber, J. Seminars in Oncology, 2010, 37, 430-439 (Year: 2010).*
Luo et al. Cell, 2009, 136, pp. 823-837 (Year: 2009).*
Liu et al. Yale Journal of Biology and Medicine 2014, 87, 481-489 (Year: 2014).*
CDC, Type 1 Diabetes, obtained from https://www.cdc.gov/diabetes/basics/type1.html on Oct. 1, 2020 (Year: 2020).*
Zhang et al., "Benzoylbenzimidazole-based Selective Inhibitors Targeting *Cryptosporidium Parvum* and *Toxoplasma Gondii* Calcium-dependent Protein Kinase-1", Bioorganic & Medicinal Chemistry Letters, vol. 22, No. 16, 2012, pp. 5264-5267.
Poon et al., "A Synthesis of the Tetracyclic Carboskeleton of Isaindigotidione", Tetrahedron Letters, vol. 45, No. 14, 2004, pp. 2985-2988.

(Continued)

*Primary Examiner* — Matthew P Coughlin
(74) *Attorney, Agent, or Firm* — Marshall, Gerstein & Borun LLP

(57) ABSTRACT

The present invention relates to a heterocyclic compound represented by Chemical Formula 1 that can be used for the prevention or treatment of diseases caused by abnormality in a PRS (prolyl-tRNA synthetase) activity, or a pharmaceutically acceptable salt thereof, a method for preparing the same, and a pharmaceutical composition comprising the same.

16 Claims, No Drawings

(56) References Cited

OTHER PUBLICATIONS

Bava et al., "CPEB1 Coordinates Alternative 3'-UTR Formation With Translational Regulation", Nature, 494, 2013, 7 pages.
Kim et al., "Aminoacyl-tRNA Synthetases and Tumorigenesis: More Than Housekeeping", Nat. Rev. Cancer, vol. 11, Oct. 2011, pp. 708-718.
Keller et al., "Halofuginone and Other Febrifugine Derivatives Inhibit Prolyl-tRNA Synthetase", Nat. Chem. Biol., vol. 8, Mar. 2012, pp. 311-317.
Carlson et al., "Halofuginone-induced Amino Acid Starvation Regulates Stat3-Dependent Th17 Effector Function and Reduces Established Autoimmune Inflammation", J. Immunol., 192(5), 2014, 11 pages.
Park et al., "Halofuginone Ameliorates Autoimmune Arthritis in Mice by Regulating the Balance Between Th17 and Treg Cells and Inhibiting Osteoclastogenesis", Arthritis Rheumatol, vol. 66, No. 5, May 2014, pp. 1195-1207.
Mark Pines, "Halofuginone for Fibrosis, Regeneration and Cancer in the Gastrointestinal Tract", World J. Gastroenterol, vol. 20, Issue 40, 2014, pp. 14778-14786.
McLaughlin et al., "The Chemistry and Biology of Febrifugine and Halofuginone", Bioorganic & Medicinal Chemistry, vol. 22, 2014, pp. 1993-2004.
"Opinion of the Scientific Panel on Additives and Products or Substances Used in Animal Feed on a Request From the Commission on the Re-evaluation of Coccidiostat Stenorol in Accordance With Article 9G of Council Directive 70/524/EEC", The EFSA Journal, 8, 2003, 45 pages.
Search Report and Written Opinion in International Application No. PCT/KR2018/001625 dated May 31, 2018, 11 pages.
Office Action in KR Application No. 10-2018-0015091 dated May 31, 2019, 15 pages.
Office Action in RU Application No. 2019124878/04(048562) dated Jan. 27, 2020, 18 pages.
Office Action in IN Application No. 201917028635 dated Mar. 18, 2020, 6 pages.
Naud et al., Structure-based Design of Orally Bioavailable 1H-Pyrrolo[3,2-c]pyridine Inhibitors of Mitotic Kinase Monopolar Spindle 1 (MPS1), Journal of Medicinal Chemistry, vol. 56, No. 24, Dec. 27, 2013, pp. 10045-10065.
Office Action in CL Application No. 201902019 dated Jul. 15, 2020, 12 pages.
Office Action in CO Application No. NC20196/0007834 dated Jul. 29, 2020, 10 pages.

* cited by examiner

HETEROCYCLIC COMPOUND, ITS PREPARATION METHOD, AND PHARMACEUTICAL COMPOSITION COMPRISING THE SAME

TECHNICAL FIELD

The present invention relates to a heterocyclic compound having a novel structure that can be used for the prevention or treatment of diseases caused by abnormality in a PRS (prolyl-tRNA synthetase) activity, a method for preparing the same, and a pharmaceutical composition comprising the same.

BACKGROUND OF ART

PRS (prolyl-tRNA synthetase) is one of the aminoacyl-tRNA synthetase (ARS) family and serves to activate an amino acid for protein synthesis. That is, ARS performs a translational function to form aminoacyl adenylate (AA-AMP) and then transfer the activated amino acid to the 3-end of the corresponding tRNA. Since ARS plays an important role in the synthesis of protein, ARS inhibitors suppress the growth of all cells. Thus, ARS has been recognized as a promising target for a therapeutic agent for treating diseases that should suppress antibiotics or cell overexpression (Nature, 2013, 494:121-125).

PRS is present in, or functions as, a multi-synthetase complex (MSC) in the form of EPRS (Glutamyl-Prolyl-tRNA Synthetase). In particular, among various MSCs, EPRS functions as a translational silencer that suppresses the production of VEGF A (vascular endothelial growth factor A) which is a key factor in angiogenesis. In addition, it is reported that EPRS is closely related with various solid tumors (Nat. Rev. Cancer, 2011, 11, 708-718).

The only substance, known as the PRS inhibitor, is halofuginone. Halofuginone is a derivative of febrifugine derived from natural products and has anti-malarial effects and various anti-inflammatory effects. It can also be used as an animal feed additive. In addition, it has been reported that halofuginone increases the phosphorylation of GCN2 kinase through PRS inhibition, which induces ATF4 and CHOP expression, and thus promotes cell death (Nat. Chem. Biol. 2012, 8, 311-317). Currently, halofuginone is being clinically studied as anti-cancer agent, an anti-inflammatory agent (J Immunol, 2014, 192(5), 2167-76), therapeutic agents for the treatment of autoimmune diseases (Arthritis Rheumatol, 2014, 66 (5), 1195-207), therapeutic agents for the treatment of fibrosis diseases (World J Gastroenterol, 2014, 20 (40), 14778-14786), and the like (Bioorg. Med. Chem. 2014, 22, 1993-2004).

However, it has been reported that halofuginone acts on various targets and has a very severe toxicity and further there is a risk of genotoxicity (The EFSA Journal, 2003, 8: 1-45). Therefore, discovering PRS inhibitors having higher safety to the human body among substances capable of inhibiting PRS like halofuginone has a significance in terms of developing an anti-cancer agent of the next generation that can be used as an antifibrosis agent, an anti-inflammatory agent, an autoimmune therapeutic agent alone or in combination with an existing targeted anti-cancer agent.

In this regard, the present inventors have conducted numerous studies to develop a novel compound with reduced toxicity while having a PRS enzyme inhibitory effect, and found that the compound having a novel structure which will be described later selectively inhibits the PRS, thereby completing the present invention. The compounds belonging to the present invention themselves have mainly a PRS enzyme inhibitory activity, but do not exclude a possibility of exhibiting a pharmacological action as an efficacious agent by a special body environment or by products of metabolic process, after absorption into the body.

DETAILED DESCRIPTION OF THE INVENTION

Technical Problem

It is an object of the present invention to provide a heterocyclic compound having a novel structure that can be used for the prevention or treatment of cancers, inflammatory diseases, autoimmune diseases or fibrosis, a method for preparing the same, and a pharmaceutical composition comprising the same.

Technical Solution

In order to achieve the above object, the present invention provides a compound represented by the following Chemical Formula 1, or a pharmaceutically acceptable salt thereof:

[Chemical Formula 1]

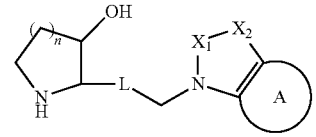

in Chemical Formula 1,
n is 1, or 2,
L is —$CH_2CH_2$—, —CH=C(R')—, or —C≡C—,
  wherein R' is hydrogen, $C_{1-4}$ alkyl, or halogen,
$X_1$ is $CR_1R_2$, $NR_1$, or —CO—,
$X_2$ is $CR_3R_4$, or $NR_3$,
  wherein $R_1$ to $R_4$ are each independently hydrogen, $C_{1-4}$ alkyl, $C_{1-4}$ hydroxyalkyl, hydroxy, amino, carboxy, —COO($C_{1-4}$ alkyl), —$CONH_2$, —CONH($C_{1-4}$ alkyl), —CON($C_{1-4}$ alkyl)$_2$, or pyrazolyl unsubstituted or substituted with $C_{1-4}$ haloalkyl; or $R_1$ and $R_3$, together with each other, link $X_1$ and $X_2$ via a double bond, and
A is benzene, pyridine, pyrimidine, or pyrimidinedione ring,
  wherein A is unsubstituted or substituted with one to three substituents each independently selected from the group consisting of a ring-type substituent selected from the group consisting of furanyl, imidazolyl, isoxazolyl, phenyl, pyrazolyl, pyridinonyl, pyridinyl, pyrrolyl, thiazolyl, and thiophenyl; $C_{1-4}$ alkyl; $C_{1-4}$ alkoxy; $C_{1-4}$ haloalkyl; $C_{1-4}$ haloalkoxy; halogen; di($C_{1-4}$ alkyl) amino; nitro; —COO($C_{1-4}$ alkyl); dihydropyranyl; morpholino; piperidinyl; and pyrrolidinyl; and
  wherein the ring-type substituent is unsubstituted or substituted with one or two substituents each independently selected from the group consisting of $C_{1-5}$ alkyl, $C_{1-4}$ haloalkyl, $C_{3-6}$ cycloalkyl, monovalent of $C_{2-5}$ alkylene carbonate, —COO($C_{1-4}$ alkyl), halogen, cyano, thiazolyl, and (1,3-dioxolan-2-yl)methyl.

Preferably, when the ring-type substituent is furanyl, it is unsubstituted or substituted with —COO($C_{1-4}$ alkyl). When the ring-type substituent is imidazolyl, it is unsubstituted or substituted with $C_{1-5}$ alkyl. When the ring-type substituent is isoxazolyl, it is unsubstituted or substituted with two $C_{1-5}$ alkyls. When the ring-type substituent is phenyl, it is unsubstituted or substituted with halogen, or $C_{1-4}$ haloalkyl. When the ring-type substituent is pyrazolyl, it is unsubstituted or substituted with $C_{1-5}$ alkyl, $C_{1-4}$ haloalkyl, monovalent of $C_{2-5}$ alkylene carbonate, thiazolyl, and (1,3-dioxolan-2-yl) methyl. When the ring-type substituent is pyridinonyl, it is unsubstituted or substituted with $C_{1-5}$ alkyl. When the ring-type substituent is pyridinyl, it is unsubstituted or substituted with halogen. When the ring-type substituent is pyrrolyl, it is unsubstituted or substituted with $C_{1-5}$ alkyl and —COO ($C_{1-4}$ alkyl). When the ring-type substituent is thiazolyl, it is unsubstituted or substituted with $C_{1-5}$ alkyl, $C_{3-6}$ cycloalkyl, cyano, or monovalent of $C_{2-6}$ alkylene carbonate. When the ring-type substituent is thiophenyl, it is unsubstituted or substituted with one or two substituents each independently selected from the group consisting of $C_{1-5}$ alkyl, and —COO ($C_{1-4}$ alkyl).

Preferably, A is unsubstituted or substituted with one to three substituents each independently selected from the group consisting of $C_{1-4}$ alkyl; $C_{1-4}$ alkoxy; $C_{1-4}$ haloalkyl; halogen; phenyl unsubstituted or substituted with halogen, or $C_{1-4}$ haloalkyl; pyrazolyl unsubstituted or substituted with $C_{1-5}$ alkyl, thiazolyl, or $C_{1-4}$ haloalkyl; thiopheny unsubstituted or substituted with $C_{1-5}$ alkyl, or —COO($C_{1-4}$ alkyl); pyrrolyl unsubstituted or substituted with $C_{1-5}$ alkyl and/or —COO($C_{1-4}$ alkyl); di($C_{1-4}$ alkyl)amino; morpholino; piperidinyl; furanyl; and pyrrolidinyl.

Preferably, L is —CH$_2$CH$_2$—, —CH═CH—, —CH═CF—, —CH═C(CH$_3$)—, or —C≡C—.

Preferably, according to X$_1$ and X$_2$, the compound represented by Chemical Formula 1 is represented by the following Chemical Formulas 1-1 to 1-5:

[Chemical Formula 1-1]

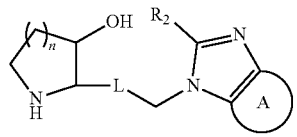

[Chemical Formula 1-2]

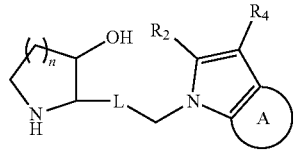

[Chemical Formula 1-3]

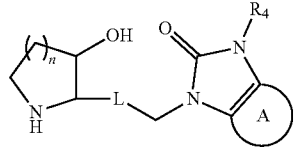

[Chemical Formula 1-4]

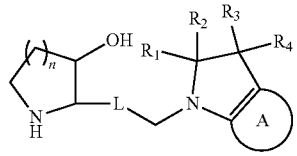

[Chemical Formula 1-5]

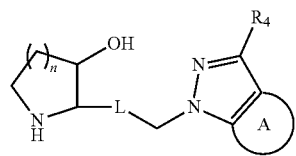

in Chemical Formulas 1-1 to 1-5, n, L, $R_1$ to $R_4$ and A are as previously defined.

Preferably, $R_1$ to $R_4$ are each independently hydrogen, methyl, hydroxymethyl, hydroxy, amino, carboxy, —COOCH$_3$, —CONH$_2$, —CONHCH$_3$, or —CON(CH$_3$)$_2$; or $R_1$ and $R_3$, together with each other, link $X_1$ and $X_2$ via a double bond.

Preferably, A is benzene, pyridine, pyrimidine, or pyrimidinedione ring, wherein A is unsubstituted or substituted with one to three substituents each independently selected from the group consisting of methyl, isobutyl, methoxy, trifluoromethyl, fluoro, chloro, bromo, phenyl, phenyl substituted with fluoro, phenyl substituted with chloro, phenyl substituted with trifluoromethyl, thiophenyl, thiopheny substituted with methyl, thiopheny substituted with —COOCH$_3$, pyrazolyl substituted with difluoromethyl, pyrazolyl substituted with methyl, pyrazolyl substituted with thiazolyl, pyrrolyl substituted with methyl and —COOCH$_2$CH$_3$, furanyl, dimethylamino, diethylamino, methylethylamino, morpholino, piperidinyl, and pyrrolidinyl.

Preferably, A is benzene, wherein A is unsubstituted or substituted with one to three substituents each independently selected from the group consisting of $C_{1-4}$ alkyl; $C_{1-4}$ alkoxy; halogen; and phenyl unsubstituted or substituted with halogen or $C_{1-4}$ haloalkyl.

Preferably, A is pyridine, wherein A is unsubstituted or substituted with one or two substituents each independently selected from the group consisting of $C_{1-4}$ alkyl; $C_{1-4}$ haloalkyl; halogen; and phenyl substituted with halogen.

Preferably, A is pyrimidine, wherein A is substituted with a substituent selected from the group consisting of halogen; di($C_{1-4}$ alkyl)amino; morpholino; piperidinyl; and pyrrolidinyl.

Preferably, A is pyrimidinedione, wherein A is unsubstituted or substituted with one or two $C_{1-4}$ alkyl.

Typical examples of the compounds represented by Chemical Formula 1 are as follows:
1) (2R,3S)-2-(3-(6-chloro-1H-benzo[d]imidazol-1-yl)propyl)piperidin-3-ol,
2) (2R,3S)-2-(3-(4-bromo-1H-benzo[d]imidazol-1-yl)propyl)piperidin-3-ol,
3) (2R,3S)-2-(3-(5-bromo-1H-benzo[d]imidazol-1-yl)propyl)piperidin-3-ol,
4) (2R,3S)-2-(3-(6-bromo-1H-benzo[d]imidazol-1-yl)propyl)piperidin-3-ol,
5) (2R,3S)-2-(3-(7-bromo-1H-benzo[d]imidazol-1-yl)propyl)piperidin-3-ol,
6) (2R,3S)-2-(3-(4-fluoro-1H-benzo[d]imidazol-1-yl)propyl)piperidin-3-ol,
7) (2R,3S)-2-(3-(5-fluoro-1H-benzo[d]imidazol-1-yl)propyl)piperidin-3-ol,
8) (2R,3S)-2-(3-(6-fluoro-1H-benzo[d]imidazol-1-yl)propyl)piperidin-3-ol,
9) (2R,3S)-2-(3-(7-fluoro-1H-benzo[d]imidazol-1-yl)propyl)piperidin-3-ol, 10) (2R,3S)-2-(3-(4-chloro-1H-benzo[d]imidazol-1-yl)propyl)piperidin-3-ol,
11) (2R,3S)-2-(3-(5-chloro-1H-benzo[d]imidazol-1-yl)propyl)piperidin-3-ol,
12) (2R,3S)-2-(3-(7-chloro-1H-benzo[d]imidazol-1-yl)propyl)piperidin-3-ol,
13) (2R,3S)-2-(3-(6-methyl-1H-benzo[d]imidazol-1-yl)propyl)piperidin-3-ol,
14) (2R,3S)-2-(3-(5-methyl-1H-benzo[d]imidazol-1-yl)propyl)piperidin-3-ol,
15) (2R,3S)-2-(3-(6-(trifluoromethyl)-1H-benzo[d]imidazol-1-yl)propyl)piperidin-3-ol,
16) (2R,3S)-2-(3-(7-(trifluoromethyl)-1H-benzo[d]imidazol-1-yl)propyl)piperidin-3-ol,
17) (2R,3S)-2-(3-(7-(trifluoromethoxy)-1H-benzo[d]imidazol-1-yl)propyl)piperidin-3-ol,
18) (2R,3S)-2-(3-(4-(pyrrolidin-1-yl)-1H-benzo[d]imidazol-1-yl)propyl)piperidin-3-ol,
19) (2R,3S)-2-(3-(4-(piperidin-1-yl)-1H-benzo[d]imidazol-1-yl)propyl)piperidin-3-ol,
20) (2R,3S)-2-(3-(4-(3-fluorophenyl)-1H-benzo[d]imidazol-1-yl)propyl)piperidin-3-ol,
21) (2R,3S)-2-(3-(4-(3-chlorophenyl)-1H-benzo[d]imidazol-1-yl)propyl)piperidin-3-ol,
22) (2R,3S)-2-(3-(5-(3-fluorophenyl)-1H-benzo[d]imidazol-1-yl)propyl)piperidin-3-ol,
23) (2R,3S)-2-(3-(6-(2-fluorophenyl)-1H-benzo[d]imidazol-1-yl)propyl)piperidin-3-ol,
24) (2R,3S)-2-(3-(6-(3-fluorophenyl)-1H-benzo[d]imidazol-1-yl)propyl)piperidin-3-ol,
25) (2R,3S)-2-(3-(6-(4-fluorophenyl)-1H-benzo[d]imidazol-1-yl)propyl)piperidin-3-ol,
26) (2R,3S)-2-(3-(7-(2-fluorophenyl)-1H-benzo[d]imidazol-1-yl)propyl)piperidin-3-ol,
27) (2R,3S)-2-(3-(7-(3-fluorophenyl)-1H-benzo[d]imidazol-1-yl)propyl)piperidin-3-ol,
28) (2R,3S)-2-(3-(7-(4-fluorophenyl)-1H-benzo[d]imidazol-1-yl)propyl)piperidin-3-ol,
29) (2R,3S)-2-(3-(5-(1H-pyrazol-4-yl)-1H-benzo[d]imidazol-1-yl)propyl)piperidin-3-ol,
30) (2R,3S)-2-(3-(6-(1H-pyrazol-4-yl)-1H-benzo[d]imidazol-1-yl)propyl)piperidin-3-ol,
31) (2R,3S)-2-(3-(7-(1H-pyrazol-4-yl)-1H-benzo[d]imidazol-1-yl)propyl)piperidin-3-ol,
32) (2R,3S)-2-(3-(6-chloro-5-fluoro-1H-benzo[d]imidazol-1-yl)propyl)piperidin-3-ol,
33) (2R,3S)-2-(3-(6-bromo-5-fluoro-1H-benzo[d]imidazol-1-yl)propyl)piperidin-3-ol,
34) (2R,3S)-2-(3-(5-chloro-6-fluoro-1H-benzo[d]imidazol-1-yl)propyl)piperidin-3-ol,
35) (2R,3S)-2-(3-(5-bromo-6-fluoro-1H-benzo[d]imidazol-1-yl)propyl)piperidin-3-ol,
36) (2R,3S)-2-(3-(6-bromo-5-chloro-1H-benzo[d]imidazol-1-yl)propyl)piperidin-3-ol,
37) (2R,3S)-2-(3-(6-chloro-5-methoxy-1H-benzo[d]imidazol-1-yl)propyl)piperidin-3-ol,
38) (2R,3S)-2-(3-(6-fluoro-5-methoxy-1H-benzo[d]imidazol-1-yl)propyl)piperidin-3-ol,
39) (2R,3S)-2-(3-(5-fluoro-6-methyl-1H-benzo[d]imidazol-1-yl)propyl)piperidin-3-ol,
40) (2R,3S)-2-(3-(4,5-dichloro-1H-benzo[d]imidazol-1-yl)propyl)piperidin-3-ol,
41) (2S,3S)-2-(3-(4,5-dichloro-1H-benzo[d]imidazol-1-yl)propyl)piperidin-3-ol,
42) (2S,3R)-2-(3-(4,5-dichloro-1H-benzo[d]imidazol-1-yl)propyl)piperidin-3-ol,
43) (2R,3R)-2-(3-(4,5-dichloro-1H-benzo[d]imidazol-1-yl)propyl)piperidin-3-ol,
44) (2R,3S)-2-(3-(4-chloro-5-methyl-1H-benzo[d]imidazol-1-yl)propyl)piperidin-3-ol,
45) (2R,3S)-2-(3-(5-bromo-4-methyl-1H-benzo[d]imidazol-1-yl)propyl)piperidin-3-ol,
46) (2R,3S)-2-(3-(5-chloro-4-methyl-1H-benzo[d]imidazol-1-yl)propyl)piperidin-3-ol,
47) (2R,3S)-2-(3-(5-bromo-4-fluoro-1H-benzo[d]imidazol-1-yl)propyl)piperidin-3-ol,
48) (2R,3S)-2-(3-(6-bromo-7-fluoro-1H-benzo[d]imidazol-1-yl)propyl)piperidin-3-ol,
49) (2R,3S)-2-(3-(4,5-difluoro-1H-benzo[d]imidazol-1-yl)propyl)piperidin-3-ol,
50) (2R,3S)-2-(3-(6,7-difluoro-1H-benzo[d]imidazol-1-yl)propyl)piperidin-3-ol,
51) (2R,3S)-2-(3-(4,5-dimethyl-1H-benzo[d]imidazol-1-yl)propyl)piperidin-3-ol,
52) (2R,3S)-2-(3-(5,6-difluoro-1H-benzo[d]imidazol-1-yl)propyl)piperidin-3-ol,
53) (2R,3S)-2-(3-(5,6-dichloro-1H-benzo[d]imidazol-1-yl)propyl)piperidin-3-ol,
54) (2R,3S)-2-(3-(5,6-dibromo-1H-benzo[d]imidazol-1-yl)propyl)piperidin-3-ol,
55) (2R,3S)-2-(3-(5,6-dimethyl-1H-benzo[d]imidazol-1-yl)propyl)piperidin-3-ol,
56) (2R,3S)-2-(3-(6,7-dichloro-1H-benzo[d]imidazol-1-yl)propyl)piperidin-3-ol,
57) (2R,3S)-2-(3-(4,6-difluoro-1H-benzo[d]imidazol-1-yl)propyl)piperidin-3-ol,
58) (2R,3S)-2-(3-(5,7-difluoro-1H-benzo[d]imidazol-1-yl)propyl)piperidin-3-ol,
59) (2R,3S)-2-(3-(4-chloro-5-methoxy-1H-benzo[d]imidazol-1-yl)propyl)piperidin-3-ol,
60) (2R,3S)-2-(3-(7-chloro-6-methoxy-1H-benzo[d]imidazol-1-yl)propyl)piperidin-3-ol,
61) (2R,3S)-2-(3-(6-chloro-4-methyl-1H-benzo[d]imidazol-1-yl)propyl)piperidin-3-ol,
62) (2R,3S)-2-(3-(4-chloro-5-fluoro-1H-benzo[d]imidazol-1-yl)propyl)piperidin-3-ol,
63) (2R,3S)-2-(3-(6-bromo-4-methyl-1H-benzo[d]imidazol-1-yl)propyl)piperidin-3-ol,
64) (2R,3S)-2-(3-(5-fluoro-4-methyl-1H-benzo[d]imidazol-1-yl)propyl)piperidin-3-ol,
65) (2R,3S)-2-(3-(6-fluoro-7-methyl-1H-benzo[d]imidazol-1-yl)propyl)piperidin-3-ol,
66) (2R,3S)-2-(3-(4-chloro-5-(trifluoromethyl)-1H-benzo[d]imidazol-1-yl)propyl)piperidin-3-ol,
67) (2R,3S)-2-(3-(7-chloro-6-(trifluoromethyl)-1H-benzo[d]imidazol-1-yl)propyl)piperidin-3-ol,
68) methyl 7-bromo-1-(3-((2R,3S)-3-hydroxypiperidin-2-yl)propyl)-1H-benzo[d]imidazole-5-carboxylate,
69) (2R,3S)-2-(3-(7-bromo-5-chloro-1H-benzo[d]imidazol-1-yl)propyl)piperidin-3-ol,
70) (2R,3S)-2-(3-(5-bromo-7-chloro-1H-benzo[d]imidazol-1-yl)propyl)piperidin-3-ol,
71) (2R,3S)-2-(3-(7-bromo-5-(trifluoromethyl)-1H-benzo[d]imidazol-1-yl)propyl)piperidin-3-ol,
72) (2R,3S)-2-(3-(6-bromo-4-fluoro-1H-benzo[d]imidazol-1-yl)propyl)piperidin-3-ol,
73) (2R,3S)-2-(3-(5-bromo-7-fluoro-1H-benzo[d]imidazol-1-yl)propyl)piperidin-3-ol,
74) (2R,3S)-2-(3-(7-chloro-4-fluoro-1H-benzo[d]imidazol-1-yl)propyl)piperidin-3-ol,
75) (2R,3S)-2-(3-(5-bromo-4-nitro-1H-benzo[d]imidazol-1-yl)propyl)piperidin-3-ol, 76) (2R,3S)-2-(3-(6-bromo-7-nitro-1H-benzo[d]imidazol-1-yl)propyl)piperidin-3-ol,
77) (2R,3S)-2-(3-(4-chloro-5-nitro-1H-benzo[d]imidazol-1-yl)propyl)piperidin-3-ol,
78) (2R,3S)-2-(3-(7-chloro-5-(trifluoromethyl)-1H-benzo[d]imidazol-1-yl)propyl)piperidin-3-ol,
79) (2R,3S)-2-(3-(5-chloro-7-fluoro-1H-benzo[d]imidazol-1-yl)propyl)piperidin-3-ol,
80) (2R,3S)-2-(3-(5,7-dichloro-1H-benzo[d]imidazol-1-yl)propyl)piperidin-3-ol,
81) (2R,3S)-2-(3-(5-chloro-7-(1H-pyrazol-4-yl)-1H-benzo[d]imidazol-1-yl)propyl)piperidin-3-ol,
82) (2R,3S)-2-(3-(7-(1H-pyrazol-4-yl)-5-(trifluoromethyl)-1H-benzo[d]imidazol-1-yl)propyl)piperidin-3-ol,
83) (2R,3S)-2-(3-(5-chloro-7-(3-fluorophenyl)-1H-benzo[d]imidazol-1-yl)propyl)piperidin-3-ol,
84) (2R,3S)-2-(3-(7-(3-fluorophenyl)-5-(trifluoromethyl)-1H-benzo[d]imidazol-1-yl)propyl)piperidin-3-ol,
85) (2R,3S)-2-(3-(5-chloro-7-(2-methylthiazol-5-yl)-1H-benzo[d]imidazol-1-yl)propyl)piperidin-3-ol,
86) (2R,3S)-2-(3-(5-chloro-7-(pyridin-3-yl)-1H-benzo[d]imidazol-1-yl)propyl)piperidin-3-ol,
87) (2R,3S)-2-(3-(5-chloro-7-(5-fluoropyridin-3-yl)-1H-benzo[d]imidazol-1-yl)propyl)piperidin-3-ol,
88) 5-(5-chloro-1-(3-((2R,3S)-3-hydroxypiperidin-2-yl)propyl)-1H-benzo[d]imidazol-7-yl)-1-methylpyridin-2(1H)-one,
89) (2R,3S)-2-(3-(5-chloro-7-(1-(difluoromethyl)-1H-pyrazol-4-yl)-1H-benzo[d]imidazol-1-yl)propyl)piperidin-3-ol,
90) (2R,3S)-2-(3-(5-chloro-7-(isoxazol-3-yl)-1H-benzo[d]imidazol-1-yl)propyl)piperidin-3-ol,
91) (2R,3S)-2-(3-(5-chloro-7-(thiophen-3-yl)-1H-benzo[d]imidazol-1-yl)propyl)piperidin-3-ol,
92) (2R,3S)-2-(3-(5-chloro-7-(2-methylthiophen-3-yl)-1H-benzo[d]imidazol-1-yl)propyl)piperidin-3-ol,
93) (2R,3S)-2-(3-(5-chloro-7-(3,5-dimethylisoxazol-4-yl)-1H-benzo[d]imidazol-1-yl)propyl)piperidin-3-ol,
94) (2R,3S)-2-(3-(5-chloro-7-(3,6-dihydro-2H-pyran-4-yl)-1H-benzo[d]imidazol-1-yl)propyl)piperidin-3-ol,
95) (2R,3S)-2-(3-(7-(1-((1,3-dioxolan-2-yl)methyl)-1H-pyrazol-4-yl)-5-chloro-1H-benzo[d]imidazol-1-yl)propyl)piperidin-3-ol,
96) (2R,3S)-2-(3-(5-chloro-7-(1-methyl-1H-imidazol-5-yl)-1H-benzo[d]imidazol-1-yl)propyl)piperidin-3-ol,
97) (2R,3S)-2-(3-(5-chloro-7-(1-methyl-1H-pyrazol-4-yl)-1H-benzo[d]imidazol-1-yl)propyl)piperidin-3-ol,
98) (2R,3S)-2-(3-(7-(pyrrolidin-1-yl)-1H-benzo[d]imidazol-1-yl)propyl)piperidin-3-ol,
99) (2R,3S)-2-(3-(5-chloro-7-(pyrrolidin-1-yl)-1H-benzo[d]imidazol-1-yl)propyl)piperidin-3-ol,
100) (2R,3S)-2-(3-(5-chloro-7-(2-cyclopropylthiazol-5-yl)-1H-benzo[d]imidazol-1-yl)propyl)piperidin-3-ol,
101) (2R,3S)-2-(3-(5-chloro-7-(1-(thiazol-2-yl)-1H-pyrazol-4-yl)-1H-benzo[d]imidazol-1-yl)propyl)piperidin-3-ol,
102) (2R,3S)-2-(3-(5-chloro-7-(1-(oxetan-3-yl)-1H-pyrazol-4-yl)-1H-benzo[d]imidazol-1-yl)propyl)piperidin-3-ol,
103) (2R,3S)-2-(3-(5-chloro-7-(2-(tetrahydro-2H-pyran-4-yl)thiazol-4-yl)-1H-benzo[d]imidazol-1-yl)propyl)piperidin-3-ol,
104) (2R,3S)-2-(3-(5-chloro-7-(furan-3-yl)-1H-benzo[d]imidazol-1-yl)propyl)piperidin-3-ol,
105) 4-(5-chloro-1-(3-((2R,3S)-3-hydroxypiperidin-2-yl)propyl)-1H-benzo[d]imidazol-7-yl)thiazole-2-carbonitrile,
106) (2R,3S)-2-(3-(7-(1-(tert-butyl)-1H-pyrazol-4-yl)-5-chloro-1H-benzo[d]imidazol-1-yl)propyl)piperidin-3-ol,
107) (2R,3S)-2-(3-(5-chloro-7-(1-isopentyl-1H-pyrazol-4-yl)-1H-benzo[d]imidazol-1-yl)propyl)piperidin-3-ol,
108) (2R,3S)-2-(3-(5-chloro-7-(1-isopropyl-1H-pyrazol-4-yl)-1H-benzo[d]imidazol-1-yl)propyl)piperidin-3-ol,
109) (2R,3S)-2-(3-(5-chloro-7-(4-methylthiophen-3-yl)-1H-benzo[d]imidazol-1-yl)propyl)piperidin-3-ol,
110) ethyl 3-(5-chloro-1-(3-((2R,3S)-3-hydroxypiperidin-2-yl)propyl)-1H-benzo[d]imidazol-7-yl)furan-2-carboxylate,
111) methyl 4-(5-chloro-1-(3-((2R,3S)-3-hydroxypiperidin-2-yl)propyl)-1H-benzo[d]imidazol-7-yl)thiophene-2-carboxylate,
112) (2R,3S)-2-(3-(5-chloro-7-(1-(2-fluoroethyl)-1H-pyrazol-4-yl)-1H-benzo[d]imidazol-1-yl)propyl)piperidin-3-ol,
113) (2R,3S)-2-(3-(7-(1-butyl-1H-pyrazol-4-yl)-5-chloro-1H-benzo[d]imidazol-1-yl)propyl)piperidin-3-ol,
114) (2R,3S)-2-(3-(5-chloro-7-(2,5-dimethylthiophen-3-yl)-1H-benzo[d]imidazol-1-yl)propyl)piperidin-3-ol,
115) (2R,3S)-2-(3-(5-chloro-7-(1-isobutyl-1H-pyrazol-4-yl)-1H-benzo[d]imidazol-1-yl)propyl)piperidin-3-ol,
116) ethyl 4-(5-chloro-1-(3-((2R,3S)-3-hydroxypiperidin-2-yl)propyl)-1H-benzo[d]imidazol-7-yl)-1-methyl-1H-pyrrole-2-carboxylate,
117) (2R,3S)-2-(3-(5-chloro-1H-imidazo[4,5-b]pyridin-1-yl)propyl)piperidin-3-ol,
118) (2R,3S)-2-(3-(5-chloro-3H-imidazo[4,5-b]pyridin-3-yl)propyl)piperidin-3-ol,
119) (2R,3S)-2-(3-(5-bromo-1H-imidazo[4,5-b]pyridin-1-yl)propyl)piperidin-3-ol,
120) (2R,3S)-2-(3-(6-bromo-1H-imidazo[4,5-b]pyridin-1-yl)propyl)piperidin-3-ol,
121) (2R,3S)-2-(3-(5-methyl-1H-imidazo[4,5-b]pyridin-1-yl)propyl)piperidin-3-ol,
122) (2R,3S)-2-(3-(6-chloro-1H-imidazo[4,5-c]pyridin-1-yl)propyl)piperidin-3-ol.
123) (2R,3S)-2-(3-(6-chloro-3H-imidazo[4,5-c]pyridin-3-yl)propyl)piperidin-3-ol,
124) (2R,3S)-2-(3-(6-bromo-1H-imidazo[4,5-c]pyridin-1-yl)propyl)piperidin-3-ol,
125) (2R,3S)-2-(3-(6-bromo-3H-imidazo[4,5-c]pyridin-3-yl)propyl)piperidin-3-ol,
126) (2R,3S)-2-(3-(7-chloro-1H-imidazo[4,5-b]pyridin-1-yl)propyl)piperidin-3-ol,
127) (2R,3S)-2-(3-(5,6-dichloro-1H-imidazo[4,5-b]pyridin-1-yl)propyl)piperidin-3-ol,
128) (2R,3S)-2-(3-(7-bromo-1H-imidazo[4,5-c]pyridin-1-yl)propyl)piperidin-3-ol,
129) (2R,3S)-2-(3-(5-(trifluoromethyl)-3H-imidazo[4,5-b]pyridin-3-yl)propyl)piperidin-3-ol,
130) (2R,3S)-2-(3-(6,7-dichloro-3H-imidazo[4,5-b]pyridin-3-yl)propyl)piperidin-3-ol,
131) (2R,3S)-2-(3-(6-chloro-7-methyl-3H-imidazo[4,5-b]pyridin-3-yl)propyl)piperidin-3-ol,
132) (2R,3S)-2-(3-(6-bromo-7-methyl-3H-imidazo[4,5-b]pyridin-3-yl)propyl)piperidin-3-ol,
133) (2R,3S)-2-(3-(6-bromo-7-chloro-3H-imidazo[4,5-b]pyridin-3-yl)propyl)piperidin-3-ol,
134) (2R,3S)-2-(3-(7-chloro-6-(3-chlorophenyl)-3H-imidazo[4,5-b]pyridin-3-yl)propyl)piperidin-3-ol,
135) (2R,3S)-2-(3-(2-chloro-7H-purin-7-yl)propyl)piperidin-3-ol,
138) (2R,3S)-2-(3-(2-chloro-9H-purin-9-yl)propyl)piperidin-3-ol, 137) (2R,3S)-2-(3-(6-(dimethylamino)-9H-purin-9-yl)propyl)piperidin-3-ol,
138) (2R,3S)-2-(3-(6-(diethylamino)-9H-purin-9-yl)propyl)piperidin-3-ol,
139) (2R,3S)-2-(3-(6-(ethyl(methyl)amino)-9H-purin-9-yl)propyl)piperidin-3-ol,
140) (2R,3S)-2-(3-(6-morpholino-9H-purin-9-yl)propyl)piperidin-3-ol,
141) (2R,3S)-2-(3-(6-(piperidin-1-yl)-9H-purin-9-yl)propyl)piperidin-3-ol,
142) (2R,3S)-2-(3-(6-(pyrrolidin-1-yl)-9H-purin-9-yl)propyl)piperidin-3-ol,
143) 1-(3-((2R,3S)-3-hydroxypiperidin-2-yl)propyl)-1H-benzo[d]imidazol-2-ol,
144) 5,6-dichloro-1-(3-((2R,3S)-3-hydroxypiperidin-2-yl)propyl)-1H-benzo[d]imidazol-2-ol,
145) (2R,3S)-2-(3-(2-(hydroxymethyl)-1H-benzo[d]imidazol-1-yl)propyl)piperidin-3-ol,
146) (2R,3S)-2-(3-(2-(hydroxymethyl)-4,5-dimethyl-1H-benzo[d]imidazol-1-yl)propyl)piperidin-3-ol,
147) (2R,3S)-2-(3-(5,6-dichloro-2-(hydroxymethyl)-1H-benzo[d]imidazol-1-yl)propyl)piperidin-3-ol,
148) (2R,3S)-2-(3-(2-amino-5,6-dichloro-1H-benzo[d]imidazol-1-yl)propyl)piperidin-3-ol,
149) methyl 7-bromo-1-(3-((2R,3S)-3-hydroxypiperidin-2-yl)propyl)-1H-indole-3-carboxylate,
150) methyl 5-bromo-1-(3-((2R,3S)-3-hydroxypiperidin-2-yl)propyl)-1H-indole-3-carboxylate,
151) methyl 6-bromo-1-(3-((2R,3S)-3-hydroxypiperidin-2-yl)propyl)-1H-indole-3-carboxylate,
152) methyl 4-chloro-1-(3-((2R,3S)-3-hydroxypiperidin-2-yl)propyl)-1H-indole-3-carboxylate,
153) methyl 6-chloro-1-(3-((2R,3S)-3-hydroxypiperidin-2-yl)propyl)-1H-indole-3-carboxylate,
154) methyl 7-chloro-1-(3-((2R,3S)-3-hydroxypiperidin-2-yl)propyl)-1H-indole-3-carboxylate,
155) (2R,3S)-2-(3-(5-chloro-3-cyclopropyl-1H-indazol-1-yl)propyl)piperidin-3-ol,
156) (2R,3S)-2-(3-(5-chloro-3-(trifluoromethyl)-1H-indazol-1-yl)propyl)piperidin-3-ol,
157) (2R,3S)-2-(3-(5-chloro-3-(1-(difluoromethyl)-1H-pyrazol-4-yl)-1H-indazol-1-yl)propyl)piperidin-3-ol,
158) (2R,3S)-2-(3-(6-chloro-3-(1-(difluoromethyl)-1H-pyrazol-4-yl)-1H-indazol-1-yl)propyl)piperidin-3-ol,
159) 1-(3-((2R,3S)-3-hydroxypiperidin-2-yl)propyl)-3-methyl-1H-benzo[d]imidazol-2(3H)-one,
160) 5-bromo-1-(3-((2R,3S)-3-hydroxypiperidin-2-yl)propyl)-1H-benzo[d]imidazol-2(3H)-one,
161) 6-bromo-1-(3-((2R,3S)-3-hydroxypiperidin-2-yl)propyl)-1H-benzo[d]imidazol-2(3H)-one,
162) 7-(3-((2R,3S)-3-hydroxypiperidin-2-yl)propyl)-1,3-dimethyl-1H-purine-2,6(3H,7H)-dione,
163) 7-(3-((2R,3S)-3-hydroxypiperidin-2-yl)propyl)-3-methyl-1H-purine-2,6(3H,7H)-dione,
164) 9-(3-((2R,3S)-3-hydroxypiperidin-2-yl)propyl)-1-methyl-1H-purine-2,6(3H,9H)-dione,
165) 7-(3-((2R,3S)-3-hydroxypiperidin-2-yl)propyl)-3-isobutyl-1-methyl-1H-purine-2,6(3H,7H)-dione,
166) (2R,3S)-2-((E)-3-(5,6-dichloro-1H-benzo[d]imidazol-1-yl)prop-1-enyl)piperidin-3-ol,
167) (2R,3S)-2-((E)-3-(5-fluoro-4-methyl-1H-benzo[d]imidazol-1-yl)prop-1-enyl)piperidin-3-ol,
168) (2R,3S)-2-((E)-3-(5-bromo-4-methyl-1H-benzo[d]imidazol-1-yl)prop-1-enyl)piperidin-3-ol,
169) (2R,3S)-2-((E)-3-(5,6-dimethyl-1H-benzo[d]imidazol-1-yl)prop-1-enyl)piperidin-3-ol,
170) (2R,3S)-2-((E)-3-(5,6-dibromo-1H-benzo[d]imidazol-1-yl)prop-1-enyl)piperidin-3-ol,
171) (2R,3S)-2-((E)-3-(5,6-difluoro-1H-benzo[d]imidazol-1-yl)prop-1-enyl)piperidin-3-ol,
172) (2R,3S)-2-((E)-3-(4,5-dimethyl-1H-benzo[d]imidazol-1-yl)prop-1-enyl)piperidin-3-ol,
173) (2R,3S)-2-((E)-3-(5-chloro-4-methyl-1H-benzo[d]imidazol-1-yl)prop-1-enyl)piperidin-3-ol,
174) (2R,3S)-2-((E)-3-(4,5-dichloro-1H-benzo[d]imidazol-1-yl)prop-1-en-1-yl)piperidin-3-ol,
175) (2R,3S)-2-((E)-3-(4-chloro-5-methyl-1H-benzo[d]imidazol-1-yl)prop-1-en-1-yl)piperidin-3-ol,
176) (2R,3S)-2-((E)-3-(5-bromo-4-nitro-1H-benzo[d]imidazol-1-yl)prop-1-en-1-yl)piperidin-3-ol,
177) (2R,3S)-2-((E)-3-(6-bromo-7-nitro-1H-benzo[d]imidazol-1-yl)prop-1-en-1-yl)piperidin-3-ol,
178) (2R,3S)-2-((E)-3-(4-chloro-5-nitro-1H-benzo[d]imidazol-1-yl)prop-1-en-1-yl)piperidin-3-ol,
179) (2R,3S)-2-((E)-3-(4,6-difluoro-1H-benzo[d]imidazol-1-yl)prop-1-en-1-yl)piperidin-3-ol,
180) (2R,3S)-2-((E)-3-(6-chloro-4-methyl-1H-benzo[d]imidazol-1-yl)prop-1-en-1-yl)piperidin-3-ol,
181) (2R,3S)-2-((E)-3-(7-chloro-5-(trifluoromethyl)-1H-benzo[d]imidazol-1-yl)prop-1-en-1-yl)piperidin-3-ol,
182) (2R,3S)-2-((E)-3-(5,7-dichloro-1H-benzo[d]imidazol-1-yl)prop-1-en-1-yl)piperidin-3-ol,
183) (2R,3S)-2-((E)-3-(5-chloro-7-fluoro-1H-benzo[d]imidazol-1-yl)prop-1-en-1-yl)piperidin-3-ol,
184) (2R,3S)-2-((E)-3-(5-bromo-1H-imidazo[4,5-b]pyridin-1-yl)prop-1-enyl)piperidin-3-ol,
185) (2R,3S)-2-((E)-3-(7-chloro-6-(3-chlorophenyl)-3H-imidazo[4,5-b]pyridin-3-yl)prop-1-enyl)piperidin-3-ol,
188) (2R,3S)-2-((E)-3-(6-bromo-7-methyl-3H-imidazo[4,5-b]pyridin-3-yl)prop-1-enyl)piperidin-3-ol,
187) (2R,3S)-2-((E)-3-(6-bromo-7-chloro-3H-imidazo[4,5-b]pyridin-3-yl)prop-1-enyl)piperidin-3-ol,
188) (2R,3S)-2-((E)-3-(6-chloro-7-methyl-3H-imidazo[4,5-b]pyridin-3-yl)prop-1-enyl)piperidin-3-ol,
189) (2R,3S)-2-((E)-3-(6,7-dichloro-3H-imidazo[4,5-b]pyridin-3-yl)prop-1-enyl)piperidin-3-ol,
190) (2R,3S)-2-((E)-3-(6-(3-chlorophenyl)-1H-benzo[d]imidazol-1-yl)prop-1-enyl)piperidin-3-ol,
191) (2R,3S)-2-((E)-3-(6-(3-fluorophenyl)-1H-benzo[d]imidazol-1-yl)prop-1-enyl)piperidin-3-ol,
192) (2R,3S)-2-((E)-3-(6-(3-(trifluoromethyl)phenyl)-1H-benzo[d]imidazol-1-yl)prop-1-enyl)piperidin-3-ol,
193) (2R,3S)-2-((E)-3-(5-bromo-6,7-difluoro-2-methyl-1H-benzo[d]imidazol-1-yl)prop-1-enyl)piperidin-3-ol,
194) (2R,3S)-2-((E)-3-(indolin-1-yl)prop-1-enyl)piperidin-3-ol,
195) (2R,3S)-2-((E)-3-(5-chloroindolin-1-yl)prop-1-enyl)piperidin-3-ol,
196) (2R,3S)-2-((E)-3-(1H-pyrrolo[2,3-b]pyridin-1-yl)prop-1-enyl)piperidin-3-ol,
197) (2R,3S)-2-((E)-3-(6-chloro-1H-indol-1-yl)prop-1-enyl)piperidin-3-ol,
198) (2R,3S)-2-((E)-3-(6-chloro-1H-indazol-1-yl)prop-1-enyl)piperidin-3-ol,
199) (2R,3S)-2-((E)-3-(4-chloro-7H-pyrrolo[2,3-d]pyrimidin-7-yl)prop-1-enyl)piperidin-3-ol,
200) (2R,3S)-2-((E)-3-(5-chloro-1H-pyrazolo[3,4-b]pyridin-1-yl)prop-1-enyl)piperidin-3-ol,
201) (2R,3S)-2-((E)-3-(3,5-dimethyl-1H-indazol-1-yl)prop-1-enyl)piperidin-3-ol,
202) methyl 7-bromo-1-((E)-3-((2R,3S)-3-hydroxypiperidin-2-yl)allyl)-1H-indole-3-carboxylate, 203) 7-bromo-1-((E)-3-((2R,3S)-3-hydroxypiperidin-2-yl) allyl)-1H-indole-3-carboxylic acid,
204) 5-bromo-1-((E)-3-((2R,3S)-3-hydroxypiperidin-2-yl) allyl)-1H-indole-3-carboxylic acid,
205) 4-chloro-1-((E)-3-((2R,3S)-3-hydroxypiperidin-2-yl) allyl)-1H-indole-3-carboxylic acid,
206) 6-chloro-1-((E)-3-((2R,3S)-3-hydroxypiperidin-2-yl) allyl)-1H-indole-3-carboxylic acid,
207) 7-chloro-1-((E)-3-((2R,3S)-3-hydroxypiperidin-2-yl) allyl)-1H-indole-3-carboxylic acid,
208) 6-fluoro-1-((E)-3-((2R,3S)-3-hydroxypiperidin-2-yl) allyl)-1H-indole-3-carboxylic acid,
209) 1-((E)-3-((2R,3S)-3-hydroxypiperidin-2-yl)allyl)-1H-indole-3-carboxylic acid,
210) methyl 4-chloro-1-((E)-3-((2R,3S)-3-hydroxypiperidin-2-yl)allyl)-1H-indole-3-carboxylate,
211) methyl 6-chloro-1-((E)-3-((2R,3S)-3-hydroxypiperidin-2-yl)allyl)-1H-indole-3-carboxylate,
212) methyl 7-chloro-1-((E)-3-((2R,3S)-3-hydroxypiperidin-2-yl)allyl)-1H-indole-3-carboxylate,
213) methyl 5-bromo-1-((E)-3-((2R,3S)-3-hydroxypiperidin-2-yl)allyl)-1H-indole-3-carboxylate,
214) methyl 6-bromo-1-((E)-3-((2R,3S)-3-hydroxypiperidin-2-yl)allyl)-1H-indole-3-carboxylate,
215) 5-bromo-1-((E)-3-((2R,3S)-3-hydroxypiperidin-2-yl) allyl)-N-methyl-1H-indole-3-carboxamide,
216) 5-bromo-1-((E)-3-((2R,3S)-3-hydroxypiperidin-2-yl) allyl)-N,N-dimethyl-1H-indole-3-carboxamide,
217) (2R,3S)-2-((Z)-3-(5-chloro-4-methyl-1H-benzo[d]imidazol-1-yl)-2-fluoroprop-1-enyl)piperidin-3-ol,
218) (2R,3S)-2-((Z)-3-(5-bromo-4-methyl-1H-benzo[d]imidazol-1-yl)-2-fluoroprop-1-enyl)piperidin-3-ol,
219) (2R,3S)-2-((Z)-3-(5,6-dichloro-1H-benzo[d]imidazol-1-yl)-2-fluoroprop-1-enyl)piperidin-3-ol,
220) (2R,3S)-2-((Z)-3-(5,6-dichloro-2-(hydroxymethyl)-1H-benzo[d]imidazol-1-yl)-2-fluoroprop-1-enyl)piperidin-3-ol,
221) (2R,3S)-2-((E)-3-(5-chloro-4-methyl-1H-benzo[d]imidazol-1-yl)-2-methylprop-1-enyl)piperidin-3-ol,
222) (2R,3S)-2-((E)-3-(5-bromo-4-methyl-1H-benzo[d]imidazol-1-yl)-2-methylprop-1-enyl)piperidin-3-ol,
223) (2R,3S)-2-((E)-3-(5,6-dichloro-1H-benzo[d]imidazol-1-yl)-2-methylprop-1-enyl)piperidin-3-ol,
224) (2R,3S)-2-((E)-3-(5,6-dichloro-2-(hydroxymethyl)-1H-benzo[d]imidazol-1-yl)-2-methylprop-1-enyl)piperidin-3-ol,
225) (2R,3S)-2-(3-(5,6-dichloro-1H-benzo[d]imidazol-1-yl)prop-1-ynyl)piperidin-3-ol,
226) (2R,3S)-2-(3-(5-bromo-4-methyl-1H-benzo[d]imidazol-1-yl)prop-1-ynyl)piperidin-3-ol,
227) (2R,3S)-2-(3-(5-chloro-4-methyl-1H-benzo[d]imidazol-1-yl)prop-1-ynyl)piperidin-3-ol,
228) (2R,3S)-2-(3-(5,6-dibromo-1H-benzo[d]imidazol-1-yl)prop-1-ynyl)piperidin-3-ol,
229) (2R,3S)-2-(3-(5-fluoro-4-methyl-1H-benzo[d]imidazol-1-yl)prop-1-ynyl)piperidin-3-ol, and
230) (2R,3S)-2-((E)-3-(5,6-dichloro-1H-benzo[d]imidazol-1-yl)prop-1-enyl)pyrrolidin-3-ol.

In addition, the compounds of the present invention may exist in the form of a pharmaceutically acceptable salt. As salt, an acid addition salt formed by a pharmaceutically acceptable free acid is useful. As the free acid, an inorganic acid and an organic acid may be used. Examples of the inorganic acid may include hydrochloric acid, bromic acid, sulfuric acid, phosphoric acid, and the like. Examples of the organic acid may include citric acid, acetic acid, lactic acid, maleic acid, gluconic acid, methanesulfonic acid, succinic acid, 4-toluene sulfonic acid, glutamic acid, aspartic acid or the like.

Salts or solvates of the compounds represented by Chemical Formula 1 that are pharmaceutically not acceptable can be used as intermediates in the preparation of the compound represented by Chemical Formula 1, a pharmaceutically acceptable salt or solvate thereof.

The compound represented by Chemical Formula 1 according to the present invention includes pharmaceutically acceptable salts thereof as well as both solvates and hydrates which can be prepared therefrom. The salts or solvates of the compound represented by Chemical Formula 1 can be prepared from the compounds represented by Chemical Formula 1 using conventional methods in the technical field to which the present invention pertains.

Further, the compound represented by Chemical Formula 1 according to the present invention can be prepared in crystalline form or non-crystalline form. When the compound represented by Chemical Formula 1 is produced in crystalline form, it may be optionally hydrated or solvated. The present invention may include not only stoichiometric hydrates of the compound represented by Chemical Formula 1 but also compounds containing a various amount of water. The solvates of the compound represented by Chemical Formula 1 according to the present invention include both stoichiometric solvates and non-stoichiometric solvates.

The present invention also provides a method for preparing a compound represented by Chemical Formula 1 as shown in the following Reaction Scheme 1:

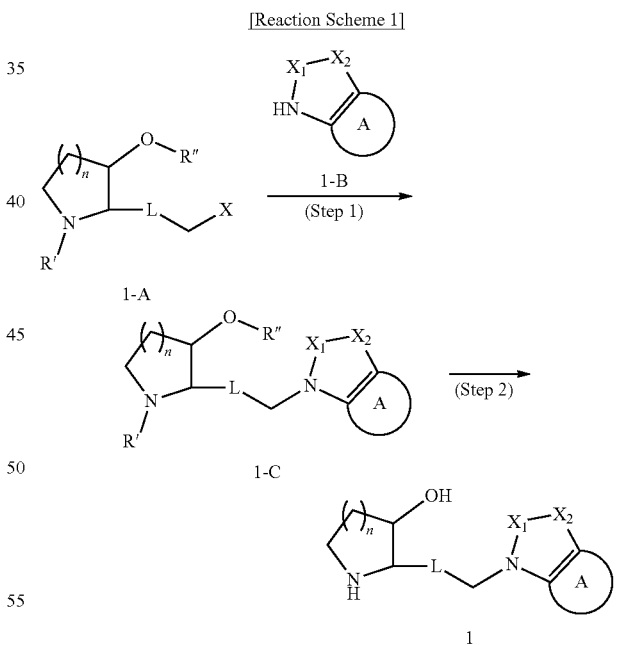

(in Reaction Scheme 1, n, L, $X_1$, $X_2$ and A are as previously defined, X is halogen (preferably bromo), and R' and R" means each independently a protecting group. The protecting group can be tert-butyldimethylsilyl, or tert-butyloxycarbonyl.)

The step 1 is a step of preparing a compound represented by Chemical Formula 1-C by reacting a compound represented by Chemical Formula 1-A with a compound represented by Chemical Formula 1-B in the presence of a base.

Conventional inorganic bases and organic bases can be used as the base. Non-limiting examples of the organic bases may include diisopropylethylamine or triethylamine. Non-limiting examples of the inorganic bases may include potassium carbonate, sodium carbonate, sodium hydrogen carbonate, cesium carbonate, or calcium carbonate. Further, the reaction may be carried out in a polar solvent such as methanol, ethanol, butanol, tetrahydrofuran, acetone, toluene, dimethylformamide, dimethylformsulfoxide, chloroform, dioxane, acetonitrile diethyl ether, or dichloromethane at 20° C. to 150° C. for 10 minutes to 24 hours.

The step 2 is a step of preparing a compound represented by Chemical Formula 1 by reacting a compound represented by Chemical Formula 1-C in the presence of an acid. Non-limiting examples of the acid may include hydrochloric acid, bromic acid, hydrofluoric acid, trifluoroacetic acid or the like. Preferably, the reaction solvent may or may not use a polar organic solvent. Preferably, when using a polar organic solvent, dichloromethane, chloroform, toluene, dimethylfomiamide, dioxane, tetrahydrofuran or the like may be used, and the reaction can be carried out at 20° C. to 100° C. for 10 minutes to 6 hours.

As another example, the compound represented by Chemical Formula 1-1 can be prepared as shown in the following Reaction Scheme 2:

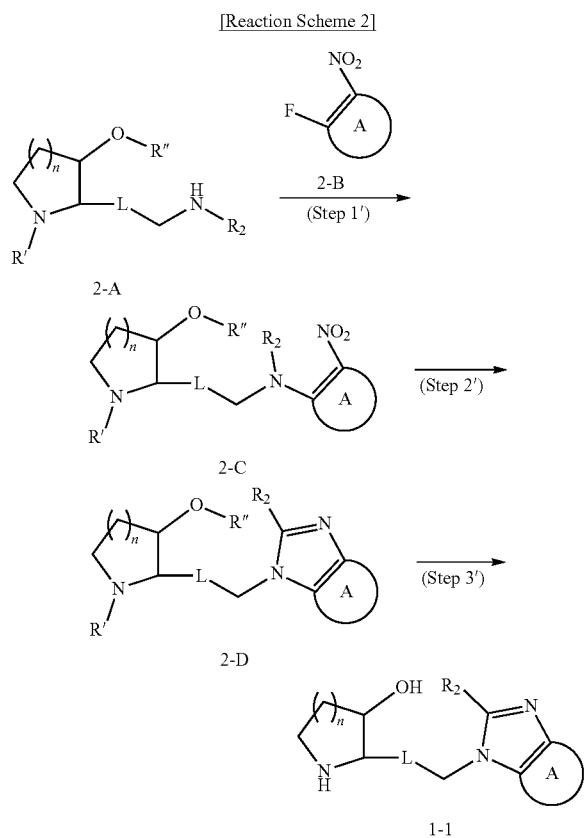

(in Reaction Scheme 2, n, L, $R_2$, and A are as previously defined, and R' and R" means each independently a protecting group. The protecting group can be tert-butyldimethylsilyl, or tert-butyloxycarbonyl.)

The step 1' is a step of preparing a compound represented by Chemical Formula 2-C by reacting a compound represented by Chemical Formula 2-A with a compound represented by Chemical Formula 2-B in the presence of a base. Conventional inorganic bases and organic bases can be used as the base. Non-limiting examples of the organic bases may include diisopropylethylamine or triethylamine. Non-limiting examples of the inorganic bases may include potassium carbonate, sodium carbonate, sodium hydrogen carbonate, cesium carbonate, or calcium carbonate. Further, the reaction may be carried out in a polar solvent such as methanol, ethanol, butanol, tetrahydrofuran, acetone, toluene, dimethylformamide, dimethylformsulfoxide, chloroform, dioxane, acetonitrile diethyl ether, or dichloromethane at 20° C. to 150° C. for 10 minutes to 24 hours.

The step 2' is a step of preparing a compound represented by Chemical Formula 2-D by reacting an amine group and a nitro group of the compound represented by Chemical Formula 2-C to form a ring. The above step is carried out substantially in two stages. First, a compound represented by Chemical Formula 2-C is reacted with hydrogen in the presence of Raney nickel and then reacted with trimethyl orthoformate. The former reaction is carried out in a polar solvent such as methanol, ethanol, butanol, tetrahydrofuran, acetone, toluene, dimethylformamide, dimethylformsulfoxide, chloroform, dioxane, acetonitrile diethyl ether, or dichloromethane at 20° C. to 150° C. for 10 minutes to 24 hours. The latter reaction is preferably carried out in the presence of para-toluene sulfonic acid, and the reaction may be carried out in a polar solvent such as methanol, ethanol, butanol, tetrahydrofuran, acetone, toluene, dimethylformamide, dimethylformsulfoxide, chloroform, dioxane, acetonitrile diethyl ether, or dichloromethane at 20° C. to 150° C. for 10 minutes to 24 hours.

The step 3' is a step of preparing a compound represented by Chemical Formula 1-1 by reacting a compound represented by Chemical Formula 2-D in the presence of an acid. The specific reaction conditions of the step 3' can be applied similarly to the reaction conditions of the step 2 of Reaction Scheme 1 described above.

Further, as an example, among the compounds of Chemical Formula 2-A shown in Reaction Scheme 2, a compound where L is ethylene and $R_2$ is hydrogen (a compound represented by the following Chemical Formula 3) can be prepared by a method as shown in the following Reaction Scheme 3:

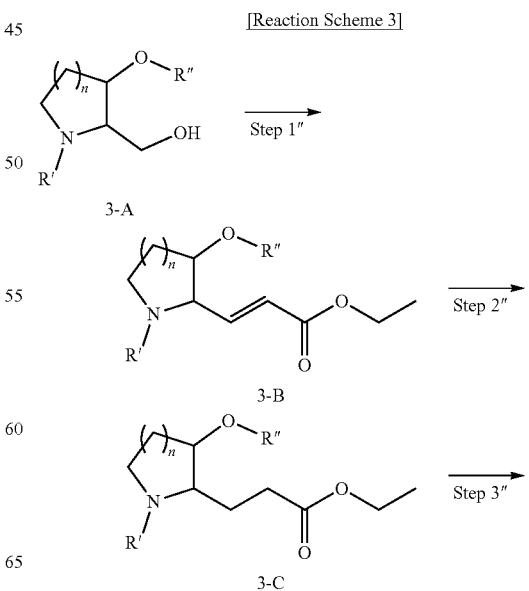

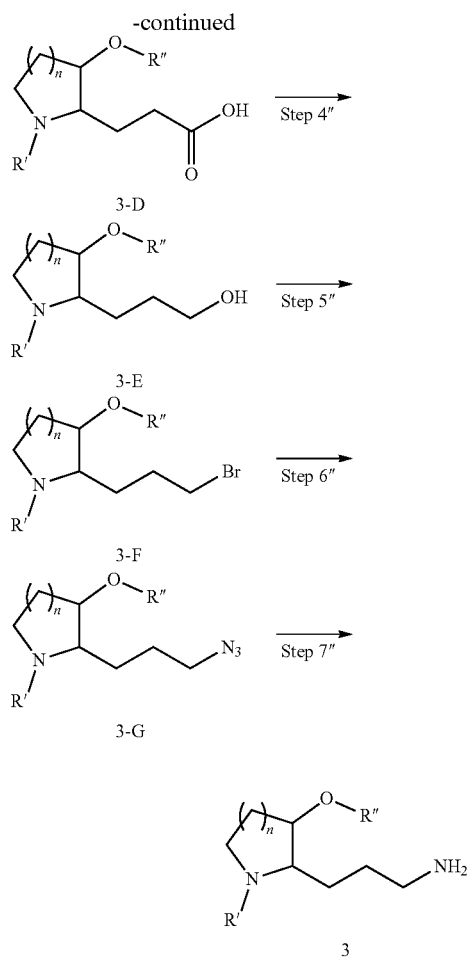

(in Reaction Scheme 3, n is as previously defined, and R' and R'' means each independently a protecting group. The protecting group can be tert-butyldimethylsilyl, or tert-butyloxycarbonyl.)

The step 1'' is a step of preparing a compound represented by Chemical Formula 3-B by reacting the compound represented by Chemical Formula 3-A with (carbethoxymethylene) triphenylphosphorane. Preferably, the compound represented by Chemical Formula 3-A is first reacted with oxalyl chloride and then reacted with triphenylphosphorane. The former reaction is preferably carried out in the presence of methylene chloride, N,N-dimethylsulfoxide, and triethylamine. The former reaction may also be carried out at −78° C. to 20° C. for 10 minutes to 12 hours. Further, in the reaction with triphenylphosphorane, dichloromethane may be used as the solvent, and the reaction can be carried out at 20° C. to 150° C. for 10 minutes to 24 hours.

The step 2'' is a step of preparing a compound represented by Chemical Formula 3-C by hydrogenating the compound represented by Chemical Formula 3-B. Preferably, the reaction is carried out in the presence of hydrogen and a hydrogenation catalyst (e.g., palladium hydroxide). In addition, tetrahydrofuran can be used as a solvent for the reaction. Further, the reaction can be carried out at 20° C. to 150° C. for 10 minutes to 24 hours.

The step 3'' is a step of preparing a compound represented by Chemical Formula 3-D by hydrolyzing the compound represented by Chemical Formula 3-C. Preferably, the reaction can be carried out under a basic condition, and sodium hydroxide may be used as the base. In addition, water or methanol may be used as a solvent for the reaction. Further, the reaction can be carried out at 20° C. to 150° C. for 10 minutes to 24 hours.

The step 4'' is a step of preparing a compound represented by Chemical Formula 3-E by subjecting the compound represented by Chemical Formula 3-D to a carbonyl reduction reaction. Preferably, the reaction may be carried out in the presence of lithium aluminum hydride. In addition, tetrahydrofuran can be used as a solvent for the reaction. Further, the reaction can be carried out at −78° C. to 20° C. for 10 minutes to 12 hours.

The step 5'' is a step of preparing a compound represented by Chemical Formula 3-F by brominating the compound represented by Chemical Formula 3-F. Preferably, the reaction is carried out in the presence of triphenylphosphine and tetrabromomethane. In addition, methylene chloride can be used as a solvent for the reaction. Further, the reaction may be carried out at 20° C. to 150° C. for 10 minutes to 24 hours.

The step 6'' is a step of preparing a compound represented by Chemical Formula 3-G by subjecting the compound represented by Chemical Formula 3-F to an azide reaction. Preferably, the reaction is carried out in the presence of sodium azide. In addition, N,N-dimethylformamide can be used as a solvent for the reaction. Further, the reaction may be carried out at 20° C. to 150° C. for 10 minutes to 24 hours.

The step 7'' is a step of preparing a compound represented by Chemical Formula 3 by aminating the compound represented by Chemical Formula 3-G. Preferably, the reaction is carried out in the presence of triphenylphosphine. In addition, tetrahydrofuran can be used as a solvent for the reaction. Further, the reaction can be carried out at 20° C. to 150° C. for 10 minutes to 24 hours.

Further, the present invention provides a pharmaceutical composition for the prevention or treatment of diseases caused by abnormality in a PRS (prolyl-tRNA synthetase) activity, comprising a compound represented by Chemical Formula 1 or a pharmaceutically acceptable salt thereof.

The compound represented by Chemical Formula 1 according to the present invention can inhibit PRS enzymatic activity and thus can be used for the prevention or treatment of diseases caused by abnormality in a PRS (prolyl-tRNA synthetase) activity. Examples of diseases caused by abnormality in the PRS (prolyl-tRNA synthetase) activity may include a cancer, an inflammatory disease, an autoimmune disease and a fibrosis.

As shown in Examples which will be described below, the compound represented by Chemical Formula 1 according to the present invention can significantly inhibit PRS enzymatic activity and also inhibit the growth of cancer cells. Thus, this compound may be effectively used for the prevention or treatment of the diseases.

The pharmaceutical composition according to the present invention can be formulated in types for oral or parenteral administrations according to a standard pharmaceutical practice. These formulations may contain additives such as pharmaceutically acceptable carrier, adjuvant or diluent in addition to the active ingredient. Suitable carriers may include, for example, physiological saline, polyethylene glycol, ethanol, vegetable oil, and isopropyl myristate, and the diluent may include, for example, lactose, dextrose, sucrose, mannitol, sorbitol, cellulose and/or glycine, but are not limited thereto. Further, the compounds of the present invention can be dissolved in oils, propylene glycol or other solvents which are usually used for the preparation of injectable solutions. In addition, the compounds of the present invention may be formulated as ointments or creams for topical application.

A preferred dose of the compound represented by Chemical Formula 1 according to the present invention may be varied depending on the condition and weight of a patient, the severity of a disease, the type of a drug, and the route and duration of administration, but it may be suitably selected by those skilled in the art. In order to achieve the desirable effects, however, the compound represented by Chemical Formula 1 according to the present invention may be administrated daily at a dose of 0.0001 to 100 mg/kg (body weight), and preferably 0.001 to 100 mg/kg (body weight). The administration may be performed once a day or in divided doses each day through an oral or parenteral route.

Depending on the method of administration, the pharmaceutical composition according to the present invention may contain the compound represented by Chemical Formula 1 or a pharmaceutically acceptable salt thereof in an amount of 0.001 to 99% by weight, preferably 0.01 to 60% by weight The pharmaceutical composition according to the present invention may be administered to mammals such as a rat, a mouse, a domestic animal, a human or the like, through various routes. The administration may be carried out through all possible methods, for example, oral, rectal, intravenous, intramuscular, subcutaneous, intra-endometrial, intracerebroventricular injection.

Advantageous Effects

The compound represented by Chemical Formula 1 according to the present invention can inhibit PRS enzymatic activity and thus may be effectively used for the prevention or treatment of diseases caused by abnormality in a PRS (prolyl-tRNA synthetase) activity, for example, cancers, inflammatory diseases, autoimmune diseases and fibrosis.

DETAILED DESCRIPTION OF THE EMBODIMENTS

Below, the present invention will be described in more detail by way of examples. However, these examples are provided only for illustration of the present invention, and should not be construed as limiting the scope of the present invention to these examples.

Example 1: Preparation of (2R,3S)-2-(3-(6-chloro-1H-benzo[d]imidazol-1-yl)propyl)piperidin-3-ol dihydrochloride

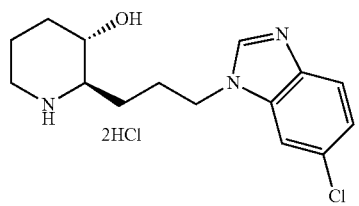 [SMILES: O[C@H]1CCCN[C@@H]1CCCn1cnc2ccc(Cl)cc21 ; "2HCl"]

Step 1-1: Preparation of tert-butyl (2R,3S)-3-((tert-butyldimethylsilyl)oxy)-2-(E)-3-ethoxy-3-oxoprop-1-en-1-yl)piperidine-1-carboxylate Methylene chloride (47 mL, 0.12 M) and oxalyl chloride (1.0 mL, 11.6 mmol) were added to a flask filled with nitrogen and the reaction solution was cooled to −78° C. N,N-dimethylsulfoxide (1.7 mL, 23.2 mmol) was then added at the same temperature and stirred for 30 minutes. Then, tert-butyl (2R,3S)-3-((tert-butyldimethylsilyl)oxy)-2-(hydroxymethyl)piperidine-1-carboxylate (2.0 g, 5.8 mmol) was dissolved in a small amount of methylene chloride and slowly added. After stirring at the same temperature for 1 hour, triethylamine (3.3 mL, 23.2 mmol) was added and the temperature of the reaction solution was raised to room temperature from −78° C. When the reaction was completed, the solvent was removed, and the resulting mixture was diluted with ethyl acetate and washed with saturated sodium chloride solution. The organic layer was collected, dried with magnesium sulfate, filtered and concentrated under reduced pressure, and then dissolved in methylene chloride (47 mL, 0.12 M). (Carbethoxymethylene)triphenylphosphorane (4.0 g, 11.6 mmol) was added thereto at room temperature and stirred for 2 hours. When the reaction was completed, the solvent was removed, and the resulting mixture was diluted with ethyl acetate and washed with saturated sodium chloride solution. The organic layer was collected, dried over magnesium sulfate, filtered and concentrated under reduced pressure, and then purified by column chromatography (hexane:ethyl acetate=4:1) to give the title compound (2.1 g, 89% yield over two steps).

Step 1-2: Preparation of tert-butyl (2R,3S)-3-((tert-butyldimethylsilyl)oxy)-2-(3-ethoxy-3-oxopropyl)piperidine-1-carboxylate Tert-butyl (2R,3S)-3-((tert-butyldimethylsilyl)oxy)-2-(E)-3-ethoxy-3-oxoprop-1-en-1-yl)piperidine-1-carboxylate (3.2 g, 7.7 mmol) obtained from Step 1-1 was dissolved in tetrahydrofuran (50 mL, 0.15 M), and then palladium hydroxide (104 mg, 0.77 mmol) was added thereto. After connection a hydrogen balloon, the mixture was stirred at room temperature for 5 hours. When the reaction was completed, the reaction solution was filtered through celite and concentrated under reduced pressure. Subsequent reactions were carried out without purification procedure.

Step 1-3: Preparation of 3-((2R,3S)-1-(tert-butoxycarbonyl)-3-(tert-butyldimethylsilyl)oxy)piperidin-2-yl)propenoic acid Tert-butyl (2R,3S)-3-((tert-butyldimethylsilyl)oxy)-2-(3-ethoxy-3-oxopropyl)piperidine-1-carboxylate (3.0 g, 7.2 mmol) obtained from Step 1-2 was dissolved in methanol (20 mL, 0.36 M), and then 2N aqueous sodium hydroxide solution (10 mL) was added thereto and stirred at room temperature for 3 hours. When the reaction was completed, the reaction solution was neutralized with 1N aqueous hydrochloric acid solution, acidified and then diluted with ethyl acetate, and washed with saturated sodium chloride solution. The organic layer was collected, dried over magnesium sulfate, filtered and concentrated under reduced pressure. Subsequent reactions were carried out without purification procedure.

Step 1-4: Preparation of tert-butyl (2R,3S)-3-((tert-butyldimethylsilyl)oxy)-2-(3-hydroxypropyl)piperidine-1-carboxylate 3-((2R,3S)-1-(tert-butoxycarbonyl)-3-(tert-butyldimethylsilyl)oxy)piperidin-2-yl)propenoic acid (1.6 g, 4.0 mmol) obtained from Step 1-1 was dissolved in tetrahydrofuran (50 mL, 0.08 M), and the reaction solution was cooled to 0° C.

Then, a lithium aluminum hydride solution (1.6 mL, 4.0 mmol) was slowly added thereto, reacted at the same temperature for 30 minutes and then stirred at room temperature for 2 hours. A small amount of water was added to complete the reaction, diluted with ethyl acetate and washed with saturated sodium chloride solution. The organic layer was collected, dried over magnesium sulfate, filtered and concentrated under reduced pressure, and then purified by column chromatography (dichloromethane:methanol=10:1) to give the title compound (1.3 g, yield: 85%).

Step 1-5: Preparation of tert-butyl (2R,3S)-2-(3-bromopropyl)-3-((tert-butyldimethylsilyl)oxy)piperidine-1-carboxylate Tert-butyl (2R,3S)-3-((tert-butyldimethylsilyl)oxy)-2-(3-hydroxypropyl)piperidine-1-carboxylate (5.1 g, 13.8 mmol) obtained from Step 1-4 was added to methylene chloride (100 mL, 0.14 M). The reaction solution was cooled to 0° C., and then triphenylphosphine (4.3 g, 16.5 mmol) and tetrabromomethane (5.5 g, 16.5 mmol) were sequentially added at the same temperature, followed by stirring at room temperature for 2 hours. When the reaction was completed, the solvent was removed, and the resulting mixture was diluted with ethyl acetate and washed with saturated sodium chloride solution. The organic layer was collected, dried over magnesium sulfate, filtered and then concentrated under reduced pressure, and purified by column chromatography (hexane:ethyl acetate=5:1) to give the title compound (4.6 g, yield: 76%).

Step 1-6: Preparation of tert-butyl (2R,3S)-2-(3-azidopropyl)-3-((tert-butyldimethylsilyl)oxy)piperidine-1-carboxylate Tert-butyl (2R,3S)-2-(3-bromopropyl)-3-((tert-butyldimethylsilyl)oxy)piperidine-1-carboxylate (7.4 g, 17.0 mmol) obtained from Step 1-5 was dissolved in N,N-dimethylformamide (25 mL, 0.67 M). Then, sodium azide (3.3 g, 17.0 mmol) was added thereto and the mixture was stirred at room temperature for 4 hours. When the reaction was completed, the solvent was removed, and the resulting mixture was diluted with ethyl acetate and washed with saturated sodium chloride solution. The organic layer was collected, dried over sodium sulfate, filtered and then concentrated under reduced pressure, and purified by column chromatography (hexane:ethyl acetate=7:1) to give the title compound (5.8 g, yield 85%).

Step 1-7: Preparation of tert-butyl (2R,3S)-2-(3-aminopropyl)-3-((tert-butyldimethylsilyl)oxy)piperidine-1-carboxylate Tert-butyl (2R,3S)-2-(3-azidopropyl)-3-((tert-butyldimethylsilyl)oxy)piperidine-1-carboxylate (5.5 g, 13.8 mmol) obtained from Step 1-6 was dissolved in tetrahydrofuran (24 mL, 0.57 M), and then triphenylphosphine (4.3 g, 16.5 mmol) was added thereto and stirred at room temperature for 30 minutes. Then, water (24 mL, 0.57 M) was added thereto and stirred at room temperature for 1 hour. When the reaction was completed, the resulting mixture was diluted with ethyl acetate and washed with saturated sodium chloride solution. The organic layer was collected, dried over sodium sulfate, filtered and then concentrated under reduced pressure, and purified by column chromatography (dichloromethane:methanol=10:1+triethylamine 2%) to give the title compound (4.0 g, yield: 78%).

Step 1-8: Preparation of tert-butyl (2R,3S)-3-((tert-butyldimethylsilyl)oxy)-2-(3-((4-chloro-2-nitrophenyl)amino)propyl)piperidine-1-carboxylate Tert-butyl (2R,3S)-2-(3-aminopropyl)-3-((tert-butyldimethylsilyl)oxy)piperidine-1-carboxylate (1.0 g, 2.7 mmol) obtained from Step 1-7 was dissolved in N,N-dimethylformamide (25 mL, 0.67 M). 4-Chloro-2-fluoro-1-nitrobenzene (518 mg, 3.0 mmol) and N,N-diisopropyl ethylamine (0.93 mL, 5.4 mmol) were then added thereto, and the mixture was heated and stirred at 60° C. for 2 hours. When the reaction was completed, the resulting mixture was diluted with ethyl acetate and washed with saturated sodium chloride solution. The organic layer was collected, dried over sodium sulfate, filtered and concentrated under reduced pressure, and purified by column chromatography (hexane:ethyl acetate=5:1) to give the title compound (1.2 g, yield: 87%).

Step 1-9: Preparation of tert-butyl (2R,3S)-3-((tert-butyldimethylsilyl)oxy)-2-(3-(5-chloro-1H-benzo[d]imidazol-1-yl)propyl)piperidine-1-carboxylate Tert-butyl (2R,3S)-3-((tert-butyldimethylsilyl)oxy)-2-(3-((4-chloro-2-nitrophenyl)amino)propyl)piperidine-1-carboxylate (2.6 mg, 4.9 mmol) obtained from Step 1-8 was dissolved in methanol (25 mL, 0.2 M), and then an appropriate amount of Rainy nickel was added thereto. After connecting a hydrogen balloon, the mixture was stirred at room temperature for 1 hour. When the reaction was completed, the reaction solution was filtered through celite and concentrated under reduced pressure. Subsequent reactions were carried out without purification procedure. The concentrated compound was dissolved in toluene (30 mL, 0.16 M), and then trimethyl orthoformate (1.6 mL, 14.6 mmol) and paratoluene sulfonic acid (168 mg, 0.98 mmol) was added thereto, followed by heating and stirring at 50° C. for 6 hours. When the reaction was completed, the solvent was removed, and the resulting mixture was diluted with ethyl acetate and washed with saturated sodium chloride solution. The organic layer was collected, dried over magnesium sulfate, filtered and concentrated under reduced pressure, and purified by column chromatography (hexane:ethyl acetate=1:1) to give the title compound (1.8 g, yield: 74%).

Step 1-10: Preparation of (2R,3S)-2-(3-(6-chloro-1H-benzo[d]imidazol-1-yl)propyl)piperidin-3-ol dihydrochloride Tert-butyl (2R,3S)-3-((tert-butyldimethylsilyl)oxy)-2-(3-(5-chloro-1H-benzo[d]imidazol-1-yl)propyl)piperidine-1-carboxylate (1.8 g, 3.6 mmol) obtained from Step 1-9 was dissolved in a small amount of tetrahydrofuran. 4N hydrogen chloride dioxane solution (30 mL, 0.12 M) was then added thereto, and the mixture was stirred at room temperature for 12 hours. When the reaction was completed, the reaction solution was concentrated under reduced pressure to remove the solvent, dissolved by addition of a small amount of methanol, and then crystallized with diethyl ether to give the title compound (1.1 g, yield: 81%).

$^1$H-NMR (500 MHz, MeOD): δ 9.56 (s, 1H), 8.18 (d, 1H), 7.86 (d, 1H), 7.70 (dd, 1H), 4.58 (t, 2H), 3.58 (m, 2H), 2.99 (m, 2H), 2.21 (m, 2H), 2.07 (m, 2H), 1.97 (m, 1H), 1.75 (m, 2H), 1.58 (m, 1H)

Example 2: Preparation of (2R,3S)-2-(3-(4-bromo-1H-benzo[d]imidazol-1-yl)propyl)piperidin-3-ol dihydrochloride

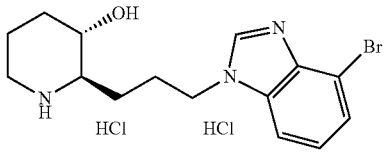 [SMILES: O[C@H]1CCCN[C@@H]1CCCn1cnc2c(Br)cccc21 ; Cl ; Cl]

The title compound (15 mg, yield: 93%) was obtained in the same manner as in Example 1, with the exception that 1-bromo-3-fluoro-2-nitrobenzene was used instead of 4-chloro-2-fluoro-1-nitrobenzene in Step 1-8 of Example 1.

$^1$H NMR (500 MHz, MeOD): 9.63 (s, 1H), 8.02 (d, 1H), 7.86 (d, 1H), 7.59 (t, 1H), 4.61 (t, 2H), 3.56 (m, 2H), 3.46 (m, 1H), 3.27 (m, 1H), 2.95 (m, 2H), 2.20 (m, 2H), 2.03 (m, 2H), 1.98 (m, 1H), 1.78 (m, 2H), 1.53 (m, 1H)

Example 3: Preparation of (2R,3S)-2-(3-(5-bromo-1H-benzo[d]imidazol-1-yl)propyl)piperidin-3-ol dihydrochloride

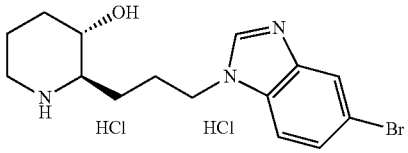 [SMILES: O[C@H]1CCCN[C@@H]1CCCn1cnc2cc(Br)ccc21 ; Cl ; Cl]

The title compound (13 mg, yield: 91%) was obtained in the same manner as in Example 1, with the exception that 4-bromo-1-fluoro-2-nitrobenzene was used instead of 4-chloro-2-fluoro-1-nitrobenzene in Step 1-8 of Example 1.

$^1$H NMR (500 MHz, MeOD): δ 9.53 (s, 1H), 8.08 (d, 1H), 7.98 (d, 1H), 7.83 (dd, 1H), 4.63 (t, 2H), 3.74 (t, 1H), 3.67 (m, 1H), 3.58 (m, 2H), 2.97 (m, 2H), 2.30 (m, 2H), 2.14 (m, 2H), 2.02 (m, 1H), 1.78 (m, 2H), 1.55 (m, 1H)

Example 4: Preparation of (2R,3S)-2-(3-(6-bromo-1H-benzo[d]imidazol-1-yl)propyl)piperidin-3-ol dihydrochloride

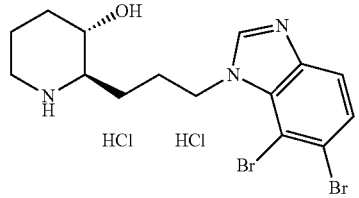 [SMILES: O[C@H]1CCCN[C@@H]1CCCn1cnc2ccc(Br)c(Br)c21 ; Cl ; Cl]

The title compound (10 mg, yield: 90%) was obtained in the same manner as in Example 1, with the exception that 4-bromo-2-fluoro-1-nitrobenzene was used instead of 4-chloro-2-fluoro-1-nitrobenzene in Step 1-8 of Example 1.

$^1$H NMR (500 MHz, MeOD): 9.51 (s, 1H), 8.32 (s, 1H), 7.81 (m, 2H), 4.59 (t, 2H), 3.58 (m, 1H), 2.97 (m, 2H), 2.20 (m, 2H), 2.12 (m, 2H), 2.02 (m, 1H), 1.79 (m, 2H), 1.59 (m, 1H)

Example 5: Preparation of (2R,3S)-2-(3-(7-bromo-1H-benzo[d]imidazol-1-yl)propyl)piperidin-3-ol dihydrochloride

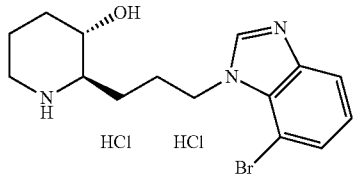 [SMILES: O[C@H]1CCCN[C@@H]1CCCn1cnc2cccc(Br)c21 ; Cl ; Cl]

The title compound (14 mg, yield: 93%) was obtained in the same manner as in Example 1, with the exception that 1-bromo-2-fluoro-3-nitrobenzene was used instead of 4-chloro-2-fluoro-1-nitrobenzene in Step 1-8 of Example 1.

$^1$H NMR (500 MHz, MeOD): 9.59 (s, 1H), 7.89 (dd, 2H), 7.56 (t, 1H), 3.59 (m, 1H), 2.98 (m, 2H), 2.30 (m, 2H), 2.13 (m, 2H), 2.04 (m, 1H), 1.79 (m, 2H), 1.56 (m, 1H)

Example 6: Preparation of (2R,3S)-2-(3-(4-fluoro-1H-benzo[d]imidazol-1-yl)propyl)piperidin-3-ol dihydrochloride

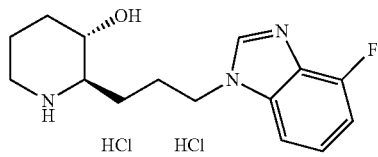 [SMILES: O[C@H]1CCCN[C@@H]1CCCn1cnc2c(F)cccc21 ; Cl ; Cl]

The title compound (13 mg, yield: 92%) was obtained in the same manner as in Example 1, with the exception that 1,3-difluoro-2-nitrobenzene was used instead of 4-chloro-2-fluoro-1-nitobenzene in Step 1-8 of Example 1.

$^1$H NMR (500 MHz, MeOD): δ 9.52 (s, 1H), 7.82 (d, 1H), 7.65 (m, 1H), 7.44 (m, 1H), 4.61 (t, 2H), 3.66 (m, 1H), 3.58 (m, 1H), 3.27 (m, 1H), 2.97 (m, 2H), 2.24 (m, 2H), 2.08 (m, 2H), 2.02 (m, 1H), 1.75 (m, 2H), 1.54 (m, 1H)

Example 7: Preparation of (2R,3S)-2-(3-(5-fluoro-1H-benzo[d]imidazol-1-yl)propyl)piperidin-3-ol dihydrochloride

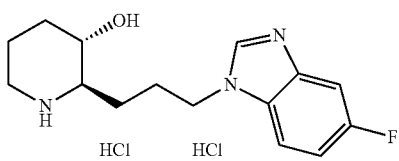 [SMILES: O[C@H]1CCCN[C@@H]1CCCn1cnc2cc(F)ccc21 ; Cl ; Cl]

The title compound (11 mg, yield: 90%) was obtained in the same manner as in Example 1, with the exception that 1,4-difluoro-2-nitrobenzene was used instead of 4-chloro-2-fluoro-1-nitrobenzene in Step 1-8 of Example 1.

$^1$H NMR (500 MHz, MeOD): δ 9.56 (s, 1H), 8.07 (m, 1H), 7.65 (d, 1H), 7.50 (t, 1H), 4.63 (m, 2H), 3.58 (m, 1H), 3.00 (m, 2H), 2.24 (m, 2H), 2.12 (m, 2H), 2.02 (m, 1H), 1.74 (m, 2H), 1.54 (m, 1H)

Example 8: Preparation of (2R,3S)-2-(3-(6-fluoro-1H-benzo[d]imidazol-1-yl)propyl)piperidin-3-ol dihydrochloride

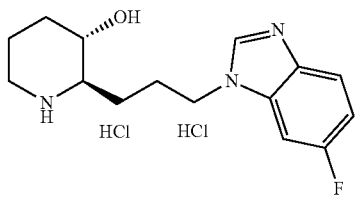 [SMILES: O[C@H]1CCCN[C@@H]1CCCn1cnc2ccc(F)cc21 ; Cl ; Cl]

The title compound (12 mg, yield: 91%) was obtained in the same manner as in Example 1, with the exception that 2,4-difluoro-1-nitrobenzene was used instead of 4-chloro-2-fluoro-1-nitobenzene in Step 1-8 of Example 1.

$^1$H NMR (500 MHz, MeOD): δ 9.56 (s, 1H), 7.89 (m, 2H), 7.48 (t, 1H), 4.59 (m, 2H), 3.57 (m, 1H), 3.03 (m, 2H), 2.29 (m, 2H), 2.11 (m, 2H), 2.03 (m, 1H), 1.76 (m, 2H), 1.54 (m, 1H)

Example 9: Preparation of (2R,3S)-2-(3-(7-fluoro-1H-benzo[d]imidazol-1-yl)propyl)piperidin-3-ol dihydrochloride

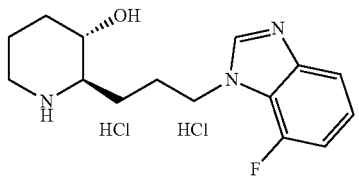 [SMILES: O[C@H]1CCCN[C@@H]1CCCn1cnc2cccc(F)c21 ; Cl ; Cl]

The title compound (10 mg, yield: 90%) was obtained in the same manner as in Example 1, with the exception that 1,2-difluoro-3-nitrobenzene was used instead of 4-chloro-2-fluoro-1-nitobenzene in Step 1-8 of Example 1.

$^1$H NMR (500 MHz, MeOD): δ 9.57 (s, 1H), 7.68 (m, 1H), 7.63 (m, 1H), 7.46 (m, 1H), 4.69 (t, 2H), 3.58 (m, 1H), 3.25 (m, 1H), 2.97 (m, 2H), 2.30 (m, 2H), 2.15 (m, 2H), 2.03 (m, 1H), 1.75 (m, 2H), 1.54 (m, 1H)

Example 10: Preparation of (2R,3S)-2-(3-(4-chloro-1H-benzo[d]imidazol-1-yl)propyl)piperidin-3-ol dihydrochloride

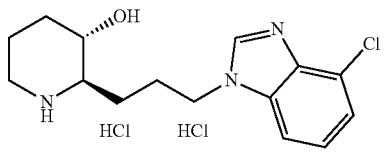 [SMILES: O[C@H]1CCCN[C@@H]1CCCn1cnc2c(Cl)cccc21 ; Cl ; Cl]

The title compound (11 mg, yield: 91%) was obtained in the same manner as in Example 1, with the exception that 1-chloro-3-fluoro-2-nitrobenzene was used instead of 4-chloro-2-fluoro-1-nitobenzene in Step 1-8 of Example 1.

$^1$H NMR (500 MHz, MeOD): δ 9.55 (s, 1H), 7.96 (d, 1H), 7.67 (d, 1H), 7.63 (m, 1H), 4.61 (t, 2H), 3.60 (m, 1H), 3.34 (m, 1H), 3.00 (m, 2H), 2.28 (m, 2H), 2.14 (m, 2H), 2.03 (m, 1H), 1.75 (m, 2H), 1.54 (m, 1H)

Example 11: Preparation of (2R,3S)-2-(3-(5-chloro-1H-benzo[d]imidazol-1-yl)propyl)piperidin-3-ol dihydrochloride

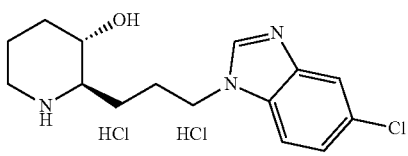 [SMILES: O[C@H]1CCCN[C@@H]1CCCn1cnc2cc(Cl)ccc21 ; Cl ; Cl]

The title compound (8 mg, yield: 87%) was obtained in the same manner as in Example 1, with the exception that 4-chloro-1-fluoro-2-nitrobenzene was used instead of 4-chloro-2-fluoro-1-nitobenzene in Step 1-8 of Example 1.

$^1$H NMR (500 MHz, MeOD): δ 9.55 (s, 1H), 8.03 (d, 1H), 7.93 (s, 1H), 7.69 (d, 1H), 4.61 (m, 2H), 3.58 (m, 1H), 3.01 (m, 2H), 2.29 (m, 2H), 2.09 (m, 2H), 2.00 (m, 1H), 1.74 (m, 2H), 1.52 (m, 1H)

Example 12: Preparation of (2R,3S)-2-(3-(7-chloro-1H-benzo[d]imidazol-1-yl)propyl)piperidin-3-ol dihydrochloride

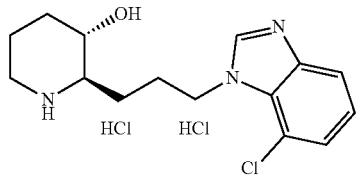 [SMILES: O[C@H]1CCCN[C@@H]1CCCn1cnc2cccc(Cl)c21 ; Cl ; Cl]

The title compound (10 mg, yield: 90%) was obtained in the same manner as in Example 1, with the exception that 1-chloro-2-fluoro-3-nitrobenzene was used instead of 4-chloro-2-fluoro-1-nitobenzene in Step 1-8 of Example 1.

$^1$H NMR (500 MHz, MeOD): δ 9.59 (s, 1H), 7.83 (d, 1H), 7.66 (d, 1H), 7.61 (d, 1H), 3.59 (m, 1H), 3.00 (m, 2H), 2.30 (m, 2H), 2.16 (m, 2H), 2.03 (m, 1H), 1.83 (m, 2H), 1.55 (m, 1H)

Example 13: Preparation of (2R,3S)-2-(3-(6-methyl-1H-benzo[d]imidazol-1-yl)propyl)piperidin-3-ol dihydrochloride

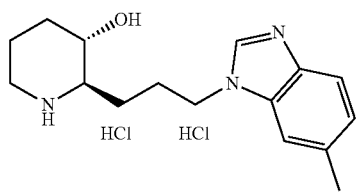 [SMILES: Cc1ccc2ncn(CCC[C@H]3NCCC[C@@H]3O)c2c1 ; Cl ; Cl]

The title compound (14 mg, yield: 85%) was obtained in the same manner as in Example 1, with the exception that 2-fluoro-4-methyl-1-nitrobenzene was used instead of 4-chloro-2-fluoro-1-nitobenzene in Step 1-8 of Example 1.

¹H NMR (500 MHz, MeOD): δ 9.42 (s, 1H), 7.83 (s, 1H), 7.73 (d, 1H), 7.52 (d, 1H), 4.59 (m, 2H), 3.57 (m, 1H), 2.95 (m, 2H), 2.59 (s, 3H), 2.24 (m, 2H), 2.11 (m, 2H), 2.01 (m, 1H), 1.74 (m, 2H), 1.54 (m, 1H)

Example 14: Preparation of (2R,3S)-2-(3-(5-methyl-1H-benzo[d]imidazol-1-yl)propyl)piperidin-3-ol dihydrochloride

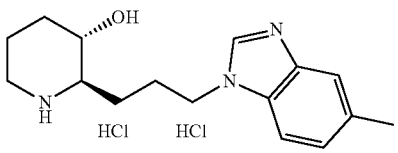 [SMILES: Cc1ccc2c(c1)ncn2CCC[C@H]1NCCC[C@@H]1O ; Cl ; Cl]

The title compound (12 mg, yield: 82%) was obtained in the same manner as in Example 1, with the exception that 1-fluoro-4-methyl-2-nitrobenzene was used instead of 4-chloro-2-fluoro-1-nitrobenzene in Step 1-8 of Example 1.

¹H NMR (500 MHz, MeOD): δ 9.41 (s, 1H), 7.89 (d, 1H), 7.65 (d, 1H), 7.52 (m, 1H), 4.56 (m, 2H), 3.36 (m, 2H), 2.95 (m, 2H), 2.66 (s, 3H), 2.24 (m, 2H), 2.07 (m 3H), 1.95 (m, 2H), 1.72 (m, 1H)

Example 15: Preparation of (2R,3S)-2-(3-(6-(trifluoromethyl)-1H-benzo[d]imidazol-1-yl)propyl)piperidin-3-ol dihydrochloride

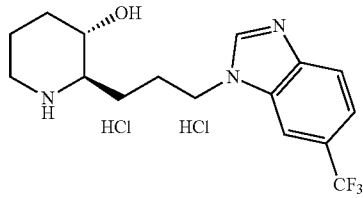 [SMILES: O[C@H]1CCCN[C@@H]1CCCn1cnc2ccc(C(F)(F)F)cc21 ; Cl ; Cl]

The title compound (17 mg, yield: 92%) was obtained in the same manner as in Example 1, with the exception that 2-fluoro-1-nitro-4-(trifluoromethyl)benzene was used instead of 4-chloro-2-fluoro-1-nitrobenzene in Step 1-8 of Example 1.

¹H NMR (500 MHz, MeOD): δ 9.62 (s, 1H), 8.45 (s, 1H), 8.06 (d, 1H), 7.95 (d, 1H), 4.67 (m, 2H), 3.62 (m, 1H), 2.98 (m, 2H), 2.22 (m, 2H), 2.08 (m, 2H), 2.01 (m, 1H), 1.71 (m, 2H), 1.54 (m, 1H)

Example 16: Preparation of (2R,3S)-2-(3-(7-(trifluoromethyl)-1H-benzo[d]imidazol-1-yl)propyl)piperidin-3-ol dihydrochloride

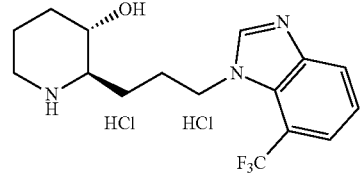 [SMILES: O[C@H]1CCCN[C@@H]1CCCn1cnc2cccc(C(F)(F)F)c21 ; Cl ; Cl]

The title compound (15 mg, yield: 89%) was obtained in the same manner as in Example 1, with the exception that 2-fluoro-1-nitro-3-(trifluoromethyl)benzene was used instead of 4-chloro-2-fluoro-1-nitrobenzene in Step 1-8 of Example 1.

¹H NMR (500 MHz, MeOD): δ 9.32 (m, 1H), 8.35 (m, 2H), 7.97 (m, 1H), 5.02 (m, 1H), 4.89 (m, 1H), 3.77 (m, 1H), 3.59 (m, 2H), 3.01 (m, 2H), 2.39 (m, 4H), 1.78 (m, 3H)

Example 17: Preparation of (2R,3S)-2-(3-(7-(trifluoromethoxy)-1H-benzo[d]imidazol-1-yl)propyl)piperidin-3-ol dihydrochloride

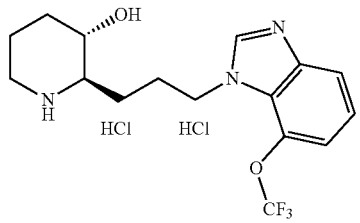 [SMILES: O[C@H]1CCCN[C@@H]1CCCn1cnc2cccc(OC(F)(F)F)c21 ; Cl ; Cl]

The title compound (14 mg, yield: 87%) was obtained in the same manner as in Example 1, with the exception that 2-fluoro-1-nitro-3-(trifluoromethoxy)benzene was used instead of 4-chloro-2-fluoro-1-nitrobenzene in Step 1-8 of Example 1.

¹H NMR (500 MHz, MeOD): δ 9.68 (s, 1H), 7.87-7.64 (m, 3H), 4.81 (m, 3H), 3.59 (m, 1H), 2.99 (m, 2H), 2.24 (m, 2H), 2.08 (m, 3H), 1.77 (m, 2H), 1.56 (m, 1H)

Example 18: Preparation of (2R,3S)-2-(3-(4-(pyrrolidin-1-yl)-1H-benzo[d]imidazol-1-yl)propyl)piperidin-3-ol dihydrochloride

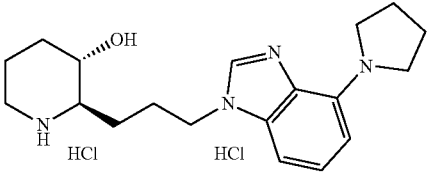 [SMILES: O[C@H]1CCCN[C@@H]1CCCn1cnc2c(N3CCCC3)cccc21 ; Cl ; Cl]

Step 18-1: Preparation of tert-butyl (2R,3S)-2-(3-(4-bromo-1H-benzo[d]imidazol-1-yl)propyl)-3-((tert-butyldimethylsilyl)oxy)piperidine-1-carboxylate The title compound (1.7 g, yield: 73%) was obtained in the same manner as in Steps 1-1 to 1-9 of Example 1.

Step 18-2: Preparation of tert-butyl (2R,3S)-3-((tert-butyldimethylsilyl)oxy)-2-(3-(4-(pyrrolidin-1-yl)-1H-benzo[d]imidazol-1-yl)propyl)piperidine-1-carboxylate (2R,3S)-2-(3-(4-bromo-1H-benzo[d]imidazol-1-yl)propyl)-3-((tert-butyldimethylsilyl)oxy)piperidine-1-carboxylate (100 mg, 0.2 mmol) obtained in Step 18-1 was dissolved in N,N-dimethylformamide (2 mL, 0.09 M). Pyrrolidine (14 mg, 0.2 mmol), 2,2'-bis(diphenylphosphino)-1,1'-binaphthyl) (25 mg, 0.04 mmol), palladium acetate (II) (5 mg, 0.02 mmol) and cesium carbonate (130 mg, 0.4 mmol) were added thereto, and then stirred in a microwave at 100° C. for 30 minutes. When the reaction was completed, it was filtered with celite, diluted with ethyl acetate, and washed with saturated sodium chloride solution. The organic layer was collected and dried over magnesium sulfate, filtered and concentrated under reduced pressure. The residue was purified by column chromatography (hexane:ethyl acetate=1:5) to give the title compound (60 mg, yield: 45%).

Step 18-3: Preparation of (2R,3S)-2-(3-(4-(pyrrolidin-1-yl)-1H-benzo[d]imidazol-1-yl)propyl)piperidin-3-ol dihydrochloride The title compound (10 mg, yield: 90%) was obtained in the same manner as in Step 1-9 of Example 1.
$^1$H NMR (500 MHz, MeOD): δ 9.32 (s, 1H), 7.45 (t, 1H), 7.17 (d, 1H), 6.76 (d, 1H), 4.52 (t, 2H), 3.64 (m, 3H), 3.57 (m, 1H), 3.48 (m, 1H), 2.92 (m, 2H), 2.27 (m, 1H), 2.18 (m, 4H), 2.11 (m, 2H), 2.02 (m, 1H), 1.72 (m, 2H), 1.55 (m, 1H)

Example 19: Preparation of (2R,3S)-2-(3-(4-(piperidin-1-yl)-1H-benzo[d]imidazol-1-yl)propyl)piperidin-3-ol dihydrochloride

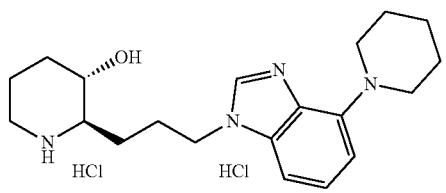 [SMILES: O[C@H]1CCCN[C@@H]1CCCn1cnc2c(N3CCCCC3)cccc21 ; Cl ; Cl]

The title compound (15 mg, yield: 96%) was obtained in the same manner as in Example 18, with the exception that piperidine was used instead of pyrrolidine in Step 18-2 of Example 18.
$^1$H NMR (500 MHz, MeOD): δ 9.05 (s, 1H), 7.69 (d, 1H), 7.53 (t, 1H), 7.35 (d, 1H), 4.52 (t, 2H), 3.50 (m, 5H), 3.34 (m, 1H), 3.26 (m, 1H), 2.95 (m, 2H), 2.25 (m, 2H), 2.09 (m, 2H), 2.02 (m, 4H), 1.75 (m, 4H), 1.53 (m, 1H)

Example 20: Preparation of (2R,3S)-2-(3-(4-(3-fluorophenyl)-1H-benzo[d]imidazol-1-yl)propyl)piperidin-3-ol dihydrochloride

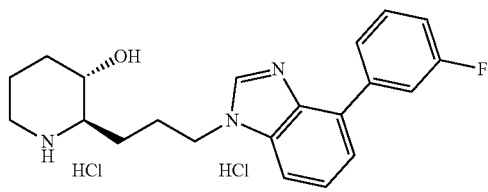 [SMILES: O[C@H]1CCCN[C@@H]1CCCn1cnc2c(-c3cccc(F)c3)cccc21 ; Cl ; Cl]

Step 20-1: tert-butyl (2R,3S)-2-(3-(4-bromo-1H-benzo[d]imidazol-1-yl)propyl)-3-((tert-butyldimethylsilyl)oxy)piperidine-1-carboxylate The title compound (1.7 g, yield: 73%) was obtained in the same manner as in Steps 1-1 to 1-9 of Example 1.

Step 20-2: tert-butyl (2R,3S)-3-((tert-butyldimethylsilyl)oxy)-2-(3-(4-(3-fluorophenyl)-1H-benzo[d]imidazol-1-yl)propyl)piperidine-1-carboxylate Tert-butyl (2R,3S)-2-(3-(4-bromo-1H-benzo[d]imidazol-1-yl)propyl)-3-((tert-butyldimethylsilyl)oxy)piperidine-1-carboxylate (100 mg, 0.2 mmol) obtained in Step 20-1 was dissolved in N,N-dimethylformamide (2 mL, 0.09 M). (3-fluorophenyl)boronic acid (22 mg, 0.2 mmol), tetrakis (triphenylphosphine)palladium(0) (23 mg, 0.04 mmol), and 2N sodium carbonate (0.3 mL, 0.76 mmol) were added thereto, and stirred in a microwave at 130° C. for 45 minutes. When the reaction was completed, it was filtered with celite, diluted with ethyl acetate, and washed with saturated sodium chloride solution. The organic layer was collected and dried over magnesium sulfate, filtered and concentrated under reduced pressure. The residue was purified by column chromatography (hexane:ethyl acetate=1:5) to give the title compound (60 mg, yield: 45%).

Step 20-3: Preparation of (2R,3S)-2-(3-(4-(3-fluorophenyl)-1H-benzo[d]imidazol-1-yl)propyl)piperidin-3-ol dihydrochloride The title compound (19 mg, yield: 91%) was obtained in the same manner as in Step 1-9 of Example 1.
$^1$H NMR (500 MHz, MeOD): δ 9.57 (d, 1H), 8.03 (d, 1H), 7.77 (t, 1H), 7.72 (d, 1H), 7.62 (m, 1H), 7.49 (d, 1H), 7.45 (m, 1H), 7.29 (t, 1H), 4.66 (t, 2H), 3.57 (m, 1H), 2.97 (m, 2H), 2.25 (m, 2H), 2.14 (m, 2H), 2.02 (m, 1H), 1.75 (m, 2H), 1.55 (m, 1H)

Example 21: Preparation of (2R,3S)-2-(3-(4-(3-chlorophenyl)-1H-benzo[d]imidazol-1-yl)propyl) piperidin-3-ol dihydrochloride

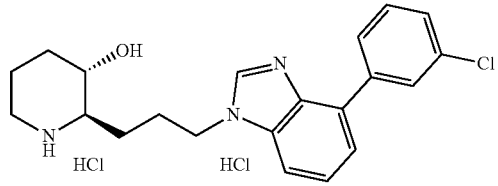 [SMILES: O[C@H]1CCCN[C@@H]1CCCn1cnc2c(-c3cccc(Cl)c3)cccc21 ; Cl ; Cl]

The title compound (18 mg, yield: 89%) was obtained in the same manner as in Example 20, with the exception that (3-chlorophenyl)boronic acid was used instead of (3-fluorophenyl)boronic acid in Step 20-2 of Example 20.
$^1$H NMR (500 MHz, MeOD): δ 9.63 (s, 1H), 8.07 (d, 1H), 7.79 (t, 1H), 7.71 (m, 2H), 7.58 (m, 3H), 4.67 (t, 2H), 3.60 (m, 1H), 2.97 (m, 2H), 2.28 (m, 2H) 2.10 (m, 2H), 2.02 (m, 1H), 1.85 (m, 2H), 1.55 (m, 1H)

Example 22: Preparation of (2R,3S)-2-(3-(5-(3-fluorophenyl)-1H-benzo[d]imidazol-1-yl)propyl) piperidin-3-ol dihydrochloride

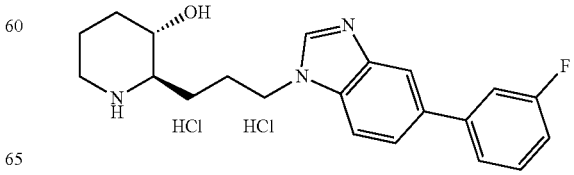

The title compound (7 mg, yield: 26%) was obtained in the same manner as in Example 20, with the exception that tert-butyl (2R,3S)-2-(3-(5-bromo-1H-benzo[d]imidazol-1-yl)propyl)-3-((tert-butyldimethylsilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate in Step 20-2 of Example 20.

$^1$H NMR (500 MHz, MeOD): δ 9.56 (s, 1H), 8.11 (m, 2H), 7.98 (m, 1H), 7.54 (m, 2H), 7.20 (m, 1H), 7.16 (m, 1H), 4.67 (m, 2H), 3.61 (m, 2H), 3.03 (m, 2H), 2.30 (m, 2H), 2.12 (m, 2H), 1.98 (m, 1H), 1.78 (m, 2H), 1.59 (m, 1H)

Example 23: Preparation of (2R,3S)-2-(3-(6-(2-fluorophenyl)-1H-benzo[d]imidazol-1-yl)propyl) piperidin-3-ol dihydrochloride

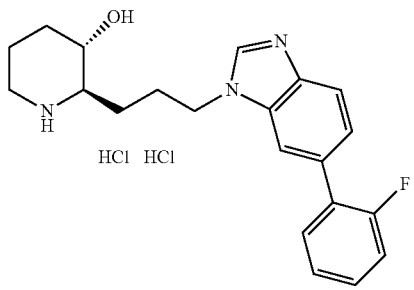 [SMILES: O[C@H]1CCCN[C@@H]1CCCn1cnc2ccc(-c3ccccc3F)cc21 ; Cl ; Cl]

The title compound (13 mg, yield: 34%) was obtained in the same manner as in Example 20, with the exception that tert-butyl (2R,3S)-2-(3-(6-bromo-1H-benzo[d]imidazol-1-yl)propyl)-3-((tert-butyldimethylsilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate, and that (2-fluorophenyl)boronic acid was used instead of (3-fluorophenyl)boronic acid in Step 20-2 of Example 20.

$^1$H NMR (500 MHz, MeOD): δ 7.98 (s, 1H), 7.88 (m, 1H), 7.71 (m, 1H), 7.59 (m, 1H), 7.44 (m, 1H), 7.32 (m, 1H), 7.25 (m, 1H), 4.58 (m, 2H), 3.55 (m, 1H), 2.94 (m, 2H), 2.19 (m, 2H), 2.06 (m, 2H), 2.00 (m, 1H), 1.70 (m, 2H), 1.53 (m, 1H)

Example 24: Preparation of (2R,3S)-2-(3-(6-(3-fluorophenyl)-1H-benzo[d]imidazol-1-yl)propyl) piperidin-3-ol dihydrochloride

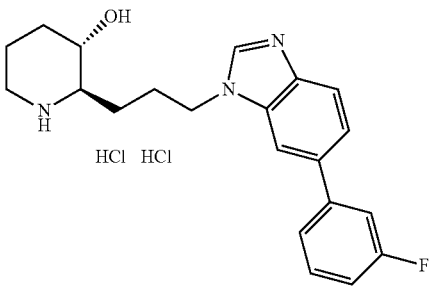 [SMILES: O[C@H]1CCCN[C@@H]1CCCn1cnc2ccc(-c3cccc(F)c3)cc21 ; Cl ; Cl]

The title compound (11 mg, yield: 30%) was obtained in the same manner as in Example 20, with the exception that tert-butyl (2R,3S)-2-(3-(6-bromo-1H-benzo[d]imidazol-1-yl)propyl)-3-((tert-butyldimethylsilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate in Step 20-2 of Example 20.

$^1$H NMR (500 MHz, MeOD): δ 9.27 (s, 1H), 8.18 (m, 1H), 7.91 (m, 2H), 7.58 (m, 1H), 7.52 (m, 2H), 7.17 (t, 1H), 4.65 (m, 2H), 3.57 (m, 1H), 2.96 (m, 2H), 2.23 (m, 2H), 2.08 (m, 2H), 2.00 (m, 1H), 1.73 (m, 2H), 1.57 (m, 1H)

Example 25: Preparation of (2R,3S)-2-(3-(6-(4-fluorophenyl)-1H-benzo[d]imidazol-1-yl)propyl) piperidin-3-ol dihydrochloride

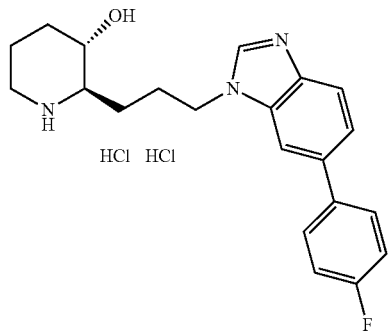 [SMILES: O[C@H]1CCCN[C@@H]1CCCn1cnc2ccc(-c3ccc(F)cc3)cc21 ; Cl ; Cl]

The title compound (8 mg, yield: 28%) was obtained in the same manner as in Example 20, with the exception that tert-butyl (2R,3S)-2-(3-(6-bromo-1H-benzo[d]imidazol-1-yl)propyl)-3-((tert-butyldimethylsilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate, and that (4-fluorophenyl)boronic acid was used instead of (3-fluorophenyl)boronic acid in Step 20-2 of Example 20.

$^1$H NMR (500 MHz, MeOD): δ 7.97 (s, 1H), 7.83-7.74 (m, 4H), 7.23 (m, 2H), 4.55 (m, 2H), 3.54 (m, 1H), 2.94 (m, 2H), 2.20 (m, 2H), 2.05 (m, 2H), 2.00 (m, 1H), 1.69 (m, 2H), 1.53 (m, 1H)

Example 26: Preparation of (2R,3S)-2-(3-(7-(2-fluorophenyl)-1H-benzo[d]imidazol-1-yl)propyl) piperidin-3-ol dihydrochloride

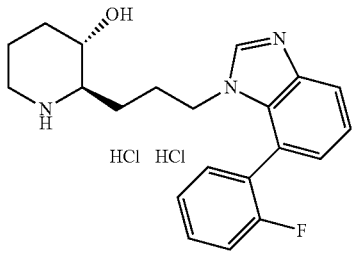 [SMILES: O[C@H]1CCCN[C@@H]1CCCn1cnc2cccc(-c3ccccc3F)c21 ; Cl ; Cl]

The title compound (11 mg, yield: 30%) was obtained in the same manner as in Example 20, with the exception that tert-butyl (2R,3S)-2-(3-(7-bromo-1H-benzo[d]imidazol-1-yl)propyl)-3-((tert-butyldimethylsilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate, and that (2-fluorophenyl)boronic acid was used instead of (3-fluorophenyl)boronic acid in Step 20-2 of Example 20.

¹H NMR (500 MHz, MeOD): δ 9.50 (s, 1H), 7.94 (d, 1H), 7.75 (t, 1H), 7.62 (m, 1H), 7.57 (m, 1H), 7.53 (d, 1H), 7.43 (m, 1H), 7.38 (t, 1H), 4.27 (m, 1H), 4.09 (m, 1H), 3.42 (m, 1H), 3.16 (m, 1H), 2.90 (m, 1H), 2.73 (m, 1H), 1.97 (m, 2H), 1.77-1.62 (m, 3H), 1.47 (m, 2H), 1.27 (m, 1H)

Example 27: Preparation of (2R,3S)-2-(3-(7-(3-fluorophenyl)-1H-benzo[d]imidazol-1-yl)propyl)piperidin-3-ol dihydrochloride

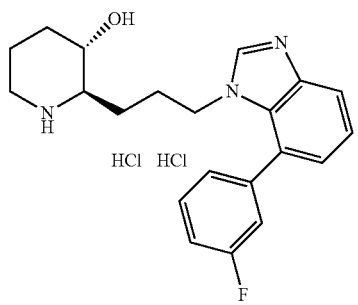 [SMILES: O[C@H]1CCCN[C@@H]1CCCn1cnc2cccc(-c3cccc(F)c3)c21 ; Cl ; Cl]

The title compound (7 mg, yield: 28%) was obtained in the same manner as in Example 20, with the exception that tert-butyl (2R,3S)-2-(3-(7-bromo-1H-benzo[d]imidazol-1-yl)propyl)-3-((tert-butyldimethylsilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate in Step 20-2 of Example 20.

¹H NMR (500 MHz, MeOD): δ 9.49 (s, 1H), 7.91 (d, 1H), 7.72 (t, 1H), 7.59 (m, 1H), 7.50 (d, 1H), 7.36 (m, 3H), 4.17 (m, 2H), 3.37 (m, 1H), 3.16 (m, 1H), 2.90 (m, 1H), 2.73 (m, 1H), 1.96 (m, 2H), 1.67 (m, 3H), 1.50 (m, 2H), 1.32 (m, 1H)

Example 28: Preparation of (2R,3S)-2-(3-(7-(4-fluorophenyl)-1H-benzo[d]imidazol-1-yl)propyl)piperidin-3-ol dihydrochloride

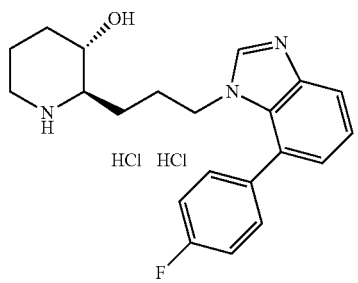 [SMILES: O[C@H]1CCCN[C@@H]1CCCn1cnc2cccc(-c3ccc(F)cc3)c21 ; Cl ; Cl]

The title compound (13 mg, yield: 32%) was obtained in the same manner as in Example 20, with the exception that tert-butyl (2R,3S)-2-(3-(7-bromo-1H-benzo[d]imidazol-1-yl)propyl)-3-((tert-butyldimethylsilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate, and that (4-fluorophenyl)boronic acid was used instead of (3-fluorophenyl)boronic acid in Step 20-2 of Example 20.

¹H NMR (500 MHz, MeOD): δ 9.48 (s, 1H), 7.89 (d, 1H), 7.68 (t, 1H), 7.54 (m, 2H), 7.50 (d, 1H), 7.33 (t, 2H), 4.14 (m, 2H), 3.42 (m, 1H), 3.16 (m, 1H), 2.90 (m, 1H), 2.72 (m, 1H), 1.97 (m, 2H), 1.72 (m, 3H), 1.50 (m, 2H), 1.31 (m, 1H)

Example 29: Preparation of (2R,3S)-2-(3-(5-(1H-pyrazol-4-yl)-1H-benzo[d]imidazol-1-yl)propyl)piperidin-3-ol dihydrochloride

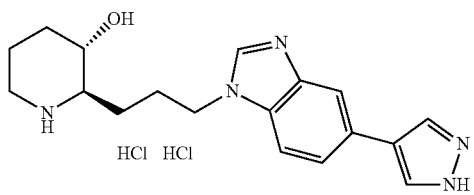 [SMILES: O[C@H]1CCCN[C@@H]1CCCn1cnc2cc(-c3cn[nH]c3)ccc21 ; Cl ; Cl]

The title compound (7 mg, yield: 19%) was obtained in the same manner as in Example 20, with the exception that tert-butyl (2R,3S)-2-(3-(6-bromo-1H-benzo[d]imidazol-1-yl)propyl)-3-((tert-butyldimethylsilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate, and that (1H-pyrazol-4-yl)boronic acid was used instead of (3-fluorophenyl)boronic acid in Step 20-2 of Example 20.

¹H NMR (500 MHz, MeOD): δ 9.53 (s, 1H), 8.32 (s, 1H), 8.07 (m, 1H), 7.70 (m, 2H), 7.58 (m, 1H), 4.63 (m, 2H), 3.60 (m, 1H), 3.00 (m, 2H), 2.30 (m, 2H), 2.14 (m, 2H), 2.05 (m, 1H), 1.78 (m, 2H), 1.55 (m, 1H)

Example 30: Preparation of (2R,3S)-2-(3-(6-(1H-pyrazol-4-yl)-1H-benzo[d]imidazol-1-yl)propyl)piperidin-3-ol dihydrochloride

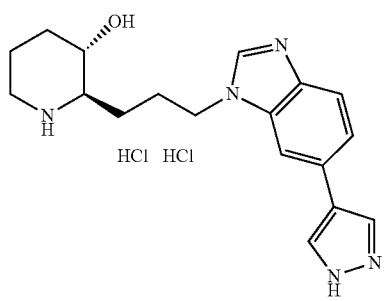 [SMILES: O[C@H]1CCCN[C@@H]1CCCn1cnc2ccc(-c3cn[nH]c3)cc21 ; Cl ; Cl]

The title compound (6 mg, yield: 15%) was obtained in the same manner as in Example 20, with the exception that tert-butyl (2R,3S)-2-(3-(6-bromo-1H-benzo[d]imidazol-1-yl)propyl)-3-((tert-butyldimethylsilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate, and that (1H-pyrazol-4-yl)boronic acid was used instead of (3-fluorophenyl)boronic acid in Step 20-2 of Example 20.

¹H NMR (500 MHz, MeOD): δ 9.52 (s, 1H), 8.48 (s, 1H), 8.03 (d, 1H), 7.87 (d, 1H), 7.68 (m, 1H), 7.58 (m, 1H), 4.66 (m, 2H), 3.60 (m, 2H), 2.97 (m, 2H), 2.31 (m, 2H), 2.14 (m, 2H), 2.00 (m, 1H), 1.77 (m, 2H), 1.54 (m, 1H)

Example 31: Preparation of (2R,3S)-2-(3-(7-(1H-pyrazol-4-yl)-1H-benzo[d]imidazol-1-yl)propyl)piperidin-3-ol dihydrochloride

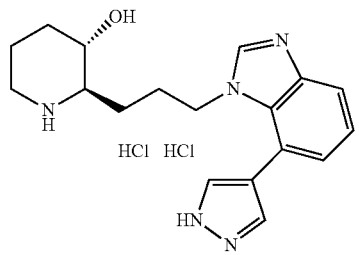 [SMILES: O[C@H]1CCCN[C@@H]1CCCn1cnc2cccc(-c3cn[nH]c3)c21 ; Cl ; Cl]

The title compound (5 mg, yield: 12%) was obtained in the same manner as in Example 20, with the exception that tert-butyl (2R,3S)-2-(3-(7-bromo-1H-benzo[d]imidazol-1-yl)propyl)-3-((tert-butyldimethylsilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate, and that (1H-pyrazol-4-yl)boronic acid was used instead of (3-fluorophenyl)boronic acid in Step 20-2 of Example 20.

$^1$H NMR (500 MHz, MeOD): δ 9.55 (s, 1H), 7.99 (s, 1H), 7.87 (d, 1H), 7.69 (t, 1H), 7.51 (d, 1H), 4.35 (m, 2H), 3.50 (m, 2H), 3.21 (m, 1H), 2.97 (m, 1H), 2.77 (m, 1H), 2.01 (m, 2H), 1.76 (m, 2H), 1.70 (m, 2H), 1.55 (m, 1H), 1.45 (m, 1H)

Example 32: Preparation of (2R,3S)-2-(3-(6-chloro-5-fluoro-1H-benzo[d]imidazol-1-yl)propyl)piperidin-3-ol dihydrochloride

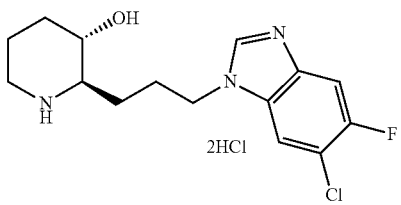 [SMILES: O[C@H]1CCCN[C@@H]1CCCn1cnc2cc(F)c(Cl)cc21 ; "2HCl"]

The title compound (25 mg, yield: 83%) was obtained in the same manner as in Example 1, with the exception that 1-chloro-2,5-difluoro-4-nitrobenzene was used instead of 4-chloro-2-fluoro-1-nitrobenzene in step 1-8 of Example 1.

$^1$H-NMR (500 MHz, MeOD): δ 9.55 (s, 1H), 8.33 (d, 1H), 7.82 (d, 1H), 4.58 (td, 2H), 3.59 (m, 2H), 2.98 (m, 2H), 2.23 (m, 2H), 2.08 (m, 2H), 1.98 (m, 1H), 1.77 (m, 2H), 1.76 (m, 1H)

Example 33: Preparation of (2R,3S)-2-(3-(6-bromo-5-fluoro-1H-benzo[d]imidazol-1-yl)propyl)piperidin-3-ol dihydrochloride

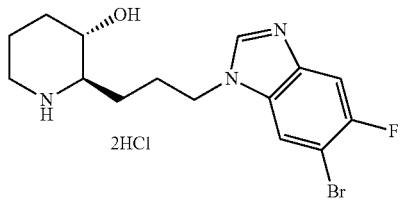 [SMILES: O[C@H]1CCCN[C@@H]1CCCn1cnc2cc(F)c(Br)cc21 ; "2HCl"]

The title compound (15 mg, yield: 81%) was obtained in the same manner as in Example 1, with the exception that 1-bromo-2,5-difluoro-4-nitrobenzene was used instead of 4-chloro-2-fluoro-1-nitrobenzene in step 1-8 of Example 1.

$^1$H-NMR (500 MHz, MeOD): δ 9.55 (s, 1H), 8.46 (d, 1H), 7.79 (d, 1H), 4.59 (t, 2H), 3.59 (m, 1H), 2.97 (m, 2H), 2.22 (m, 2H), 2.08 (m, 2H), 1.97 (m, 1H), 1.76 (m, 2H), 1.56 (m, 1H)

Example 34: Preparation of (2R,3S)-2-(3-(5-chloro-6-fluoro-1H-benzo[d]imidazol-1-yl)propyl)piperidin-3-ol dihydrochloride

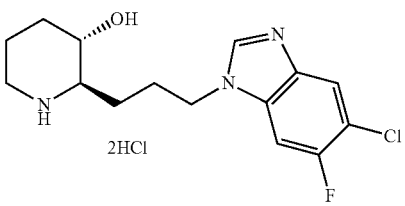 [SMILES: O[C@H]1CCCN[C@@H]1CCCn1cnc2cc(Cl)c(F)cc21 ; "2HCl"]

The title compound (20 mg, yield: 80%) was obtained in the same manner as in Example 1, with the exception that 1-chloro-2,4-difluoro-5-nitrobenzene was used instead of 4-chloro-2-fluoro-1-nitrobenzene in step 1-8 of Example 1.

$^1$H-NMR (500 MHz, MeOD): δ 9.55 (s, 1H), 8.09 (d, 1H), 8.06 (d, 1H), 4.58 (t, 2H), 3.60 (m, 2H), 2.98 (m, 2H), 2.21 (m, 2H), 2.09 (m, 2H), 1.97 (m, 1H), 1.76 (m, 2H), 1.56 (m, 1H)

Example 35: Preparation of (2R,3S)-2-(3-(5-bromo-6-fluoro-1H-benzo[d]imidazol-1-yl)propyl)piperidin-3-ol dihydrochloride

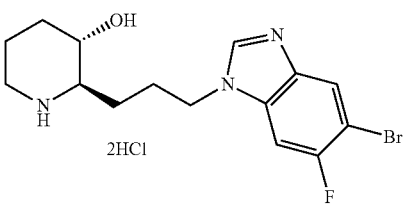 [SMILES: O[C@H]1CCCN[C@@H]1CCCn1cnc2cc(Br)c(F)cc21 ; "2HCl"]

The title compound (22 mg, yield: 83%) was obtained in the same manner as in Example 1, with the exception that 1-bromo-2,4-difluoro-5-nitrobenzene was used instead of 4-chloro-2-fluoro-1-nitrobenzene in step 1-8 of Example 1.

¹H-NMR (500 MHz, MeOD): δ 9.58 (s, 1H), 8.19 (d, 1H), 8.07 (d, 1H), 4.58 (t, 2H), 3.59 (m, 2H), 2.98 (m, 2H), 2.22 (m, 2H), 2.08 (m, 2H), 1.96 (m, 1H), 1.76 (m, 2H), 1.56 (m, 1H)

Example 36: Preparation of (2R,3S)-2-(3-(6-bromo-5-chloro-1H-benzo[d]imidazol-1-yl)propyl)piperidin-3-ol dihydrochloride

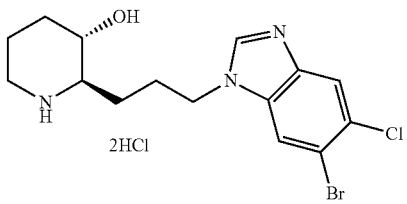 [SMILES: O[C@H]1CCCN[C@@H]1CCCn1cnc2cc(Cl)c(Br)cc21 ; "2HCl"]

The title compound (22 mg, yield: 83%) was obtained in the same manner as in Example 1, with the exception that 1-bromo-2-chloro-5-fluoro-4-nitrobenzene was used instead of 4-chloro-2-fluoro-1-nitrobenzene in step 1-8 of Example 1.

¹H-NMR (500 MHz, MeOD): δ 9.54 (s, 1H), 8.51 (s, 1H), 8.10 (s, 1H), 4.58 (t, 2H), 3.66 (m, 2H), 2.98 (m, 2H), 2.23 (m, 2H), 2.08 (m, 2H), 1.97 (m, 1H), 1.76 (m, 2H), 1.56 (m, 1H)

Example 37: Preparation of (2R,3S)-2-(3-(6-chloro-5-methoxy-1H-benzo[d]imidazol-1-yl)propyl)piperidin-3-ol dihydrochloride

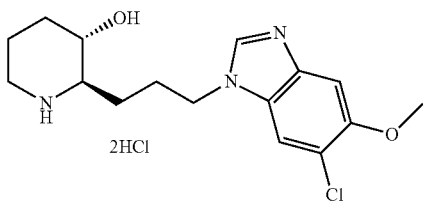 [SMILES: COc1cc2ncn(CCC[C@H]3NCCC[C@@H]3O)c2cc1Cl ; "2HCl"]

The title compound (18 mg, yield: 81%) was obtained in the same manner as in Example 1, with the exception that 1-chloro-5-fluoro-2-methoxy-4-nitrobenzene was used instead of 4-chloro-2-fluoro-1-nitrobenzene in step 1-8 of Example 1.

¹H-NMR (500 MHz, MeOD): δ 9.44 (s, 1H), 8.17 (s, 1H), 7.45 (s, 1H), 4.56 (t, 2H), 4.02 (s, 3H), 3.58 (t, 1H), 2.98 (m, 2H), 2.21 (m, 2H), 2.05 (m, 2H), 1.97 (m, 1H), 1.76 (m, 2H), 1.54 (m, 1H)

Example 38: Preparation of (2R,3S)-2-(3-(6-fluoro-5-methoxy-1H-benzo[d]imidazol-1-yl)propyl)piperidin-3-ol dihydrochloride

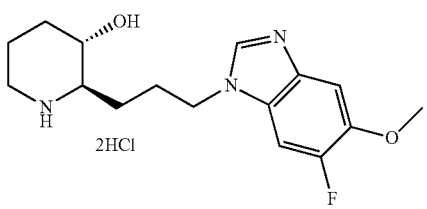 [SMILES: COc1cc2ncn(CCC[C@H]3NCCC[C@@H]3O)c2cc1F ; "2HCl"]

The title compound (18 mg, yield: 81%) was obtained in the same manner as in Example 1, with the exception that 1,5-difluoro-2-methoxy-4-nitrobenzene was used instead of 4-chloro-2-fluoro-1-nitrobenzene in step 1-8 of Example 1.

¹H-NMR (500 MHz, MeOD): δ 9.45 (s, 1H), 7.92 (d, 1H), 7.48 (d, 1H), 4.55 (t, 2H), 4.00 (s, 3H), 3.58 (m, 2H), 2.99 (m, 2H), 2.22 (m, 2H), 2.06 (m, 2H), 1.97 (m, 1H), 1.77 (m, 2H)

Example 39: Preparation of (2R,3S)-2-(3-(5-fluoro-6-methyl-1H-benzo[d]imidazol-1-yl)propyl)piperidin-3-ol dihydrochloride

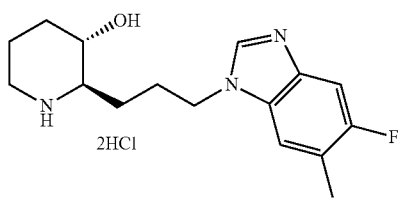 [SMILES: Cc1cc2c(cc1F)ncn2CCC[C@H]1NCCC[C@@H]1O ; "2HCl"]

The title compound (15 mg, yield: 79%) was obtained in the same manner as in Example 1, with the exception that 1,4-difluoro-2-methyl-5-nitrobenzene was used instead of 4-chloro-2-fluoro-1-nitrobenzene in step 1-8 of Example 1.

¹H-NMR (500 MHz, MeOD): δ 9.49 (s, 1H), 7.96 (d, 2H), 7.58 (d, 1H), 4.59 (t, 2H), 3.59 (m, 1H), 3.00 (m, 2H), 2.50 (s, 3H), 2.22 (m, 2H), 2.08 (m, 2H), 1.97 (m, 1H), 1.77 (m, 2H), 1.56 (m, 1H)

Example 40: Preparation of (2R,3S)-2-(3-(4,5-dichloro-1H-benzo[d]imidazol-1-yl)propyl)piperidin-3-ol dihydrochloride

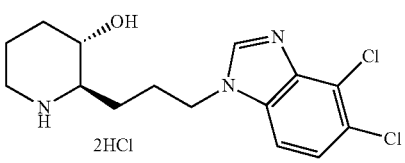 [SMILES: O[C@H]1CCCN[C@@H]1CCCn1cnc2c(Cl)c(Cl)ccc21 ; "2HCl"]

The title compound (26 mg, yield: 81%) was obtained in the same manner as in Example 1, with the exception that 1,2-dichloro-4-fluoro-3-nitrobenzene was used instead of 4-chloro-2-fluoro-1-nitrobenzene in step 1-8 of Example 1.

¹H-NMR (500 MHz, MeOD): δ 9.67 (s, 1H). 8.02 (d, 1H), 7.82 (d, 1H), 4.62 (m, 2H), 3.60 (m, 1H), 3.28 (m, 1H), 2.99 (m, 2H), 2.25 (m, 2H), 2.08 (m, 2H), 1.99 (m, 1H), 1.78 (m, 2H), 1.54 (m, 1H)

Example 41: Preparation of (2S,3S)-2-(3-(4,5-dichloro-1H-benzo[d]imidazol-1-yl)propyl)piperidin-3-ol dihydrochloride

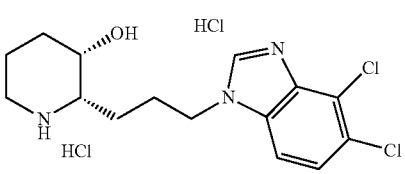 [SMILES: Cl ; O[C@H]1CCCN[C@H]1CCCn1cnc2c(Cl)c(Cl)ccc21 ; Cl]

The title compound (19 mg, yield: 85%) was obtained in the same manner as in Example 1, with the exception that tert-butyl (2S,3S)-3-((tert-butyldimethylsilyl)oxy)-2-(3-hydroxypropyl)piperidine-1-carboxylate was used instead of tert-butyl (2R,3S)-3-((tert-butyldimethylsilyl)oxy)-2-(3-hydroxypropyl)piperidine-1-carboxylate in Step 1-5 of Example 1.

¹H NMR (500 MHz, MeOD): δ 9.58 (d, 1H), 7.97 (d, 1H), 7.81 (d, 1H), 4.59 (m, 2H), 4.02 (s, 1H), 3.27 (s, 1H), 3.20 (m, 1H), 3.00 (t, 1H), 2.18-2.05 (m, 3H), 1.94 (m, 1H), 1.87 (m, 1H), 1.72-1.67 (m, 3H)

Example 42: Preparation of (2S,3R)-2-(3-(4,5-dichloro-1H-benzo[d]imidazol-1-yl)propyl)piperidin-3-ol dihydrochloride

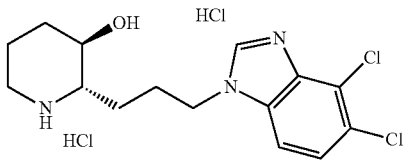 [SMILES: Cl ; O[C@@H]1CCCN[C@H]1CCCn1cnc2c(Cl)c(Cl)ccc21 ; Cl]

The title compound (33 mg, yield: 84%) was obtained in the same manner as in Example 1, with the exception that tert-butyl (2S,3R)-3-((tert-butyldimethylsilyl)oxy)-2-(3-hydroxypropyl)piperidine-1-carboxylate was used instead of tert-butyl (2R,3S)-3-((tert-butyldimethylsilyl)oxy)-2-(3-hydroxypropyl)piperidine-1-carboxylate in Step 1-5 of Example 1.

¹H NMR (500 MHz, MeOD): δ 9.64 (d, 1H), 8.00 (dd, 1H), 7.82 (d, 1H), 4.61 (m, 2H), 3.59 (m, 1H), 3.27 (s, 1H), 3.02-2.93 (m, 2H), 2.29-2.18 (m, 2H), 2.07 (m, 2H), 1.99 (m, 1H), 1.58 (m, 2H), 1.51 (m, 1H)

Example 43: Preparation of (2R,3R)-2-(3-(4,5-dichloro-1H-benzo[d]imidazol-1-yl)propyl)piperidin-3-ol dihydrochloride

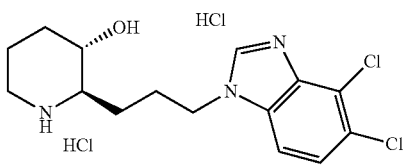 [SMILES: Cl ; O[C@H]1CCCN[C@@H]1CCCn1cnc2c(Cl)c(Cl)ccc21 ; Cl]

The title compound (23 mg, yield: 85%) was obtained in the same manner as in Example 1, with the exception that tert-butyl (2R,3R)-3-((tert-butyldimethylsilyl)oxy)-2-(3-hydroxypropyl)piperidine-1-carboxylate was used instead of tert-butyl (2R,3S)-3-((tert-butyldimethylsilyl)oxy)-2-(3-hydroxypropyl)piperidine-1-carboxylate in Step 1-5 of Example 1.

¹H NMR (500 MHz, MeOD): δ 9.66 (d, 1H), 7.97 (d, 1H), 7.83 (d, 1H), 4.60 (t, 2H), 4.01 (s, 1H), 3.27 (s, 1H), 3.20 (t, 1H), 3.00 (t, 1H), 2.20-2.05 (m, 3H), 1.94 (m, 1H), 1.88 (m, 1H), 1.73-1.66 (m, 3H)

Example 44: Preparation of (2R,3S)-2-(3-(4-chloro-5-methyl-1H-benzo[d]imidazol-1-yl)propyl)piperidin-3-ol dihydrochloride

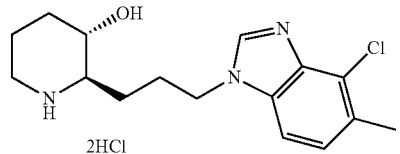 [SMILES: Cc1ccc2c(ncn2CCC[C@H]2NCCC[C@@H]2O)c1Cl]

The title compound (25 mg, yield: 80%) was obtained in the same manner as in Example 1, with the exception that 2-chloro-4-fluoro-1-methyl-3-nitrobenzene was used instead of 4-chloro-2-fluoro-1-nitrobenzene in step 1-8 of Example 1.

¹H-NMR (500 MHz, MeOD): δ 9.61 (s, 1H), 7.88 (d, 1H), 7.62 (d, 1H), 4.60 (t, 2H), 3.58 (m, 2H), 2.97 (m, 2H), 2.58 (s, 3H), 2.23 (m, 2H), 2.06 (m, 2H), 1.96 (m, 1H), 1.76 (m, 2H), 1.54 (m, 1H)

Example 45: Preparation of (2R,3S)-2-(3-(5-bromo-4-methyl-1H-benzo[d]imidazol-1-yl)propyl)piperidin-3-ol dihydrochloride

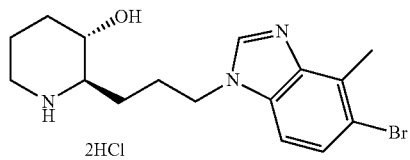 [SMILES: Cc1c(Br)ccc2c1ncn2CCC[C@H]1NCCC[C@@H]1O]

Step 45-1: Preparation of tert-butyl(2R,3S)-2-(3-(5-bromo-4-methyl-1H-benzo[d]imidazol-1-yl)propyl)-3-(tert-butyldimethylsilyl)oxy)piperidine-1-carboxylate Tert-butyl (2R,3S)-2-(3-bromopropyl)-3-((tert-butyldimethylsilyl)oxy)piperidine-1-carboxylate (40 mg, 0.09 mmol) obtained from Step 1-5 of Example 1 was dissolved in N,N-dimethylformamide (2 mL, 0.05 M). Then, potassium carbonate (25 mg, 0.18 mmol) and 5-bromo-4-methyl-1H-benzo[d]imidazole (18 mg, 0.09 mmol) were added thereto, and the mixture was stirred at room temperature for 4 hours. When the reaction was completed, the solvent was removed, and the resulting mixture was diluted with ethyl acetate and washed with saturated sodium chloride solution. The organic layer was collected, dried over sodium sulfate, filtered and concentrated under reduced pressure, and then purified by column chromatography (hexane:ethyl acetate=1:1) to give the title compound (43 mg, yield: 85%).

Step 45-2: Preparation of (2R,3S)-2-(3-(5-bromo-4-methyl-1H-benzo[d]imidazol-1-yl)propyl)piperidin-3-ol dihydrochloride Tert-butyl(2R,3S)-2-(3-(5-bromo-4-methyl-1H-benzo[d]imidazol-1-yl)propyl)-3-(tert-butyldimethylsilyl)oxy)piperidin-1-carboxylate (43 mg, 0.08 mmol) obtained from Step 45-1 was dissolved in a small amount of tetrahydrofuran. Then, 4N hydrogen chloride dioxane solution (2.0 mL, 0.04

M) was added, and the mixture was stirred at room temperature for 12 hours. When the reaction was completed, the reaction solution was concentrated under reduced pressure to remove the solvent, dissolved by addition of a small amount of methanol, and then crystallized with diethyl ether to obtain the title compound (27 mg, yield: 85%).

$^1$H-NMR (500 MHz, DMSO-$d_6$): δ 9.19 (s, 1H), 7.82 (d, 1H), 7.76 (s, 1H), 4.47 (m, 2H), 3.38 (m, 1H), 3.09 (d, 1H), 2.81 (m, 2H), 2.65 (s, 3H), 2.19 (m, 1H), 2.10 (m, 1H), 1.88 (m, 2H), 1.75 (m, 1H), 1.72 (m, 1H), 1.58 (m, 1H), 1.37 (m, 1H)

Example 46: Preparation of (2R,3S)-2-(3-(5-chloro-4-methyl-1H-benzo[d]imidazol-1-yl)propyl)piperidin-3-ol dihydrochloride

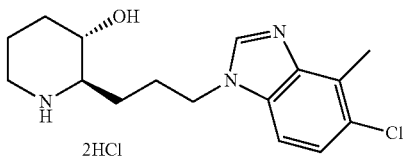 [SMILES: Cc1c(Cl)ccc2c1ncn2CCC[C@H]1NCCC[C@@H]1O]

The title compound (30 mg, yield: 80%) was obtained in the same manner as in Example 45, with the exception that 5-chloro-4-methyl-1H-benzo[d]imidazole was used instead of 5-bromo-4-methyl-1H-benzo[d]imidazole in step 45-1 of Example 45.

$^1$H-NMR (500 MHz, MeOD): δ 9.53 (s, 1H), 7.83 (d, 1H), 7.69 (d, 1H), 4.58 (t, 2H), 3.58 (m, 1H), 3.28 (m, 1H), 2.96 (m, 2H), 2.70 (s, 3H), 2.22 (m, 2H), 2.05 (m, 2H), 2.00 (m, 1H), 1.75 (m, 2H), 1.55 (m, 1H)

Example 47: Preparation of (2R,3S)-2-(3-(5-bromo-4-fluoro-1H-benzo[d]imidazol-1-yl)propyl)piperidin-3-ol dihydrochloride

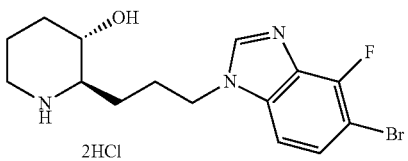 [SMILES: O[C@H]1CCCN[C@@H]1CCCn1cnc2c(F)c(Br)ccc21]

The title compound (10 mg, yield: 40%) was obtained in the same manner as in Example 45, with the exception that 5-bromo-4-fluoro-1H-benzo[d]imidazole was used instead of 5-bromo-4-methyl-1H-benzo[d]imidazole in step 45-1 of Example 45.

$^1$H-NMR (500 MHz, MeOD): δ 9.47 (s, 1H), 7.84 (dd, 1H), 7.79 (d, 1H), 4.60 (m, 2H), 3.59 (m, 1H), 3.27 (m, 1H), 2.99 (m, 2H), 2.20 (m, 2H), 2.07 (m, 2H), 1.98 (m, 1H), 1.75 (m, 2H), 1.56 (m, 1H)

Example 48: Preparation of (2R,3S)-2-(3-(6-bromo-7-fluoro-1H-benzo[d]imidazol-1-yl)propyl)piperidin-3-ol dihydrochloride

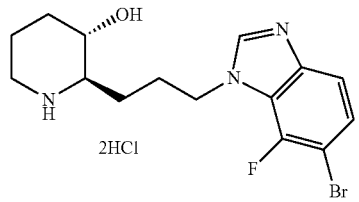 [SMILES: O[C@H]1CCCN[C@@H]1CCCn1cnc2ccc(Br)c(F)c21]

The title compound (11 mg, yield: 43%) was obtained in the same manner as in Example 45, with the exception that 6-bromo-7-fluoro-1H-benzo[d]imidazole was used instead of 5-bromo-4-methyl-1H-benzo[d]imidazole in step 45-1 of Example 45.

$^1$H-NMR (500 MHz, MeOD): δ 9.53 (S, 1H), 7.85 (dd, 1H), 7.64 (d, 1H), 4.67 (m, 2H), 3.59 (m, 1H), 3.27 (m, 1H), 2.98 (m, 2H), 2.23 (m, 2H), 2.09 (m, 2H), 1.98 (m, 1H), 1.77 (m, 2H), 1.54 (m, 1H)

Example 49: Preparation of (2R,3S)-2-(3-(4,5-difluoro-1H-benzo[d]imidazol-1-yl)propyl)piperidin-3-ol dihydrochloride

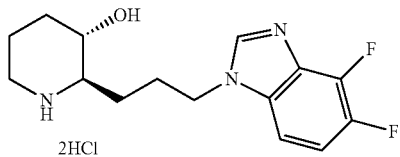 [SMILES: O[C@H]1CCCN[C@@H]1CCCn1cnc2c(F)c(F)ccc21]

The title compound (9 mg, yield: 39%) was obtained in the same manner as in Example 45, with the exception that 4,5-difluoro-1H-benzo[d]imidazole was used instead of 5-bromo-4-methyl-1H-benzo[d]imidazole in step 45-1 of Example 45.

$^1$H-NMR (500 MHz, DMSO-$d_6$): δ 8.58 (s, 1H), 7.58 (dd, 1H), 7.40 (dd, 1H), 4.33 (m, 2H), 3.38 (m, 1H), 3.09 (d, 1H), 2.98 (m, 2H), 2.10 (m, 1H), 1.96 (m, 1H), 1.87 (m, 2H), 1.77 (m, 1H), 1.65 (m, 1H), 1.54 (m, 1H), 1.36 (m, 1H)

Example 50: Preparation of (2R,3S)-2-(3-(6,7-difluoro-1H-benzo[d]imidazol-1-yl)propyl)piperidin-3-ol dihydrochloride

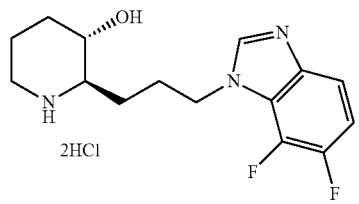 [SMILES: O[C@H]1CCCN[C@@H]1CCCn1cnc2ccc(F)c(F)c21]

The title compound (10 mg, yield: 41%) was obtained in the same manner as in Example 45, with the exception that 6,7-difluoro-1H-benzo[d]imidazole was used instead of 5-bromo-4-methyl-1H-benzo[d]imidazole in step 45-1 of Example 45.

¹H-NMR (500 MHz, DMSO-d₆): δ 8.94 (s, 1H), 7.59 (dd, 1H), 7.44 (dd, 1H), 4.44 (m, 2H), 3.41 (m, 1H), 3.09 (d, 1H), 2.78 (m, 2H), 2.13 (m, 1H), 2.03 (m, 1H), 1.89 (m, 2H), 1.76 (d, 1H), 1.66 (m, 1H), 1.57 (m, 1H), 1.35 (m, 1H)

Example 51: Preparation of (2R,3S)-2-(3-(4,5-dimethyl-1H-benzo[d]imidazol-1-yl)propyl)piperidin-3-ol dihydrochloride

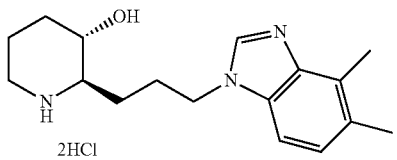 [SMILES: Cc1ccc2c(ncn2CCC[C@H]2NCCC[C@@H]2O)c1C]

The title compound (30 mg, yield: 86%) was obtained in the same manner as in Example 45, with the exception that 4,5-dimethyl-1H-benzo[d]imidazole was used instead of 5-bromo-4-methyl-1H-benzo[d]imidazole in step 45-1 of Example 45.

¹H-NMR (500 MHz, MeOD): δ 9.48 (s, 1H), 7.71 (d, 1H), 7.51 (d, 1H), 4.57 (t, 2H), 3.58 (m, 1H), 3.27 (m, 1H), 2.98 (m, 2H), 2.56 (s, 3H), 2.48 (s, 3H), 2.23 (m, 2H), 2.06 (m, 2H), 1.98 (m, 1H), 1.76 (m, 2H), 1.55 (m, 1H)

Example 52: Preparation of (2R,3S)-2-(3-(5,6-difluoro-1H-benzo[d]imidazol-1-yl)propyl)piperidin-3-ol dihydrochloride

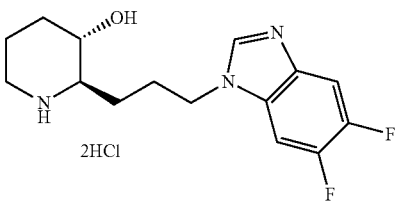 [SMILES: O[C@H]1CCCN[C@@H]1CCCn1cnc2cc(F)c(F)cc21]

The title compound (32 mg, yield: 84%) was obtained in the same manner as in Example 45, with the exception that 5,6-difluoro-1H-benzo[d]imidazole was used instead of 5-bromo-4-methyl-1H-benzo[d]imidazole in step 45-1 of Example 45.

¹H-NMR (500 MHz, MeOD): δ 9.58 (s, 1H), 8.17 (dd, 1H), 7.88 (dd, 1H), 4.59 (t, 2H), 3.59 (m, 1H), 3.28 (m, 1H), 2.99 (m, 2H), 2.23 (m, 2H), 2.08 (m, 2H), 1.97 (m, 1H), 1.77 (m, 2H), 1.56 (m, 1H)

Example 53: Preparation of (2R,3S)-2-(3-(5,6-dichloro-1H-benzo[d]imidazol-1-yl)propyl)piperidin-3-ol dihydrochloride

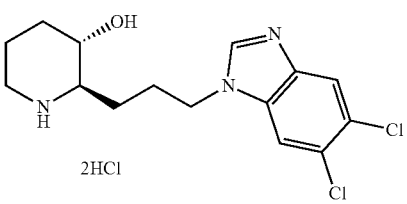 [SMILES: O[C@H]1CCCN[C@@H]1CCCn1cnc2cc(Cl)c(Cl)cc21]

The title compound (37 mg, yield: 85%) was obtained in the same manner as in Example 45, with the exception that 5,6-dichloro-1H-benzo[d]imidazole was used instead of 5-bromo-4-methyl-1H-benzo[d]imidazole in step 45-1 of Example 45.

¹H-NMR (500 MHz, DMSO-d₆): δ 9.10 (s, 1H), 8.08 (s, 1H), 4.39 (m, 2H), 3.41 (m, 1H), 3.10 (m, 1H), 2.80 (m, 2H), 2.11 (m, 1H), 2.01 (m, 1H), 1.90 (m, 2H), 1.77 (m, 1H), 1.67 (m, 1H), 1.57 (m, 1H), 1.35 (m, 1H)

Example 54: Preparation of (2R,3S)-2-(3-(5,6-dibromo-1H-benzo[d]imidazol-1-yl)propyl)piperidin-3-ol dihydrochloride

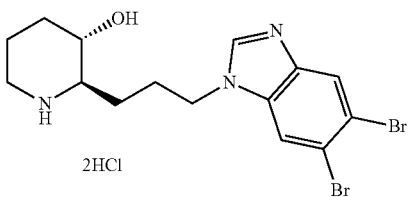 [SMILES: O[C@H]1CCCN[C@@H]1CCCn1cnc2cc(Br)c(Br)cc21]

The title compound (31 mg, yield: 80%) was obtained in the same manner as in Example 45, with the exception that 5,6-dibromo-1H-benzo[d]imidazole was used instead of 5-bromo-4-methyl-1H-benzo[d]imidazole in step 45-1 of Example 45.

¹H-NMR (500 MHz, DMSO-d₆): δ8.93 (s, 1H), 8.38 (s, 1H), 8.17 (2, 1H), 4.37 (m, 2H), 3.40 (m, 1H), 3.10 (d, 1H), 2.79 (m, 2H), 2.07 (m, 1H), 1.99 (m, 1H), 1.89 (m, 2H), 1.77 (d, 1H), 1.65 (m, 1H), 1.53 (m, 1H), 1.35 (m, 1H)

Example 55: Preparation of (2R,3S)-2-(3-(5,6-dimethyl-1H-benzo[d]imidazol-1-yl)propyl)piperidin-3-ol dihydrochloride

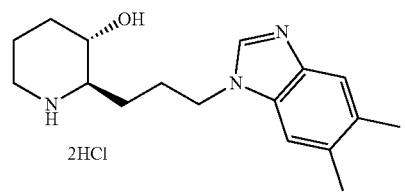 [SMILES: Cc1cc2ncn(CCC[C@H]3NCCC[C@@H]3O)c2cc1C]

The title compound (36 mg, yield: 85%) was obtained in the same manner as in Example 45, with the exception that 5,6-dimethyl-1H-benzo[d]imidazole was used instead of 5-bromo-4-methyl-1H-benzo[d]imidazole in step 45-1 of Example 45.

¹H-NMR (500 MHz, MeOD): δ 9.38 (s, 1H), 7.80 (s, 1H), 7.62 (s, 1H), 4.59 (m, 2H), 3.59 (m, 1H), 3.27 (m, 1H), 2.99 (m, 2H), 2.51 (s, 3H), 2.49 (s, 3H), 2.24 (m, 2H), 2.08 (m, 2H), 1.97 (m, 1H), 1.77 (m, 2H), 1.56 (m, 1H)

Example 56: Preparation of (2R,3S)-2-(3-(6,7-dichloro-1H-benzo[d]imidazol-1-yl)propyl)piperidin-3-ol dihydrochloride

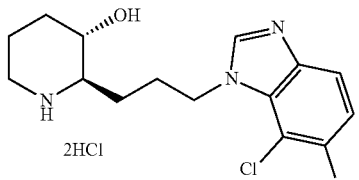

The title compound (15 mg, yield: 30%) was obtained in the same manner as in Example 45, with the exception that 6,7-dichloro-1H-benzo[d]imidazole was used instead of 5-bromo-4-methyl-1H-benzo[d]imidazole in step 45-1 of Example 45.

$^1$H-NMR (500 MHz, MeOD): δ 9.43 (s, 1H), 7.80 (s, 2H), 4.83 (m, 2H), 3.58 (t, 1H), 3.28 (m, 1H), 2.99 (m, 2H), 2.21 (m, 2H), 2.10 (m, 2H), 2.09 (m, 1H), 1.77 (m, 2H), 1.76 (m, 1H)

Example 57: Preparation of (2R,3S)-2-(3-(4,6-difluoro-1H-benzo[d]imidazol-1-yl)propyl)piperidin-3-ol dihydrochloride

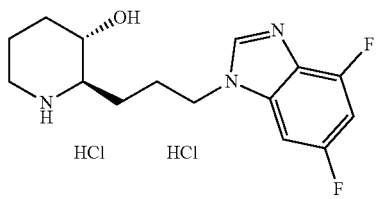 [SMILES: O[C@H]1CCCN[C@@H]1CCCn1cnc2c(F)cc(F)cc21 ; Cl ; Cl]

The title compound (26 mg, yield: 92%) was obtained in the same manner as in Example 45, with the exception that 4,6-difluoro-1H-benzo[d]imidazole was used instead of 5-bromo-4-methyl-1H-benzo[d]imidazole in Step 45-1 of Example 45.

$^1$H NMR (500 MHz, MeOD): δ 9.56 (s, 1H), 7.76 (d, 1H), 7.39 (t, 1H), 4.57 (m, 2H), 3.62 (m, 1H), 2.99 (m, 2H), 2.68 (m, 1H), 2.28 (m, 2H), 2.12 (m, 2H), 2.05 (m, 1H), 1.80 (m, 2H), 1.55 (m, 1H)

Example 58: Preparation of (2R,3S)-2-(3-(5,7-difluoro-1H-benzo[d]imidazol-1-yl)propyl)piperidin-3-ol dihydrochloride

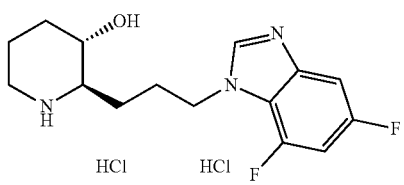 [SMILES: O[C@H]1CCCN[C@@H]1CCCn1cnc2cc(F)cc(F)c21 ; Cl ; Cl]

The title compound (25 mg, yield: 90%) was obtained in the same manner as in Example 45, with the exception that 4,6-difluoro-1H-benzo[d]imidazole was used instead of 5-bromo-4-methyl-1H-benzo[d]imidazole in Step 45-1 of Example 45.

$^1$H NMR (500 MHz, MeOD): δ 9.60 (d, 1H), 7.51 (d, 1H), 7.42 (t, 1H), 4.66 (m, 2H), 3.58 (m, 1H), 2.98 (m, 2H), 2.30 (m, 2H), 2.12 (m, 2H), 2.02 (m, 1H), 1.74 (m, 2H), 1.54 (m, 1H)

Example 59: Preparation of (2R,3S)-2-(3-(4-chloro-5-methoxy-1H-benzo[d]imidazol-1-yl)propyl)piperidin-3-ol dihydrochloride

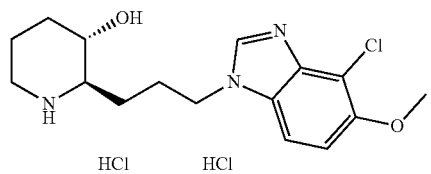 [SMILES: COc1ccc2c(ncn2CCC[C@H]2NCCC[C@@H]2O)c1Cl ; Cl ; Cl]

The title compound (23 mg, yield: 91%) was obtained in the same manner as in Example 45, with the exception that 4-chloro-5-methoxy-1H-benzo[d]imidazole was used instead of 5-bromo-4-methyl-1H-benzo[d]imidazole in Step 45-1 of Example 45.

$^1$H NMR (500 MHz, MeOD): δ 9.55 (s, 1H), 7.97 (d, 1H), 7.52 (d, 1H), 4.59 (t, 2H), 4.04 (s, 3H), 3.57 (m, 1H), 2.99 (m, 2H), 2.31 (m, 2H), 2.10 (m, 2H), 2.02 (m, 1H), 1.79 (m, 2H), 1.55 (m, 1H)

Example 60: Preparation of (2R,3S)-2-(3-(7-chloro-6-methoxy-1H-benzo[d]imidazol-1-yl)propyl)piperidin-3-ol dihydrochloride

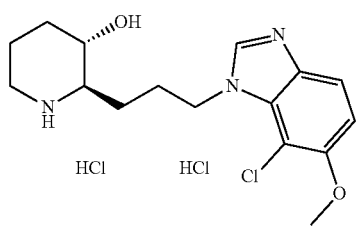 [SMILES: COc1ccc2ncn(CCC[C@H]3NCCC[C@@H]3O)c2c1Cl ; Cl ; Cl]

The title compound (22 mg, yield: 90%) was obtained in the same manner as in Example 45, with the exception that 4-chloro-5-methoxy-1H-benzo[d]imidazole was used instead of 5-bromo-4-methyl-1H-benzo[d]imidazole in Step 45-1 of Example 45.

$^1$H NMR (500 MHz, MeOD): δ 9.48 (s, 1H), 7.79 (d, 1H), 7.52 (d, 1H), 4.82 (m, 2H), 4.03 (s, 3H), 3.62 (m, 1H), 2.99 (m, 2H), 2.30 (m, 2H), 2.14 (m, 2H), 2.02 (m, 1H), 1.80 (m, 2H), 1.55 (m, 1H)

Example 61: Preparation of (2R,3S)-2-(3-(6-chloro-4-methyl-1H-benzo[d]imidazol-1-yl)propyl)piperidin-3-ol dihydrochloride

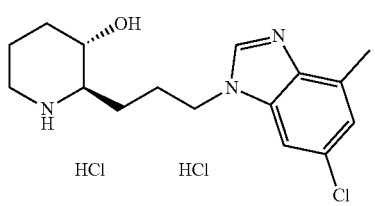 [SMILES: Cc1cc(Cl)cc2c1ncn2CCC[C@H]1NCCC[C@@H]1O ; Cl ; Cl]

The title compound (24 mg, yield: 91%) was obtained in the same manner as in Example 45, with the exception that 6-chloro-4-methyl-1H-benzo[d]imidazole was used instead of 5-bromo-4-methyl-1H-benzo[d]imidazole in Step 45-1 of Example 45.

$^1$H NMR (500 MHz, MeOD): δ 9.59 (s, 1H), 7.97 (s, 1H), 7.52 (s, 1H), 4.58 (m, 2H), 3.59 (m, 1H), 2.97 (m, 2H), 2.67 (s, 3H), 2.20 (m, 2H), 2.10 (m, 2H), 2.01 (m, 1H), 1.76 (m, 2H), 1.55 (m, 1H)

Example 62: Preparation of (2R,3S)-2-(3-(4-chloro-5-fluoro-1H-benzo[d]imidazol-1-yl)propyl)piperidin-3-ol dihydrochloride

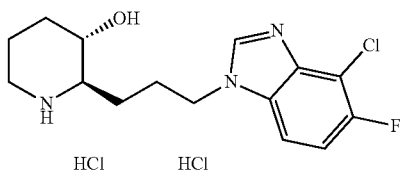 [SMILES: O[C@H]1CCCN[C@@H]1CCCn1cnc2c(Cl)c(F)ccc21 ; Cl ; Cl]

The title compound (19 mg, yield: 89%) was obtained in the same manner as in Example 45, with the exception that 4-chloro-5-fluoro-1H-benzo[d]imidazole was used instead of 5-bromo-4-methyl-1H-benzo[d]imidazole in Step 45-1 of Example 45.

$^1$H NMR (500 MHz, MeOD): δ 9.54 (s, 1H), 7.95 (d, 1H), 7.50 (d, 1H), 4.58 (t, 2H), 3.56 (m, 1H), 3.42 (m, 1H), 2.98 (m, 2H), 2.30 (m, 2H), 2.08 (m, 2H), 2.00 (m, 1H), 1.72 (m, 2H), 1.52 (m, 1H)

Example 63: Preparation of (2R,3S)-2-(3-(6-bromo-4-methyl-1H-benzo[d]imidazol-1-yl)propyl)piperidin-3-ol dihydrochloride

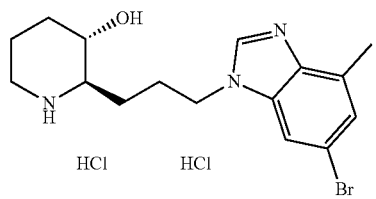 [SMILES: Cc1cc(Br)cc2c1ncn2CCC[C@H]1NCCC[C@@H]1O ; Cl ; Cl]

The title compound (26 mg, yield: 93%) was obtained in the same manner as in Example 45, with the exception that 6-bromo-4-methyl-1H-benzo[d]imidazole was used instead of 5-bromo-4-methyl-1H-benzo[d]imidazole in Step 45-1 of Example 45.

$^1$H NMR (500 MHz, MeOD): δ 9.58 (s, 1H), 8.12 (s, 1H), 7.66 (s, 1H), 4.57 (m, 2H), 3.60 (m, 1H), 2.99 (m, 2H), 2.65 (s, 3H), 2.24 (m, 2H), 2.10 (m, 2H), 2.02 (m, 1H), 1.79 (m, 2H), 1.59 (m, 1H)

Example 64: Preparation of (2R,3S)-2-(3-(5-fluoro-4-methyl-1H-benzo[d]imidazol-1-yl)propyl)piperidin-3-ol dihydrochloride

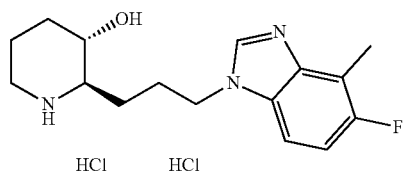 [SMILES: Cc1c(F)ccc2c1ncn2CCC[C@H]1NCCC[C@@H]1O ; Cl ; Cl]

The title compound (22 mg, yield: 90%) was obtained in the same manner as in Example 45, with the exception that 5-fluoro-4-methyl-1H-benzo[d]imidazole was used instead of 5-bromo-4-methyl-1H-benzo[d]imidazole in Step 45-1 of Example 45.

$^1$H NMR (500 MHz, MeOD): δ 9.62 (s, 1H), 7.88 (dd, 1H), 7.46 (t, 1H), 4.61 (m, 2H), 3.58 (m, 1H), 2.99 (m, 2H), 2.59 (s, 3H), 2.25 (m, 2H), 2.12 (m 2H), 2.01 (m, 1H), 1.79 (m, 2H), 1.59 (m, 1H)

Example 65: Preparation of (2R,3S)-2-(3-(6-fluoro-7-methyl-1H-benzo[d]imidazol-1-yl)propyl)piperidin-3-ol dihydrochloride

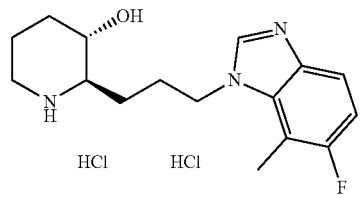 [SMILES: Cc1c(F)ccc2ncn(CCC[C@H]3NCCC[C@@H]3O)c12 ; Cl ; Cl]

The title compound (20 mg, yield: 88%) was obtained in the same manner as in Example 45, with the exception that 5-fluoro-4-methyl-1H-benzo[d]imidazole was used instead of 5-bromo-4-methyl-1H-benzo[d]imidazole in Step 45-1 of Example 45.

$^1$H NMR (500 MHz, MeOD): δ 9.50 (s, 1H), 7.69 (dd, 1H), 7.46 (t, 1H), 4.76 (m, 2H), 3.61 (m, 1H), 3.00 (m, 2H), 2.77 (s, 3H), 2.25 (m, 2H), 2.13 (m, 2H), 2.02 (m, 1H), 1.79 (m, 2H), 1.57 (m, 1H)

Example 66: Preparation of (2R,3S)-2-(3-(4-chloro-5-(trifluoromethyl)-1H-benzo[d]imidazol-1-yl)propyl)piperidin-3-ol dihydrochloride

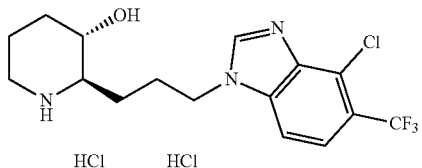 [SMILES: O[C@H]1CCCN[C@@H]1CCCn1cnc2c(Cl)c(C(F)(F)F)ccc21 ; Cl ; Cl]

The title compound (27 mg, yield: 95%) was obtained in the same manner as in Example 45, with the exception that 4-chloro-5-(trifluoromethyl)-1H-benzo[d]imidazole was used instead of 5-bromo-4-methyl-1H-benzo[d]imidazole in Step 45-1 of Example 45.

¹H NMR (500 MHz, MeOD): δ 9.65 (s, 1H), 8.13 (d, 1H), 8.01 (d, 1H), 4.64 (m, 2H), 3.61 (m, 2H), 2.98 (m, 2H), 2.26 (m, 2H), 2.10 (m, 2H), 1.98 (m, 1H), 1.76 (m, 2H), 1.56 (m, 1H)

Example 67: Preparation of (2R,3S)-2-(3-(7-chloro-6-(trifluoromethyl)-1H-benzo[d]imidazol-1-yl)propyl)piperidin-3-ol dihydrochloride

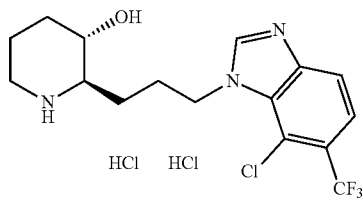 [SMILES: O[C@H]1CCCN[C@@H]1CCCn1cnc2ccc(C(F)(F)F)c(Cl)c21 ; Cl ; Cl]

The title compound (23 mg, yield: 91%) was obtained in the same manner as in Example 45, with the exception that 4-chloro-5-(trifluoromethyl)-1H-benzo[d]imidazole was used instead of 5-bromo-4-methyl-1H-benzo[d]imidazole in Step 45-1 of Example 45.
¹H NMR (500 MHz, MeOD): δ 9.59 (s, 1H), 8.01 (d, 1H), 7.96 (d, 1H), 4.91 (m, 2H), 3.61 (m, 1H), 2.98 (m, 2H), 2.27 (m, 2H), 2.10 (m, 2H), 2.01 (m, 1H), 1.80 (m, 2H), 1.56 (m, 1H)

Example 68: methyl 7-bromo-1-(3-((2R,3S)-3-hydroxypiperidin-2-yl)propyl)-1H-benzo[d]imidazole-5-carboxylate dihydrochloride

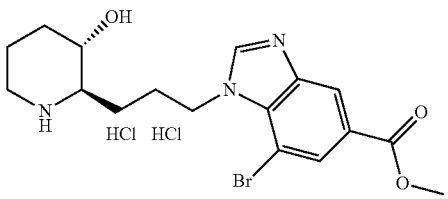 [SMILES: COC(=O)c1cc(Br)c2c(c1)ncn2CCC[C@H]1NCCC[C@@H]1O ; Cl ; Cl]

The title compound (22 mg, yield: 89%) was obtained in the same manner as in Example 1, with the exception that methyl 3-bromo-4-fluoro-5-nitrobenzoate was used instead of 4-chloro-2-fluoro-1-nitrobenzene in Step 1-8 of Example 1.
¹H NMR (500 MHz, MeOD): δ 8.85 (s, 1H), 8.38 (s, 1H), 8.27 (s, 1H), 4.75 (m, 2H), 3.96 (s, 3H), 3.57 (m, 1H), 2.98 (m, 2H), 2.25-1.98 (m, 5H), 1.72 (m, 2H), 1.54 (m, 1H)

Example 69: Preparation of (2R,3S)-2-(3-(7-bromo-5-chloro-1H-benzo[d]imidazol-1-yl)propyl)piperidin-3-ol dihydrochloride

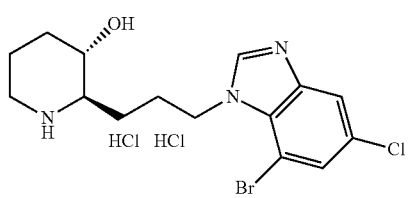 [SMILES: O[C@H]1CCCN[C@@H]1CCCn1cnc2cc(Cl)cc(Br)c21 ; Cl ; Cl]

The title compound (24 mg, yield: 90%) was obtained in the same manner as in Example 1, with the exception that 1-bromo-5-chloro-2-fluoro-3-nitrobenzene was used instead of 4-chloro-2-fluoro-1-nitrobenzene in Step 1-8 of Example 1.
¹H NMR (500 MHz, MeOD): δ 9.28 (s, 1H), 7.87 (m, 2H), 4.77 (m, 2H), 3.59 (m, 1H), 2.93 (m, 2H), 2.18 (m, 2H), 2.08 (m, 2H), 2.02 (m, 1H), 1.75 (m, 2H), 1.55 (m, 1H)

Example 70: Preparation of (2R,3S)-2-(3-(5-bromo-7-chloro-1H-benzo[d]imidazol-1-yl)propyl)piperidin-3-ol dihydrochloride

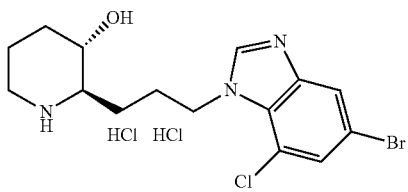 [SMILES: O[C@H]1CCCN[C@@H]1CCCn1cnc2cc(Br)cc(Cl)c21 ; Cl ; Cl]

The title compound (23 mg, yield: 89%) was obtained in the same manner as in Example 1, with the exception that 5-bromo-1-chloro-2-fluoro-3-nitrobenzene was used instead of 4-chloro-2-fluoro-1-nitrobenzene in Step 1-8 of Example 1.
¹H NMR (500 MHz, MeOD): δ 9.35 (s, 1H), 8.00 (s, 1H), 7.84 (s, 1H), 4.78 (m, 2H), 3.58 (m, 1H), 2.97 (m, 2H), 2.21 (m, 2H), 2.08 (m, 2H), 1.99 (m, 1H), 1.74 (m, 2H), 1.53 (m, 1H)

Example 71: Preparation of (2R,3S)-2-(3-(7-bromo-5-(trifluoromethyl)-1H-benzo[d]imidazol-1-yl)propyl)piperidin-3-ol dihydrochloride

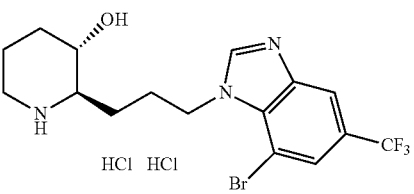 [SMILES: O[C@H]1CCCN[C@@H]1CCCn1cnc2cc(C(F)(F)F)cc(Br)c21 ; Cl ; Cl]

The title compound (19 mg, yield: 89%) was obtained in the same manner as in Example 1, with the exception that 1-bromo-2-fluoro-3-nitro-5-(trifluoromethyl)benzene was used instead of 4-chloro-2-fluoro-1-nitrobenzene in Step 1-8 of Example 1.
¹H NMR (500 MHz, MeOD): δ 9.26 (s, 1H), 8.11 (s, 1H), 8.02 (s, 1H), 3.55 (m, 1H), 2.90 (m, 2H), 2.18 (m, 2H), 2.05 (m, 2H), 1.94 (m, 1H), 1.71 (m, 2H), 1.52 (m, 1H)

Example 72: Preparation of (2R,3S)-2-(3-(6-bromo-4-fluoro-1H-benzo[d]imidazol-1-yl)propyl)piperidin-3-ol dihydrochloride

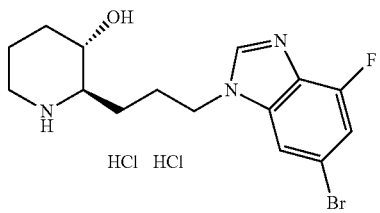 [SMILES: O[C@H]1CCCN[C@@H]1CCCn1cnc2c(F)cc(Br)cc21 ; Cl ; Cl]

The title compound (23 mg, yield: 90%) was obtained in the same manner as in Example 45, with the exception that 6-bromo-4-fluoro-1H-benzo[d]imidazole was used instead of 5-bromo-4-methyl-1H-benzo[d]imidazole in Step 45-1 of Example 45.

$^1$H NMR (500 MHz, MeOD): δ 9.44 (s, 1H), 8.12 (s, 1H), 7.65 (d, 1H), 4.55 (m, 2H), 3.65 (m, 1H), 3.57 (m, 1H), 2.98 (m, 2H), 2.26 (m, 2H), 2.10 (m, 2H), 1.98 (m, 1H), 1.74 (m, 2H), 1.54 (m, 1H)

Example 73: Preparation of (2R,3S)-2-(3-(5-bromo-7-fluoro-1H-benzo[d]imidazol-1-yl)propyl)piperidin-3-ol dihydrochloride

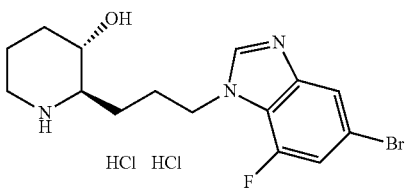 [SMILES: O[C@H]1CCCN[C@@H]1CCCn1cnc2cc(Br)cc(F)c21 ; Cl ; Cl]

The title compound (24 mg, yield: 92%) was obtained in the same manner as in Example 45, with the exception that 6-bromo-4-fluoro-1H-benzo[d]imidazole was used instead of 5-bromo-4-methyl-1H-benzo[d]imidazole in Step 45-1 of Example 45.

$^1$H NMR (500 MHz, MeOD): δ 9.55 (s, 1H), 7.92 (s, 1H), 7.69 (d, 1H), 4.65 (m, 2H), 3.61 (m, 1H), 2.96 (m, 2H), 2.15 (m, 2H), 2.07 (m, 2H), 1.98 (m, 1H), 1.75 (m, 2H), 1.53 (m, 1H)

Example 74: Preparation of (2R,3S)-2-(3-(7-chloro-4-fluoro-1H-benzo[d]imidazol-1-yl)propyl)piperidin-3-ol dihydrochloride

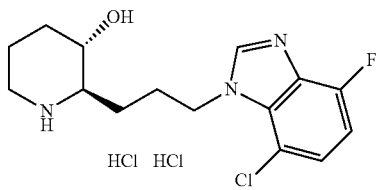 [SMILES: O[C@H]1CCCN[C@@H]1CCCn1cnc2c(F)ccc(Cl)c21 ; Cl ; Cl]

The title compound (9 mg, yield: 45%) was obtained in the same manner as in Example 45, with the exception that 7-chloro-4-fluoro-1H-benzo[d]imidazole was used instead of 5-bromo-4-methyl-1H-benzo[d]imidazole in Step 45-1 of Example 45.

$^1$H NMR (500 MHz, MeOD): δ 9.43 (s, 1H), 7.60 (dd, 1H), 7.38 (t, 1H), 4.82 (m, 2H), 3.54 (m, 1H), 2.98 (m, 2H), 2.24 (m, 2H), 2.16 (m, 2H), 1.99 (m, 1H), 1.72 (m, 2H), 1.55 (m, 1H)

Example 75: Preparation of (2R,3S)-2-(3-(5-bromo-4-nitro-1H-benzo[d]imidazol-1-yl)propyl)piperidin-3-ol dihydrochloride

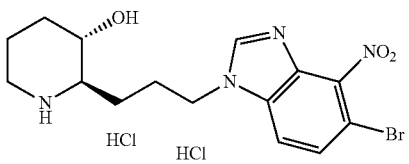 [SMILES: O=[N+]([O-])c1c(Br)ccc2c1ncn2CCC[C@H]1NCCC[C@@H]1O ; Cl ; Cl]

The title compound (23 mg, yield: 90%) was obtained in the same manner as in Example 45, with the exception that 5-bromo-4-nitro-1H-benzo[d]imidazole was used instead of 5-bromo-4-methyl-1H-benzo[d]imidazole in Step 45-1 of Example 45.

$^1$H NMR (500 MHz, MeOD): δ 8.81 (s, 1H), 7.95 (d, 1H), 7.82 (d, 1H), 4.51 (m, 2H), 3.53 (m, 1H), 2.92 (m, 2H), 2.10 (m, 2H), 2.04 (m, 3H), 1.68 (m, 2H), 1.57 (m, 1H)

Example 76: Preparation of (2R,3S)-2-(3-(6-bromo-7-nitro-1H-benzo[d]imidazol-1-yl)propyl)piperidin-3-ol dihydrochloride

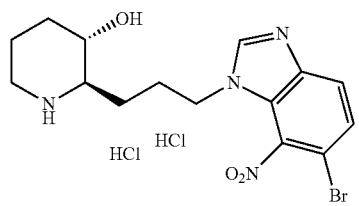 [SMILES: O=[N+]([O-])c1c(Br)ccc2ncn(CCC[C@H]3NCCC[C@@H]3O)c12 ; Cl ; Cl]

The title compound (18 mg, yield: 87%) was obtained in the same manner as in Example 45, with the exception that 5-bromo-4-nitro-1H-benzo[d]imidazole was used instead of 5-bromo-4-methyl-1H-benzo[d]imidazole in Step 45-1 of Example 45.

$^1$H NMR (500 MHz, MeOD): δ 8.51 (s, 1H), 7.84 (d, 1H), 7.68 (d, 1H), 4.24 (t, 1H), 3.52 (m, 1H), 2.97 (m, 2H), 2.00 (m, 5H), 1.73 (m, 1H), 1.63 (m, 1H), 1.53 (m, 1H)

Example 77: Preparation of (2R,3S)-2-(3-(4-chloro-5-nitro-1H-benzo[d]imidazol-1-yl)propyl)piperidin-3-ol dihydrochloride

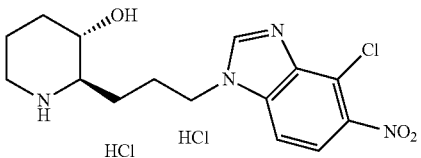 [SMILES: O=[N+]([O-])c1ccc2c(ncn2CCC[C@H]2NCCC[C@@H]2O)c1Cl ; Cl ; Cl]

The title compound (23 mg, yield: 92%) was obtained in the same manner as in Example 45, with the exception that 4-chloro-5-nitro-1H-benzo[d]imidazole was used instead of 5-bromo-4-methyl-1H-benzo[d]imidazole in Step 45-1 of Example 45.

$^1$H NMR (500 MHz, MeOD): δ 8.76 (s, 1H), 8.06 (d, 1H), 7.86 (d, 1H), 4.51 (m, 2H), 3.66 (m, 1H), 2.98 (m, 2H), 2.08 (m, 2H), 1.99 (m 3H), 1.74 (m, 3H), 1.56 (m, 1H)

Example 78: Preparation of (2R,3S)-2-(3-(7-chloro-5-(trifluoromethyl)-1H-benzo[d]imidazol-1-yl)propyl)piperidin-3-ol dihydrochloride

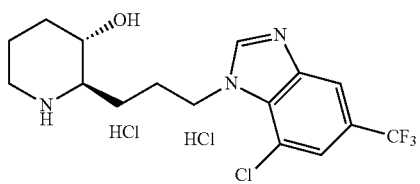 [SMILES: O[C@H]1CCCN[C@@H]1CCCn1cnc2cc(C(F)(F)F)cc(Cl)c21 ; Cl ; Cl]

The title compound (19 mg, yield: 87%) was obtained in the same manner as in Example 1, with the exception that 1-chloro-2-fluoro-3-nitro-5-(trifluoromethyl)benzene was used instead of 4-chloro-2-fluoro-1-nitrobenzene in Step 1-8 of Example 1.

$^1$H NMR (500 MHz, MeOD): δ 9.32 (m, 1H), 8.07 (d, 1H), 7.83 (d, 1H), 4.78 (s, 1H), 3.58 (m, 1H), 3.44 (m, 1H), 3.00 (m, 1H), 2.93 (m, 2H), 2.20-2.05 (m, 4H), 2.02 (m, 1H), 1.97 (m, 2H), 1.52 (m, 1H)

Example 79: Preparation of (2R,3S)-2-(3-(5-chloro-7-fluoro-1H-benzo[d]imidazol-1-yl)propyl)piperidin-3-ol dihydrochloride

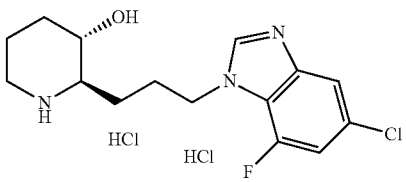 [SMILES: O[C@H]1CCCN[C@@H]1CCCn1cnc2cc(Cl)cc(F)c21 ; Cl ; Cl]

The title compound (22 mg, yield: 88%) was obtained in the same manner as in Example 1, with the exception that 5-chloro-1,2-difluoro-3-nitrobenzene was used instead of 4-chloro-2-fluoro-1-nitrobenzene in Step 1-8 of Example 1.

$^1$H NMR (500 MHz, MeOD): δ 9.39 (m, 1H), 7.71 (m, 1H), 7.49 (m, 1H), 4.59 (m, 2H), 3.57 (m, 1H), 3.44 (m, 1H), 3.29 (m, 1H), 2.97 (m, 2H), 2.18 (m, 2H), 2.07 (m, 1H), 1.72 (m, 2H), 1.51 (m, 1H)

Example 80: Preparation of (2R,3S)-2-(3-(5,7-dichloro-1H-benzo[d]imidazol-1-yl)propyl)piperidin-3-ol dihydrochloride

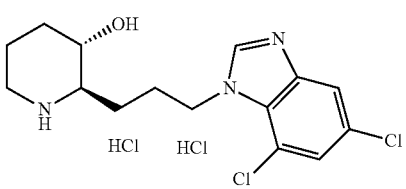 [SMILES: O[C@H]1CCCN[C@@H]1CCCn1cnc2cc(Cl)cc(Cl)c21 ; Cl ; Cl]

The title compound (7 mg, yield: 31%) was obtained in the same manner as in Example 1, with the exception that 1,5-dichloro-2-fluoro-3-nitrobenzene was used instead of 4-chloro-2-fluoro-1-nitrobenzene in Step 1-8 of Example 1.

$^1$H NMR (500 MHz, MeOD): δ 9.30 (s, 1H), 7.84 (s, 1H), 7.69 (s, 1H), 4.78 (m, 2H), 3.69 (m, 1H), 3.30 (m, 1H), 2.99 (m, 2H), 2.25 (m, 2H), 2.16 (m, 2H), 2.06 (m, 1H), 1.78 (m, 2H), 1.51 (m, 1H)

Example 81: Preparation of (2R,3S)-2-(3-(5-chloro-7-(1H-pyrazol-4-yl)-1H-benzo[d]imidazol-1-yl)propyl)piperidin-3-ol dihydrochloride

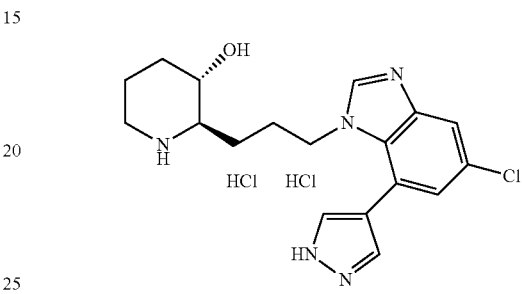

The title compound (8 mg, yield: 14%) was obtained in the same manner as in Example 20, with the exception that tert-butyl (2R,3S)-2-(3-(7-bromo-5-chloro-1H-benzo[d]imidazol-1-yl)propyl)-3-((tert-butyldimethysilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate, and that (1H-pyrazol-4-yl)boronic acid was used instead of (3-fluorophenyl)boronic acid in Step 20-2 of Example 20.

$^1$H NMR (500 MHz, MeOD): δ 9.37 (s, 1H), 7.97 (s, 2H), 7.88 (s, 1H), 7.49 (s, 1H), 4.28 (m, 2H), 3.44 (m, 1H), 2.91 (m, 1H), 2.75 (m, 1H), 1.96 (m, 2H), 1.74-1.62 (m, 3H), 1.50 (m, 1H), 1.36 (m, 1H)

Example 82: Preparation of (2R,3S)-2-(3-(7-(1H-pyrazol-4-yl)-5-(trifluoromethyl)-1H-benzo[d]imidazol-1-yl)propyl)piperidin-3-ol dihydrochloride

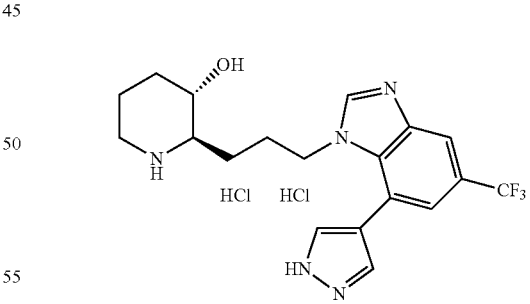

The title compound (9 mg, yield: 15%) was obtained in the same manner as in Example 20, with the exception that tert-butyl (2R,3S)-2-(3-(7-bromo-5-(trifluoromethyl)-1H-benzo[d]imidazol-1-yl)propyl)-3-((tert-butyldimethysilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate in Step 20-2 of Example 20.

$^1$H NMR (500 MHz, MeOD): δ 9.06 (m, 1H), 8.10 (s, 1H), 7.97 (s, 2H), 7.61 (s, 1H), 4.26 (m, 2H), 3.44 (m, 1H), 3.17 (m, 1H), 2.93 (m, 1H), 2.76 (m, 1H), 1.99 (m, 2H), 1.67 (m, 3H), 1.53 (m, 1H), 1.49 (m, 1H)

Example 83: Preparation of (2R,3S)-2-(3-(5-chloro-7-(3-fluorophenyl)-1H-benzo[d]imidazol-1-yl)propyl)piperidin-3-ol dihydrochloride

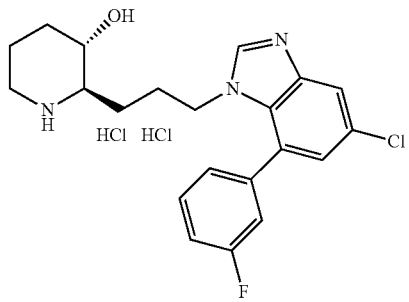 [SMILES: O[C@H]1CCCN[C@@H]1CCCn1cnc2cc(Cl)cc(-c3cccc(F)c3)c21 ; Cl ; Cl]

The title compound (13 mg, yield: 22%) was obtained in the same manner as in Example 20, with the exception that tert-butyl (2R,3S)-2-(3-(7-bromo-5-chloro-1H-benzo[d]imidazol-1-yl)propyl)-3-((tert-butyldimethysilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate in Step 20-2 of Example 20.
$^1$H NMR (500 MHz, MeOD): δ 9.39 (s, 1H), 7.95 (d, 1H), 7.64 (m, 1H), 7.62 (m, 1H), 7.39 (m, 2H), 7.34 (m, 1H), 4.15 (m, 1H), 4.05 (m, 2H), 3.44 (m, 1H), 3.18 (m, 1H), 2.91 (t, 1H), 2.87 (s, 1H), 2.01 (m, 2H), 1.96 (m, 2H), 1.50 (m, 2H), 1.33 (m, 1H)

Example 84: Preparation of (2R,3S)-2-(3-(7-(3-fluorophenyl)-5-(trifluoromethyl)-1H-benzo[d]imidazol-1-yl)propyl)piperidin-3-ol dihydrochloride

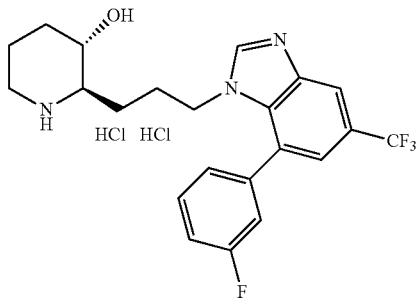 [SMILES: O[C@H]1CCCN[C@@H]1CCCn1cnc2cc(C(F)(F)F)cc(-c3cccc(F)c3)c21 ; Cl ; Cl]

The title compound (11 mg, yield: 20%) was obtained in the same manner as in Example 20, with the exception that tert-butyl (2R,3S)-2-(3-(7-bromo-5-(trifluoromethyl)-1H-benzo[d]imidazol-1-yl)propyl)-3-((tert-butyldimethylsilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate in Step 20-2 of Example 20.
$^1$H NMR (500 MHz, MeOD): δ 9.62 (s, 1H), 8.24 (m, 2H), 7.74 (m, 1H), 7.64 (m, 1H), 7.42 (m, 3H), 4.15 (m, 2H), 3.43 (m, 1H), 3.21 (m, 1H), 2.91 (m, 1H), 2.74 (m, 1H), 1.97 (m, 2H), 1.73 (m, 3H), 1.52 (m, 2H), 1.33 (m, 1H)

Example 85: Preparation of (2R,3S)-2-(3-(5-chloro-7-(2-methylthiazol-5-yl)-1H-benzo[d]imidazol-1-yl)propyl)piperidin-3-ol

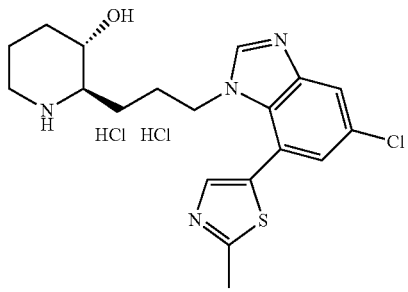 [SMILES: Cc1ncc(-c2cc(Cl)cc3ncn(CCC[C@H]4NCCC[C@@H]4O)c23)s1 ; Cl ; Cl]

The title compound (6 mg, yield: 12%) was obtained in the same manner as in Example 20, with the exception that tert-butyl (2R,3S)-2-(3-(7-bromo-5-chloro-1H-benzo[d]imidazol-1-yl)propyl)-3-((tert-butyldimethysilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1l-carboxylate, and that (2-methylthiazol-5-yl)boronic acid was used instead of (3-fluorophenyl)boronic acid in Step 20-2 of Example 20.
$^1$H NMR (500 MHz, MeOD): δ 9.68 (s, 1H), 8.06 (m, 2H), 7.71 (s, 1H), 4.30 (t, 2H), 3.52 (m, 1H), 3.27 (m, 1H), 2.95 (m, 1H), 2.84 (s, 3H), 2.83 (s, 1H), 2.05-1.89 (m, 4H), 1.88 (m, 2H), 1.74 (m, 2H)

Example 86: Preparation of (2R,3S)-2-(3-(5-chloro-7-(pyridin-3-yl)-1H-benzo[d]imidazol-1-yl)propyl)piperidin-3-ol trihydrochloride

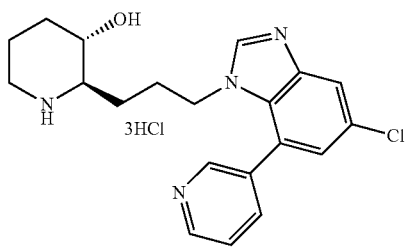 [SMILES: O[C@H]1CCCN[C@@H]1CCCn1cnc2cc(Cl)cc(-c3cccnc3)c21 ; "3HCl"]

The title compound (8 mg, yield: 15%) was obtained in the same manner as in Example 20, with the exception that tert-butyl (2R,3S)-2-(3-(7-bromo-5-chloro-1H-benzo[d]imidazol-1-yl)propyl)-3-((tert-butyldimethysilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate, and that pyridin-3-ylboronic acid was used instead of (3-fluorophenyl)boronic acid in Step 20-2 of Example 20.
$^1$H NMR (500 MHz, MeOD): δ 9.55 (s, 1H), 9.16 (s, 1H), 9.03 (s, 1H), 8.74 (s, 1H), 8.18 (s, 1H), 8.09 (s, 1H), 7.68 (s, 1H), 4.10 (m, 2H), 3.46 (m, 1H), 3.24 (m, 1H), 2.92 (m, 1H), 2.78 (m, 1H), 2.03 (m, 1H), 1.98 (m, 1H), 1.95-1.93 (m, 3H), 1.52 (m, 1H), 1.44 (m 2H)

Example 87: Preparation of (2R,3S)-2-(3-(5-chloro-7-(5-fluoropyridin-3-yl)-1H-benzo[d]imidazol-1-yl)propyl)piperidin-3-ol trihydrochloride

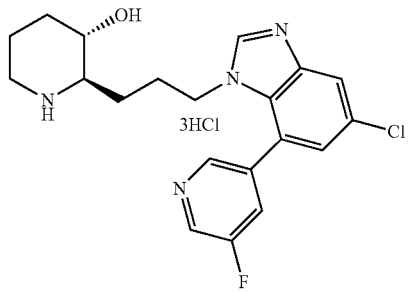 [SMILES: O[C@H]1CCCN[C@@H]1CCCn1cnc2cc(Cl)cc(-c3cncc(F)c3)c21 ; "3HCl"]

The title compound (9 mg, yield: 16%) was obtained in the same manner as in Example 20, with the exception that tert-butyl (2R,3S)-2-(3-(7-bromo-5-chloro-1H-benzo[d]imidazol-1-yl)propyl)-3-((tert-butyldimethysilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1l-carboxylate, and that (5-fluoropyridin-3-yl)boronic acid was used instead of (3-fluorophenyl)boronic acid in Step 20-2 of Example 20.

$^1$H NMR (500 MHz, MeOD): δ 9.70 (s, 1H), 8.86-8.75 (m, 2H), 8.19 (m, 1H), 8.07 (s, 1H), 7.67 (s, 1H), 4.11 (m, 2H), 3.47 (m, 1H), 3.24 (m, 1H), 2.93 (td, 1H), 2.77 (s, 1H), 2.01-2.00 (m, 2H), 1.93-1.82 (m, 3H), 1.73 (s, 1H), 1.65 (m, 1H)

Example 88: 5-(5-chloro-1-(3-((2R,3S)-3-hydroxypiperidin-2-yl)propyl)-1H-benzo[d]imidazol-7-yl)-1-methylpyridin-2(1H)-one dihydrochloride

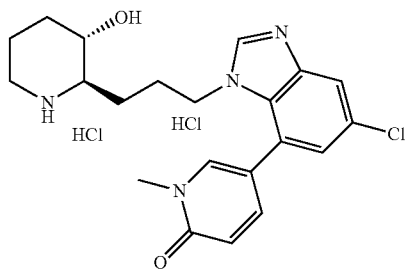 [SMILES: Cn1cc(-c2cc(Cl)cc3ncn(CCC[C@H]4NCCC[C@@H]4O)c23)ccc1=O ; Cl ; Cl]

The title compound (10 mg, yield: 16%) was obtained in the same manner as in Example 20, with the exception that tert-butyl (2R,3S)-2-(3-(7-bromo-5-chloro-1H-benzo[d]imidazol-1-yl)propyl)-3-((tert-butyldimethylsilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate, and that (1-methyl-6-oxo-1,6-dihydropyridin-3-yl)boronic acid was used instead of (3-fluorophenyl)boronic acid in Step 20-2 of Example 20.

$^1$H NMR (500 MHz, MeOD): δ 9.55 (m, 1H), 7.98 (d, 2H), 7.74 (d, 1H), 7.57 (s, 1H), 6.71 (d, 1H), 4.32 (m, 2H), 3.67 (s, 3H), 3.44 (s, 1H), 3.24 (m, 1H), 2.88 (t, 1H), 2.80 (s, 1H), 2.03-1.89 (m, 4H), 1.71 (m, 2H), 1.49 (m, 2H)

Example 89: Preparation of (2R,3S)-2-(3-(5-chloro-7-(1-(difluoromethyl)-1H-pyrazol-4-yl)-1H-benzo[d]imidazol-1-yl)propyl)piperidin-3-ol dihydrochloride

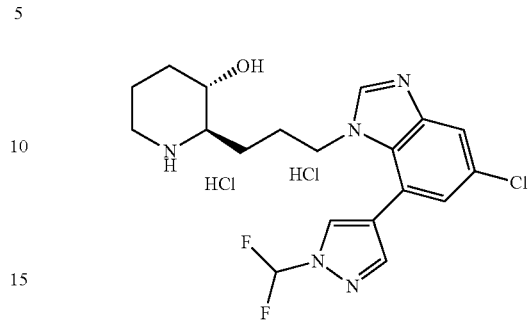

The title compound (9 mg, yield: 14%) was obtained in the same manner as in Example 20, with the exception that tert-butyl (2R,3S)-2-(3-(7-bromo-5-chloro-1H-benzo[d]imidazol-1-yl)propyl)-3-((tert-butyldimethylsilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate, and that (1-(difluoromethyl)-1H-pyrazol-4-yl)boronic acid was used instead of (3-fluorophenyl)boronic acid in Step 20-2 of Example 20.

$^1$H NMR (500 MHz, MeOD): δ 9.46 (s, 1H), 8.50 (s, 1H), 8.05 (s, 1H), 7.94 (s, H), 7.56 (s, 1H), 4.28 (m, 2H), 3.49 (m, 1H), 3.24 (m, 1H), 2.94 (t, 1H), 2.89 (m, 1H), 2.01 (m, 2H), 1.80 (m, 2H), 1.72 (m, 2H), 1.64 (m, 1H), 1.55 (m, 1H)

Example 90: Preparation of (2R,3S)-2-(3-(5-chloro-7-(Isoxazol-3-yl)-1H-benzo[d]imidazol-1-yl)propyl)piperidin-3-ol dihydrochloride

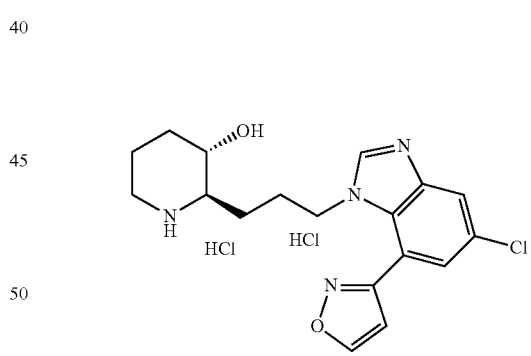

The title compound (7 mg, yield: 12%) was obtained in the same manner as in Example 20, with the exception that tert-butyl (2R,3S)-2-(3-(7-bromo-5-chloro-1H-benzo[d]imidazol-1-yl)propyl)-3-((tert-butyldimethysilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate, and that isoxazol-3-ylboronic acid was used instead of (3-fluorophenyl)boronic acid in Step 20-2 of Example 20.

$^1$H NMR (500 MHz, MeOD): δ 9.53 (s, 1H), 8.04 (m, 2H), 7.92 (s, 1H), 7.69 (m, 1H), 4.61 (m, 2H), 3.61 (m, 1H), 3.02 (m, 2H), 2.28 (m, 2H), 2.04 (m, 2H), 1.99 (m, H), 1.78 (m, 2H), 1.52 (m, 1H)

Example 91: Preparation of (2R,3S)-2-(3-(5-chloro-7-(thiophen-3-yl)-1H-benzo[d]imidazol-1-yl)propyl)piperidin-3-ol dihydrochloride

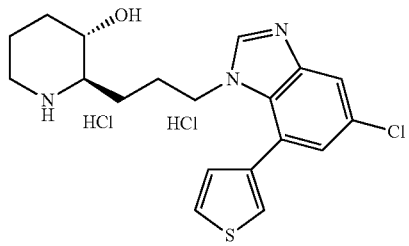 [SMILES: O[C@H]1CCCN[C@@H]1CCCn1cnc2cc(Cl)cc(-c3ccsc3)c21 ; Cl ; Cl]

The title compound (24 mg, yield: 31%) was obtained in the same manner as in Example 20, with the exception that tert-butyl (2R,3S)-2-(3-(7-bromo-5-chloro-1H-benzo[d]imidazol-1-yl)propyl)-3-((tert-butyldimethysilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate, and that thiophen-3-ylboronic acid was used instead of (3-fluorophenyl)boronic acid in Step 20-2 of Example 20.

$^1$H NMR (500 MHz, MeOD): δ 9.52 (s 1H), 7.93 (s, 1H), 7.73 (d, 2H), 7.52 (s, 1H), 7.36 (d, 1H), 4.22 (m, 2H), 3.48 (m, 1H), 3.23 (m, 1H), 2.93 (t, 1H), 2.76 (m, 1H), 2.02 (m, 2H), 1.78-1.63 (m, 3H), 1.62 (m, 1H), 1.57 (m, 1H), 1.55 (m, 1H)

Example 92: Preparation of (2R,3S)-2-(3-(5-chloro-7-(2-methylthiophen-3-yl)-1H-benzo[d]imidazol-1-yl)propyl)piperidin-3-ol dihydrochloride

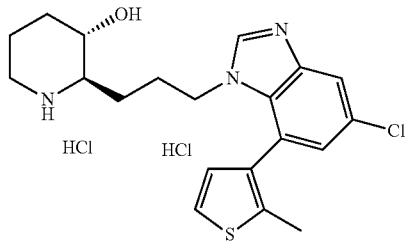 [SMILES: Cc1sccc1-c1cc(Cl)cc2ncn(CCC[C@H]3NCCC[C@@H]3O)c12 ; Cl ; Cl]

The title compound (20 mg, yield: 25%) was obtained in the same manner as in Example 20, with the exception that tert-butyl (2R,3S)-2-(3-(7-bromo-5-chloro-1H-benzo[d]imidazol-1-yl)propyl)-3-((tert-butyldimethysilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate, and that (2-methylthiophen-3-yl)boronic acid was used instead of (3-fluorophenyl)boronic acid in Step 20-2 of Example 20.

$^1$H NMR (500 MHz, MeOD): δ 9.56 (s, 1H), 7.95 (s, 1H), 7.47 (d, 2H), 7.15 (d, 1H), 4.22 (m, 1H), 4.15 (m, 1H), 3.50 (m, 1H), 3.25 (m, 1H), 2.91 (t, 1H), 2.81 (m, 1H), 2.34 (d, 3H), 2.01 (m, 2H), 1.99-1.96 (m, 3H), 1.79 (m, 1H), 1.65 (m, 1H), 1.56 (m, 1H)

Example 93: Preparation of (2R,3S)-2-(3-(5-chloro-7-(3,5-dimethylisoxazol-4-yl)-1H-benzo[d]imidazol-1-yl)propyl)piperidin-3-ol dihydrochloride

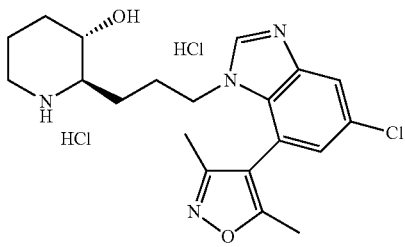 [SMILES: Cc1noc(C)c1-c1cc(Cl)cc2ncn(CCC[C@H]3NCCC[C@@H]3O)c12 ; Cl ; Cl]

The title compound (19 mg, yield: 24%) was obtained in the same manner as in Example 20, with the exception that tert-butyl (2R,3S)-2-(3-(7-bromo-5-chloro-1H-benzo[d]imidazol-1-yl)propyl)-3-((tert-butyldimethysilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate, and that (3,5-dimethylisoxazol-4-yl)boronic acid was used instead of (3-fluorophenyl)boronic acid in Step 20-2 of Example 20.

$^1$H NMR (500 MHz, MeOD): δ 9.58 (s, 1H), 8.04 (s, 1H), 7.71 (s, 1H), 4.23 (m, 2H), 3.61 (m, 1H), 3.01 (m, 1H), 2.97 (m, 1H), 2.39 (s, 3H), 2.18 (s, 3H), 2.17-2.11 (m, 3H), 2.04 (m, 2H), 1.86 (m, 2H), 1.71 (m, 2H)

Example 94: Preparation of (2R,3S)-2-(3-(5-chloro-7-(3,6-dihydro-2H-pyran-4-yl)-1H-benzo[d]imidazol-1-yl)propyl)piperidin-3-ol dihydrochloride

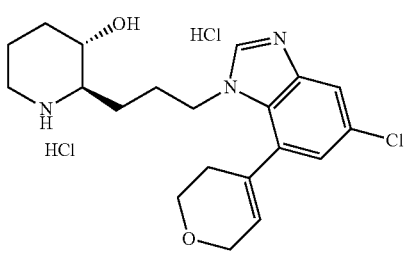 [SMILES: O[C@H]1CCCN[C@@H]1CCCn1cnc2cc(Cl)cc(C3=CCOCC3)c21 ; Cl ; Cl]

The title compound (22 mg, yield: 27%) was obtained in the same manner as in Example 20, with the exception that tert-butyl (2R,3S)-2-(3-(7-bromo-5-chloro-1H-benzo[d]imidazol-1-yl)propyl)-3-((tert-butyldimethysilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate, and that (3,6-dihydro-2H-pyran-4-yl)boronic acid was used instead of (3-fluorophenyl)boronic acid in Step 20-2 of Example 20.

$^1$H NMR (500 MHz, MeOD): δ 9.60 (s, 1H), 7.85 (s, 1H), 7.51 (s, 1H), 6.08 (s, 1H), 4.60 (t, 2H), 4.39 (s, 2H), 4.03 (t, 2H), 3.61 (m, 1H), 2.99 (m, 2H), 2.58 (s, 2H), 2.12-1.96 (m, 5H), 1.72 (m, 2H), 1.51 (m, 1H)

Example 95: Preparation of (2R,3S)-2-(3-(7-(1-((1,3-dioxolan-2-yl)methyl)-1H-pyrazol-4-yl)-5-chloro-1H-benzo[d]imidazol-1-yl)propyl)piperidin-3-ol dihydrochloride

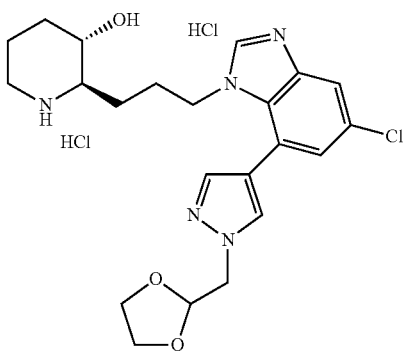 [SMILES: O[C@H]1CCCN[C@@H]1CCCn1cnc2cc(Cl)cc(-c3cnn(CC4OCCO4)c3)c21 ; Cl ; Cl]

The title compound (17 mg, yield: 22%) was obtained in the same manner as in Example 20, with the exception that tert-butyl (2R,3S)-2-(3-(7-bromo-5-chloro-1H-benzo[d]imidazol-1-yl)propyl)-3-((tert-butyldimethylsilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate, and that (1-((1,3-dioxolan-2-yl)methyl)-1H-pyrazol-4-yl)boronic acid was used instead of (3-fluorophenyl)boronic acid in Step 20-2 of Example 20.

$^1$H NMR (500 MHz, MeOD): δ 9.62 (s, 1H), 8.07 (s, 1H), 7.93 (s, 1H), 7.82 (s, 1H), 7.53 (s, 1H), 4.43 (m, 2H), 4.41 (m, 2H), 3.97 (m, 2H), 3.56 (m, 1H), 3.25 (m, 1H), 2.96 (t, 1H), 2.96 (s, 1H), 2.01 (m, 1H), 1.82-1.65 (m, 5H), 1.56 (m, 1H), 1.51 (m, 1H)

Example 96: Preparation of (2R,3S)-2-(3-(5-chloro-7-(1-methyl-1H-imidazol-5-yl)-1H-benzo[d]imidazol-1-yl)propyl)piperidin-3-ol trihydrochloride

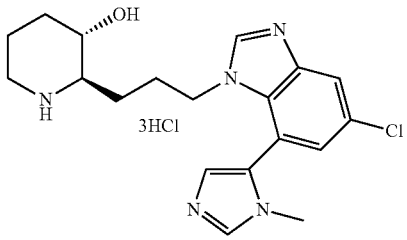 [SMILES: Cn1cncc1-c1cc(Cl)cc2ncn(CCC[C@H]3NCCC[C@@H]3O)c12 ; "3HCl"]

The title compound (20 mg, yield: 29%) was obtained in the same manner as in Example 20, with the exception that tert-butyl (2R,3S)-2-(3-(7-bromo-5-chloro-1H-benzo[d]imidazol-1-yl)propyl)-3-((tert-butyldimethysilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate, and that (1-methyl-1H-imidazol-5-yl)boronic acid was used instead of (3-fluorophenyl)boronic acid in Step 20-2 of Example 20.

$^1$H NMR (500 MHz, MeOD): δ 9.20 (s, 1H), 9.12 (d, 1H), 8.01 (s, 1H), 8.00 (s, 1H), 7.68 (s, 1H), 4.20 (s, 1H), 3.94 (s, 1H), 3.78 (s, 3H), 3.47 (m, 1H), 2.94 (t, 1H), 2.89 (m, 1H), 2.06 (m, 1H), 1.97 (m, 1H), 1.85 (m, 2H), 1.83-1.74 (m, 3H), 1.53 (m, 2H)

Example 97: Preparation of (2R,3S)-2-(3-(5-chloro-7-(1-methyl-1H-pyrazol-4-yl)-1H-benzo[d]imidazol-1-yl)propyl)piperidin-3-ol dihydrochloride

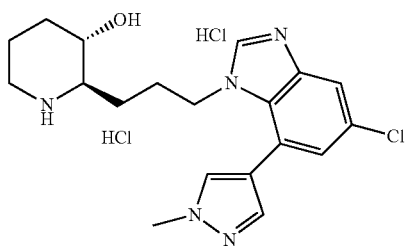 [SMILES: Cn1cc(-c2cc(Cl)cc3ncn(CCC[C@H]4NCCC[C@@H]4O)c23)cn1 ; Cl ; Cl]

The title compound (15 mg, yield: 25%) was obtained in the same manner as in Example 20, with the exception that tert-butyl (2R,3S)-2-(3-(7-bromo-5-chloro-1H-benzo[d]imidazol-1-yl)propyl)-3-((tert-butyldimethysilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate, and that (1-methyl-1H-pyrazol-4-yl)boronic acid was used instead of (3-fluorophenyl)boronic acid in Step 20-2 of Example 20.

$^1$H NMR (500 MHz, MeOD): δ 9.30 (s, 1H), 7.97 (s, 1H), 7.87 (s, 1H), 7.76 (s, 1H), 7.45 (s, 1H), 4.32 (m, 2H), 4.02 (s, 3H), 3.24 (m, 1H), 2.92 (m, 1H), 2.77 (m, 1H), 2.00 (m, 2H), 1.71 (m, 4H), 1.51 (m, 1H), 1.40 (m, 1H)

Example 98: Preparation of (2R,3S)-2-(3-(7-(pyrrolidin-1-yl)-1H-benzo[d]imidazol-1-yl)propyl)piperidin-3-ol dihydrochloride

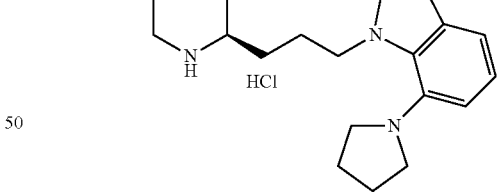

The title compound (12 mg, yield: 20%) was obtained in the same manner as in Example 18, with the exception that tert-butyl (2R,3S)-2-(3-(7-bromo-1H-benzo[d]imidazol-1-yl)propyl)-3-((tert-butyldimethylsilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate in Step 18-2 of Example 18.

$^1$H NMR (500 MHz, MeOD): δ 9.44 (s, 1H), 7.55 (m, 3H), 4.76 (t, 2H), 3.56 (m, 1H), 3.20 (m, 4H), 2.94 (m, 2H), 2.20 (m, 2H), 2.07 (m, 5H), 2.00 (m, 3H), 1.74 (m, 2H), 1.53 (m, 1H)

Example 99: Preparation of (2R,3S)-2-(3-(5-chloro-7-(pyrrolidin-1-yl)-1H-benzo[d]imidazol-1-yl)propyl)piperidin-3-ol dihydrochloride

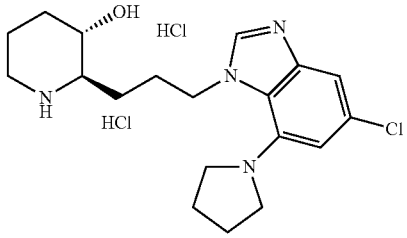 [SMILES: O[C@H]1CCCN[C@@H]1CCCn1cnc2cc(Cl)cc(N3CCCC3)c21 ; Cl ; Cl]

The title compound (13 mg, yield: 21%) was obtained in the same manner as in Example 18, with the exception that tert-butyl (2R,3S)-2-(3-(7-bromo-5-chloro-1H-benzo[d]imidazol-1-yl)propyl)-3-((tert-butyldimethylsilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate in Step 18-2 of Example 18.

$^1$H NMR (500 MHz, MeOD): δ 9.46 (s, 1H), 7.58 (d, 1H), 7.47 (d, 1H), 4.72 (m, 2H), 3.53 (m, 1H), 3.21 (m, 4H), 2.94 (m, 2H), 2.20 (m, 2H), 2.11 (m, 5H), 1.96 (m, 2H), 1.77 (m, 1H), 1.63 (m, 1H), 1.52 (m, 1H)

Example 100: Preparation of (2R,3S)-2-(3-(5-chloro-7-(2-cyclopropylthiazol-5-yl)-1H-benzo[d]imidazol-1-yl)propyl)piperidin-3-ol dihydrochloride

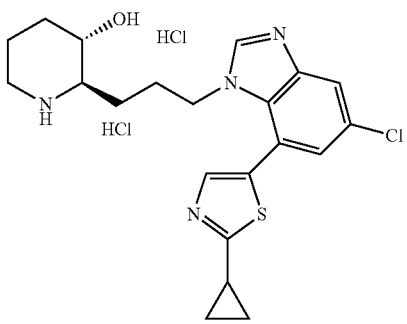 [SMILES: O[C@H]1CCCN[C@@H]1CCCn1cnc2cc(Cl)cc(-c3cnc(C4CC4)s3)c21 ; Cl ; Cl]

The title compound (12 mg, yield: 25%) was obtained in the same manner as in Example 20, with the exception that tert-butyl (2R,3S)-2-(3-(7-bromo-5-chloro-1H-benzo[d]imidazol-1-yl)propyl)-3-((tert-butyldimethylsilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate, and that (2-cyclopropylthiazol-5-yl)boronic acid was used instead of (3-fluorophenyl)boronic acid in Step 20-2 of Example 20.

$^1$H NMR (500 MHz, MeOD): δ 9.51 (s, 1H), 7.97 (s, 1H), 7.73 (s, 1H), 7.70 (s, 1H), 4.63 (m, 2H), 3.42 (m, 1H), 3.22 (m, 1H), 2.93 (m, 1H), 2.77 (m, 1H), 2.50 (m, 1H), 1.95 (m, 2H), 1.68 (m, 4H), 1.50 (m, 2H), 1.23 (m, 2H), 1.11 (m, 2H)

Example 101: Preparation of (2R,3S)-2-(3-(5-chloro-7-(1-(thiazol-2-yl)-1H-pyrazol-4-yl)-1H-benzo[d]imidazol-1-yl)propyl)piperidin-3-ol dihydrochloride

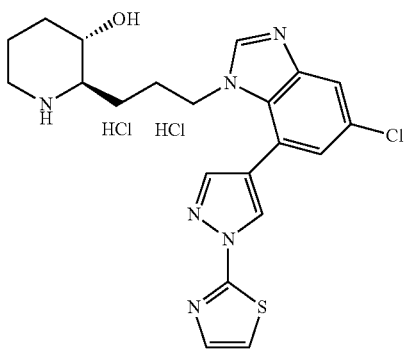 [SMILES: O[C@H]1CCCN[C@@H]1CCCn1cnc2cc(Cl)cc(-c3cnn(-c4nccs4)c3)c21 ; Cl ; Cl]

The title compound (17 mg, yield: 30%) was obtained in the same manner as in Example 20, with the exception that tert-butyl (2R,3S)-2-(3-(7-bromo-5-chloro-1H-benzo[d]imidazol-1-yl)propyl)-3-((tert-butyldimethysilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate, and that (1-(thiazol-2-yl)-1H-pyrazol-4-yl)boronic acid was used instead of (3-fluorophenyl)boronic acid in Step 20-2 of Example 20.

$^1$H NMR (500 MHz, MeOD): δ 9.41 (s, 1H), 8.83 (s, 1H), 8.10 (s, 1H), 7.95 (s, 1H), 7.65 (s, 1H), 7.61 (s, 1H), 7.47 (s, 1H), 4.37 (m, 2H), 3.44 (m, 1H), 3.18 (m, 1H), 2.87 (m, 1H), 2.78 (m, 1H), 1.92 (m, 2H), 1.82 (m, 2H), 1.65 (m, 2H), 1.43 (m, 2H)

Example 102: Preparation of (2R,3S)-2-(3-(5-chloro-7-(1-(oxetan-3-yl)-1H-pyrazol-4-yl)-1H-benzo[d]imidazol-1-yl)propyl)piperidin-3-ol dihydrochloride

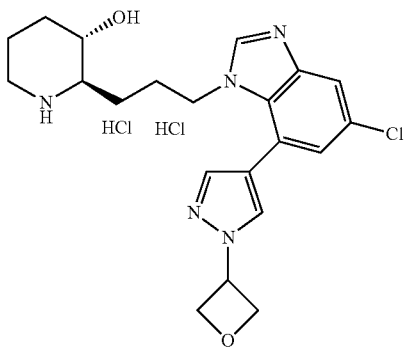 [SMILES: O[C@H]1CCCN[C@@H]1CCCn1cnc2cc(Cl)cc(-c3cnn(C4COC4)c3)c21 ; Cl ; Cl]

The title compound (12 mg, yield: 23%) was obtained in the same manner as in Example 20, with the exception that tert-butyl (2R,3S)-2-(3-(7-bromo-5-chloro-1H-benzo[d]imidazol-1-yl)propyl)-3-((tert-butyldimethysilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate, and that (1-(oxetan-3-yl)-1H-pyrazol-4-yl)boronic acid was used instead of (3-fluorophenyl)boronic acid in Step 20-2 of Example 20.

¹H NMR (500 MHz, MeOD): δ 9.58 (s, 1H), 8.15 (s, 1H), 7.92 (s, 1H), 7.87 (s, 1H), 7.54 (s, 1H), 4.68 (m, 1H), 4.34 (m, 2H), 4.03 (m, 2H), 3.50 (m, 1H), 3.22 (m, 1H), 2.92 (m, 1H), 2.85 (m, 1H), 1.95 (m, 2H), 1.78 (m, 4H), 1.64 (m, 1H), 1.42 (m, 1H)

Example 103: Preparation of (2R,3S)-2-(3-(5-chloro-7-(2-(tetrahydro-2H-pyran-4-yl)thiazol-4-yl)-1H-benzo[d]imidazol-1-yl)propyl)piperidin-3-ol dihydrochloride

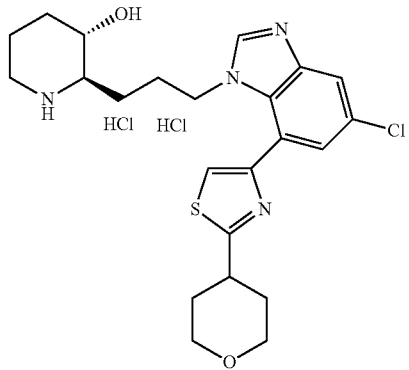 [SMILES: O[C@H]1CCCN[C@@H]1CCCn1cnc2cc(Cl)cc(-c3csc(C4CCOCC4)n3)c21 ; Cl ; Cl]

The title compound (10 mg, yield: 18%) was obtained in the same manner as in Example 20, with the exception that tert-butyl (2R,3S)-2-(3-(7-bromo-5-chloro-1H-benzo[d]imidazol-1-yl)propyl)-3-((tert-butyldimethylsilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate, and that (2-(tetrahydro-2H-pyran-4-yl)thiazol-5-yl)boronic acid was used instead of (3-fluorophenyl)boronic acid in Step 20-2 of Example 20.

¹H NMR (500 MHz, MeOD): δ 9.63 (s, 1H), 7.98 (s, 1H), 7.73 (S, 1H), 7.21 (s, 1H), 4.65 (m, 2H), 3.84 (m, 4H), 3.62 (m, 4H), 3.48 (m, 1H), 3.25 (m, 1H), 2.94 (m, 1H), 2.81 (m, 1H), 1.99 (m, 3H), 1.82 (m, 4H), 1.54 (m, 2H)

Example 104: Preparation of (2R,3S)-2-(3-(5-chloro-7-(furan-3-yl)-1H-benzo[d]imidazol-1-yl)propyl)piperidin-3-ol dihydrochloride

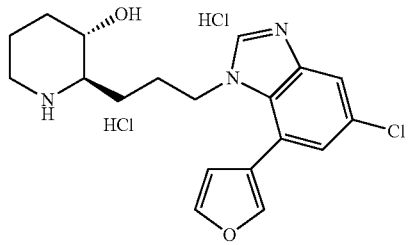 [SMILES: O[C@H]1CCCN[C@@H]1CCCn1cnc2cc(Cl)cc(-c3ccoc3)c21 ; Cl ; Cl]

The title compound (9 mg, yield: 15%) was obtained in the same manner as in Example 20, with the exception that tert-butyl (2R,3S)-2-(3-(7-bromo-5-chloro-1H-benzo[d]imidazol-1-yl)propyl)-3-((tert-butyldimethysilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1l-carboxylate, and that furan-3-ylboronic acid was used instead of (3-fluorophenyl)boronic acid in Step 20-2 of Example 20.

¹H NMR (500 MHz, MeOD): δ 9.55 (s, 1H), 8.05 (d, 1H), 7.93 (s, 1H), 7.69 (d, 1H), 7.50 (m, 1H), 7.32 (m, 1H), 4.63 (m, 2H), 3.61 (m, 1H), 3.02 (m, 1H), 2.94 (m, 1H), 2.26 (m, 2H), 2.09 (m, 2H), 2.01 (m, 1H), 1.78 (m, 2H), 1.53 (m, 1H)

Example 105: 4-(5-chloro-1-(3-((2R,3S)-3-hydroxypiperidin-2-yl)propyl)-1H-benzo[d]imidazol-7-yl)thiazole-2-carbonitrile dihydrochloride

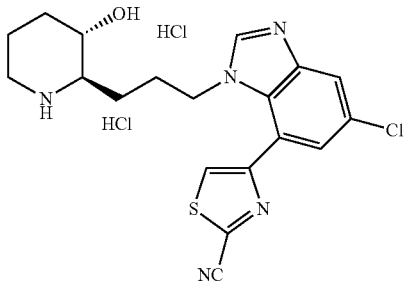 [SMILES: N#Cc1nc(-c2cc(Cl)cc3ncn(CCC[C@H]4NCCC[C@@H]4O)c23)cs1 ; Cl ; Cl]

The title compound (14 mg, yield: 20%) was obtained in the same manner as in Example 20, with the exception that tert-butyl (2R,3S)-2-(3-(7-bromo-5-chloro-1H-benzo[d]imidazol-1-yl)propyl)-3-((tert-butyldimethysilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1l-carboxylate, and that (2-cyanothiazol-4-yl)boronic acid was used instead of (3-fluorophenyl)boronic acid in Step 20-2 of Example 20.

¹H NMR (500 MHz, MeOD): δ 9.54 (s, 1H), 8.29 (s, 1H), 8.02 (s, 1H), 7.79 (s, 1H), 4.57 (m, 2H), 3.42 (m, 1H), 3.20 (m, 1H), 2.91 (m, 1H), 2.76 (m, 1H), 1.95 (m, 2H), 1.60 (m, 4H), 1.52 (m, 1H), 1.41 (m, 1H)

Example 106: Preparation of (2R,3S)-2-(3-(7-(1-(tert-butyl)-1H-pyrazol-4-yl)-5-chloro-1H-benzo[d]imidazol-1-yl)propyl)piperidin-3-ol dihydrochloride

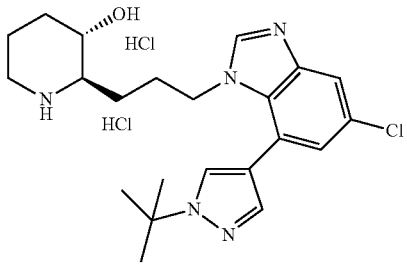 [SMILES: CC(C)(C)n1cc(-c2cc(Cl)cc3ncn(CCC[C@H]4NCCC[C@@H]4O)c23)cn1 ; Cl ; Cl]

The title compound (10 mg, yield: 18%) was obtained in the same manner as in Example 20, with the exception that tert-butyl (2R,3S)-2-(3-(7-bromo-5-chloro-1H-benzo[d]imidazol-1-yl)propyl)-3-((tert-butyldimethylsilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate, and that (1-(tert-butyl)-1H-pyrazol-4-yl)boronic acid was used instead of (3-fluorophenyl)boronic acid in Step 20-2 of Example 20.

$^1$H NMR (500 MHz, MeOD): δ 9.52 (s, 1H), 8.14 (s, 1H), 7.89 (s, 1H), 7.80 (s, 1H), 7.51 (s, 1H), 4.36 (m, 2H), 3.48 (m, 1H), 3.23 (m, 1H), 2.95 (m, 1H), 2.82 (m, 1H), 2.01 (m, 2H), 1.81 (m, 2H), 1.73 (m, 11H), 1.53 (m, 1H), 1.43 (m, 1H)

Example 107: Preparation of (2R,3S)-2-(3-(5-chloro-7-(1-isopentyl-1H-pyrazol-4-yl)-1H-benzo[d]imidazol-1-yl)propyl)piperidin-3-ol dihydrochloride

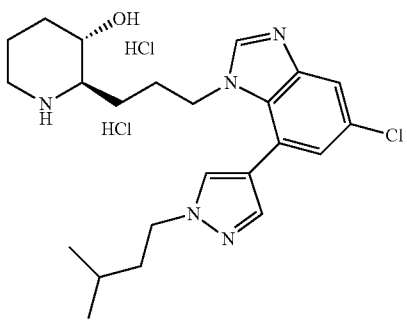 [SMILES: CC(C)CCn1cc(-c2cc(Cl)cc3ncn(CCC[C@H]4NCCC[C@@H]4O)c23)cn1 ; Cl ; Cl]

The title compound (17 mg, yield: 25%) was obtained in the same manner as in Example 20, with the exception that tert-butyl (2R,3S)-2-(3-(7-bromo-5-chloro-1H-benzo[d]imidazol-1-yl)propyl)-3-((tert-butyldimethylsilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate, and that (1-isopentyl-1H-pyrazol-4-yl)boronic acid was used instead of (3-fluorophenyl)boronic acid in Step 20-2 of Example 20.

$^1$H NMR (500 MHz, MeOD): δ 9.47 (s, 1H), 8.04 (s, 1H), 7.89 (s, 1H), 7.78 (s, 1H), 7.50 (s, 1H), 4.32 (m, 4H), 3.45 (m, 1H), 3.23 (m, 1H), 2.95 (m, 1H), 2.78 (m, 1H), 2.00 (m, 2H), 1.87 (m, 2H), 1.76 (m, 2H), 1.64 (m, 4H), 1.54 (m, 1H), 1.42 (m, 1H), 1.02 (s, 6H)

Example 108: Preparation of (2R,3S)-2-(3-(5-chloro-7-(1-isopropyl-1H-pyrazol-4-yl)-1H-benzo[d]imidazol-1-yl)propyl)piperidin-3-ol dihydrochloride

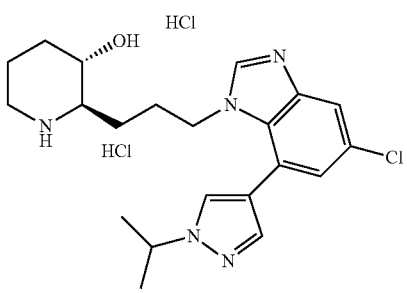 [SMILES: Cl ; CC(C)n1cc(-c2cc(Cl)cc3ncn(CCC[C@H]4NCCC[C@@H]4O)c23)cn1 ; Cl]

The title compound (15 mg, yield: 21%) was obtained in the same manner as in Example 20, with the exception that tert-butyl (2R,3S)-2-(3-(7-bromo-5-chloro-1H-benzo[d]imidazol-1-yl)propyl)-3-((tert-butyldimethylsilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate, and that (1-isopropyl-1H-pyrazol-4-yl)boronic acid was used instead of (3-fluorophenyl)boronic acid in Step 20-2 of Example 20.

$^1$H NMR (500 MHz, MeOD): δ 9.48 (s, 1H), 8.07 (s, 1H), 7.90 (s, 1H), 7.79 (s, 1H), 7.52 (s, 1H), 4.70 (m, 1H), 4.30 (m, 2H), 3.45 (m, 1H), 3.24 (m, 1H), 2.93 (m, 1H), 2.80 (m, 1H), 1.99 (m, 2H), 1.71 (m, 2H), 1.67 (m, 2H), 1.59 (s, 6H), 1.53 (m, 1H), 1.40 (m, 1H)

Example 109: Preparation of (2R,3S)-2-(3-(5-chloro-7-(4-methylthiophen-3-yl)-1H-benzo[d]imidazol-1-yl)propyl)piperidin-3-ol dihydrochloride

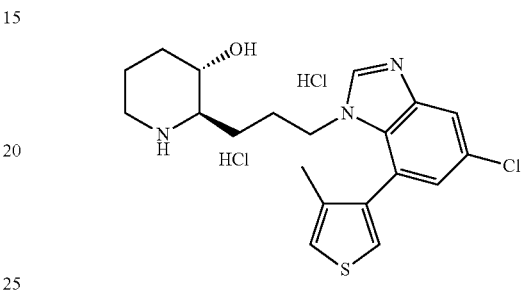

The title compound (20 mg, yield: 31%) was obtained in the same manner as in Example 20, with the exception that tert-butyl (2R,3S)-2-(3-(7-bromo-5-chloro-1H-benzo[d]imidazol-1-yl)propyl)-3-((tert-butyldimethysilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate, and that (4-methylthiophen-3-yl)boronic acid was used instead of (3-fluorophenyl)boronic acid in Step 20-2 of Example 20.

$^1$H NMR (500 MHz, MeOD): δ 9.53 (s, 1H), 7.95 (s, 1H), 7.63 (s, 1H), 7.48 (s, 1H), 7.34 (s, 1H), 4.23 (m, 1H), 3.96 (m, 1H), 3.51 (m, 1H), 3.23 (m, 1H), 2.96 (m, 1H), 2.81 (m, 1H), 2.06 (d, 3H), 1.99 (m, 2H), 1.76 (m, 3H), 1.57 (m, 2H), 1.42 (m, 1H)

Example 110: ethyl 3-(5-chloro-1-(3-((2R,3S)-3-hydroxypiperidin-2-yl)propyl)-1H-benzo[d]imidazol-7-yl)furan-2-carboxylate dihydrochloride

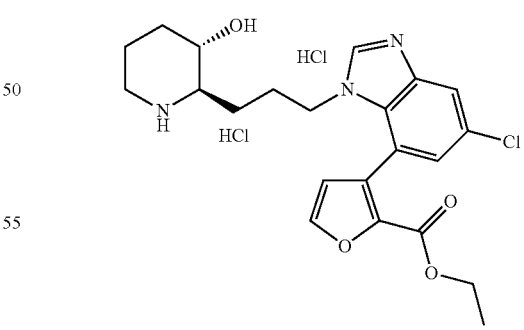

The title compound (10 mg, yield: 21%) was obtained in the same manner as in Example 20, with the exception that tert-butyl (2R,3S)-2-(3-(7-bromo-5-chloro-1H-benzo[d]imidazol-1-yl)propyl)-3-((tert-butyldimethysilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate, and that (2-(ethoxycarbonyl)furan-3-yl)boronic acid was used instead of (3-fluorophenyl)boronic acid in Step 20-2 of Example 20.

¹H NMR (500 MHz, MeOD): δ 9.53 (s, 1H), 8.00 (s, 1H), 7.97 (s, 1H), 7.55 (s, 1H), 6.96 (s, 1H), 4.29 (m, 1H), 4.15 (m, 3H), 3.47 (m, 1H), 3.24 (m, 2H), 2.94 (m, 1H), 2.79 (m, 1H), 1.97 (m, 3H), 1.84 (m, 2H), 1.72 (m, 2H), 1.53 (m, 2H), 1.08 (t, 3H)

Example 111: methyl 4-(5-chloro-1-(3-((2R,3S)-3-hydroxypiperidin-2-yl)propyl)-1H-benzo[d]imidazol-7-yl)thiophene-2-carboxylate dihydrochloride

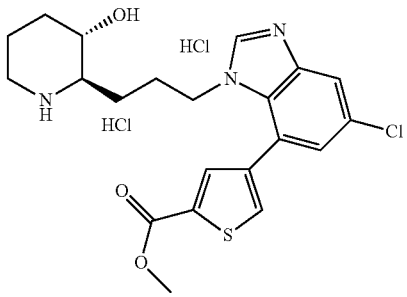 [SMILES: COC(=O)c1cc(-c2cc(Cl)cc3ncn(CCC[C@H]4NCCC[C@@H]4O)c23)cs1 ; Cl ; Cl]

The title compound (9 mg, yield: 19%) was obtained in the same manner as in Example 20, with the exception that tert-butyl (2R,3S)-2-(3-(7-bromo-5-chloro-1H-benzo[d]imidazol-1-yl)propyl)-3-((tert-butyldimethysilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate, and that (5-(methoxycarbonyl)thiophen-3-yl)boronic acid was used instead of (3-fluorophenyl)boronic acid in Step 20-2 of Example 20.

¹H NMR (500 MHz, MeOD): δ 9.54 (s, 1H), 8.05 (d, 2H), 7.97 (s, 1H), 7.57 (s, 1H), 4.80 (m, 1H), 4.22 (m, 2H), 3.93 (s, 3H), 3.43 (m, 1H), 3.22 (m, 2H), 2.93 (m, 1H), 2.78 (m, 1H), 2.01 (m, 2H), 1.78 (m, 3H), 1.63 (m, 1H), 1.53 (m, 1H), 1.41 (m, 1H)

Example 112: Preparation of (2R,3S)-2-(3-(5-chloro-7-(1-(2-fluoroethyl)-1H-pyrazol-4-yl)-1H-benzo[d]imidazol-1-yl)propyl)piperidin-3-ol dihydrochloride

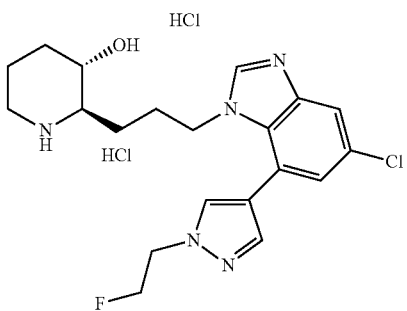 [SMILES: Cl ; O[C@H]1CCCN[C@@H]1CCCn1cnc2cc(Cl)cc(-c3cnn(CCF)c3)c21 ; Cl]

The title compound (15 mg, yield: 29%) was obtained in the same manner as in Example 20, with the exception that tert-butyl (2R,3S)-2-(3-(7-bromo-5-chloro-1H-benzo[d]imidazol-1-yl)propyl)-3-((tert-butyldimethysilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate, and that (1-(2-fluoroethyl)-1H-pyrazol-4-yl)boronic acid was used instead of (3-fluorophenyl)boronic acid in Step 20-2 of Example 20.

¹H NMR (500 MHz, MeOD): δ 9.53 (s, 1H), 8.09 (s, 1H), 7.91 (s, 1H), 7.85 (s, 1H), 7.53 (s, 1H), 4.92 (m, 1H), 4.64 (m, 1H), 4.56 (m, 1H), 4.32 (m, 2H), 3.49 (m, 1H), 3.23 (m, 1H), 2.94 (m, 1H), 2.80 (m, 1H), 1.96 (m, 3H), 1.74 (m, 4H), 1.54 (m, 1H), 1.47 (m, 1H)

Example 113: Preparation of (2R,3S)-2-(3-(7-(1-butyl-1H-pyrazol-4-yl)-5-chloro-1H-benzo[d]imidazol-1-yl)propyl)piperidin-3-ol dihydrochloride

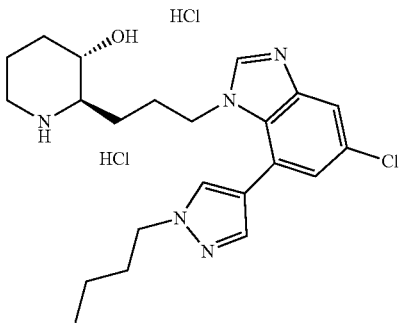 [SMILES: Cl ; CCCCn1cc(-c2cc(Cl)cc3ncn(CCC[C@H]4NCCC[C@@H]4O)c23)cn1 ; Cl]

The title compound (18 mg, yield: 34%) was obtained in the same manner as in Example 20, with the exception that tert-butyl (2R,3S)-2-(3-(7-bromo-5-chloro-1H-benzo[d]imidazol-1-yl)propyl)-3-((tert-butyldimethysilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate, and that (1-butyl-1H-pyrazol-4-yl)boronic acid was used instead of (3-fluorophenyl)boronic acid in Step 20-2 of Example 20.

¹H NMR (500 MHz, MeOD): δ 9.43 (s, 1H), 8.02 (S, 1H), 7.89 (s, 1H), 7.79 (s, 1H), 7.50 (s, 1H), 4.30 (m, 3H), 3.45 (m, 1H), 3.36 (m, 1H), 3.22 (m, 1H), 2.95 (m, 1H), 2.78 (m, 1H), 2.01 (m, 4H), 1.75 (m, 4H), 1.54 (m, 1H), 1.42 (m, 3H), 1.01 (m, 3H)

Example 114: Preparation of (2R,3S)-2-(3-(5-chloro-7-(2,5-dimethylthiophen-3-yl)-1H-benzo[d]imidazol-1-yl)propyl)piperidin-3-ol dihydrochloride

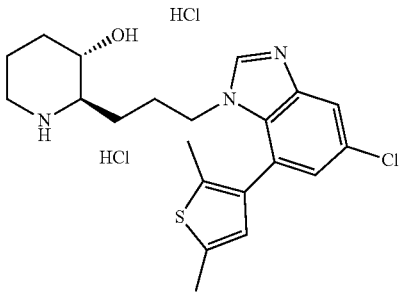 [SMILES: Cl ; Cc1cc(-c2cc(Cl)cc3ncn(CCC[C@H]4NCCC[C@@H]4O)c23)c(C)s1 ; Cl]

The title compound (12 mg, yield: 20%) was obtained in the same manner as in Example 20, with the exception that tert-butyl (2R,3S)-2-(3-(7-bromo-5-chloro-1H-benzo[d]imidazol-1-yl)propyl)-3-((tert-butyldimethylsilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate, and that (2,5-dimethylthiophen-3-yl)boronic acid was used instead of (3-fluorophenyl)boronic acid in Step 20-2 of Example 20.

¹H NMR (500 MHz, MeOD): δ 9.54 (m, 1H), 7.92 (s, 1H), 7.44 (s, 1H), 6.80 (s, 1H), 4.25 (m, 1H), 4.09 (m, 1H), 3.48 (m, 1H), 3.25 (m, 2H), 2.95 (m, 1H), 2.80 (m, 1H), 2.51 (s, 3H), 2.24 (d, 3H), 1.99 (m, 3H), 1.80 (m, 2H), 1.66 (m, 3H), 1.56 (m, 1H), 1.47 (m, 1H)

Example 115: Preparation of (2R,3S)-2-(3-(5-chloro-7-(1-isobutyl-1H-pyrazol-4-yl)-1H-benzo[d]imidazol-1-yl)propyl)piperidin-3-ol dihydrochloride

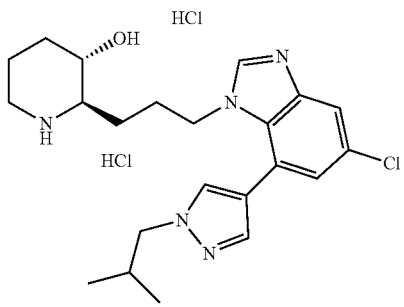 [SMILES: Cl ; CC(C)Cn1cc(-c2cc(Cl)cc3ncn(CCC[C@H]4NCCC[C@@H]4O)c23)cn1 ; Cl]

The title compound (18 mg, yield: 27%) was obtained in the same manner as in Example 20, with the exception that tert-butyl (2R,3S)-2-(3-(7-bromo-5-chloro-1H-benzo[d]imidazol-1-yl)propyl)-3-((tert-butyldimethylsilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate, and that (1-isobutyl-1H-pyrazol-4-yl)boronic acid was used instead of (3-fluorophenyl)boronic acid in Step 20-2 of Example 20.

¹H NMR (500 MHz, MeOD): δ 9.53 (s, 1H), 8.03 (s, 1H), 7.90 (s, 1H), 7.80 (s, 1H), 7.50 (s, 1H), 4.33 (m, 2H), 4.10 (m, 2H), 3.48 (m, 1H), 3.23 (m, 1H), 2.92 (m, 1H), 2.81 (m, 1H), 2.30 (m, 1H), 1.99 (m, 2H), 1.81 (m, 2H), 1.74 (m, 2H), 1.54 (m, 1H), 1.44 (m, 1H), 0.99 (d, 6H)

Example 116: ethyl 4-(5-chloro-1-(3-((2R,3S)-3-hydroxypiperidin-2-yl)propyl)-1H-benzo[d]imidazol-7-yl)-1-methyl-1H-pyrrole-2-carboxylate dihydrochloride

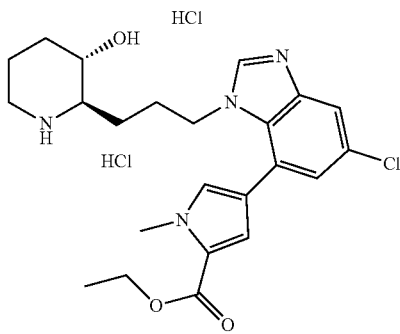 [SMILES: Cl ; CCOC(=O)c1cc(-c2cc(Cl)cc3ncn(CCC[C@H]4NCCC[C@@H]4O)c23)cn1C ; Cl]

The title compound (18 mg, yield: 31%) was obtained in the same manner as in Example 20, with the exception that tert-butyl (2R,3S)-2-(3-(7-bromo-5-chloro-1H-benzo[d]imidazol-1-yl)propyl)-3-((tert-butyldimethysilyl)oxy)piperidine-1-carboxylate was used instead of tert-butyl (2R,3S)-2-(3-(4-bromo-1H-benzo[d]imidazol-1-yl)propyl)-3-((tert-butyldimethylsilyl)oxy)piperidine-1-carboxylate, and that (5-(ethoxycarbonyl)-1-methyl-1H-pyrrol-3-yl)boronic acid was used instead of (3-fluorophenyl)boronic acid in Step 20-2 of Example 20.

¹H NMR (500 MHz, MeOD): δ 9.50 (s, 1H), 7.87 (s, 1H), 7.49 (s, 1H), 7.31 (s, 1H), 7.15 (s, 1H), 4.41 (m, 2H), 4.32 (m, 2H), 4.04 (s, 3H), 3.42 (m, 1H), 3.21 (m, 1H), 2.92 (m, 1H), 2.76 (m, 1H), 1.96 (m, 2H), 1.88-1.62 (m, 5H), 1.52 (m, 2H), 1.40 (m, 3H)

Example 117: Preparation of (2R,3S)-2-(3-(5-chloro-1H-imidazo[4,5-b]pyridin-1-yl)propyl)piperidin-3-ol dihydrochloride

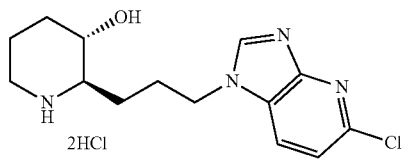 [SMILES: O[C@H]1CCCN[C@@H]1CCCn1cnc2nc(Cl)ccc21 ; "2HCl"]

The title compound (17 mg, yield: 35%) was obtained in the same manner as in Example 45, with the exception that 5-chloro-1H-imidazo[4,5-b]pyridine was used instead of 5-bromo-4-methyl-1H-benzo[d]imidazole in step 45-1 of Example 45.

¹H-NMR (500 MHz, MeOD): δ 9.48 (s, 1H), 8.29 (d, 1H), 7.68 (d, 1H), 4.58 (t, 2H), 3.66 (m, 2H), 3.00 (m, 2H), 2.20 (m, 2H), 2.07 (m, 2H), 1.98 (m, 1H), 1.74 (m, 2H), 1.56 (m, 1H)

Example 118: Preparation of (2R,3S)-2-(3-(5-chloro-3H-imidazo[4,5-b]pyridin-3-yl)propyl)piperidin-3-ol dihydrochloride

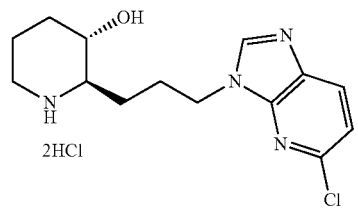 [SMILES: O[C@H]1CCCN[C@@H]1CCCn1cnc2ccc(Cl)nc21 ; "2HCl"]

The title compound (15 mg, yield: 40%) was obtained in the same manner as in Example 45, with the exception that 5-chloro-3H-imidazo[4,5-b]pyridine was used instead of 5-bromo-4-methyl-1H-benzo[d]imidazole in step 45-1 of Example 45.

¹H-NMR (500 MHz, MeOD): δ9.50 (s, 1H), 8.46 (d, 1H), 7.69 (d, 1H), 4.59 (t, 2H), 3.65 (m, 1H), 3.58 (m, 1H), 2.99 (m, 2H), 2.20 (m, 2H), 2.05 (m, 2H), 1.97 (m, 1H), 1.73 (m, H), 1.54 (m, 1H)

Example 119: Preparation of (2R,3S)-2-(3-(5-bromo-1H-imidazo[4,5-b]pyridin-1-yl)propyl)piperidin-3-ol dihydrochloride

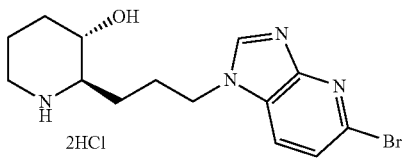 [SMILES: O[C@H]1CCCN[C@@H]1CCCn1cnc2nc(Br)ccc21 ; "2HCl"]

The title compound (30 mg, yield: 80%) was obtained in the same manner as in Example 45, with the exception that 5-bromo-1H-imidazo[4,5-b]pyridine was used instead of 5-bromo-4-methyl-1H-benzo[d]imidazole in step 45-1 of Example 45.

$^1$H-NMR (500 MHz, MeOD): δ 9.54 (s, 1H), 8.20 (d, 1H), 7.84 (d, 1H), 4.59 (t, 2H), 3.58 (m, 2H), 2.99 (m, 2H), 2.24 (m, 2H), 2.07 (m, 2H), 1.98 (m, 1H), 1.74 (m, 2H), 1.56 (m, 1H)

Example 120: Preparation of (2R,3S)-2-(3-(6-bromo-1H-imidazo[4,5-b]pyridin-1-yl)propyl)piperidin-3-ol dihydrochloride

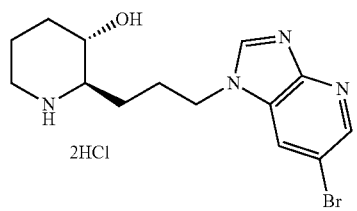 [SMILES: O[C@H]1CCCN[C@@H]1CCCn1cnc2ncc(Br)cc21 ; "2HCl"]

The title compound (33 mg, yield: 82%) was obtained in the same manner as in Example 45, with the exception that 6-bromo-1H-imidazo[4,5-b]pyridine was used instead of 5-bromo-4-methyl-1H-benzo[d]imidazole in step 45-1 of Example 45.

$^1$H-NMR (500 MHz, MeOD): δ 9.50 (s, 1H), 8.78 (d, 1H), 8.53 (d, 1H), 4.60 (t, 2H), 3.56 (t, 1H), 2.98 (m, 2H), 2.26 (m, 2H), 2.21 (m, 2H), 1.97 (m, 1H), 1.74 (m, 2H), 1.55 (m, 1H)

Example 121: Preparation of (2R,3S)-2-(3-(5-methyl-1H-imidazo[4,5-b]pyridin-1-yl)propyl)piperidin-3-ol dihydrochloride

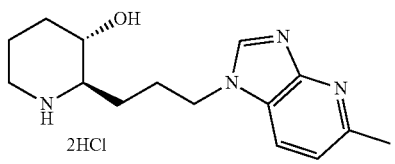 [SMILES: Cc1ccc2c(ncn2CCC[C@H]2NCCC[C@@H]2O)n1 ; "2HCl"]

The title compound (19 mg, yield: 49%) was obtained in the same manner as in Example 45, with the exception that 5-methyl-1H-imidazo[4,5-b]pyridine was used instead of 5-bromo-4-methyl-1H-benzo[d]imidazole in step 45-1 of Example 45.

$^1$H-NMR (500 MHz, MeOD): δ 9.55 (s, 1H), 8.18 (d, 1H), 7.58 (d, 1H), 4.63 (t, 2H), 3.58 (m, 2H), 3.00 (m, 2H), 2.74 (s, 3H), 2.24 (m, 2H), 2.06 (m, 2H), 1.98 (m, 1H), 1.74 (m, 2H), 1.56 (m, 2H), 1.56 (m, 1H)

Example 122: Preparation of (2R,3S)-2-(3-(6-chloro-1H-imidazo[4,5-c]pyridin-1-yl)propyl)piperidin-3-ol dihydrochloride

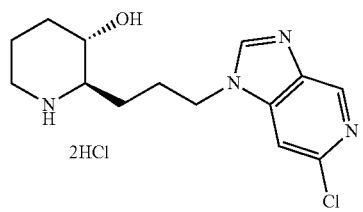 [SMILES: O[C@H]1CCCN[C@@H]1CCCn1cnc2cnc(Cl)cc21 ; "2HCl"]

The title compound (15 mg, yield: 40%) was obtained in the same manner as in Example 45, with the exception that 6-chloro-1H-imidazo[4,5-c]pyridine was used instead of 5-bromo-4-methyl-1H-benzo[d]imidazole in step 45-1 of Example 45.

$^1$H-NMR (500 MHz, MeOD): δ 9.30 (s, 1H), 9.09 (s, 1H), 7.91 (s, 1H), 4.62 (t, 2H), 3.60 (m, 2H), 2.99 (m, 2H), 2.22 (m, 2H), 2.06 (m, 2H), 1.98 (m, 1H), 1.73 (m, 2H), 1.56 (m, 1H)

Example 123: Preparation of (2R,3S)-2-(3-(6-chloro-3H-imidazo[4,5-c]pyridin-3-yl)propyl)piperidin-3-ol dihydrochloride

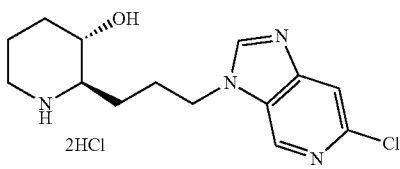 [SMILES: O[C@H]1CCCN[C@@H]1CCCn1cnc2cc(Cl)ncc21 ; "2HCl"]

The title compound (18 mg, yield: 37%) was obtained in the same manner as in Example 45, with the exception that 6-chloro-3H-imidazo[4,5-c]pyridine was used instead of 5-bromo-4-methyl-1H-benzo[d]imidazole in step 45-1 of Example 45.

$^1$H-NMR (500 MHz, MeOD): δ9.21 (s, 1H), 8.97 (s, 1H), 8.18 (s, 1H), 4.52 (t, 2H), 3.58 (m, 1H), 2.98 (m, 2H), 2.19 (m, 2H), 2.05 (m, 2H), 1.97 (m, 1H), 1.73 (m, 2H), 1.56 (m, 1H)

Example 124: Preparation of (2R,3S)-2-(3-(6-bromo-1H-imidazo[4,5-c]pyridin-1-yl)propyl)piperidin-3-ol dihydrochloride

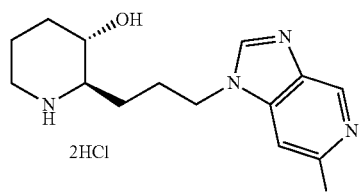

The title compound (18 mg, yield: 35%) was obtained in the same manner as in Example 45, with the exception that 6-bromo-3H-imidazo[4,5-c]pyridine was used instead of 5-bromo-4-methyl-1H-benzo[d]imidazole in step 45-1 of Example 45.

¹H-NMR (500 MHz, MeOD): δ9.43 (s, 1H), 9.16 (s, 1H), 8.12 (s, 1H), 4.64 (t, 2H), 3.65 (m, 2H), 3.01 (m, 2H), 2.26 (m, 2H), 2.07 (m, 2H), 1.97 (m, 1H), 1.75 (m, 2H), 1.56 (m, 1H)

Example 125: Preparation of (2R,3S)-2-(3-(6-bromo-3H-imidazo[4,5-c]pyridin-3-yl)propyl)piperidin-3-ol dihydrochloride

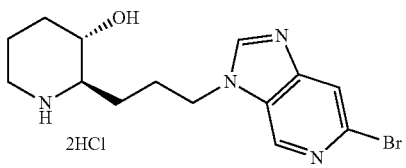 [SMILES: O[C@H]1CCCN[C@@H]1CCCn1cnc2cc(Br)ncc21 ; "2HCl"]

The title compound (20 mg, yield: 40%) was obtained in the same manner as in Example 45, with the exception that 6-bromo-3H-imidazo[4,5-c]pyridine was used instead of 5-bromo-4-methyl-1H-benzo[d]imidazole in step 45-1 of Example 45.

¹H-NMR (500 MHz, MeOD): δ 9.18 (s, 1H), 9.01 (s, 1H), 8.38 (s, 1H), 4.53 (t, 2H), 3.58 (m, 2H), 2.97 (m, 2H), 2.19 (m, 2H), 2.05 (m, 2H), 1.97 (m, 1H), 1.74 (m, 2H), 1.56 (m, 1H)

Example 126: Preparation of (2R,3S)-2-(3-(7-chloro-1H-imidazo[4,5-b]pyridin-1-yl)propyl)piperidin-3-ol dihydrochloride

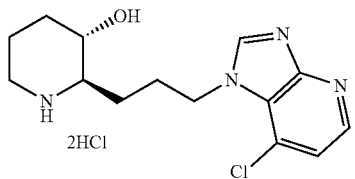 [SMILES: O[C@H]1CCCN[C@@H]1CCCn1cnc2nccc(Cl)c21 ; "2HCl"]

The title compound (25 mg, yield: 32%) was obtained in the same manner as in Example 45, with the exception that 7-chloro-1H-imidazo[4,5-b]pyridine was used instead of 5-bromo-4-methyl-1H-benzo[d]imidazole in step 45-1 of Example 45.

Example 127: Preparation of (2R,3S)-2-(3-(5,6-dichloro-1H-imidazo[4,5-b]pyridin-1-yl)propyl)piperidin-3-ol dihydrochloride

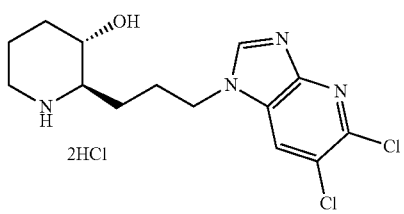 [SMILES: O[C@H]1CCCN[C@@H]1CCCn1cnc2nc(Cl)c(Cl)cc21 ; "2HCl"]

The title compound (35 mg, yield: 48%) was obtained in the same manner as in Example 45, with the exception that 5,6-dichloro-1H-imidazo[4,5-b]pyridine was used instead of 5-bromo-4-methyl-1H-benzo[d]imidazole in step 45-1 of Example 45.

¹H-NMR (500 MHz, MeOD): δ9.10 (s, 1H), 8.45 (s, 1H), 4.50 (t, 2H), 3.56 (m, 1H), 2.98 (m, 2H), 2.21 (m, 2H), 2.03 (m, 3H), 1.69 (m, 2H), 1.53 (m, 1H)

Example 128: Preparation of (2R,3S)-2-(3-(7-bromo-1H-imidazo[4,5-c]pyridin-1-yl)propyl)piperidin-3-ol dihydrochloride

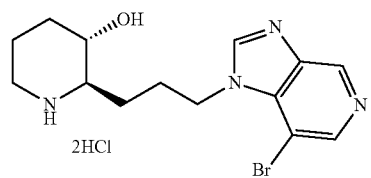 [SMILES: O[C@H]1CCCN[C@@H]1CCCn1cnc2cncc(Br)c21 ; "2HCl"]

The title compound (18 mg, yield: 35%) was obtained in the same manner as in Example 45, with the exception that 7-bromo-1H-imidazo[4,5-c]pyridine was used instead of 5-bromo-4-methyl-1H-benzo[d]imidazole in step 45-1 of Example 45.

¹H-NMR (500 MHz, MeOD): δ 9.66 (s, 1H), 9.07 (s, 1H), 8.89 (s, 1H), 4.62 (t, 2H), 3.58 (m, 2H), 2.99 (m, 2H), 2.21 (m, 2H), 2.00 (m, 3H), 1.74 (m, 2H), 1.55 (m, 1H)

Example 129: Preparation of (2R,3S)-2-(3-(5-(trifluoromethyl)-3H-imidazo[4,5-b]pyridin-3-yl)propyl)piperidin-3-ol dihydrochloride

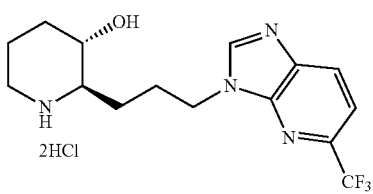 [SMILES: O[C@H]1CCCN[C@@H]1CCCn1cnc2ccc(C(F)(F)F)nc21 ; "2HCl"]

The title compound (20 mg, yield: 45%) was obtained in the same manner as in Example 45, with the exception that 5-(trifluoromethyl)-3H-imidazo[4,5-b]pyridine was used instead of 5-bromo-4-methyl-1H-benzo[d]imidazole in step 45-1 of Example 45.

¹H-NMR (500 MHz, MeOD): δ9.71 (s, 1H), 8.53 (d, 1H), 8.08 (d, 1H), 4.67 (t, 2H), 3.59 (m, 1H), 2.95 (m, 2H), 2.28 (m, 2H), 2.07 (m, 2H), 1.98 (m, 1H), 1.75 (m, 2H), 1.55 (m, 1H)

Example 130: Preparation of (2R,3S)-2-(3-(6,7-dichloro-3H-imidazo[4,5-b]pyridin-3-yl)propyl)piperidin-3-ol dihydrochloride

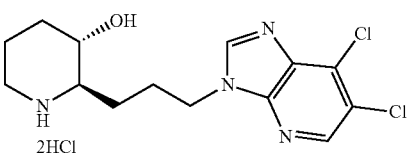 [SMILES: O[C@H]1CCCN[C@@H]1CCCn1cnc2c(Cl)c(Cl)cnc21 ; "2HCl"]

The title compound (25 mg, yield: 80%) was obtained in the same manner as in Example 45, with the exception that 6,7-dichloro-3H-imidazo[4,5-b]pyridine was used instead of 5-bromo-4-methyl-1H-benzo[d]imidazole in step 45-1 of Example 45.
¹H-NMR (500 MHz, MeOD): δ 8.62 (s, 1H), 8.51 (s, 1H), 4.43 (m, 2H), 3.51 (m, 1H), 3.22 (m, 1H), 2.91 (m, 2H), 2.08 (m, 2H), 1.96 (m, 3H), 1.55 (m, 3H)

Example 131: Preparation of (2R,3S)-2-(3-(6-chloro-7-methyl-3H-imidazo[4,5-b]pyridin-3-yl)propyl)piperidin-3-ol dihydrochloride

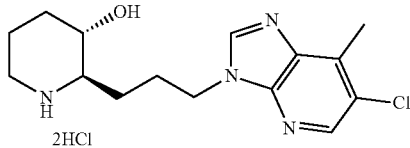 [SMILES: Cc1c(Cl)cnc2c1ncn2CCC[C@H]1NCCC[C@@H]1O ; "2HCl"]

The title compound (31 mg, yield: 84%) was obtained in the same manner as in Example 45, with the exception that 6-chloro-7-methyl-3H-imidazo[4,5-b]pyridine was used instead of 5-bromo-4-methyl-1H-benzo[d]imidazole in step 45-1 of Example 45.
¹H-NMR (500 MHz, MeOD): δ 9.68 (s, 1H), 8.67 (s, 1H), 4.62 (t, 2H), 3.57 (m, 2H), 2.97 (m, 2H), 2.74 (s, 3H), 2.25 (m, 2H), 2.06 (m, 2H), 1.97 (m, 1H), 1.75 (m, 2H), 1.53 (m, 1H)

Example 132: Preparation of (2R,3S)-2-(3-(6-bromo-7-methyl-3H-imidazo[4,5-b]pyridin-3-yl)propyl)piperidin-3-ol dihydrochloride

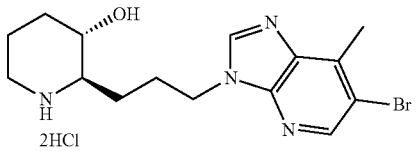 [SMILES: Cc1c(Br)cnc2c1ncn2CCC[C@H]1NCCC[C@@H]1O ; "2HCl"]

The title compound (35 mg, yield: 85%) was obtained in the same manner as in Example 45, with the exception that 6-bromo-7-methyl-3H-imidazo[4,5-b]pyridine was used instead of 5-bromo-4-methyl-1H-benzo[d]imidazole in step 45-1 of Example 45.
¹H-NMR (500 MHz, MeOD): δ 9.74 (s, 1H), 8.80 (d, 1H), 4.63 (t, 2H), 3.57 (m, 1H), 2.96 (m, 2H), 2.76 (s, 3H), 2.28 (m, 2H), 2.06 (m, 2H), 1.97 (m, 1H), 1.74 (m, 2H), 1.55 (m, 1H)

Example 133: Preparation of (2R,3S)-2-(3-(6-bromo-7-chloro-3H-imidazo[4,5-b]pyridin-3-yl)propyl)piperidin-3-ol dihydrochloride

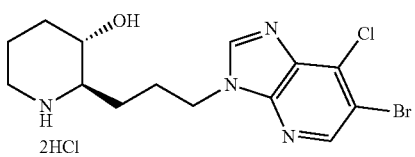 [SMILES: O[C@H]1CCCN[C@@H]1CCCn1cnc2c(Cl)c(Br)cnc21 ; "2HCl"]

The title compound (30 mg, yield: 78%) was obtained in the same manner as in Example 45, with the exception that 6-bromo-7-chloro-3H-imidazo[4,5-b]pyridine was used instead of 5-bromo-4-methyl-1H-benzo[d]imidazole in step 45-1 of Example 45.
¹H-NMR (500 MHz, MeOD): δ 9.24 (s, 1H), 8.77 (s, 1H), 4.55 (t, 2H), 3.55 (m, 1H), 3.26 (m, 1H), 2.97 (m, 2H), 2.23 (m, 2H), 2.03 (m, 3H), 1.70 (m, 2H), 1.54 (m, 1H)

Example 134: Preparation of (2R,3S)-2-(3-(7-chloro-6-(3-chlorophenyl)-3H-imidazo[4,5-b]pyridin-3-yl)propyl)piperidin-3-ol dihydrochloride

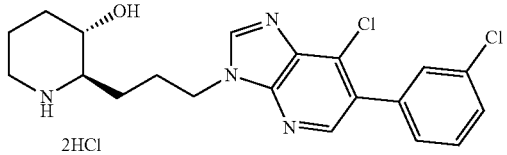 [SMILES: O[C@H]1CCCN[C@@H]1CCCn1cnc2c(Cl)c(-c3cccc(Cl)c3)cnc21 ; "2HCl"]

The title compound (28 mg, yield: 70%) was obtained in the same manner as in Example 45, with the exception that 7-chloro-6-(3-chlorophenyl)-3H-imidazo[4,5-b]pyridine was used instead of 5-bromo-4-methyl-1H-benzo[d]imidazole in step 45-1 of Example 45.
¹H-NMR (500 MHz, MeOD): δ 9.69 (s, 1H), 8.67 (s, 1H), 7.55 (m, 4H), 4.66 (t, 2H), 3.59 (m, 1H), 3.02 (m, 2H), 2.33 (m, 2H), 2.07 (m, 2H), 1.97 (m, 1H), 1.56 (m, 2H), 1.55 (m, 1H)

Example 135: Preparation of (2R,3S)-2-(3-(2-chloro-7H-purin-7-yl)propyl)piperidin-3-ol trihydrochloride

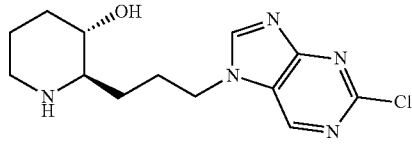

The title compound (15 mg, yield: 35%) was obtained in the same manner as in Example 45, with the exception that 2-chloro-7H-purine was used instead of 5-bromo-4-methyl-1H-benzo[d]imidazole in step 45-1 of Example 45.
¹H-NMR (500 MHz, MeOD): δ 9.05 (s, 1H), 8.81 (s, 1H), 4.44 (t, 2H), 3.55 (m, 1H), 3.28 (m, 1H), 2.98 (m, 2H), 2.19 (m, 2H), 2.03 (m, 3H), 1.70 (m, 2H), 1.55 (m, 1H)

Example 136: Preparation of (2R,3S)-2-(3-(2-chloro-9H-purin-9-yl)propyl)piperidin-3-ol trihydrochloride

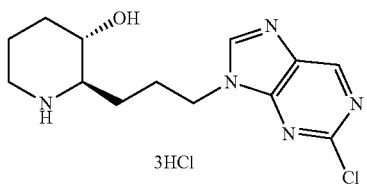 [SMILES: O[C@H]1CCCN[C@@H]1CCCn1cnc2cnc(Cl)nc21 ; "3HCl"]

The title compound (12 mg, yield: 30%) was obtained in the same manner as in Example 45, with the exception that 2-chloro-9H-purine was used instead of 5-bromo-4-methyl-1H-benzo[d]imidazole in step 45-1 of Example 45.

¹H-NMR (500 MHz, MeOD): δ 9.19 (s, 1H), 8.87 (s, 1H), 4.52 (m, 2H), 3.55 (m, 1H), 3.25 (m, 1H), 2.97 (m, 2H), 2.16 (m, 2H), 2.00 (m, 3H), 1.65 (m, 2H), 1.55 (m, 1H)

Example 137: Preparation of (2R,3S)-2-(3-(6-(dimethylamino)-9H-purin-9-yl)propyl)piperidin-3-ol trihydrochloride

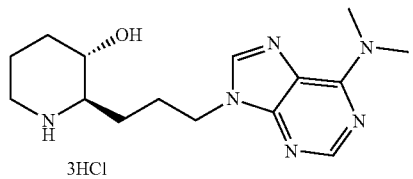 [SMILES: CN(C)c1ncnc2c1ncn2CCC[C@H]1NCCC[C@@H]1O ; "3HCl"]

3HCl

The title compound (25 mg, yield: 75%) was obtained in the same manner as in Example 45, with the exception that N,N-dimethyl-9H-purin-6-amine was used instead of 5-bromo-4-methyl-1H-benzo[d]imidazole in step 45-1 of Example 45.

¹H-NMR (500 MHz, MeOD): δ 8.38 (s, 1H), 8.37 (s, 1H), 4.41 (t, 2H), 3.98 (br, 2H), 3.56 (t, 1H), 3.42 (br, 3H), 3.26 (m, 1H), 2.97 (m, 2H), 2.19 (m, 5H), 1.78 (m, 1H), 1.67 (m, 1H), 1.53 (m, 1H)

Example 138: Preparation of (2R,3S)-2-(3-(6-(diethylamino)-9H-purin-9-yl)propyl)piperidin-3-ol trihydrochloride

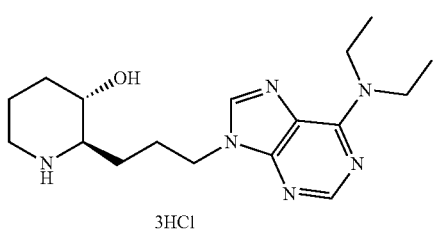 [SMILES: CCN(CC)c1ncnc2c1ncn2CCC[C@H]1NCCC[C@@H]1O ; "3HCl"]

3HCl

The title compound (27 mg, yield: 77%) was obtained in the same manner as in Example 45, with the exception that N,N-diethylamino-9H-purin-6-amine was used instead of 5-bromo-4-methyl-1H-benzo[d]imidazole in step 45-1 of Example 45.

¹H-NMR (500 MHz, MeOD): δ 8.34 (s, 1H), 8.32 (d, 1H), 4.38 (m, 2H), 3.66 (br, 4H), 3.55 (m, 1H), 3.27 (m, 1H), 2.96 (m, 2H), 2.14-2.00 (m, 6H), 1.68 (m, 1H), 1.53 (m, 1H), 1.38 (br, 6H)

Example 139: Preparation of (2R,3S)-2-(3-(6-(ethyl(methyl)amino)-9H-purin-9-yl)propyl)piperidin-3-ol trihydrochloride

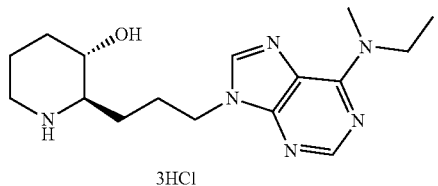 [SMILES: CCN(C)c1ncnc2c1ncn2CCC[C@H]1NCCC[C@@H]1O ; "3HCl"]

3HCl

The title compound (28 mg, yield: 78%) was obtained in the same manner as in Example 45, with the exception that N-ethyl-N-methyl-9H-purin-6-amine was used instead of 5-bromo-4-methyl-1H-benzo[d]imidazole in step 45-1 of Example 45.

¹H-NMR (500 MHz, MeOD): δ 8.39 (s, 1H), 8.38 (s, 1H), 4.51 (br, 2H), 4.41 (t, 2H), 3.56 (m, 1H), 3.41 (m, 1H), 3.27 (m, 3H), 2.96 (m, 2H), 2.19-1.99 (m, 5H), 1.75 (m, 1H), 1.68 (m, 1H), 1.53 (t, 3H)

Example 140: Preparation of (2R,3S)-2-(3-(6-morpholino-9H-purin-9-yl)propyl)piperidin-3-ol trihydrochloride

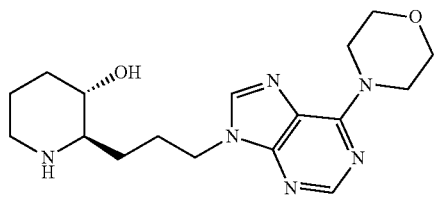

3HCl

The title compound (27 mg, yield: 80%) was obtained in the same manner as in Example 45, with the exception that 4-(9H-purin-6-yl)morpholine was used instead of 5-bromo-4-methyl-1H-benzo[d]imidazole in step 45-1 of Example 45.

¹H-NMR (500 MHz, MeOD): δ 8.35 (s, 1H), 8.33 (d, 1H), 4.39 (m, 2H), 3.66 (s, 6H), 3.54 (m, 1H), 3.25 (m, 1H), 2.96 (m, 2H), 2.14-1.98 (m, 5H), 1.84 (s, 6H), 1.72 (m, 2H), 1.53 (m, 1H)

Example 141: Preparation of (2R,3S)-2-(3-(6-(piperidin-1-yl)-9H-purin-9-yl)propyl)piperidin-3-ol trihydrochloride

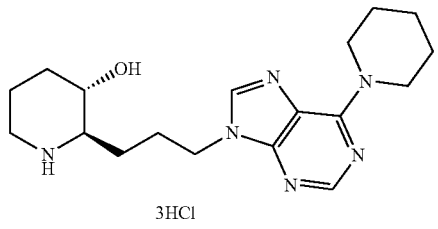 [SMILES: O[C@H]1CCCN[C@@H]1CCCn1cnc2c(N3CCCCC3)ncnc21 ; "3HCl"]

3HCl

The title compound (30 mg, yield: 81%) was obtained in the same manner as in Example 45, with the exception that 6-(piperidin-1-yl)-9H-purine was used instead of 5-bromo-4-methyl-1H-benzo[d]imidazole in step 45-1 of Example 45.

¹H-NMR (500 MHz, MeOD): δ 8.43 (s, 1H), 8.36 (s, 1H), 4.40 (m, 4H), 3.91 (m, 4H), 3.66 (s, 6H), 3.27 (m, 1H), 2.96 (m, 2H), 2.03 (m, 5H), 1.69 (m, 2H), 1.53 (m, 1H)

Example 142: Preparation of (2R,3S)-2-(3-(6-(pyrrolidin-1-yl)-9H-purin-9-yl)propyl)piperidin-3-ol trihydrochloride

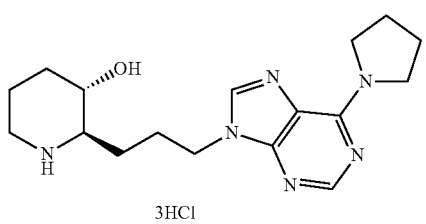 [SMILES: O[C@H]1CCCN[C@@H]1CCCn1cnc2c(N3CCCC3)ncnc21 ; "3HCl"]

The title compound (29 mg, yield: 80%) was obtained in the same manner as in Example 45, with the exception that 6-(pyrrolidin-1-yl)-9H-purine was used instead of 5-bromo-4-methyl-1H-benzo[d]imidazole in step 45-1 of Example 45.

¹H-NMR (500 MHz, MeOD): δ 8.33 (br, 2H), 4.37 (m, 4H), 3.75 (br, 2H), 3.66 (m, 1H), 2.96 (m, 2H), 2.17 (br, 6H), 2.00 (m, 4H), 1.73 (m, 2H), 1.53 (m, 1H)

Example 143: Preparation of 1-(3-((2R,3S)-3-hydroxypiperidin-2-yl)propyl)-1H-benzo[d]imidazol-2-ol dihydrochloride

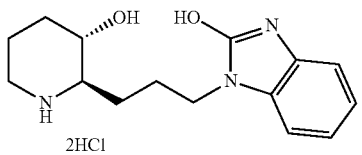 [SMILES: Oc1nc2ccccc2n1CCC[C@H]1NCCC[C@@H]1O]

The title compound (25 mg, yield: 79%) was obtained in the same manner as in Example 45, with the exception that 1H-benzo[d]imidazol-2-ol was used instead of 5-bromo-4-methyl-1H-benzo[d]imidazole in step 45-1 of Example 45.

¹H-NMR (500 MHz, MeOD): δ 7.16 (d, 1H), 7.10 (m, 3H), 3.96 (m, 2H), 3.53 (m, 1H), 3.20 (m, 1H), 2.91 (m, 2H), 2.00 (m, 5H), 1.62 (m, 2H), 1.51 (m, 1H)

Example 144: Preparation of 5,6-dichloro-1-(3-((2R,3S)-3-hydroxypiperidin-2-yl)propyl)-1H-benzo[d]imidazol-2-ol dihydrochloride

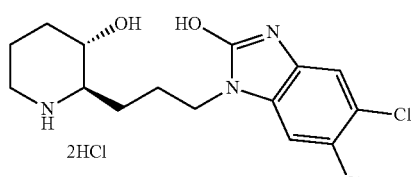

The title compound (27 mg, yield: 84%) was obtained in the same manner as in Example 45, with the exception that 5,6-dichloro-1H-benzo[d]imidazol-2-ol was used instead of 5-bromo-4-methyl-1H-benzo[d]imidazole in step 45-1 of Example 45.

¹H-NMR (500 MHz, MeOD): δ 7.38 (s, 1H), 7.21 (s, 1H), 3.92 (m, 2H), 3.48 (m, 2H), 3.20 (m, 3H), 2.89 (m, 3H), 2.04-1.92 (m, 7H), 1.67 (m, 5H)

Example 145: Preparation of (2R,3S)-2-(3-(2-(hydroxymethyl)-1H-benzo[d]imidazol-1-yl)propyl)piperidin-3-ol dihydrochloride

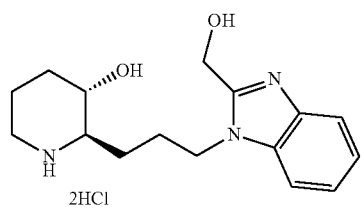 [SMILES: OCc1nc2ccccc2n1CCC[C@H]1NCCC[C@@H]1O]

The title compound (25 mg, yield: 80%) was obtained in the same manner as in Example 45, with the exception that (1H-benzo[d]imidazol-2-yl)methanol was used instead of 5-bromo-4-methyl-1H-benzo[d]imidazole in step 45-1 of Example 45.

¹H-NMR (500 MHz, MeOD): δ7.99 (d, 1H), 7.81 (d, 1H), 7.64 (m, 2H), 5.20 (s, 2H), 4.51 (m, 2H), 3.59 (m, 1H), 3.27 (m, 1H), 2.97 (m, 2H), 2.20 (m, 1H), 2.08 (m, 3H), 1.96 (m, 1H), 1.87 (m, 2H), 1.55 (m, 1H)

Example 146: Preparation of (2R,3S)-2-(3-(2-(hydroxymethyl)-4,5-dimethyl-1H-benzo[d]imidazol-1-yl)propyl)piperidin-3-ol dihydrochloride

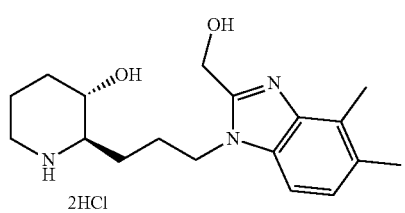 [SMILES: Cc1ccc2c(nc(CO)n2CCC[C@H]2NCCC[C@@H]2O)c1C]

The title compound (31 mg, yield: 83%) was obtained in the same manner as in Example 45, with the exception that (4,5-dimethyl-1H-benzo[d]imidazol-2-yl)methanol was used instead of 5-bromo-4-methyl-1H-benzo[d]imidazole in step 45-1 of Example 45.

¹H-NMR (500 MHz, MeOD): δ 7.67 (d, 1H), 7.47 (d, 1H), 5.14 (s, 2H), 4.53 (m, 2H), 3.59 (m, 1H), 3.28 (m, 1H), 2.97 (m, 2H), 2.57 (s, 3H), 2.47 (s, 3H), 2.20 (m, 1H), 2.10 (m, 3H), 1.97 (m, 1H), 1.76 (m, 2H), 1.54 (m, 1H)

Example 147: Preparation of (2R,3S)-2-(3-(5,6-dichloro-2-(hydroxymethyl)-1H-benzo[d]imidazol-1-yl)propyl)piperidin-3-ol dihydrochloride

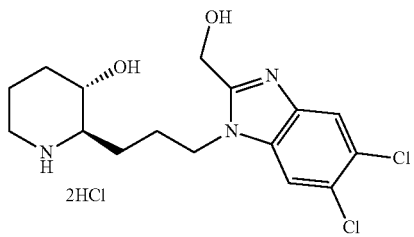 [SMILES: OCc1nc2cc(Cl)c(Cl)cc2n1CCC[C@H]1NCCC[C@@H]1O]

The title compound (28 mg, yield: 79%) was obtained in the same manner as in Example 45, with the exception that (5,6-dichloro-1H-benzo[d]imidazol-2-yl)methanol was used instead of 5-bromo-4-methyl-1H-benzo[d]imidazole in step 45-1 of Example 45.
$^1$H-NMR (500 MHz, DMSO-d$_6$): δ 8.37 (s, 1H), 7.99 (s, 1H), 4.99 (s, 2H), 4.40 (m, 2H), 3.41 (m, 1H), 3.09 (d, 1H), 2.78 (m, 2H), 2.08 (m, 1H), 1.98 (m, 2H), 1.89 (m, 1H), 1.77 (m, 1H), 1.64 (m, 2H), 1.35 (m, 1H)

Example 148: Preparation of (2R,3S)-2-(3-(2-amino-5,6-dichloro-1H-benzo[d]imidazol-1-yl)propyl)piperidin-3-ol dihydrochloride

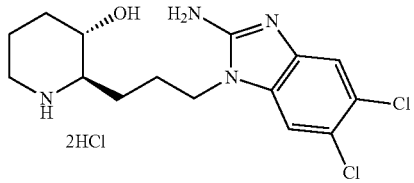 [SMILES: Nc1nc2cc(Cl)c(Cl)cc2n1CCC[C@H]1NCCC[C@@H]1O]

The title compound (25 mg, yield: 81%) was obtained in the same manner as in Example 45, with the exception that 5,6-dichloro-1H-benzo[d]imidazol-2-amine was used instead of 5-bromo-4-methyl-1H-benzo[d]imidazole in step 45-1 of Example 45.
$^1$H-NMR (500 MHz, MeOD): δ 7.84 (s, 1H), 7.57 (s, 1H), 4.20 (t, 2H), 3.58 (m, 1H), 2.97 (m, 1H), 2.98 (m, 2H), 2.07-1.95 (m, 5H), 1.77 (m, 2H), 1.54 (m, 1H)

Example 149: Preparation of methyl 7-bromo-1-(3-((2R,3S)-3-hydroxypiperidin-2-yl)propyl)-1H-indole-3-carboxylate dihydrochloride

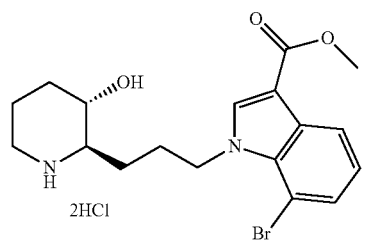 [SMILES: COC(=O)c1cn(CCC[C@H]2NCCC[C@@H]2O)c2c(Br)cccc12]

The title compound (30 mg, yield: 75%) was obtained in the same manner as in Example 45, with the exception that methyl 7-bromo-1H-indole-3-carboxylate was used instead of 5-bromo-4-methyl-1H-benzo[d]imidazole in step 45-1 of Example 45.
$^1$H-NMR (500 MHz, MeOD): δ8.13 (d, 1H), 8.05 (s, 1H), 7.45 (d, 1H), 7.09 (t, 1H), 4.69 (m, 2H), 3.88 (s, 3H), 3.48 (m, 1H), 3.16 (m, 1H), 2.88 (m, 2H), 2.00 (m, 5H), 1.64 (m, 2H), 1.52 (m, 1H)

Example 150: Preparation of methyl 5-bromo-1-(3-((2R,3S)-3-hydroxypiperidin-2-yl)propyl)-1H-indole-3-carboxylate dihydrochloride

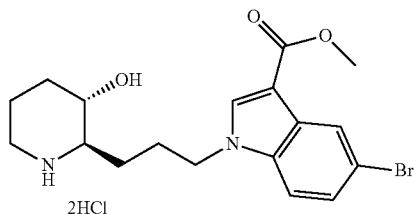 [SMILES: COC(=O)c1cn(CCC[C@H]2NCCC[C@@H]2O)c2ccc(Br)cc12]

The title compound (29 mg, yield: 73%) was obtained in the same manner as in Example 45, with the exception that methyl 5-bromo-1H-indole-3-carboxylate was used instead of 5-bromo-4-methyl-1H-benzo[d]imidazole in step 45-1 of Example 45.
$^1$H-NMR (500 MHz, MeOD): δ8.20 (s, 1H), 8.05 (s, 1H), 7.49 (d, 1H), 7.38 (d, 1H), 4.33 (m, 2H), 3.88 (s, 3H), 3.50 (m, 1H), 3.20 (d, 1H), 2.90 (m, 2H), 1.99 (m, 5H), 1.65 (m, 1H), 1.52 (m, 2H)

Example 151: Preparation of methyl 6-bromo-1-(3-((2R,3S)-3-hydroxypiperidin-2-yl)propyl)-1H-indole-3-carboxylate dihydrochloride

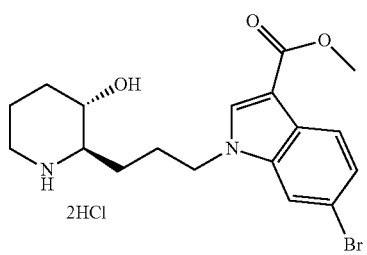 [SMILES: COC(=O)c1cn(CCC[C@H]2NCCC[C@@H]2O)c2cc(Br)ccc12]

The title compound (25 mg, yield: 77%) was obtained in the same manner as in Example 45, with the exception that methyl 6-bromo-1H-indole-3-carboxylate was used instead of 5-bromo-4-methyl-1H-benzo[d]imidazole in step 45-1 of Example 45.
$^1$H-NMR (500 MHz, MeOD): δ8.03 (s, 1H), 7.97 (d, 1H), 7.78 (s, 1H), 7.34 (d, 1H), 4.30 (m, 2H), 3.87 (s, 3H), 3.50 (m, 1H), 3.20 (d, 1H), 2.91 (m, 2H), 1.97 (m, 5H), 1.67 (m, 1H), 1.53 (m, 2H)

Example 152: Preparation of methyl 4-chloro-1-(3-((2R,3S)-3-hydroxypiperidin-2-yl)propyl)-1H-indole-3-carboxylate dihydrochloride

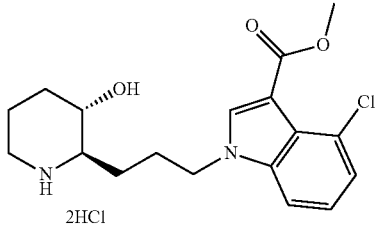 [SMILES: COC(=O)c1cn(CCC[C@H]2NCCC[C@@H]2O)c2cccc(Cl)c12]

The title compound (27 mg, yield: 70%) was obtained in the same manner as in Example 45, with the exception that methyl 4-chloro-1H-indole-3-carboxylate was used instead of 5-bromo-4-methyl-1H-benzo[d]imidazole in step 45-1 of Example 45.

$^1$H-NMR (500 MHz, MeOD): δ 8.07 (s, 1H), 7.51 (d, 1H), 7.24 (s, 1H), 7.23 (s, 1H), 4.33 (m, 2H), 3.84 (s, 3H), 3.20 (m, 1H), 2.91 (m, 2H), 2.00 (m, 5H), 1.67 (m, 1H), 1.52 (m, 2H)

Example 153: Preparation of methyl 6-chloro-1-(3-((2R,3S)-3-hydroxypiperidin-2-yl)propyl)-1H-indole-3-carboxylate dihydrochloride

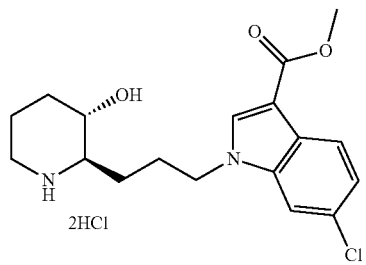 [SMILES: COC(=O)c1cn(CCC[C@H]2NCCC[C@@H]2O)c2cc(Cl)ccc12]

The title compound (21 mg, yield: 73%) was obtained in the same manner as in Example 45, with the exception that methyl 6-chloro-1H-indole-3-carboxylate was used instead of 5-bromo-4-methyl-1H-benzo[d]imidazole in step 45-1 of Example 45.

$^1$H-NMR (500 MHz, MeOD): δ 8.04 (s, 1H), 8.02 (d, 1H), 7.62 (s, 1H), 7.21 (d, 1H), 4.31 (m, 2H), 3.87 (s, 3H), 3.50 (m, 1H), 3.19 (d, 1H), 2.91 (m, 2H), 1.97 (m, 5H), 1.65 (m, 1H), 1.53 (m, 2H)

Example 154: Preparation of methyl 7-chloro-1-(3-((2R,3S)-3-hydroxypiperidin-2-yl)propyl)-1H-indole-3-carboxylate dihydrochloride

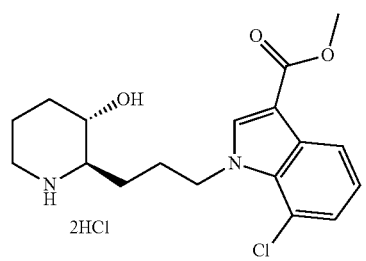 [SMILES: COC(=O)c1cn(CCC[C@H]2NCCC[C@@H]2O)c2c(Cl)cccc12]

The title compound (19 mg, yield: 77%) was obtained in the same manner as in Example 45, with the exception that methyl 7-chloro-1H-indole-3-carboxylate was used instead of 5-bromo-4-methyl-1H-benzo[d]imidazole in step 45-1 of Example 45.

$^1$H-NMR (500 MHz, MeOD): δ 8.07 (d, 1H), 8.04 (s, 1H), 7.25 (d, 1H), 7.17 (t, 1H), 4.66 (m, 2H), 3.88 (s, 3H), 3.51 (m, 1H), 3.20 (d, 1H), 2.91 (m, 2H), 3.11 (m, 1H), 2.08 (m, 4H), 1.69 (m, 2H), 1.55 (m, 1H)

Example 155: Preparation of (2R,3S)-2-(3-(5-chloro-3-cyclopropyl-1H-indazol-1-yl)propyl)piperidin-3-ol dihydrochloride

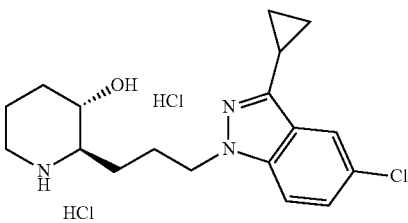 [SMILES: O[C@H]1CCCN[C@@H]1CCCn1nc(C2CC2)c2cc(Cl)ccc21 ; Cl ; Cl]

The title compound (20 mg, yield: 65%) was obtained in the same manner as in Example 45, with the exception that 5-chloro-3-cyclopropyl-1H-indazole was used instead of 5-bromo-4-methyl-1H-benzo[d]imidazole in Step 45-1 of Example 45.

$^1$H NMR (500 MHz, MeOD): δ 7.93 (s, 1H), 7.47 (s, 2H), 4.35 (m, 2H), 3.51 (m, 1H), 3.20 (m, 1H), 2.92 (m, 2H), 2.22 (m, 1H), 2.10-1.91 (m, 4H), 1.68 (m, 1H), 1.51 (m, 2H), 1.04) m, 2H), 0.97 (m, 2H)

Example 156: Preparation of (2R,3S)-2-(3-(5-chloro-3-(trifluoromethyl)-1H-indazol-1-yl)propyl)piperidin-3-ol dihydrochloride

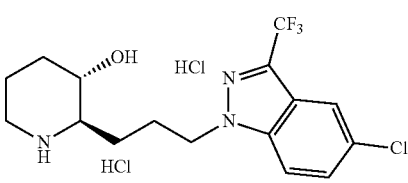 [SMILES: O[C@H]1CCCN[C@@H]1CCCn1nc(C(F)(F)F)c2cc(Cl)ccc21 ; Cl ; Cl]

The title compound (17 mg, yield: 31%) was obtained in the same manner as in Example 45, with the exception that 5-chloro-3-(trifluoromethyl)-1H-indazole was used instead of 5-bromo-4-methyl-1H-benzo[d]imidazole in Step 45-1 of Example 45.

$^1$H NMR (500 MHz, MeOD): δ 7.96 (s, 1H), 7.72 (d, 1H), 7.65 (d, 1H), 4.57 (m, 2H), 3.52 (m, 1H), 3.22 (m, 1H), 2.92 (m, 2H), 2.20 (m, 1H), 2.12 (m, 1H), 2.00 (m, 3H), 1.68 (m, 1H), 1.62 (m, 1H), 1.50 (m, 1H)

Example 157: Preparation of (2R,3S)-2-(3-(5-chloro-3-(1-(difluoromethyl)-1H-pyrazol-4-yl)-1H-indazol-1-yl)propyl)piperidin-3-ol dihydrochloride

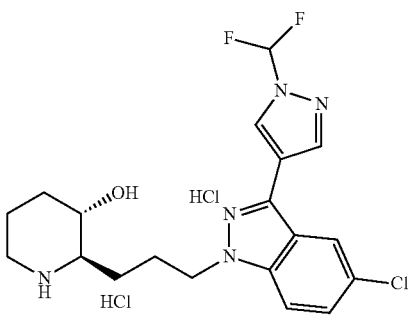 [SMILES: O[C@H]1CCCN[C@@H]1CCCn1nc(-c2cnn(C(F)F)c2)c2cc(Cl)ccc21 ; Cl ; Cl]

The title compound (16 mg, yield: 29%) was obtained in the same manner as in Example 45, with the exception that 5-chloro-3-(1-(difluoromethyl)-1H-pyrazol-4-yl)-1H-indazole was used instead of 5-bromo-4-methyl-1H-benzo[d]imidazole in Step 45-1 of Example 45.

$^1$H NMR (500 MHz, MeOD): δ 8.69 (s, 1H), 8.27 (s, 1H), 8.03 (s, 1H), 7.65 (d, 1H), 7.44 (d, 1H), 4.52 (m, 2H), 3.50 (m, 1H), 3.16 (m, 1H), 2.90 (m, 2H), 2.21 (m, 1H), 2.12 (m, 1H), 2.07 (m, 3H), 1.66 (m, 2H), 1.50 (m, 1H)

Example 158: Preparation of (2R,3S)-2-(3-(6-chloro-3-(1-(difluoromethyl)-1H-pyrazol-4-yl)-1H-indazol-1-yl)propyl)piperidin-3-ol dihydrochloride

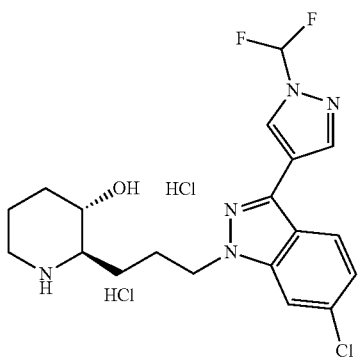 [SMILES: O[C@H]1CCCN[C@@H]1CCCn1nc(-c2cnn(C(F)F)c2)c2ccc(Cl)cc21 ; Cl ; Cl]

The title compound (17 mg, yield: 30%) was obtained in the same manner as in Example 45, with the exception that 6-chloro-3-(1-(difluoromethyl)-1H-pyrazol-4-yl)-1H-indazole was used instead of 5-bromo-4-methyl-1H-benzo[d]imidazole in Step 45-1 of Example 45.

$^1$H NMR (500 MHz, MeOD): δ 8.66 (s, 1H), 8.27 (s, 1H), 7.99 (d, 1H), 7.70 (s, 1H), 7.23 (d, 1H), 4.51 (m, 2H), 3.50 (m, 1H), 3.21 (m, 1H), 2.92 (m, 2H), 2.18 (m, 1H), 2.10 (m, 1H), 2.07 (m, 3H), 1.66 (m, 2H), 1.55 (m, 1H)

Example 159: Preparation of 1-(3-((2R,3S)-3-hydroxypiperidin-2-yl)propyl)-3-methyl-1H-benzo[d]imidazol-2(3H)-one dihydrochloride

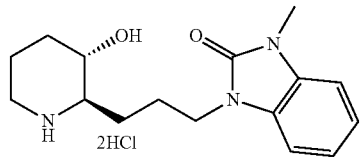 [SMILES: Cn1c(=O)n(CCC[C@H]2NCCC[C@@H]2O)c2ccccc21 ; "2HCl"]

The title compound (18 mg, yield: 69%) was obtained in the same manner as in Example 45, with the exception that 1-methyl-1,3-dihydro-2H-benzo[d]imidazol-2-one was used instead of 5-bromo-4-methyl-1H-benzo[d]imidazole in step 45-1 of Example 45.

$^1$H-NMR (500 MHz, MeOD): δ 7.16 (m, 4H), 3.99 (m, 2H), 3.66 (s, 2H), 3.53 (m, 2H), 3.43 (s, 3H), 2.94 (m, 2H), 2.00 (m, 4H), 1.88 (m, 1H), 1.62 (m, 2H), 1.52 (m, 1H)

Example 160: Preparation of 5-bromo-1-(3-((2R,3S)-3-hydroxypiperidin-2-yl)propyl)-1H-benzo[d]imidazol-2(3H)-one dihydrochloride

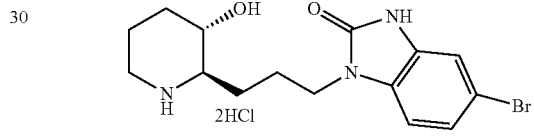

The title compound (15 mg, yield: 42%) was obtained in the same manner as in Example 45, with the exception that 5-bromo-1,3-dihydro-2H-benzo[d]imidazol-2-one was used instead of 5-bromo-4-methyl-1H-benzo[d]imidazole in step 45-1 of Example 45.

$^1$H-NMR (500 MHz, MeOD): δ7.37 (s, 1H), 7.21 (d, 1H), 6.99 (d, 1H), 3.94 (m, 2H), 3.54 (m, 1H), 3.23 (m, 1H), 2.94 (m, 2H), 2.05-1.87 (m, 5H), 1.65 (m, 2H), 1.53 (m, 1H)

Example 161: Preparation of 6-bromo-1-(3-((2R,3S)-3-hydroxypiperidin-2-yl)propyl)-1H-benzo[d]imidazol-2(3H)-one dihydrochloride

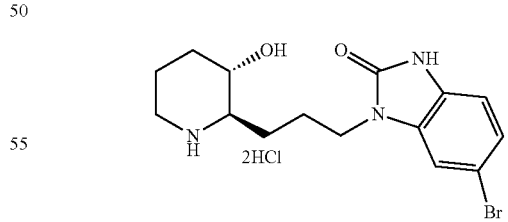

The title compound (14 mg, yield: 40%) was obtained in the same manner as in Example 45, with the exception that 5-bromo-1,3-dihydro-2H-benzo[d]imidazol-2-one was used instead of 5-bromo-4-methyl-1H-benzo[d]imidazole in step 45-1 of Example 45.

$^1$H-NMR (500 MHz, MeOD): δ 7.23 (d, 1H), 7.22 (s, 1H), 7.09 (d, 1H), 3.95 (m, 2H), 3.53 (m, 1H), 3.23 (m, 1H), 2.94 (m, 2H), 2.02-1.87 (m, 5H), 1.66 (m, 2H), 1.53 (m, 1H)

Example 162: Preparation of 7-(3-((2R,3S)-3-hydroxypiperidin-2-yl)propyl)-1,3-dimethyl-1H-purine-2,6(3H,7H)-dione dihydrochloride

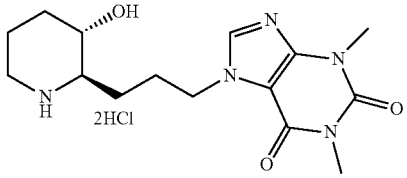 [SMILES: Cn1c(=O)c2c(ncn2CCC[C@H]2NCCC[C@@H]2O)n(C)c1=O ; "2HCl"]

The title compound (21 mg, yield: 75%) was obtained in the same manner as in Example 45, with the exception that 1,3-dimethyl-3,7-dihydro-1H-purine-2,6-dione was used instead of 5-bromo-4-methyl-1H-benzo[d]imidazole in step 45-1 of Example 45.

$^1$H-NMR (500 MHz, MeOD): δ 8.15 (s, 1H), 4.40 (br, 2H), 3.57 (m, 1H), 3.34 (s, 6H), 3.26 (m, 1H), 2.98 (m, 2H), 2.00 (m, 5H), 1.72 (m, 2H), 1.55 (m, 1H)

Example 163: Preparation of 7-(3-((2R,3S)-3-hydroxypiperidin-2-yl)propyl)-3-methyl-1H-purine-2,6(3H,7H)-dione dihydrochloride

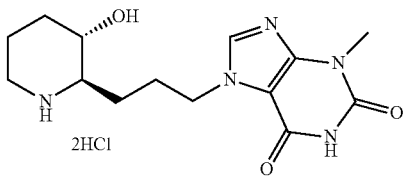 [SMILES: Cn1c(=O)[nH]c(=O)c2c1ncn2CCC[C@H]1NCCC[C@@H]1O]

The title compound (21 mg, yield: 72%) was obtained in the same manner as in Example 45, with the exception that 3-methyl-3,7-dihydro-1H-purine-2,6-dione was used instead of 5-bromo-4-methyl-1H-benzo[d]imidazole in step 45-1 of Example 45.

$^1$H-NMR (500 MHz, MeOD): δ 7.95 (s, 1H), 4.34 (m, 2H), 3.48 (m, 3H), 3.22 (m, 1H), 2.89 (m, 2H), 1.95 (m, 5H), 1.68 (m, 1H), 1.52 (m, 2H)

Example 164: Preparation of 9-(3-((2R,3S)-3-hydroxypiperidin-2-yl)propyl)-1-methyl-1H-purine-2,6(3H,9H)-dione dihydrochloride

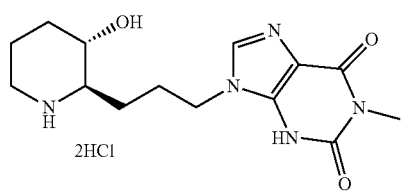 [SMILES: Cn1c(=O)[nH]c2c(ncn2CCC[C@H]2NCCC[C@@H]2O)c1=O]

The title compound (25 mg, yield: 70%) was obtained in the same manner as in Example 45, with the exception that 1-methyl-3,9-dihydro-1H-purine-2,6-dione was used instead of 5-bromo-4-methyl-1H-benzo[d]imidazole in step 45-1 of Example 45.

$^1$H-NMR (500 MHz, MeOD): δ7.89 (s, 1H), 4.36 (m, 2H), 3.66 (m, 1H), 3.23 (m, 1H), 2.98 (m, 2H), 1.99 (m, 5H), 1.69 (m, 1H), 1.56 (m, 2H)

Example 165: Preparation of 7-(3-((2R,3S)-3-hydroxypiperidin-2-yl)propyl)-3-isobutyl-1-methyl-1H-purine-2,6(3H,7H)-dione dihydrochloride

The title compound (25 mg, yield: 70%) was obtained in the same manner as in Example 45, with the exception that 3-isobutyl-1-methyl-3,7-dihydro-1H-purine-2,6-dione was used instead of 5-bromo-4-methyl-1H-benzo[d]imidazole in step 45-1 of Example 45.

$^1$H-NMR (500 MHz, MeOD): δ 7.95 (s, 1H), 4.38 (m, 2H), 3.90 (m, 3H), 3.54 (m, 1H), 3.36 (m, 4H), 3.28 (m, 1H), 2.99 (m, 2H), 2.26 (m, 1H), 2.04 (m, 5H), 1.69 (m, 1H), 1.63 (m, 1H), 1.54 (m, 1H), 0.94 (m, 8H)

Example 166: Preparation of (2R,3S)-2-((E)-3-(5,6-dichloro-1H-benzo[d]imidazol-1-yl)prop-1-enyl)piperidin-3-ol dihydrochloride

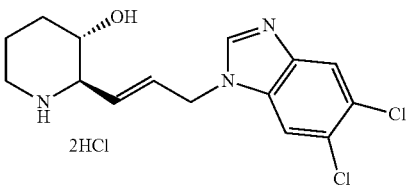 [SMILES: O[C@H]1CCCN[C@@H]1/C=C/Cn1cnc2cc(Cl)c(Cl)cc21]

Step 166-1: Preparation of tert-butyl (2R,3S)-3-((tert-butyldimethylsilyl)oxy)-2-((E)-3-ethoxy-3-oxoprop-1-en-1-yl)piperidine-1-carboxylate Methylene chloride (47 mL, 0.12 M) and oxalyl chloride (1.0 mL, 11.6 mmol) were added to a flask filled with nitrogen and the reaction solution was cooled to −78° C. Dimethylsulfoxide (1.7 mL, 23.2 mmol) was then added at the same temperature and stirred for 30 minutes. Then, tert-butyl (2R,3S)-3-((tert-butyldimethylsilyl)oxy)-2-(hydroxymethyl)piperidine-1-carboxylate (2.0 g, 5.8 mmol) was dissolved in a small amount of methylene chloride and slowly added. After stirring at the same temperature for 1 hour, triethylamine (3.3 mL, 23.2 mmol) was added and the temperature of the reaction solution was raised to room temperature from −78° C. When the reaction was completed, the solvent was removed, and the resulting mixture was diluted with ethyl acetate and washed with saturated sodium chloride solution. The organic layer was collected, dried with magnesium sulfate, filtered and concentrated under reduced pressure, and then dissolved in methylene chloride (47 mL, 0.12 M). Then, (carbethoxymethylene)triphenylphosphorane (4.0 g, 11.6 mmol) was added thereto and stirred for 2 hours. When the reaction was completed, the solvent was removed, and the resulting mixture was diluted with ethyl acetate and washed with saturated sodium chloride solution. The organic layer was collected, dried over magnesium sulfate, filtered and then concentrated under reduced pressure, and purified by column chromatography (hexane:ethyl acetate=4:1) to give the title compound (2.1 g, yield: 89%).

Step 166-2: Preparation of (E)-3-((2R,3S)-1-(tert-butoxycarbonyl)-3-((tert-butyldimethylsilyl)oxy) piperidin-2-yl)acrylic acid Tert-butyl (2R,3S)-3-((tert-butyldimethylsilyl)oxy)-2-((E)-3-ethoxy-3-oxoprop-1-en-1-yl)piperidine-1-carboxylate (3.0 g, 7.2 mmol) obtained from Step 166-1 was dissolved in methanol (20 mL, 0.36 mmol). Then, 2N sodium hydroxide aqueous solution (10 mL) was added thereto and stirred at room temperature for 3 hours. When the reaction was completed, the reaction solution was neutralized with 1N aqueous hydrochloric acid solution, acidified, diluted with ethyl acetate and then washed with saturated sodium chloride solution. The organic layer was collected, dried over magnesium sulfate, filtered and concentrated under reduced pressure. Subsequent reactions were carried out without purification procedure.

Step 166-3: Preparation of tert-butyl (2R,3S)-3-((tert-butyldimethylsilyl)oxy)-2-((E)-3-hydroxyprop-en-1-yl) piperidine-1-carboxylate (E)-3-((2R,3S)-1-(tert-butoxycarbonyl)-3-((tert-butyldimethylsilyl)oxy)piperidin-2-yl)acrylic acid (1.6 g, 4.0 mmol) obtained from Step 166-2 was dissolved in tetrahydrofuran (50 mL, 0.08 M), and the reaction solution was cooled to 0° C. Then, a lithium aluminum hydride solution (1.6 mL, 4.0 mmol) was slowly added thereto, reacted at the same temperature for 30 minutes and then stirred at room temperature for 2 hours. A small amount of water was added to complete the reaction, diluted with ethyl acetate and washed with saturated sodium chloride solution. The organic layer was collected, dried over magnesium sulfate, filtered and concentrated under reduced pressure, and then purified by column chromatography (dichloromethane:methanol=10:1) to give the title compound (1.3 g, yield: 85%).

Step 166-4: Preparation of tert-butyl (2R,3S)-2-((E)-3-bromoprop-1l-en-1-yl)-3-((tert-butyldimethyl-silyl)oxy)piperidine-1-carboxylate Tert-butyl (2R,3S)-3-((tert-butyldimethylsilyl)oxy)-2-((E)-3-hydroxyprop-en-1-yl)piperidine-1l-carboxylate (100 mg, 0.27 mmol) obtained from Step 166-3 was added to methylene chloride (10 mL, 0.03 M). The reaction solution was cooled to 0° C., and then triphenylphosphine (106 g, 0.40 mmol) and tetrabromomethane (134 mg, 0.40 mmol) were sequentially added at the same temperature, followed by stirring at room temperature for 2 hours. When the reaction was completed, the solvent was removed, and the resulting mixture was diluted with ethyl acetate and washed with saturated sodium chloride solution. The organic layer was collected, dried over magnesium sulfate, filtered and concentrated under reduced pressure, and then purified by column chromatography (hexane:ethyl acetate=5:1) to give the title compound (89 mg, yield: 76%).

Step 166-5: Preparation of tert-butyl (2R,3S)-3-((tert-butyldimethylsilyl)oxy)-2-((E)-3-(5,6-dichloro-1H-benzo[d]imidazol-1-yl)prop-1-en-1-yl) piperidine-1-carboxylate Tert-butyl (2R,3S)-2-((E)-3-bromoprop-1l-en-1-yl)-3-((tert-butyldimethylsilyl)oxy)piperidine-1l-carboxylate (83 mg, 0.19 mmol) obtained from Step 166-4 was dissolved in N,N-dimethylformamide (3 mL, 0.06 M). Potassium carbonate (53 mg, 0.38 mmol) and 5,6-dichloro-1H-benzo[d]imidazole (35 mg, 0.19 mmol) were added thereto and the mixture was stirred at room temperature for 4 hours. When the reaction was completed, the solvent was removed, and the resulting mixture was diluted with ethyl acetate and washed with saturated sodium chloride solution. The organic layer was collected, dried over sodium sulfate, filtered and concentrated under reduced pressure, and then purified by column chromatography (hexane:ethyl acetate=1:2) to give the title compound (88 g, yield: 85%).

Step 166-6: Preparation of (2R,3S)-2-((E)-3-(5,6-dichloro-1H-benzo[d]imidazol-yl)prop-1-en-1-yl) piperidin-3-ol dihydrochloride Tert-butyl (2R,3S)-3-((tert-butyldimethylsilyl)oxy)-2-((E)-3-(5,6-dichloro-1H-benzo[d]imidazol-1-yl)prop-1-en-1-yl)piperidine-1-carboxylate (85 mg, 0.16 mmol) obtained from Step 166-5 was dissolved in a small amount of tetrahydrofuran. Then, 4N hydrogen chloride dioxane solution (5 mL, 0.03 M) was added thereto and stirred at room temperature for 12 hours. When the reaction was completed, the reaction solution was concentrated under reduced pressure to remove the solvent, dissolved by addition of a small amount of methanol and then crystallized with diethyl ether to obtain the title compound (51 mg, yield: 81%).

$^1$H-NMR (500 MHz, DMSO-$d_6$): δ 8.86 (s, 1H), 8.12 (s, 1H), 8.04 (s, 1H), 6.11 (dt, 1H), 5.85 (d, 1H), 5.03 (d, 2H), 3.54 (m, 1H), 3.40 (m, 1H), 3.13 (d, 1H), 2.79 (m, 1H), 1.94 (m, 1H), 1.79 (d, 1H), 1.68 (m, 1H), 1.41 (m, 1H)

Example 167: Preparation of (2R,3S)-2-((E)-3-(5-fluoro-4-methyl-1H-benzo[d]imidazol-1-yl)prop-1-enyl)piperidin-3-ol dihydrochloride

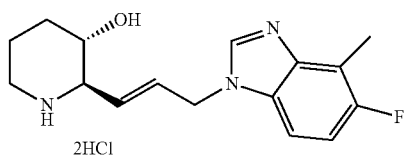 [SMILES: Cc1c(F)ccc2c1ncn2C/C=C/[C@H]1NCCC[C@@H]1O]

The title compound (24 mg, yield: 80%) was obtained in the same manner as in Example 166, with the exception that 5-fluoro-4-methyl-1H-benzo[d]imidazole was used instead of 5,6-dichloro-1H-benzo[d]imidazole in Step 166-5 of Example 166.

$^1$H-NMR (500 MHz, MeOD): δ 9.45 (d, 1H), 7.73 (m, 1H), 7.42 (m, 1H), 6.25 (m, 1H), 5.98 (m, 1H), 5.23 (s, 2H), 3.55 (m, 2H), 2.96 (m, 1H), 2.56 (s, 3H), 2.00 (m, 3H), 1.74 (m, 1H), 1.56 (m, 1H)

Example 168: Preparation of (2R,3S)-2-((E)-3-(5-bromo-4-methyl-1H-benzo[d]imidazol-1-yl)prop-1-enyl)piperidin-3-ol dihydrochloride

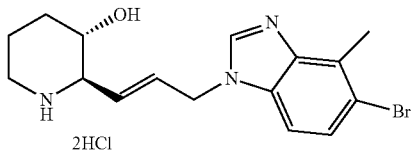 [SMILES: Cc1c(Br)ccc2c1ncn2C/C=C/[C@H]1NCCC[C@@H]1O]

The title compound (30 mg, yield: 85%) was obtained in the same manner as in Example 166, with the exception that 5-bromo-4-methyl-1H-benzo[d]imidazole was used instead of 5,6-dichloro-1H-benzo[d]imidazole in Step 166-5 of Example 166.
$^1$H-NMR (500 MHz, MeOD): δ 9.38 (d, 1H), 7.68 (m, 1H), 7.37 (m, 1H), 6.15 (m, 1H), 5.88 (m, 1H), 5.00 (s, 2H), 3.34 (m, 2H), 2.78 (m, 1H), 2.54 (s, 3H), 1.97 (m, 3H), 1.68 (m, 1H), 1.48 (m, 1H)

Example 169: Preparation of (2R,3S)-2-((E)-3-(5,6-dimethyl-1H-benzo[d]imidazol-1-yl)prop-1-en-1-yl)piperidin-3-ol dihydrochloride

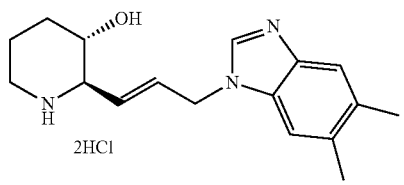 [SMILES: Cc1cc2ncn(C/C=C/[C@H]3NCCC[C@@H]3O)c2cc1C]

The title compound (30 mg, yield: 85%) was obtained in the same manner as in Example 166, with the exception that 5,6-dimethyl-1H-benzo[d]imidazole was used instead of 5,6-dichloro-1H-benzo[d]imidazole in Step 166-5 of Example 166.
$^1$H-NMR (500 MHz, MeOD): δ7.64 (m, 1H), 7.61 (s, 1H), 6.25 (m, 1H), 5.91 (m, 1H), 5.20 (s, 2H), 3.56 (m, 2H), 2.95 (m, 1H), 2.46 (m, 1H), 2.45 (s, 6H), 2.09 (m, 1H), 2.00 (m, 2H), 1.72 (m, 1H), 1.56 (m, 1H)

Example 170: Preparation of (2R,3S)-2-((E)-3-(5,6-dibromo-1H-benzo[d]imidazol-1-yl)prop-1-en-1-yl)piperidin-3-ol dihydrochloride

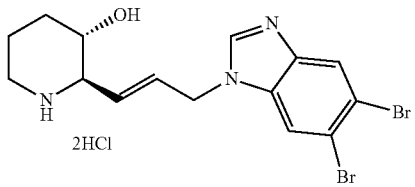 [SMILES: O[C@H]1CCCN[C@@H]1/C=C/Cn1cnc2cc(Br)c(Br)cc21]

The title compound (24 mg, yield: 80%) was obtained in the same manner as in Example 166, with the exception that 5,6-dibromo-1H-benzo[d]imidazole was used instead of 5,6-dichloro-1H-benzo[d]imidazole in Step 166-5 of Example 166.

$^1$H-NMR (500 MHz, MeOD): δ9.21 (m, 1H), 8.30 (m, 1H), 8.21 (m, 1H), 6.22 (m, 1H), 5.92 (m, 1H), 5.16 (m, 2H), 3.56 (m, 2H), 2.95 (m, 1H), 1.99 (m, 3H), 1.72 (m, 1H), 1.56 (m, 1H)

Example 171: Preparation of (2R,3S)-2-((E)-3-(5,6-difluoro-1H-benzo[d]imidazol-1-yl)prop-1-en-1-yl)piperidin-3-ol dihydrochloride

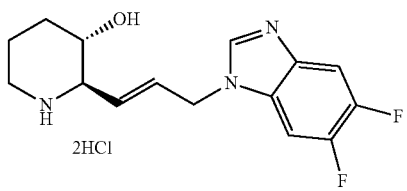 [SMILES: O[C@H]1CCCN[C@@H]1/C=C/Cn1cnc2cc(F)c(F)cc21]

The title compound (20 mg, yield: 86%) was obtained in the same manner as in Example 166, with the exception that 5,6-difluoro-1H-benzo[d]imidazole was used instead of 5,6-dichloro-1H-benzo[d]imidazole in Step 166-5 of Example 166.
$^1$H-NMR (500 MHz, MeOD): δ 7.76 (m, 1H), 6.22 (m, 1H), 5.88 (m, 1H), 5.12 (m, 2H), 3.57 (m, 3H), 2.92 (m, 1H), 2.20 (m, 4H), 1.72 (m, 1H), 1.56 (m, 1H)

Example 172: Preparation of (2R,3S)-2-((E)-3-(4,5-dimethyl-1H-benzo[d]imidazol-1-yl)prop-1-en-1-yl)piperidin-3-ol dihydrochloride

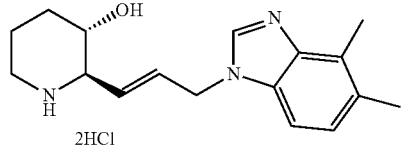 [SMILES: Cc1ccc2c(ncn2C/C=C/[C@H]2NCCC[C@@H]2O)c1C]

The title compound (19 mg, yield: 81%) was obtained in the same manner as in Example 166, with the exception that 4,5-dimethyl-1H-benzo[d]imidazole was used instead of 5,6-dichloro-1H-benzo[d]imidazole in Step 166-5 of Example 166.
$^1$H-NMR (500 MHz, MeOD): δ9.42 (m, 1H), 7.62 (m, 1H), 7.47 (m, 1H), 6.25 (m, 1H), 5.94 (m, 1H), 5.21 (m, 2H), 3.55 (m, 2H), 3.34 (m, 1H), 2.95 (m, 1H), 1.99 (m, 2H), 1.74 (m, 1H), 1.53 (m, 1H)

Example 173: Preparation of (2R,3S)-2-((E)-3-(5-chloro-4-methyl-1H-benzo[d]imidazol-1-yl)prop-1-en-1-yl)piperidin-3-ol hydrochloride

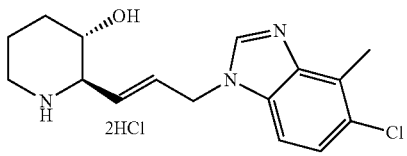 [SMILES: Cc1c(Cl)ccc2c1ncn2C/C=C/[C@H]1NCCC[C@@H]1O ; "2HCl"]

The title compound (25 mg, yield: 82%) was obtained in the same manner as in Example 166, with the exception that 5-chloro-4-methyl-1H-benzo[d]imidazole was used instead of 5,6-dichloro-1H-benzo[d]imidazole in Step 166-5 of Example 166.

¹H-NMR (500 MHz, MeOD): δ9.50 (s, 1H), 7.76 (d, 1H), 7.67 (d, 1H), 5.98 (m, 1H), 5.23 (m, 2H), 3.63 (m, 1H), 3.55 (m, 1H), 2.96 (m, 1H), 2.66 (s, 3H), 2.09 (m, 1H), 2.00 (m, 1H), 1.74 (m, 1H), 1.53 (m, 1H)

Example 174: Preparation of (2R,3S)-2-((E)-3-(4,5-dichloro-1H-benzo[d]imidazol-1-yl)prop-1-en-1-yl)piperidin-3-ol dihydrochloride

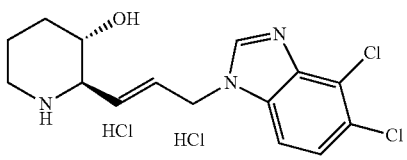 [SMILES: O[C@H]1CCCN[C@@H]1/C=C/Cn1cnc2c(Cl)c(Cl)ccc21 ; Cl ; Cl]

The title compound (20 mg, yield: 89%) was obtained in the same manner as in Example 166, with the exception that 4,5-dichloro-1H-benzo[d]imidazole was used instead of 5,6-dichloro-1H-benzo[d]imidazole in Step 166-5 of Example 166.

¹H NMR (500 MHz, MeOD): δ 9.58 (s, 1H), 7.91 (d, 1H), 7.79 (d, 1H), 6.30 (m, 1H), 6.03 (m, 1H), 5.25 (d, 2H), 3.69 (m, 1H), 3.58 (m, 1H), 3.01 (m, 1H), 2.11 (m, 1H), 2.03 (m, 1H), 1.80 (m, 1H), 1.55 (m, 1H)

Example 175: Preparation of (2R,3S)-2-((E)-3-(4-chloro-5-methyl-1H-benzo[d]imidazol-1-yl)prop-1-en-1-yl)piperidin-3-ol dihydrochloride

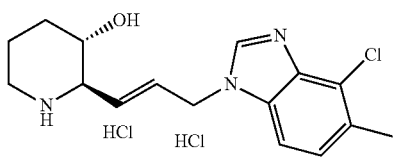 [SMILES: Cc1ccc2c(ncn2C/C=C/[C@H]2NCCC[C@@H]2O)c1Cl ; Cl ; Cl]

The title compound (23 mg, yield: 91%) was obtained in the same manner as in Example 166, with the exception that 4-chloro-5-methyl-1H-benzo[d]imidazole was used instead of 5,6-dichloro-1H-benzo[d]imidazole in Step 166-5 of Example 166.

¹H NMR (500 MHz, MeOD): δ 9.52 (s, 1H), 7.88 (d, 1H), 7.70 (d, 1H), 6.25 (m, 1H), 6.01 (m, 1H), 5.20 (d, 2H), 3.62 (m, 1H), 3.49 (m, 1H), 3.00 (m, 1H), 2.65 (s, 3H), 2.05 (m, 1H), 2.00 (m, 1H), 1.74 (m, 1H), 1.51 (m, 1H)

Example 176: Preparation of (2R,3S)-2-((E)-3-(5-bromo-4-nitro-1H-benzo[d]imidazol-1-yl)prop-1-en-1-yl)piperidin-3-ol dihydrochloride

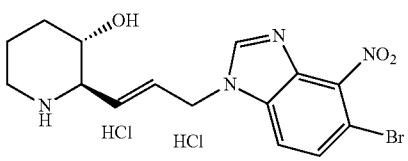 [SMILES: O=[N+]([O-])c1c(Br)ccc2c1ncn2C/C=C/[C@H]1NCCC[C@@H]1O ; Cl ; Cl]

The title compound (9 mg, yield: 45%) was obtained in the same manner as in Example 166, with the exception that 5-bromo-4-nitro-1H-benzo[d]imidazole was used instead of 5,6-dichloro-1H-benzo[d]imidazole in Step 166-5 of Example 166.

¹H NMR (500 MHz, MeOD): δ 8.94 (s, 1H), 7.93 (d, 1H), 7.83 (d, 1H), 6.27 (m, 1H), 5.84 (m, 1H), 5.20 (m, 2H), 3.62 (m, 2H), 3.58 (m 1H), 2.99 (m, 1H), 2.11 (m, 1H), 2.08 (m, 1H), 1.98 (m, 1H), 1.59 (m, 1H)

Example 177: Preparation of (2R,3S)-2-((E)-3-(6-bromo-7-nitro-1H-benzo[d]imidazol-1-yl)prop-1-en-1-yl)piperidin-3-ol dihydrochloride

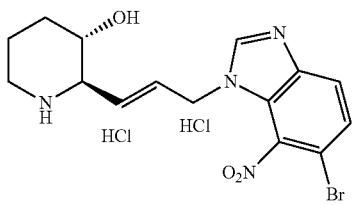 [SMILES: O=[N+]([O-])c1c(Br)ccc2ncn(C/C=C/[C@H]3NCCC[C@@H]3O)c12 ; Cl ; Cl]

The title compound (10 mg, yield: 51%) was obtained in the same manner as in Example 166, with the exception that 5-bromo-4-nitro-1H-benzo[d]imidazole was used instead of 5,6-dichloro-1H-benzo[d]imidazole in Step 166-5 of Example 166.

¹H NMR (500 MHz, MeOD): δ 8.45 (s, 1H), 7.85 (d, 1H), 7.69 (d, 1H), 6.11 (m, 1H), 5.59 (m, 1H), 4.28 (m, 2H), 3.62 (m, 2H), 2.96 (m 1H), 2.24 (m, 1H), 1.72 (m, 2H), 1.58 (m, 1H), 1.53 (m, 1H)

Example 178: Preparation of (2R,3S)-2-((E)-3-(4-chloro-5-nitro-1H-benzo[d]imidazol-1-yl)prop-1-en-1-yl)piperidin-3-ol dihydrochloride

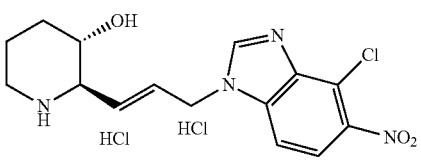 [SMILES: O=[N+]([O-])c1ccc2c(ncn2C/C=C/[C@H]2NCCC[C@@H]2O)c1Cl ; Cl ; Cl]

The title compound (11 mg, yield: 52%) was obtained in the same manner as in Example 166, with the exception that 4-chloro-5-nitro-1H-benzo[d]imidazole was used instead of 5,6-dichloro-1H-benzo[d]imidazole in Step 166-5 of Example 166.

¹H NMR (500 MHz, MeOD): δ 9.06 (s, 1H), 8.04 (m, 1H), 7.92 (m, 1H), 7.87 (m, 1H), 6.26 (m, 1H), 5.86 (m, H), 5.26 (m, 2H), 3.60 (m, 2H), 2.96 (m, 2H), 2.07 (m, 1H), 1.99 (m 2H), 1.77 (m, 1H), 1.51 (m, 1H)

Example 179: Preparation of (2R,3S)-2-((E)-3-(4,6-difluoro-1H-benzo[d]imidazol-1-yl)prop-1-en-1-yl)piperidin-3-ol dihydrochloride

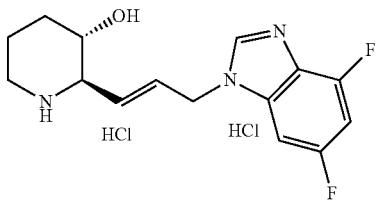 [SMILES: O[C@H]1CCCN[C@@H]1/C=C/Cn1cnc2c(F)cc(F)cc21 ; Cl ; Cl]

The title compound (15 mg, yield: 62%) was obtained in the same manner as in Example 166, with the exception that 4,6-difluoro-1H-benzo[d]imidazole was used instead of 5,6-dichloro-1H-benzo[d]imidazole in Step 166-5 of Example 166.

$^1$H NMR (500 MHz, MeOD): δ 9.22 (m, 1H), 7.58 (m, 1H), 7.32 (m, 1H), 6.38 (m, 1H), 5.99 (m, 1H), 5.27 (d, 1H), 3.65 (m, 2H), 2.99 (t, 1H), 2.19 (m, 1H), 2.08 (m, 2H), 1.87 (m, 2H), 1.65 (m, 1H)

Example 180: Preparation of (2R,3S)-2-((E)-3-(6-chloro-4-methyl-1H-benzo[d]imidazol-1-yl)prop-1-en-1-yl)piperidin-3-ol dihydrochloride

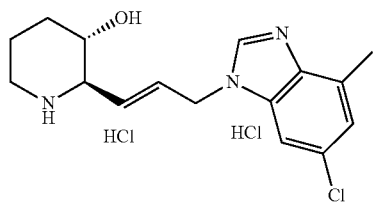 [SMILES: Cc1cc(Cl)cc2c1ncn2C/C=C/[C@H]1NCCC[C@@H]1O ; Cl ; Cl]

The title compound (14 mg, yield: 58%) was obtained in the same manner as in Example 166, with the exception that 6-chloro-4-methyl-1H-benzo[d]imidazole was used instead of 5,6-dichloro-1H-benzo[d]imidazole in Step 166-5 of Example 166.

$^1$H NMR (500 MHz, MeOD): δ 9.53 (m, 1H), 7.85 (m, 1H), 7.50 (m, 1H), 6.31 (m, 1H), 6.01 (m, 1H), 5.41 (m, 1H), 3.66 (m, 1H), 3.00 (m, 2H), 2.64 (s, 3H), 2.08 (m, 3H), 1.73 (m, 1H)

Example 181: Preparation of (2R,3S)-2-((E)-3-(7-chloro-5-(trifluoromethyl)-1H-benzo[d]imidazol-1-yl)prop-1-en-1-yl)piperidin-3-ol dihydrochloride

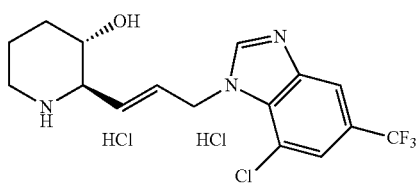 [SMILES: O[C@H]1CCCN[C@@H]1/C=C/Cn1cnc2cc(C(F)(F)F)cc(Cl)c21 ; Cl ; Cl]

The title compound (19 mg, yield: 75%) was obtained in the same manner as in Example 166, with the exception that 7-chloro-5-(trifluoromethyl)-1H-benzo[d]imidazole was used instead of 5,6-dichloro-1H-benzo[d]imidazole in Step 166-5 of Example 166.

$^1$H NMR (500 MHz, MeOD): δ 9.51 (m, 1H), 8.20 (m, 1H, 7.99 (m, 1H), 6.37 (m, 1H), 5.89 (m, 1H), 5.47 (m, 2H), 3.59 (m, 2H), 2.93 (m, 1H), 2.08 (m, 2H), 2.06 (m, 1H), 1.75 (m, 1H), 1.58 (m, 1H), 1.51 (m, 1H)

Example 182: Preparation of (2R,3S)-2-((E)-3-(5,7-dichloro-1H-benzo[d]imidazol-1-yl)prop-1-en-1-yl)piperidin-3-ol dihydrochloride

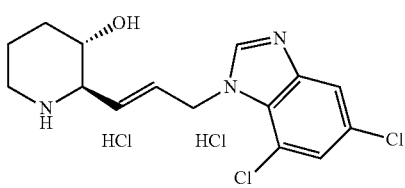 [SMILES: O[C@H]1CCCN[C@@H]1/C=C/Cn1cnc2cc(Cl)cc(Cl)c21 ; Cl ; Cl]

The title compound (22 mg, yield: 85%) was obtained in the same manner as in Example 166, with the exception that 5,7-dichloro-1H-benzo[d]imidazole was used instead of 5,6-dichloro-1H-benzo[d]imidazole in Step 166-5 of Example 166.

$^1$H NMR (500 MHz, MeOD): δ 9.04 (s, 1H), 7.81 (s, 1H), 7.61 (s, 1H), 6.36 (m, 1H), 5.74 (m, 1H), 5.42 (m, 1H). 3.63-3.53 (m, 2H), 2.99 (m, 1H), 2.09 (m, 1H), 2.01 (m, 1H), 1.76 (m, 1H), 1.59 (m, 1H), 1.51 (m, 1H)

Example 183: Preparation of (2R,3S)-2-((E)-3-(5-chloro-7-fluoro-1H-benzo[d]imidazol-1-yl)prop-1-en-1-yl)piperidin-3-ol dihydrochloride

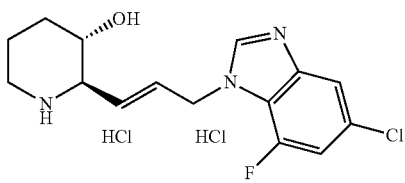 [SMILES: O[C@H]1CCCN[C@@H]1/C=C/Cn1cnc2cc(Cl)cc(F)c21 ; Cl ; Cl]

The title compound (18 mg, yield: 72%) was obtained in the same manner as in Example 166, with the exception that 5-chloro-7-fluoro-1H-benzo[d]imidazole was used instead of 5,6-dichloro-1H-benzo[d]imidazole in Step 166-5 of Example 166.

$^1$H NMR (500 MHz, MeOD): δ 9.56 (s, 1H), 7.75 (m, 1H), 7.47 (m, 1H), 6.33 (m, 1H), 6.02 (m, 1H), 5.28 (m, 2H), 3.66 (m, 2H), 2.99 (m, 1H), 2.11 (m, 2H). 1.78 (m, 2H), 1.55 (m, 1H)

Example 184: Preparation of (2R,3S)-2-((E)-3-(5-bromo-1H-imidazo[4,5-b]pyridin-1-yl)prop-1-en-1-yl)piperidin-3-ol dihydrochloride

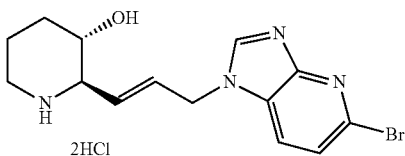 [SMILES: O[C@H]1CCCN[C@@H]1/C=C/Cn1cnc2nc(Br)ccc21]

The title compound (18 mg, yield: 40%) was obtained in the same manner as in Example 166, with the exception that 5-bromo-1H-imidazo[4,5-b]pyridine was used instead of 5,6-dichloro-1H-benzo[d]imidazole in Step 166-5 of Example 166.

¹H-NMR (500 MHz, MeOD): δ 8.37 (s, 1H), 7.94 (m, 1H), 7.46 (m, 1H), 6.24 (m, 1H), 5.70 (m, 1H), 5.08 (m, 2H), 3.49 (m, 2H), 3.24 (m, 1H), 2.91 (m, 1H), 1.97 (m, 2H), 1.68 (m, 1H), 1.51 (m, 1H)

Example 185: Preparation of (2R,3S)-2-((E)-3-(7-chloro-6-(3-chlorophenyl)-3H-imidazo[4,5-b]pyridin-3-yl)prop-1-en-1-yl)piperidin-3-ol dihydrochloride

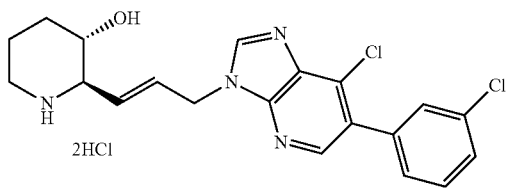 [SMILES: O[C@H]1CCCN[C@@H]1/C=C/Cn1cnc2c(Cl)c(-c3cccc(Cl)c3)cnc21]

The title compound (20 mg, yield: 41%) was obtained in the same manner as in Example 166, with the exception that 7-chloro-6-(3-chlorophenyl)-3H-imidazo[4,5-b]pyridine was used instead of 5,6-dichloro-1H-benzo[d]imidazole in Step 166-5 of Example 166.

¹H-NMR (500 MHz, MeOD): δ8.52 (s, 1H), 8.38 (s, 1H), 7.42 (m, 4H), 6.26 (m, 1H), 5.68 (m, 1H), 5.12 (m, 2H), 3.51 (m, 2H), 3.34 (m 1H), 2.92 (m, 1H), 1.99 (m, 2H), 1.53 (m, 2H)

Example 186: Preparation of (2R,3S)-2-((E)-3-(6-bromo-7-methyl-3H-imidazo[4,5-b]pyridin-3-yl)prop-1-en-1-yl)piperidin-3-ol dihydrochloride

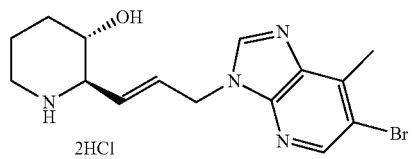 [SMILES: Cc1c(Br)cnc2c1ncn2C/C=C/[C@H]1NCCC[C@@H]1O]

The title compound (18 mg, yield: 40%) was obtained in the same manner as in Example 166, with the exception that 6-bromo-7-methyl-3H-imidazo[4,5-b]pyridine was used instead of 5,6-dichloro-1H-benzo[d]imidazole in Step 166-5 of Example 166.

¹H-NMR (500 MHz, MeOD): δ 8.39 (s, 1H), 8.34 (s, 1H), 6.24 (m, 1H), 5.70 (m, 1H), 5.08 (m, 2H), 3.49 (m, 2H), 3.24 (m, 1H), 2.91 (m, 1H), 2.23 (s, 3H), 1.97 (m, 2H), 1.68 (m, 1H), 1.51 (m, 1H)

Example 187: Preparation of (2R,3S)-2-((E)-3-(6-bromo-7-chloro-3H-imidazo[4,5-b]pyridin-3-yl)prop-1l-en-1-yl)piperidin-3-ol dihydrochloride

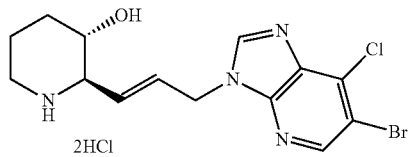 [SMILES: O[C@H]1CCCN[C@@H]1/C=C/Cn1cnc2c(Cl)c(Br)cnc21]

The title compound (25 mg, yield: 45%) was obtained in the same manner as in Example 166, with the exception that 6-bromo-7-chloro-3H-imidazo[4,5-b]pyridine was used instead of 5,6-dichloro-1H-benzo[d]imidazole in Step 166-5 of Example 166.

¹H-NMR (500 MHz, MeOD): δ 8.58 (m, 2H), 6.24 (m, 1H), 5.70 (m, 1H), 5.08 (m, 2H), 3.49 (m, 2H), 3.24 (m, 1H), 2.91 (m, 1H), 1.97 (m, 2H), 1.68 (m, 1H), 1.51 (m, 1H)

Example 188: Preparation of (2R,3S)-2-((E)-3-(6-chloro-7-methyl-3H-imidazo[4,5-b]pyridin-3-yl)prop-1-en-1-yl)piperidin-3-ol dihydrochloride

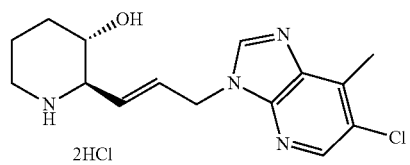

The title compound (32 mg, yield: 84%) was obtained in the same manner as in Example 166, with the exception that 6-chloro-7-methyl-3H-imidazo[4,5-b]pyridine was used instead of 5,6-dichloro-1H-benzo[d]imidazole in Step 166-5 of Example 166.

¹H-NMR (500 MHz, MeOD): δ 8.37 (s, 1H), 8.31 (s, 1H), 6.22 (m, 1H), 5.68 (m, 1H), 5.06 (m, 2H), 3.38 (m, 2H), 3.20 (m, 1H), 2.84 (m, 1H), 2.20 (s, 3H), 1.87 (m, 2H), 1.54 (m, 1H), 1.48 (m, 1H)

Example 189: Preparation of (2R,3S)-2-((E)-3-(6,7-dichloro-3H-imidazo[4,5-b]pyridin-3-yl)prop-1-en-1-yl)piperidin-3-ol dihydrochloride

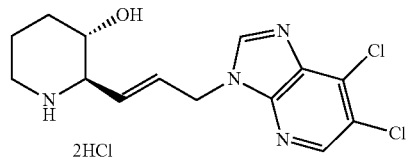 [SMILES: Cc1c(Cl)cnc2c1ncn2C/C=C/[C@H]1NCCC[C@@H]1O]

The title compound (25 mg, yield: 60%) was obtained in the same manner as in Example 166, with the exception that 6,7-dichloro-3H-imidazo[4,5-b]pyridine was used instead of 5,6-dichloro-1H-benzo[d]imidazole in Step 166-5 of Example 166.

¹H-NMR (500 MHz, DMSO-d₆): δ 8.68 (s, 1H), 8.57 (s, 1H), 6.15 (dd, 1H), 5.76 (dd, 1H), 4.98 (d, 2H), 3.52 (m,

1H), 3.40 (m, 1H), 3.09 (d, 1H), 2.78 (dd, 1H), 1.92 (m, 1H), 1.77 (m, 1H), 1.68 (m, 1H), 1.37 (m, 1H)

Example 190: Preparation of (2R,3S)-2-((E)-3-(6-(3-chlorophenyl)-1H-benzo[d]imidazol-1-yl)prop-1-en-1-yl)piperidin-3-ol dihydrochloride

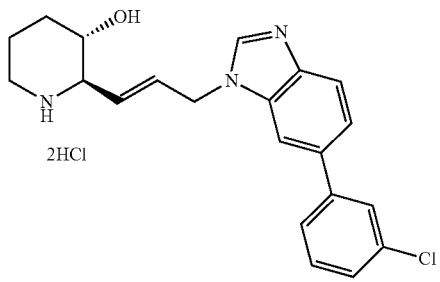 [SMILES: O[C@H]1CCCN[C@@H]1/C=C/Cn1cnc2ccc(-c3cccc(Cl)c3)cc21]

The title compound (18 mg, yield: 40%) was obtained in the same manner as in Example 166, with the exception that 6-(3-chlorophenyl)-1H-benzo[d]imidazole was used instead of 5,6-dichloro-1H-benzo[d]imidazole in Step 166-5 of Example 166.

$^1$H-NMR (500 MHz, MeOD): δ 9.53 (s, 1H), 8.18 (s, 1H), 7.96 (s, 2H), 7.80 (s, 1H), 6.69 (d, 1H), 7.50 (t, 1H), 7.45 (d, 1H) 6.34 (dd, 1H), 6.00 (dd, 1H), 5.32 (d, 2H), 3.64 (m, 2H), 2.97 (m, 1H), 2.10 (m, 1H), 1.98 (m, 1H), 1.75 (m, 1H), 1.56 (m, 1H), 1.30 (m, 1H)

Example 191: Preparation of (2R,3S)-2-((E)-3-(6-(3-fluorophenyl)-1H-benzo[d]imidazol-1-yl)prop-1-en-1-yl)piperidin-3-ol dihydrochloride

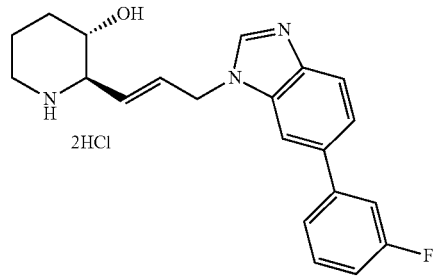 [SMILES: O[C@H]1CCCN[C@@H]1/C=C/Cn1cnc2ccc(-c3cccc(F)c3)cc21]

The title compound (15 mg, yield: 42%) was obtained in the same manner as in Example 166, with the exception that 6-(3-fluorophenyl)-1H-benzo[d]imidazole was used instead of 5,6-dichloro-1H-benzo[d]imidazole in Step 166-5 of Example 166.

$^1$H-NMR (500 MHz, MeOD): δ 9.35 (s, 1H), 8.23 (d, 1H), 7.93 (s, 2H), 7.57 (d, 1H), 7.52 (d, 2H), 7.17 (t, 1H), 6.32 (d, 1H), 5.94 (m, 1H), 5.31 (m, 2H), 3.56 (m, 3H), 2.97 (m, 1H), 2.10 (m, 1H), 2.01 (m, 1H), 1.72 (m, 1H), 1.55 (m, 1H)

Example 192: Preparation of (2R,3S)-2-((E)-3-(6-(3-(trifluoromethyl)phenyl)-1H-benzo[d]imidazol-1-yl)prop-1-enyl)piperidin-3-ol dihydrochloride

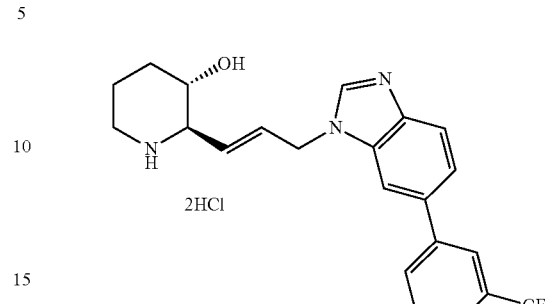

The title compound (15 mg, yield: 40%) was obtained in the same manner as in Example 166, with the exception that 6-(3-(trifluoromethyl)phenyl)-1H-benzo[d]imidazole was used instead of 5,6-dichloro-1H-benzo[d]imidazole in Step 166-5 of Example 166.

$^1$H-NMR (500 MHz, MeOD): δ 9.48 (s, 1H), 8.21 (s, 1H), 8.03 (m, 2H), 8.01 (s, 2H), 7.73 (m, 2H), 6.34 (td, 1H), 5.99 (dd, 1H), 5.34 (m, 2H), 3.60 (td, 2H), 2.95 (m, 1H), 2.10 (d, 1H), 2.01 (d, 1H), 1.74 (m, 1H), 1.55 (m, 1H), 1.31 (m, 1H)

Example 193: Preparation of (2R,3S)-2-((E)-3-(5-bromo-6,7-difluoro-2-methyl-1H-benzo[d]imidazol-1-yl)prop-1-en-1-yl)piperidin-3-ol dihydrochloride

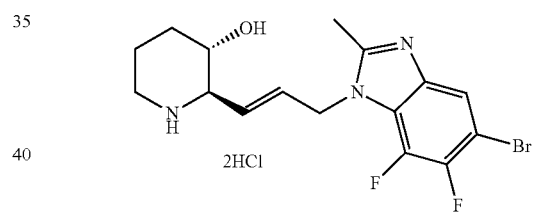

The title compound (12 mg, yield: 40%) was obtained in the same manner as in Example 166, with the exception that 5-bromo-6,7-difluoro-2-methyl-1H-benzo[d]imidazole was used instead of 5,6-dichloro-1H-benzo[d]imidazole in Step 166-5 of Example 166.

$^1$H-NMR (500 MHz, MeOD): δ 8.37 (s, 1H), 8.31 (s, 1H), 6.22 (m, 1H), 5.68 (m, 1H), 5.06 (m, 2H), 3.38 (m, 2H), 3.20 (m, 1H), 2.84 (m, 1H), 2.20 (s, 3H), 1.87 (m, 2H), 1.54 (m, 1H), 1.48 (m, 1H)

Example 194: Preparation of (2R,3S)-2-((E)-3-(indolin-1-yl)prop-1-en-1-yl)piperidin-3-ol dihydrochloride

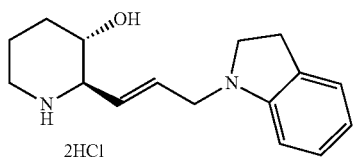 [SMILES: O[C@H]1CCCN[C@@H]1/C=C/CN1CCc2ccccc21]

The title compound (25 mg, yield: 80%) was obtained in the same manner as in Example 166, with the exception that indoline was used instead of 5,6-dichloro-1H-benzo[d]imidazole in Step 166-5 of Example 166.
¹H-NMR (500 MHz, MeOD): δ7.29 (m, 4H), 6.89 (s, 2H), 4.14 (m, 2H), 3.82 (m, 2H), 3.56 (m, 2H), 3.25 (m, 5H), 2.95 (m, 1H), 1.99 (m, 2H), 1.74 (m 1H), 1.56 (m, 1H)

Example 195: Preparation of (2R,3S)-2-((E)-3-(5-chloroindolin-1-yl)prop-1-en-1-yl)piperidin-3-ol dihydrochloride

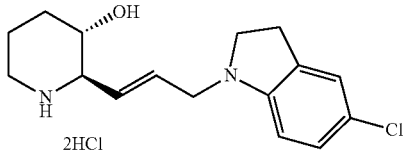 [SMILES: O[C@H]1CCCN[C@@H]1/C=C/CN1CCc2cc(Cl)ccc21]

The title compound (27 mg, yield: 82%) was obtained in the same manner as in Example 166, with the exception that 5-chloroindoline was used instead of 5,6-dichloro-1H-benzo[d]imidazole in Step 166-5 of Example 166.
¹H-NMR (500 MHz, MeOD): δ7.10 (s, 1H), 6.89 (m, 2H), 6.04 (s, 2H), 4.12 (m, 2H), 3.74 (m, 2H), 3.42 (m, 2H), 3.20 (m, 5H), 2.84 (m, 1H), 1.97 (m, 2H), 1.68 (m, 1H), 1.52 (m, 1H)

Example 196: Preparation of (2R,3S)-2-((E)-3-(1H-pyrrolo[2,3-b]pyridin-1-yl)prop-1-en-1-yl)piperidin-3-ol dihydrochloride

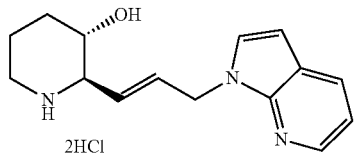 [SMILES: O[C@H]1CCCN[C@@H]1/C=C/Cn1ccc2cccnc21]

The title compound (30 mg, yield: 80%) was obtained in the same manner as in Example 166, with the exception that 1H-pyrrolo[2,3-b]pyridine was used instead of 5,6-dichloro-1H-benzo[d]imidazole in Step 166-5 of Example 166.
¹H-NMR (500 MHz, MeOD): δ8.21 (d, 1H), 7.98 (m, 1H), 7.37 (m, 1H), 7.09 (m, 1H), 6.51 (m, 1H), 6.20 (m, 1H), 5.90 (m, 1H), 4.87 (m, 2H), 3.61 (m, 1H), 3.52 (m, 1H), 3.27 (m, 1H), 2.95 (m, 1H), 2.00 (m, 2H), 1.71 (m, 1H), 1.56 (m, 1H)

Example 197: Preparation of (2R,3S)-2-((E)-3-(6-chloro-1H-indol-1-yl)prop-1-en-1-yl)piperidin-3-ol dihydrochloride

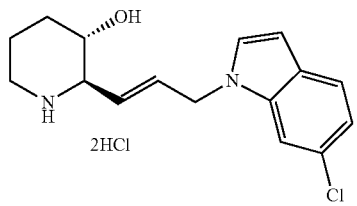 [SMILES: O[C@H]1CCCN[C@@H]1/C=C/Cn1ccc2ccc(Cl)cc21]

The title compound (37 mg, yield: 83%) was obtained in the same manner as in Example 166, with the exception that 6-chloro-1H-indole was used instead of 5,6-dichloro-1H-benzo[d]imidazole in Step 166-5 of Example 166.
¹H-NMR (500 MHz, MeOD): δ 7.36 (m, 3H), 7.08 (d, 1H), 6.90 (m, 1H), 6.13 (m, 1H), 5.38 (m, 1H), 4.87 (m, 2H), 3.44 (m, 2H), 3.15 (m, 1H), 2.88 (m, 1H), 1.94 (m, 2H), 1.65 (m, 1H), 1.48 (m, 1H)

Example 198: Preparation of (2R,3S)-2-((E)-3-(6-chloro-1H-indazol-1-yl)prop-1-en-1-yl)piperidin-3-ol dihydrochloride

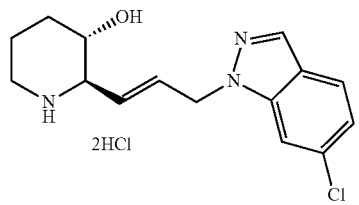 [SMILES: O[C@H]1CCCN[C@@H]1/C=C/Cn1ncc2ccc(Cl)cc21]

The title compound (25 mg, yield: 79%) was obtained in the same manner as in Example 166, with the exception that 6-chloro-1H-indazole was used instead of 5,6-dichloro-1H-benzo[d]imidazole in Step 166-5 of Example 166.
¹H-NMR (500 MHz, MeOD): δ8.02 (s, 1H), 7.71 (m, 1H), 7.63 (s, 1H), 7.12 (m, 1H), 6.20 (m, 1H), 5.62 (m, 1H), 5.21 (m 2H), 3.54 (m, 1H), 3.46 (m, 1H), 3.22 (m, 1H), 2.90 (m, 1H), 2.05 (m, 1H), 1.96 (m, 1H), 1.65 (m, 1H), 1.50 (m, 1H)

Example 199: Preparation of (2R,3S)-2-((E)-3-(4-chloro-7H-pyrrolo[2,3-d]pyrimidin-7-yl)prop-1-en-1-yl)piperidin-3-ol dihydrochloride

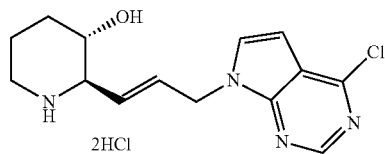 [SMILES: O[C@H]1CCCN[C@@H]1/C=C/Cn1ccc2c(Cl)ncnc21]

The title compound (27 mg, yield: 85%) was obtained in the same manner as in Example 166, with the exception that 4-chloro-7H-pyrrolo[2,3-d]pyrimidine was used instead of 5,6-dichloro-1H-benzo[d]imidazole in Step 166-5 of Example 166.
¹H-NMR (500 MHz, MeOD): δ8.53 (s, 1H), 7.60 (s, 1H), 6.69 (m, 1H), 6.18 (m, 1H), 5.53 (m, 1H), 5.04 (m, 2H), 3.46 (m, 2H), 3.21 (m, 1H), 2.90 (m, 1H), 1.96 (m, 2H), 1.56 (m, 1H), 1.50 (m, 1H)

Example 200: Preparation of (2R,3S)-2-((E)-3-(5-chloro-1H-pyrazolo[3,4-b]pyridin-1-yl)prop-1-en-1-yl)piperidin-3-ol dihydrochloride

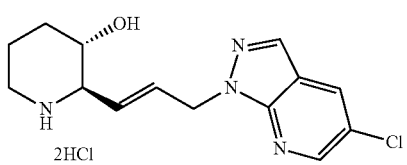 [SMILES: O[C@H]1CCCN[C@@H]1/C=C/Cn1ncc2cc(Cl)cnc21]

The title compound (25 mg, yield: 81%) was obtained in the same manner as in Example 166, with the exception that chloro-1H-pyrazolo[3,4-b]pyridine was used instead of 5,6-dichloro-1H-benzo[d]imidazole in Step 166-5 of Example 166.

$^1$H-NMR (500 MHz, MeOD): δ 8.52 (m, 1H), 8.26 (m, 1H), 8.13 (s, 1H), 6.20 (m, 1H), 5.62 (m, 1H), 5.21 (m 2H), 3.54 (m, 1H), 3.46 (m, 1H), 3.22 (m, 1H), 2.90 (m, 1H), 2.05 (m, 1H), 1.96 (m, 1H), 1.65 (m, 1H), 1.50 (m, 1H)

Example 201: Preparation of (2R,3S)-2-((E)-3-(3,5-dimethyl-1H-indazol-1-yl)prop-1-en-1-yl)piperidin-3-ol dihydrochloride

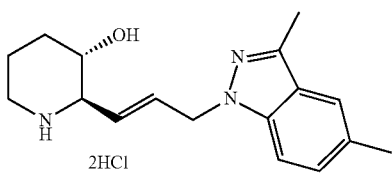 [SMILES: Cc1ccc2c(c1)c(C)nn2C/C=C/[C@H]1NCCC[C@@H]1O]

The title compound (28 mg, yield: 79%) was obtained in the same manner as in Example 166, with the exception that 3,5-dimethyl-1H-indazole was used instead of 5,6-dichloro-1H-benzo[d]imidazole in Step 166-5 of Example 166.

$^1$H-NMR (500 MHz, MeOD): δ7.74 (s, 1H), 7.50 (m, 1H), 7.37 (m, 1H), 6.13 (m, 1H), 5.49 (m, 1H), 5.02 (m, 2H), 3.50 (m, 1H), 3.44 (m, 1H), 3.32 (s, 3H), 3.21 (m, 1H), 2.90 (m, 1H), 2.51 (s, 3H), 2.04 (m, 1H), 1.95 (m, 1H), 1.56 (m, 1H), 1.49 (m, 1H)

Example 202: Preparation of methyl 7-bromo-1-((E)-3-((2R,3S)-3-hydroxypiperidin-2-yl)allyl)-1H-indole-3-carboxylate dihydrochloride

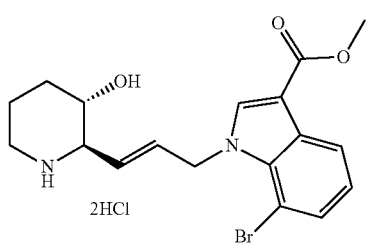 [SMILES: COC(=O)c1cn(C/C=C/[C@H]2NCCC[C@@H]2O)c2c(Br)cccc12]

The title compound (30 mg, yield: 82%) was obtained in the same manner as in Example 166, with the exception that methyl 7-bromo-1H-indole-3-carboxylate was used instead of 5,6-dichloro-1H-benzo[d]imidazole in Step 166-5 of Example 166.

$^1$H-NMR (500 MHz, MeOD): δ 8.14 (m, 1H), 8.04 (s, 1H), 7.44 (m, 1H), 7.09 (m, 1H), 6.26 (m, 1H), 5.43 (m, 1H), 5.31 (m, 1H), 3.50 (m, 2H), 3.15 (m, 1H), 2.88 (m, 1H), 1.94 (m, 2H), 1.62 (m, 1H), 1.50 (m, 1H)

Example 203: Preparation of 7-bromo-1-((E)-3-((2R,3S)-3-hydroxypiperidin-2-yl)allyl)-1H-indole-3-carboxylic acid dihydrochloride

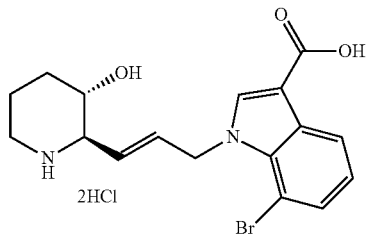 [SMILES: O=C(O)c1cn(C/C=C/[C@H]2NCCC[C@@H]2O)c2c(Br)cccc12 ; "2HCl"]

The title compound (28 mg, yield: 80%) was obtained in the same manner as in Example 166, with the exception that 7-bromo-1H-indole-3-carboxylic acid was used instead of 5,6-dichloro-1H-benzo[d]imidazole in Step 166-5 of Example 166.

$^1$H-NMR (500 MHz, MeOD): δ 8.02 (m, 2H), 7.39 (d, 1H), 7.09 (m, 1H), 6.21 (m, 1H), 5.91 (m, 1H), 4.83 (m, 2H), 3.62 (m, 1H), 3.51 (m, 1H), 3.26 (m, 1H), 2.94 (m, 1H), 1.98 (m, 2H), 1.71 (m, 1H), 1.52 (m, 1H)

Example 204: Preparation of 5-bromo-1-((E)-3-((2R,3S)-3-hydroxypiperidin-2-yl)allyl)-1H-indole-3-carboxylic acid dihydrochloride

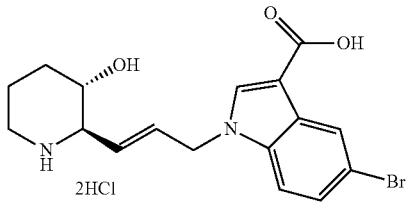 [SMILES: O=C(O)c1cn(C/C=C/[C@H]2NCCC[C@@H]2O)c2ccc(Br)cc12 ; "2HCl"]

The title compound (35 mg, yield: 82%) was obtained in the same manner as in Example 166, with the exception that 5-bromo-IH-indole-3-carboxylic acid was used instead of 5,6-dichloro-1H-benzo[d]imidazole in Step 166-5 of Example 166.

$^1$H-NMR (500 MHz, MeOD): δ 8.18 (s, 1H), 8.01 (m, 1H), 7.31 (m, 2H), 6.21 (m, 1H), 5.90 (m, 1H), 4.89 (m, 2H), 3.61 (m, 1H), 3.53 (m, 1H), 3.23 (m, 1H), 2.95 (m, 1H), 1.99 (m, 2H), 1.68 (m, 1H), 1.53 (m, 1H)

Example 205: Preparation of 4-chloro-1-((E)-3-((2R,3S)-3-hydroxypiperidin-2-yl)allyl)-1H-indole-3-carboxylic acid dihydrochloride

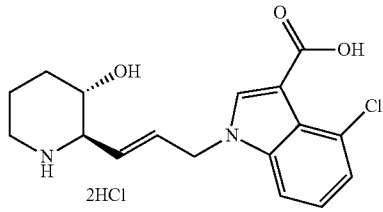 [SMILES: O=C(O)c1cn(C/C=C/[C@H]2NCCC[C@@H]2O)c2cccc(Cl)c12 ; "2HCl"]

The title compound (31 mg, yield: 83%) was obtained in the same manner as in Example 166, with the exception that 4-chloro-IH-indole-3-carboxylic acid was used instead of 5,6-dichloro-1H-benzo[d]imidazole in Step 166-5 of Example 166.

¹H-NMR (500 MHz, MeOD): δ 8.06 (s, 1H), 7.41 (d, 1H), 7.15 (m, 2H), 6.20 (m, 1H), 5.90 (m, 1H), 4.87 (m, 2H), 3.61 (m, 1H), 3.52 (m, 1H), 3.27 (m, 1H), 2.95 (m, 1H), 2.00 (m, 2H), 1.71 (m, 1H), 1.56 (m, 1H)

Example 206: Preparation of 6-chloro-1-((E)-3-((2R,3S)-3-hydroxypiperidin-2-yl)allyl)-1H-indole-3-carboxylic acid dihydrochloride

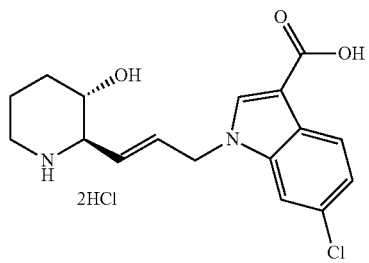 [SMILES: O=C(O)c1cn(C/C=C/[C@H]2NCCC[C@@H]2O)c2cc(Cl)ccc12 ; "2HCl"]

The title compound (27 mg, yield: 79%) was obtained in the same manner as in Example 166, with the exception that 6-chloro-1H-indole-3-carboxylic acid was used instead of 5,6-dichloro-1H-benzo[d]imidazole in Step 166-5 of Example 166.

¹H-NMR (500 MHz, MeOD): δ8.01 (d, 1H), 7.46 (m, 1H), 7.17 (d, 1H), 6.22 (m, 1H), 5.91 (m, 1H), 4.88 (m, 2H), 4.36 (m, 1H), 3.61 (m, 1H), 3.27 (m, 1H), 2.94 (m, 1H), 2.05 (m, 2H), 1.72 (m, 1H), 1.56 (m, 1H)

Example 207: Preparation of 7-chloro-1-((E)-3-((2R,3S)-3-hydroxypiperidin-2-yl)allyl)-1H-indole-3-carboxylic acid dihydrochloride

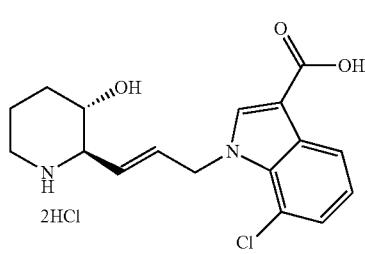 [SMILES: O=C(O)c1cn(C/C=C/[C@H]2NCCC[C@@H]2O)c2c(Cl)cccc12 ; "2HCl"]

The title compound (25 mg, yield: 77%) was obtained in the same manner as in Example 166, with the exception that 7-chloro-IH-indole-3-carboxylic acid was used instead of 5,6-dichloro-1H-benzo[d]imidazole in Step 166-5 of Example 166.

¹H-NMR (500 MHz, MeOD): δ 8.00 (m, 2H), 7.16 (m, 2H), 6.22 (m, 1H), 5.91 (m, 1H), 4.90 (m, 2H), 3.53 (m, 2H), 2.96 (m, 1H), 1.99 (m, 2H), 1.71 (m 1H), 1.55 (m, 1H)

Example 208: Preparation of 6-fluoro-1-((E)-3-((2R,3S)-3-hydroxypiperidin-2-yl)allyl)-1H-indole-3-carboxylic acid dihydrochloride

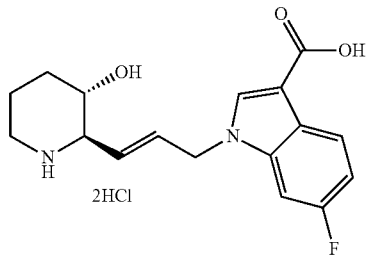 [SMILES: O=C(O)c1cn(C/C=C/[C@H]2NCCC[C@@H]2O)c2cc(F)ccc12 ; "2HCl"]

The title compound (24 mg, yield: 81%) was obtained in the same manner as in Example 166, with the exception that 6-fluoro-1H-indole-3-carboxylic acid was used instead of 5,6-dichloro-1H-benzo[d]imidazole in Step 166-5 of Example 166.

¹H-NMR (500 MHz, MeOD): δ7.99 (m, 2H), 7.15 (m, 1H), 6.95 (m, 1H), 6.21 (m, 1H), 5.90 (m, 1H), 4.87 (m, 2H), 3.60 (m, 1H), 3.51 (m, 1H), 3.26 (m, 1H), 2.94 (m, 1H), 2.01 (m, 2H), 1.71 (m, 1H), 1.56 (m, 1H)

Example 209: Preparation of 1-((E)-3-((2R,3S)-3-hydroxypiperidin-2-yl)allyl)-1H-indole-3-carboxylic acid dihydrochloride

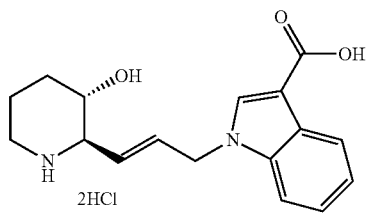 [SMILES: O=C(O)c1cn(C/C=C/[C@H]2NCCC[C@@H]2O)c2ccccc12 ; "2HCl"]

The title compound (20 mg, yield: 78%) was obtained in the same manner as in Example 166, with the exception that 1H-indole-3-carboxylic acid was used instead of 5,6-dichloro-1H-benzo[d]imidazole in Step 166-5 of Example 166.

¹H-NMR (500 MHz, MeOD): δ 8.05 (d, 1H), 7.99 (d, 1H), 7.45 (d, 1H), 7.16 (m, 2H), 6.22 (m, 1H), 5.91 (m, 1H), 4.83 (m, 2H), 4.37 (m, 1H), 3.61 (m, 1H), 3.52 (m, 1H), 2.94 (m, 1H), 2.00 (m, 2H), 1.69 (m, 1H), 1.53 (m, 1H)

Example 210: Preparation of methyl 4-chloro-1-((E)-3-((2R,3S)-3-hydroxypiperidin-2-yl)allyl)-1H-indole-3-carboxylate dihydrochloride

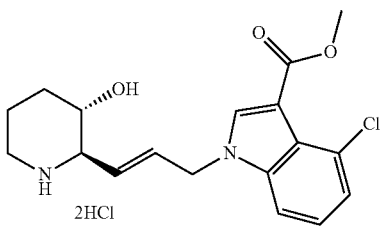 [SMILES: COC(=O)c1cn(C/C=C/[C@H]2NCCC[C@@H]2O)c2cccc(Cl)c12 ; "2HCl"]

The title compound (18 mg, yield: 82%) was obtained in the same manner as in Example 166, with the exception that methyl 4-chloro-IH-indole-3-carboxylate was used instead of 5,6-dichloro-1H-benzo[d]imidazole in Step 166-5 of Example 166.

¹H-NMR (500 MHz, MeOD): δ 8.05 (s, 1H), 7.44 (d, 1H), 7.20 (m, 2H), 6.17 (m, 1H), 5.42 (m, 1H), 4.98 (m, 2H), 3.84 (s, 3H), 3.45 (m, 2H), 3.18 (m, 1H), 2.89 (m, 1H), 1.94 (m, 2H), 1.64 (m, 1H), 1.50 (m, 1H)

Example 211: Preparation of methyl 6-chloro-1-((E)-3-((2R,3S)-3-hydroxypiperidin-2-yl)allyl)-1H-indole-3-carboxylate dihydrochloride

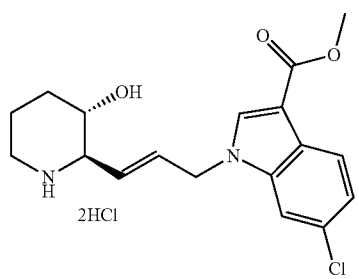 [SMILES: COC(=O)c1cn(C/C=C/[C@H]2NCCC[C@@H]2O)c2cc(Cl)ccc12 ; "2HCl"]

The title compound (28 mg, yield: 80%) was obtained in the same manner as in Example 166, with the exception that methyl 6-chloro-1H-indole-3-carboxylate was used instead of 5,6-dichloro-1H-benzo[d]imidazole in Step 166-5 of Example 166.

¹H-NMR (500 MHz, MeOD): δ8.02 (m, 2H), 7.56 (s, 1H), 7.22 (t, 1H), 6.17 (m, 1H), 5.45 (m, 1H), 4.96 (m, 2H), 3.87 (s, 3H), 3.46 (m, 2H), 3.20 (m, 1H), 2.89 (m, 1H), 1.95 (m, 2H), 1.65 (m, 1H), 1.51 (m, 1H)

Example 212: Preparation of methyl 7-chloro-1-((E)-3-((2R,3S)-3-hydroxypiperidin-2-yl)allyl)-1H-indole-3-carboxylate dihydrochloride

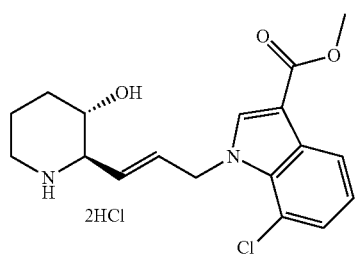 [SMILES: COC(=O)c1cn(C/C=C/[C@H]2NCCC[C@@H]2O)c2c(Cl)cccc12 ; "2HCl"]

The title compound (28 mg, yield: 84%) was obtained in the same manner as in Example 166, with the exception that methyl 7-chloro-1H-indole-3-carboxylate was used instead of 5,6-dichloro-1H-benzo[d]imidazole in Step 166-5 of Example 166.

¹H-NMR (500 MHz, MeOD): δ 8.08 (d, 1H), 8.03 (s, 1H), 7.25 (d, 1H), 7.16 (m, 1H), 6.26 (m, 1H), 5.28 (m, 2H), 3.89 (s, 3H), 3.65 (s, 1H), 3.46 (m, 2H), 3.16 (m, 1H), 2.90 (m, 1H), 1.95 (m, 2H), 1.60 (m, 1H), 1.50 (m, 1H)

Example 213: Preparation of methyl 5-bromo-1-((E)-3-((2R,3S)-3-hydroxypiperidin-2-yl)allyl)-1H-indole-3-carboxylate dihydrochloride

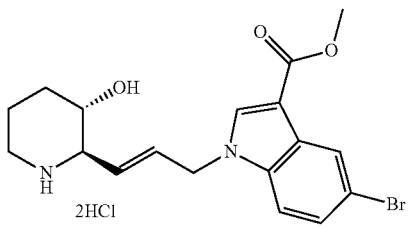 [SMILES: COC(=O)c1cn(C/C=C/[C@H]2NCCC[C@@H]2O)c2ccc(Br)cc12 ; "2HCl"]

The title compound (30 mg, yield: 85%) was obtained in the same manner as in Example 166, with the exception that methyl 5-bromo-1H-indole-3-carboxylate was used instead of 5,6-dichloro-1H-benzo[d]imidazole in Step 166-5 of Example 166.

¹H-NMR (500 MHz, MeOD): δ 8.19 (d, 1H), 8.04 (d, 1H), 7.36 (m, 2H), 6.17 (m, 1H), 5.46 (m, 1H), 4.97 (m, 2H), 3.90 (s, 3H), 3.43 (m, 2H), 3.20 (m, 1H), 2.88 (m, 1H), 1.97 (m, 2H), 1.66 (m, 1H), 1.51 (m, 1H)

Example 214: Preparation of methyl 6-bromo-1-((E)-3-((2R,3S)-3-hydroxypiperidin-2-yl)allyl)-1H-indole-3-carboxylate dihydrochloride

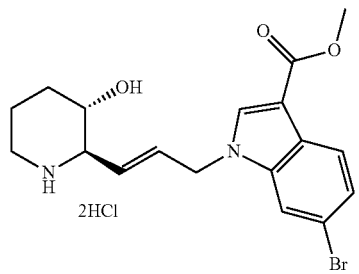

The title compound (31 mg, yield: 83%) was obtained in the same manner as in Example 166, with the exception that methyl 6-bromo-1H-indole-3-carboxylate was used instead of 5,6-dichloro-1H-benzo[d]imidazole in Step 166-5 of Example 166.

¹H-NMR (500 MHz, MeOD): δ7.96 (m, 2H), 7.71 (s, 1H), 7.33 (m, 1H), 6.17 (m, 1H), 5.44 (m, 1H), 4.96 (m, 2H), 3.87 (s, 3H), 3.47 (m, 2H), 3.19 (m, 1H), 2.89 (m, 1H), 1.97 (m, 2H), 1.65 (m, 1H), 1.51 (m, 1H)

Example 215: Preparation of 5-bromo-1-((E)-3-((2R,3S)-3-hydroxypiperidin-2-yl)allyl)-N-methyl-1H-indole-3-carboxamide dihydrochloride

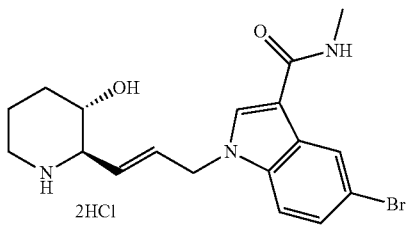 [SMILES: CNC(=O)c1cn(C/C=C/[C@H]2NCCC[C@@H]2O)c2ccc(Br)cc12 ; "2HCl"]

The title compound (21 mg, yield: 86%) was obtained in the same manner as in Example 166, with the exception that 5-bromo-N-methyl-1H-indole-3-carboxamide was used instead of 5,6-dichloro-1H-benzo[d]imidazole in Step 166-5 of Example 166.

$^1$H-NMR (500 MHz, MeOD): δ 8.25 (m, 1H), 7.84 (s, 1H), 7.34 (m, 2H), 6.16 (m, 1H), 5.38 (m, 1H), 4.89 (m, 2H), 3.44 (m, 2H), 3.16 (m, 1H), 2.86 (m, 4H), 1.94 (m, 2H), 1.63 (m, 1H), 1.48 (m, 1H)

Example 216: Preparation of 5-bromo-1-((E)-3-((2R,3S)-3-hydroxypiperidin-2-yl)allyl)-N,N-dimethyl-1H-indole-3-carboxamide dihydrochloride

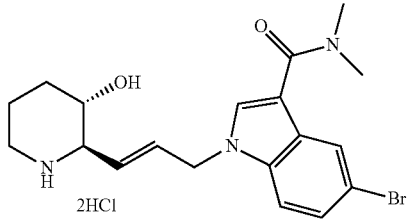 [SMILES: CN(C)C(=O)c1cn(C/C=C/[C@H]2NCCC[C@@H]2O)c2ccc(Br)cc12 ; "2HCl"]

The title compound (21 mg, yield: 86%) was obtained in the same manner as in Example 166, with the exception that 5-bromo-N,N-dimethyl-1H-indole-3-carboxylamide was used instead of 5,6-dichloro-1H-benzo[d]imidazole in Step 166-5 of Example 166.

$^1$H-NMR (500 MHz, MeOD): δ7.95 (s, 1H), 7.71 (s, 1H), 7.41 (d, 1H), 7.34 (m, 1H), 6.14 (m, 1H), 5.39 (m, 1H), 4.96 (m, 2H), 3.45 (m, 2H), 3.16 (m, 7H), 2.89 (m, 1H), 1.97 (m, 2H), 1.65 (m, 1H), 1.50 (m, 1H)

Example 217: Preparation of (2R,3S)-2-((Z)-3-(5-chloro-4-methyl-1H-benzo[d]imidazol-1-yl)-2-fluoroprop-1-enyl)piperidin-3-ol dihydrochloride

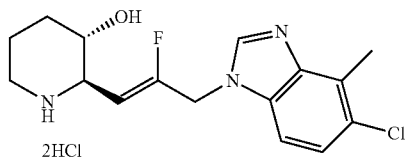 [SMILES: Cc1c(Cl)ccc2c1ncn2C/C(F)=C/[C@H]1NCCC[C@@H]1O ; "2HCl"]

The title compound (25 mg, yield: 80%) was obtained in the same manner as in Example 166, with the exception that triethyl 2-fluoro-2-phosphonoacetate was used instead of (carbethoxymethylene)triphenylphosphorane in Step 166-1 of Example 166, and 5-chloro-4-methyl-1H-benzo[d]imidazole was used instead of 5,6-dichloro-1H-benzo[d]imidazole in Step 166-5 of Example 166.

$^1$H-NMR (500 MHz, MeOD): δ 8.30 (s, 1H), 7.52 (d, 1H), 7.32 (d, 1H), 5.36 (m, 1H), 5.25 (m, 1H), 5.19 (m, 1H), 3.36 (t, 1H), 3.31 (m, 1H), 3.10 (d, 1H), 2.79 (m, 1H), 2.61 (s, 3H), 2.15 (m, 1H), 1.87 (m, 1H), 1.68 (m, 1H), 1.56 (m, 1H)

Example 218: Preparation of (2R,3S)-2-((Z)-3-(5-bromo-4-methyl-1H-benzo[d]imidazol-1-yl)-2-fluoroprop-1-en-1-yl)piperidin-3-ol dihydrochloride

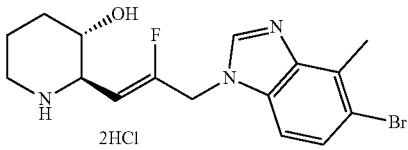

The title compound (27 mg, yield: 81%) was obtained in the same manner as in Example 166, with the exception that triethyl 2-fluoro-2-phosphonoacetate was used instead of (carbethoxymethylene)triphenylphosphorane in Step 166-1 of Example 166, and 5-bromo-4-methyl-1H-benzo[d]imidazole was used instead of 5,6-dichloro-1H-benzo[d]imidazole in Step 166-5 of Example 166.

$^1$H-NMR (500 MHz, MeOD): δ 8.29 (s, 1H), 7.46 (s, 2H), 5.35 (m, 1H), 5.25 (m, 1H), 5.21 (m, 1H), 3.54 (t, 1H), 3.41 (m, 1H), 3.12 (d, 1H), 2.77 (m, 1H), 2.63 (s, 3H), 2.15 (m, 1H), 1.87 (m, 1H), 1.68 (m, 1H), 1.56 (m, 1H)

Example 219: Preparation of (2R,3S)-2-((Z)-3-(5,6-dichloro-1H-benzo[d]imidazol-1-yl)-2-fluoroprop-1-en-1-yl)piperidin-3-ol dihydrochloride

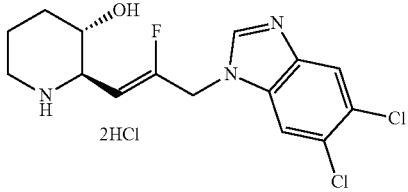 [SMILES: O[C@H]1CCCN[C@@H]1/C=C(\F)Cn1cnc2cc(Cl)c(Cl)cc21]

The title compound (35 mg, yield: 84%) was obtained in the same manner as in Example 166, with the exception that triethyl 2-fluoro-2-phosphonoacetate was used instead of (carbethoxymethylene)triphenylphosphorane in Step 166-1 of Example 166.

$^1$H-NMR (500 MHz, MeOD): δ 8.38 (s, 1H), 8.00 (s, 1H), 7.80 (s, 1H), 5.26 (m, 3H), 3.59 (t, 1H), 3.42 (m, 1H), 3.14 (d, 1H), 2.83 (t, 1H), 2.14 (m, 1H), 1.89 (d, 1H), 1.69 (m, 1H), 1.58 (m, 1H)

Example 220: Preparation of (2R,3S)-2-((Z)-3-(5,6-dichloro-2-(hydroxymethyl)-1H-benzo[d]imidazol-1-yl)-2-fluoroprop-1-en-1-yl)piperidin-3-ol dihydrochloride

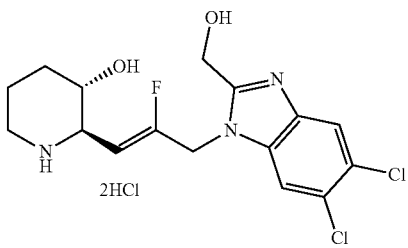 [SMILES: OCc1nc2cc(Cl)c(Cl)cc2n1C/C(F)=C/[C@H]1NCCC[C@@H]1O]

The title compound (30 mg, yield: 79%) was obtained in the same manner as in Example 166, with the exception that triethyl 2-fluoro-2-phosphonoacetate was used instead of (carbethoxymethylene)triphenylphosphorane in Step 166-1 of Example 166, and (5,6-dichloro-1H-benzo[d]imidazol-2-yl)methanol was used instead of 5,6-dichloro-1H-benzo[d]imidazole in Step 166-5 of Example 166.

$^1$H-NMR (500 MHz, MeOD): δ8.01 (s, 1H), 7.71 (s, 1H), 5.41 (m, 3H), 4.85 (m, 2H), 3.80 (m, 1H), 3.57 (m, 2H), 3.26 (s, 1H), 2.96 (t, 1H), 2.18 (m, 1H), 1.98 (m, 1H), 1.73 (m, 1H), 1.63 (m, 1H)

Example 221: Preparation of (2R,3S)-2-((E)-3-(5-chloro-4-methyl-1H-benzo[d]imidazol-1-yl)-2-methylprop-1-en-1-yl)piperidin-3-ol dihydrochloride

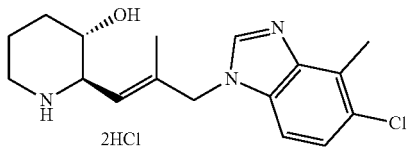 [SMILES: C/C(=C\[C@H]1NCCC[C@@H]1O)Cn1cnc2c(C)c(Cl)ccc21]

The title compound (27 mg, yield: 81%) was obtained in the same manner as in Example 166, with the exception that (1-ethoxycarbonylethylidene diene)triphenylphosphorane was used instead of (carbethoxymethylene)triphenylphosphorane in Step 166-1 of Example 166, and 5-chloro-4-methyl-1H-benzo[d]imidazole was used instead of 5,6-dichloro-1H-benzo[d]imidazole in Step 166-5 of Example 166.

$^1$H-NMR (500 MHz, MeOD): δ8.21 (s, 1H), 7.39 (d, 1H), 7.31 (d, 1H), 5.13 (d, 1H), 4.93 (m, 2H), 3.62 (t, 1H), 3.39 (m, 1H), 3.15 (m, 1H), 2.87 (m, 1H), 2.62 (s, 3H), 2.06 (m, 1H) 1.93 (m, 1H), 1.78 (s, 3H), 1.62 (m, 1H), 1.57 (m, 1H)

Example 222: Preparation of (2R,3S)-2-((E)-3-(5-bromo-4-methyl-1H-benzo[d]imidazol-1-yl)-2-methylprop-1-en-1-yl)piperidin-3-ol dihydrochloride

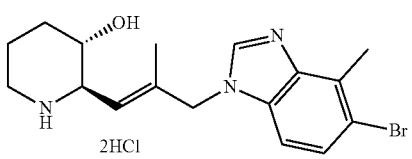 [SMILES: C/C(=C\[C@H]1NCCC[C@@H]1O)Cn1cnc2c(C)c(Br)ccc21]

The title compound (34 mg, yield: 80%) was obtained in the same manner as in Example 166, with the exception that (1-ethoxycarbonylethylidene diene)triphenylphosphorane was used instead of (carbethoxymethylene)triphenylphosphorane in Step 166-1 of Example 166, and 5-bromo-4-methyl-1H-benzo[d]imidazole was used instead of 5,6-dichloro-1H-benzo[d]imidazole in Step 166-5 of Example 166.

$^1$H-NMR (500 MHz, MeOD): δ8.20 (s, 1H), 7.47 (d, 1H), 7.35 (d, 1H), 5.12 (d, 1H), 4.93 (m, 2H), 3.62 (t, 1H), 3.40 (m, 1H), 3.15 (m, 1H), 2.86 (m, 1H), 2.64 (s, 3H), 2.06 (m, 1H), 1.92 (m, 1H), 1.78 (s, 3H), 1.66 (m, 1H), 1.56 (m, 1H)

Example 223: Preparation of (2R,3S)-2-((E)-3-(5,6-dichloro-1H-benzo[d]imidazol-1-yl)-2-methylprop-1-en-1-yl)piperidin-3-ol dihydrochloride

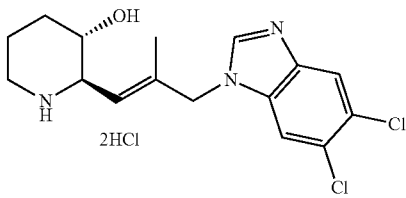 [SMILES: C/C(=C\[C@H]1NCCC[C@@H]1O)Cn1cnc2cc(Cl)c(Cl)cc21]

The title compound (28 mg, yield: 78%) was obtained in the same manner as in Example 166, with the exception that (1-ethoxycarbonylethylidene)triphenylphosphorane was used instead of (carbethoxymethylene)triphenylphosphorane in Step 166-1 of Example 166.

$^1$H-NMR (500 MHz, MeOD): δ 8.28 (s, 1H), 7.83 (s, 2H), 5.18 (d, 1H), 4.91 (m, 2H), 3.48 (t, 1H), 3.07 (d, 1H), 2.76 (t, 1H), 2.07 (m, 1H), 1.86 (m, 1H), 1.76 (s, 3H), 1.62 (m, 1H), 1.46 (m, 1H)

Example 224: Preparation of (2R,3S)-2-((E)-3-(5,6-dichloro-2-(hydroxymethyl)-1H-benzo[d]imidazol-1-yl)-2-methylprop-1-en-1-yl)piperidin-3-ol dihydrochloride

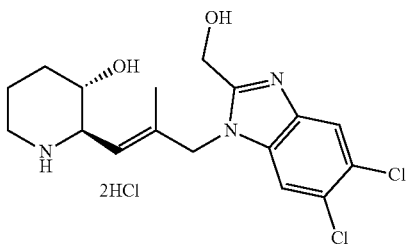 [SMILES: C/C(=C\[C@H]1NCCC[C@@H]1O)Cn1c(CO)nc2cc(Cl)c(Cl)cc21]

The title compound (31 mg, yield: 78%) was obtained in the same manner as in Example 166, with the exception that (1-ethoxycarbonylethylidene)triphenylphosphorane was used instead of (carbethoxymethylene)triphenylphosphorane in Step 166-1 of Example 166, and 5,6-dichloro-1H-benzo[d]imidazol-2-yl)methanol was used instead of 5,6-dichloro-1H-benzo[d]imidazole in Step 166-5 of Example 166.

$^1$H-NMR (500 MHz, MeOD): δ7.79 (s, 2H), 5.03 (m, 2H), 4.89 (m, 3H), 3.70 (t, 1H), 3.40 (m, 1H), 3.14 (m, 1H), 2.92 (m, 1H), 2.03 (m, 1H), 1.94 (m, 1H), 1.84 (s, 3H), 1.65 (m, 1H), 1.55 (m, 1H)

Example 225: Preparation of (2R,3S)-2-(3-(5,6-dichloro-1H-benzo[d]imidazol-1-yl)prop-1-yn-1-yl)piperidin-3-ol dihydrochloride

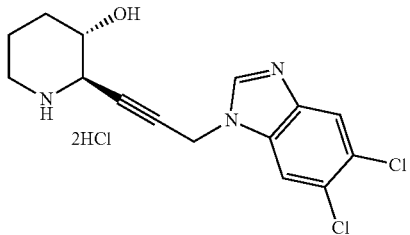 [SMILES: O[C@H]1CCCN[C@@H]1C#CCn1cnc2cc(Cl)c(Cl)cc21]

Step 225-1: Preparation of tert-butyl (2R,3S)-3-((tert-butyldimethylsilyl)oxy)-2-(E)-3-ethoxy-3-oxoprop-1-en-1-yl)piperidine-1-carboxylate Methylene chloride (47 mL, 0.12 M) and oxalyl chloride (1.0 mL, 11.6 mmol) were added to a flask filled with nitrogen and the reaction solution was cooled to −78° C. Dimethylsulfoxide (1.7 mL, 23.2 mmol) was then added at the same temperature and stirred for 30 minutes. Then, tert-butyl (2R,3S)-3-((tert-butyldimethylsilyl)oxy)-2-(hydroxymethyl)piperidine-1-carboxylate (2.0 g, 5.8 mmol) was dissolved in a small amount of methylene chloride and slowly added. After stirring at the same temperature for 1 hour, triethylamine (3.3 mL, 23.2 mmol) was added and the temperature of the reaction solution was raised to room temperature from −78° C. When the reaction was completed, the solvent was removed, and the resulting mixture was diluted with ethyl acetate and washed with saturated sodium chloride solution. The organic layer was collected and dried with magnesium sulfate, filtered and concentrated under reduced pressure, and then dissolved in methylene chloride (47 mL, 0.12 M), and (carbethoxymethylene)triphenylphosphorane (4.0 g, 11.6 mmol) was added thereto at room temperature and stirred for 2 hours. When the reaction was completed, the solvent was removed, and the resulting mixture was diluted with ethyl acetate and washed with saturated sodium chloride solution. The organic layer was collected, dried over magnesium sulfate, filtered and concentrated under reduced pressure, and purified by column chromatography (hexane:ethyl acetate=4:1) to give the title compound (2.1 g, 89% yield over two steps).

Step 225-2: Preparation of tert-butyl (2R,3S)-3-((tert-butyldimethylsilyl)oxy)-2-(3-ethoxy-3-oxoprop-1-yn-1-yl)piperidine-1-carboxylate Tert-butyl (2R,3S)-3-((tert-butyldimethylsilyl)oxy)-2-(E)-3-ethoxy-3-oxoprop-1-en-1-yl)piperidine-1l-carboxylate (3.2 g, 7.7 mmol) obtained from Step 225-1 was dissolved in methanol (50 mL, 0.15 M), and a lindlar catalyst (82 mg, 0.77 mmol) was added thereto. After connecting a hydrogen balloon, the mixture was stirred at room temperature for 5 hours. When the reaction was completed, the reaction solution was filtered through celite and concentrated under reduced pressure. Subsequent reactions were carried out without purification procedure.

Step 225-3: Preparation of 3-((2R,3S)-1-(tert-butoxycarbonyl)-3-(tert-butyldimethylsilyl)oxy)piperidin-2-yl)propenoic acid Tert-butyl (2R,3S)-3-((tert-butyldimethylsilyl)oxy)-2-(3-ethoxy-3-oxoprop-1-yn-1-yl)piperidine-1-carboxylate (3.0 g, 7.2 mmol) obtained from Step 225-2 was dissolved in methanol (20 mL, 0.36 M), and then 2N aqueous sodium hydroxide solution (10 mL) was added thereto and stirred at room temperature for 3 hours. When the reaction was completed, the reaction solution was neutralized with 1N aqueous hydrochloric acid solution, acidified, diluted with ethyl acetate and then washed with saturated sodium chloride solution. The organic layer was collected, dried over magnesium sulfate, filtered and concentrated under reduced pressure. Subsequent reactions were carried out without purification procedure.

Step 225-4: Preparation of tert-butyl (2R,3S)-3-((tert-butyldimethylsilyl)oxy)-2-(3-hydroxyprop-1-yn-1-yl)piperidine-1-carboxylate 3-((2R,3S)-1-(tert-butoxycarbonyl)-3-(tert-butyldimethylsilyl)oxy)piperidin-2-yl)propenoic acid (1.6 g, 4.0 mmol) obtained from Step 225-3 was dissolved in tetrahydrofuran (50 mL, 0.08 M), and the reaction solution was cooled to 0° C. Then, a lithium aluminum hydride solution (1.6 mL, 4.0 mmol) was slowly added thereto, reacted at the same temperature for 30 minutes and then stirred at room temperature for 2 hours. A small amount of water was added to complete the reaction, diluted with ethyl acetate and washed with saturated sodium chloride solution. The organic layer was collected, dried over magnesium sulfate, filtered and concentrated under reduced pressure, and then purified by column chromatography (dichloromethane:methanol=10:1) to give the title compound (1.3 g, yield: 85%).

Step 225-5: Preparation of tert-butyl (2R,3S)-2-(3-bromoprop-1-yn-1-yl)-3-((tert-butyldimethylsilyl)oxy)piperidine-1-carboxylate Tert-butyl (2R,3S)-3-((tert-butyldimethylsilyl)oxy)-2-(3-hydroxyprop-1-yn-1-yl)piperidine-1-carboxylate (100 mg, 0.27 mmol) obtained from Step 225-4 was added to methylene chloride (100 mL, 0.0.3 M). The reaction solution was cooled to 0° C., and then triphenylphosphine (107 g, 0.41 mmol) and tetrabromomethane (135 g, 0.41 mmol) were sequentially added at the same temperature, followed by stirring at room temperature for 2 hours. When the reaction was completed, the solvent was removed, and the resulting mixture was diluted with ethyl acetate and washed with saturated sodium chloride solution. The organic layer was collected and dried over magnesium sulfate, filtered and concentrated under reduced pressure, and then purified by column chromatography (hexane:ethyl acetate=5:1) to give the title compound (89 g, yield: 76%).

Step 225-6: Preparation of tert-butyl (2R,3S)-3-((tert-butyldimethylsilyl)oxy)-2-(3-(5,6-dichloro-1H-benzo[d]imidazol-1-yl)prop-1-yn-1-yl)piperidine-1-carboxylate Tert-butyl (2R,3S)-2-(3-bromoprop-1-yn-1-yl)-3-((tert-butyldimethylsilyl)oxy)piperidine-1-carboxylate (200 mg, 0.46 mmol) obtained from Step 225-5 was dissolved in N,N-dimethylformamide (5 mL, 0.69 M). Then, potassium carbonate (127 mg, 0.92 mmol) and 5,6-dichloro-1H-benzo[d]imidazole (86 mg, 0.46 mmol) were added thereto, and the mixture was stirred at room temperature for 4 hours. When the reaction was completed, the solvent was removed, and the resulting mixture was diluted with ethyl acetate and washed with saturated sodium chloride solution. The organic layer was collected, dried over sodium sulfate, filtered and concentrated under reduced pressure, and then purified by column chromatography (hexane:ethyl acetate=1:2) to give the title compound (293 mg, yield 85%).

Step 225-7: Preparation of (2R,3S)-2-(3-(5,6-dichloro-1H-benzo[d]imidazol-1-yl)prop-1-yn-1-yl)piperidin-3-ol dihydrochloride Tert-butyl (2R,3S)-3-((tert-butyldimethylsilyl)oxy)-2-(3-(5,6-dichloro-1H-benzo[d]imidazol-1-yl)prop-1-yn-1-yl)piperidine-1-carboxylate (293 mg, 0.54 mmol) obtained from Step 225-6 was dissolved in a small amount of tetrahydrofuran and 4N hydrogen chloride dioxane solution (5 mL, 0.10 M) was added thereto, and the mixture was heated and stirred at room temperature for 12 hours. When the reaction was completed, the reaction solution was concentrated under reduced pressure to remove the solvent, dissolved by addition of a small amount of methanol and then crystallized with diethyl ether to give the title compound (176 mg, yield: 82%).

¹H-NMR (500 MHz, MeOD): δ 8.44 (br, 1H), 7.99 (s, 1H), 7.88 (s, 1H), 5.34 (s, 2H), 4.11 (m, 1H), 3.90 (m, 1H), 3.22 (m, 1H), 3.04 (m, 1H), 1.99 (m, 2H), 1.65 (m, 2H)

Example 226: Preparation of (2R,3S)-2-(3-(5-bromo-4-methyl-1H-benzo[d]imidazol-1-yl)prop-1-yn-1-yl)piperidin-3-ol dihydrochloride

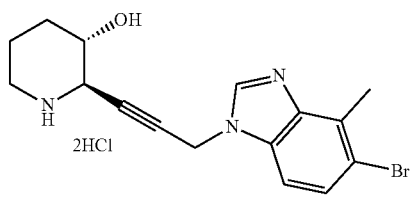 [SMILES: Cc1c(Br)ccc2c1ncn2CC#C[C@H]1NCCC[C@@H]1O]

The title compound (42 mg, yield: 85%) was obtained in the same manner as in Example 225, with the exception that 5-bromo-4-methyl-1H-benzo[d]imidazole was used instead of 5,6-dichloro-1H-benzo[d]imidazole in Step 225-6 of Example 225.

¹H-NMR (500 MHz, MeOD): δ9.61 (m, 1H), 7.86 (m, 1H), 7.78 (m, 1H), 5.57 (d, 2H), 4.86 (m, 1H), 4.16 (m, 1H), 3.97 (m, 1H), 3.06 (m, 1H), 2.72 (s, 3H), 2.02 (m, 2H), 1.65 (m, 2H)

Example 227: Preparation of (2R,3S)-2-(3-(5-chloro-4-methyl-1H-benzo[d]imidazol-1-yl)prop-1-yn-1-yl)piperidin-3-ol dihydrochloride

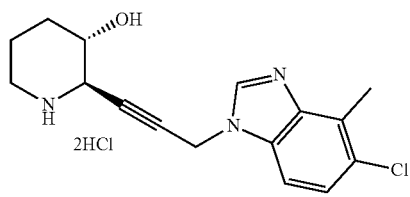 [SMILES: Cc1c(Cl)ccc2c1ncn2CC#C[C@H]1NCCC[C@@H]1O]

The title compound (35 mg, yield: 81%) was obtained in the same manner as in Example 225, with the exception that 5-chloro-4-methyl-1H-benzo[d]imidazole was used instead of 5,6-dichloro-1H-benzo[d]imidazole in Step 225-6 of Example 225.

¹H-NMR (500 MHz, MeOD): δ 9.65 (s, 1H), 7.86 (d, 1H), 7.71 (d, 1H), 5.57 (s, 2H), 4.82 (m, 1H), 4.16 (m, 1H), 3.95 (m, 1H), 3.05 (m, 1H), 2.17 (s, 3H), 2.00 (m, 2H), 1.63 (m, 2H)

Example 228: Preparation of (2R,3S)-2-(3-(5,6-dibromo-1H-benzo[d]imidazol-1-yl)prop-1-yn-1-yl)piperidin-3-ol dihydrochloride

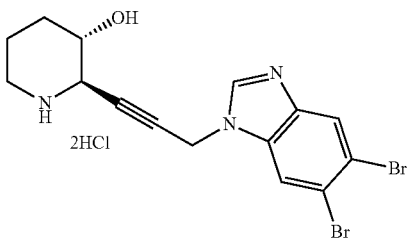 [SMILES: O[C@H]1CCCN[C@@H]1C#CCn1cnc2cc(Br)c(Br)cc21]

The title compound (30 mg, yield: 80%) was obtained in the same manner as in Example 225, with the exception that 5,6-dibromo-IH-benzo[d]imidazole was used instead of 5,6-dichloro-1H-benzo[d]imidazole in Step 225-6 of Example 225.

¹H-NMR (500 MHz, MeOD): δ 9.18 (br, 1H), 8.39 (s, 1H), 8.20 (m, 1H), 5.47 (s, 2H), 4.88 (m, 1H), 4.16 (m, 1H), 3.94 (m, 1H), 3.06 (m, 1H), 1.99 (m, 2H), 1.68 (m, 2H)

Example 229: Preparation of (2R,3S)-2-(3-(5-fluoro-4-methyl-1H-benzo[d]imidazol-1-yl)prop-1-yn-1-yl)piperidin-3-ol dihydrochloride

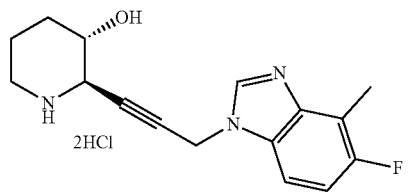 [SMILES: Cc1c(F)ccc2c1ncn2CC#C[C@H]1NCCC[C@@H]1O]

The title compound (28 mg, yield: 75%) was obtained in the same manner as in Example 225, with the exception that 5-fluoro-4-methyl-1H-benzo[d]imidazole was used instead of 5,6-dichloro-1H-benzo[d]imidazole in Step 225-6 of Example 225.

¹H-NMR (500 MHz, MeOD): δ 8.44 (br, 1H), 7.99 (s, 1H), 7.88 (s, 1H), 5.34 (s, 2H), 4.11 (m, 1H), 3.90 (m, 1H), 3.22 (m, 1H), 3.04 (m, 1H), 1.99 (m, 2H), 1.65 (m, 2H)

Example 230: Preparation of (2R,3S)-2-((E)-3-(5,6-dichloro-1H-benzo[d]imidazol-1-yl)prop-1-en-1-yl)pyrrolidin-3-ol dihydrochloride

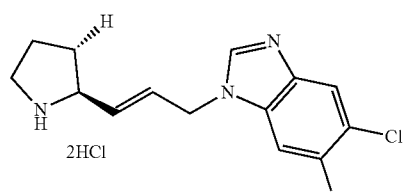

Step 230-1: Preparation of (2R,3S)-1-(tert-butoxycarbonyl)-3-((tert-butyldimethylsilyl)oxy)pyrrolidine-2-carboxylic acid (2R,3S)-1-(tert-butoxycarbonyl)-3-hydroxypyrrolidine-2-carboxylic acid (10.7 g, 46.2 mmol) was dissolved in N,N-dimethylformamide (100 mL, 0.46 M). Then, the reaction solution was cooled to 0° C., and tert-butyldimethylsilyl chloride (20.9 g, 138.6 mmol) and triethylamine (32.2 mL, 231.0 mmol) were added thereto. The reaction solution was stirred at room temperature for 12 hours. When the reaction was completed, the solvent was removed, and the resulting mixture was diluted with ethyl acetate and washed with saturated sodium chloride solution. The organic layer was collected, dried over magnesium sulfate, filtered and concentrated under reduced pressure, and then purified by column chromatography (dichloromethane:methanol=7:1) to give the title compound (14.4 g, yield: 90%).

Step 230-2: Preparation of tert-butyl (2R,3S)-3-((tert-butyldimethylsilyl)oxy)-2-(hydroxymethyl)pyrrolidine-1-carboxylate (2R,3S)-1-(tert-butoxycarbonyl)-3-((tert-butyldimethysilyl)oxy)pyrrolidine-2-carboxylic acid (2.0 g, 4.3 mmol) obtained from Step 230-1 was dissolved in tetrahydrofuran (50 mL, 0.09 M). Then, the reaction solution was cooled to 0° C. and a borane solution (5.2 mL, 4.7 mmol) was added thereto. The reaction solution was stirred at the same temperature for 1 hour and then stirred at room temperature for 2 hours. A small amount of methanol was added to complete the reaction. After removing the solvent, the reaction solution was diluted with ethyl acetate and washed with saturated sodium chloride solution. The organic layer was collected and the resulting mixture was dried over magnesium sulfate, filtered and concentrated under reduced pressure, and then purified by column chromatography (hexane:ethyl acetate=3:1) to give the title compound (1.1 g, yield 80%).

Step 230-3: Preparation of tert-butyl (2R,3S)-3-((tert-butyldimethylsilyl)oxy)-2-((E)-3-ethoxy-3-oxoprop-1-en-1-yl)pyrrolidine-1-carboxylate Methylene chloride (61 mL, 0.12 M) and oxalyl chloride (0.76 mL, 8.7 mmol) were added to a flask filled with nitrogen and the reaction solution was cooled to −78° C. N,N-dimethylsulfoxide (1.2 mL, 17.4 mmol) was then added at the same temperature and stirred for 30 minutes. Then, tert-butyl (2R,3S)-3-((tert-butyldimethylsilyl)oxy)-2-(hydroxymethyl)pyrrolidine-1-carboxylate (1.4 g, 4.3 mmol) obtained from Step 230-2 was dissolved in a small amount of methylene chloride and slowly added. After stirring at the same temperature for 1 hour, triethylamine (2.4 mL, 17.4 mmol) was added and the temperature of the reaction solution was raised to room temperature from −78° C. When the reaction was completed, the solvent was removed, and the resulting mixture was diluted with ethyl acetate and washed with saturated sodium chloride solution. The organic layer was collected, dried with magnesium sulfate, filtered and concentrated under reduced pressure, and then dissolved in methylene chloride (20 mL, 0.22 M), and (carbethoxymethylene)triphenylphosphorane (3.0 g, 8.7 mmol) was added thereto at room temperature and stirred for 2 hours. When the reaction was completed, the solvent was removed, and the resulting mixture was diluted with ethyl acetate and washed with saturated sodium chloride solution. The organic layer was collected, dried over magnesium sulfate, filtered and concentrated under reduced pressure, and then purified by column chromatography (hexane:ethyl acetate=4:1) to give the title compound (1.5 g, yield: 87%).

Step 230-4: Preparation of (E)-3-((2R,3S)-1-(tert-butoxycarbonyl)-3-((tert-butyldimethylsilyl)oxy)pyrrolidin-2-yl)acrylic acid Tert-butyl (2R,3S)-3-((tert-butyldimethylsilyl)oxy)-2-((E)-3-ethoxy-3-oxoprop-1-en-1-yl)pyrrolidine-1-carboxylate (1.5 g, 3.8 mmol) obtained from Step 230-3 was dissolved in ethanol (27 mL, 0.14 M), and then 2N aqueous sodium hydroxide solution (8 mL) was added thereto and stirred at room temperature for 3 hours. When the reaction was completed, the reaction solution was neutralized with 1N aqueous hydrochloric acid solution, acidified and then diluted with ethyl acetate, and washed with saturated sodium chloride solution. The organic layer was collected, dried over magnesium sulfate, filtered and concentrated under reduced pressure. Subsequent reactions were carried out without purification procedure.

Step 230-5: Preparation of tert-butyl (2R,3S)-3-((tert-butyldimethylsilyl)oxy)-2-((E)-3-hydroxyprop-1-en-1-yl)pyrrolidin-1-carboxylate (E)-3-((2R,3S)-1-(tert-butoxycarbonyl)-3-((tert-butydimethysilyl)oxy)pyrrolidin-2-yl)acrylic acid (400 mg, 1.1 mmol) obtained from Step 230-4 was dissolved in tetrahydrofuran (10 mL, 0.1 M), and the reaction solution was cooled to 0° C. Then, a lithium aluminum hydride solution (0.43 mL, 1.1 mmol) was slowly added thereto, reacted at the same temperature for 30 minutes and then stirred at room temperature for 2 hours. A small amount of water was added to complete the reaction, diluted with ethyl acetate and washed with saturated sodium chloride solution. The organic layer was collected, dried over magnesium sulfate, filtered and concentrated under reduced pressure, and then purified by column chromatography (dichloromethane:methanol=10:1) to give the title compound (328 g, yield: 85%).

Step 230-6: Preparation of tert-butyl (2R,3S)-3-((tert-butyldimethylsilyl)oxy)-2-((E)-3-(5,6-dichloro-1H-benzo[d]imidazol-1-yl)prop-1-en-1-yl)pyrrolidine-1-carboxylate Tert-butyl (2R,3S)-3-((tert-butyldimethylsilyl)oxy)-2-((E)-3-hydroxyprop-1-en-1-yl)pyrrolidin-1-carboxylate (177 mg, 0.49 mmol) obtained from Step 230-5 was added to methylene chloride (5 mL, 0.1 M). The reaction solution was cooled to 0° C., and then a 50% aqueous solution of potassium hydroxide (0.05 mL, 0.49 mmol) and para-toluenesulfonyl chloride (104 mg, 0.55 mmol) were sequentially added at the same temperature, followed by stirring at room temperature for 2 hours. When the reaction was completed, the solvent was removed, and the resulting mixture was diluted with ethyl acetate and washed with saturated sodium chloride solution. The organic layer was collected and dried over magnesium sulfate, filtered and then concentrated under reduced pressure, and dissolved in N,N-dimethylformamide (3 mL, 0.16 M). Then, potassium carbonate (53 mg, 0.38 mmol) and 5,6-dichloro-1H-benzo[d]imidazole (92 mg, 0.49 mmol) were added thereto and stirred at room temperature for 4 hours. When the reaction was completed, the solvent was removed, and the resulting mixture was diluted with ethyl acetate and washed with saturated sodium chloride solution. The organic layer was collected, dried over sodium sulfate, filtered and concentrated under reduced pressure, and then purified by column chromatography (hexane:ethyl acetate=1:1) to give the title compound (155 mg, yield: 60%).

Step 230-7: Preparation of (2R,3S)-2-((E)-3-(5,6-dichloro-1H-benzo[d]imidazol-1-yl)prop-1-en-1-yl) pyrrolidin-3-ol dihydrochloride Tert-butyl (2R,3S)-3-((tert-butyldimethylsilyl)oxy)-2-((E)-3-(5,6-dichloro-1H-benzo[d]imidazol-1-yl)prop-1-en-1-yl)pyrrolidine-1l-carboxylate (43 mg, 0.08 mmol) obtained from Step 230-6 was dissolved in a small amount of tetrahydrofuran and then a 4N hydrogen chloride dioxane solution (2 mL, 0.04M) was added thereto and the mixture was stirred at room temperature for 12 hours. When the reaction was completed, the reaction solution was concentrated under reduced pressure to remove the solvent, dissolved by addition of a small amount of methanol, and then crystallized with diethyl ether to give the title compound (25 mg, yield 79%).

$^1$H-NMR (500 MHz, DMSO-$d_6$): δ 8.80 (s, 1H), 8.11 (s, 1H), 8.04 (s, 1H), 6.12 (m, 1H), 5.78 (m, 1H), 5.02 (d, 2H), 4.05 (m, 1H), 3.81 (m, 1H), 3.22 (m, 2H), 2.10 (m, 1H), 1.79 (m, 1H)

Experimental Example: PRS Enzyme Activity Inhibition Experiment

In order to confirm the biological activities of the compounds prepared in Examples, % inhibition or $IC_{50}$ values of PRS enzyme (phosphoribosylpyrophosphate synthetase enzyme) activities were calculated.

Specifically, the portion corresponding to PRS in cDNA of EPRS was subcloned, and the obtained high-purity PRS protein was purified and used in the experiment. The compounds (1 μM) prepared in Examples were added into the reaction buffer (20 mM $KPO_4$ (pH 7.4), 6 mM MgAc, 5 mM ATP, 400 mg/mL tRNA, 0.5 mM DTT, 20 mCi[$^3$H]proline (1 mCi/mL)) and allowed to react at 37° C. for 5 to 10 minutes. The reaction was terminated with 3M paper that was in advance dried by addition of 5% TCA. The radioactivity was measured using a liquid scintillation counter.

% Inhibition and $IC_{50}$ values of the respective compounds were calculated and analyzed using Microsoft Excel or Sigma Plot 8.0. The results are shown in Tables 1 to 3 below. In Tables 1 to 3, the results are divided into A, B and C according to the range of $IC_{50}$. The case where the derived $IC_{50}$ is 100 nM or less is represented by "A", the case where the $IC_{50}$ is 100 to 500 nM is represented by "B", and the case where the IC50 is 500 nM or higher is represented by "C".

TABLE 1

| Example No. | PRS $IC_{50}$ |
| --- | --- |
| 1 | B |
| 2 | B |
| 3 | C |
| 4 | B |
| 5 | B |
| 6 | C |
| 7 | B |
| 8 | C |
| 9 | C |
| 10 | B |
| 11 | B |
| 12 | B |
| 13 | C |

TABLE 1-continued

| Example No. | PRS $IC_{50}$ |
| --- | --- |
| 14 | C |
| 15 | B |
| 16 | B |
| 17 | C |
| 18 | C |
| 19 | C |
| 20 | C |
| 21 | C |
| 22 | C |
| 23 | B |
| 24 | A |
| 25 | C |
| 26 | C |
| 27 | B |
| 28 | B |
| 29 | C |
| 30 | B |
| 31 | B |
| 32 | B |
| 33 | B |
| 34 | B |
| 35 | B |
| 36 | B |
| 37 | B |
| 38 | C |
| 39 | B |
| 40 | A |
| 41 | C |
| 42 | C |
| 43 | A |
| 44 | B |
| 45 | B |
| 46 | A |
| 47 | B |
| 48 | B |
| 49 | B |
| 50 | B |
| 51 | C |
| 52 | B |
| 53 | B |
| 54 | C |
| 55 | C |
| 56 | B |
| 57 | C |
| 58 | A |
| 59 | B |
| 60 | B |
| 61 | A |
| 62 | B |
| 63 | A |
| 64 | A |
| 65 | B |
| 66 | C |
| 67 | A |
| 68 | C |
| 69 | A |
| 70 | A |
| 71 | B |
| 72 | B |
| 73 | B |
| 74 | B |
| 75 | C |
| 76 | C |
| 77 | B |
| 78 | B |
| 79 | A |
| 80 | A |

TABLE 2

| Example No. | PRS $IC_{50}$ |
| --- | --- |
| 81 | C |
| 82 | C |
| 83 | A |

TABLE 2-continued

| Example No. | PRS IC$_{50}$ |
|---|---|
| 84 | C |
| 85 | B |
| 86 | B |
| 87 | B |
| 88 | C |
| 89 | A |
| 90 | B |
| 91 | A |
| 92 | B |
| 93 | C |
| 94 | B |
| 95 | B |
| 96 | C |
| 97 | A |
| 98 | B |
| 99 | A |
| 100 | B |
| 101 | A |
| 102 | B |
| 103 | C |
| 104 | A |
| 105 | C |
| 106 | B |
| 107 | B |
| 108 | B |
| 109 | A |
| 110 | C |
| 111 | A |
| 112 | B |
| 113 | B |
| 114 | B |
| 115 | B |
| 116 | A |
| 117 | B |
| 118 | C |
| 119 | C |
| 120 | C |
| 121 | B |
| 122 | B |
| 123 | C |
| 124 | C |
| 125 | C |
| 126 | B |
| 127 | B |
| 128 | C |
| 129 | C |
| 130 | B |
| 131 | B |
| 132 | B |
| 133 | C |
| 134 | C |
| 135 | C |
| 136 | C |
| 137 | C |
| 138 | C |
| 139 | C |
| 140 | C |
| 141 | C |
| 142 | C |
| 143 | C |
| 144 | C |
| 145 | C |
| 146 | C |
| 147 | C |
| 148 | B |
| 149 | B |
| 150 | C |
| 151 | B |
| 152 | C |
| 153 | B |
| 154 | B |
| 155 | C |
| 156 | C |
| 157 | C |
| 158 | C |
| 159 | C |
| 160 | C |

TABLE 3

| Example No. | PRS IC$_{50}$ |
|---|---|
| 161 | C |
| 162 | C |
| 163 | C |
| 164 | C |
| 165 | C |
| 166 | B |
| 167 | B |
| 168 | B |
| 169 | C |
| 170 | B |
| 171 | C |
| 172 | C |
| 173 | B |
| 174 | A |
| 175 | B |
| 176 | C |
| 177 | C |
| 178 | B |
| 179 | B |
| 180 | B |
| 181 | B |
| 182 | A |
| 183 | B |
| 184 | C |
| 185 | C |
| 186 | B |
| 187 | A |
| 188 | C |
| 189 | B |
| 190 | B |
| 191 | B |
| 192 | B |
| 193 | C |
| 194 | C |
| 195 | C |
| 196 | C |
| 197 | C |
| 198 | C |
| 199 | C |
| 200 | C |
| 201 | C |
| 202 | B |
| 203 | C |
| 204 | C |
| 205 | C |
| 206 | C |
| 207 | C |
| 208 | C |
| 209 | C |
| 210 | C |
| 211 | C |
| 212 | C |
| 213 | C |
| 214 | B |
| 215 | C |
| 216 | C |
| 217 | C |
| 218 | C |
| 219 | C |
| 220 | C |
| 221 | C |
| 222 | C |
| 223 | C |
| 224 | C |
| 225 | C |
| 226 | C |
| 227 | C |
| 228 | C |
| 229 | C |
| 230 | C |

What is claimed is:

1. A compound represented by the following Chemical Formula 1, or a pharmaceutically acceptable salt thereof:

[Chemical Formula 1]

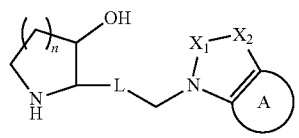

in Chemical Formula 1, n is 1 or 2,

L is —CH$_2$CH$_2$—, —CH=C(R')—, or —C≡C—, wherein R' is hydrogen, C$_{1-4}$ alkyl, or halogen, X$_1$ is CR$_1$R$_2$, NR$_1$, or —CO—, X$_2$ is CR$_3$R$_4$, or NR$_3$, wherein R$_1$ to R$_4$ are each independently hydrogen, C$_{1-4}$ alkyl, C$_{1-4}$ hydroxyalkyl, hydroxy, amino, carboxy, —COO(C$_{1-4}$ alkyl), —CONH$_2$, —CONH(C$_{1-4}$ alkyl), —CON(C$_{1-4}$ alkyl)$_2$, or pyrazolyl unsubstituted or substituted with C$_{1-4}$ haloalkyl; or R$_1$ and R$_3$, together with each other, links X$_1$ and X$_2$ via a double bond, and A is benzene, pyridine, pyrimidine, or pyrimidinedione ring, wherein A is unsubstituted or substituted with one to three substituents each independently selected from the group consisting of a ring-type substituent selected from the group consisting of furanyl, imidazolyl, isoxazolyl, phenyl, pyrazolyl, pyridinonyl, pyridinyl, pyrrolyl, thiazolyl, and thiophenyl; C$_{1-4}$ alkyl; C$_{1-4}$ alkoxy; C$_{1-4}$ haloalkyl; C$_{1-4}$ haloalkoxy; halogen; di(C$_{1-4}$ alkyl) amino; nitro; —COO(C$_{1-4}$ alkyl); dihydropyranyl; morpholino; piperidinyl; and pyrrolidinyl; and wherein the ring-type substituent is unsubstituted or substituted with one or two substituents each independently selected from the group consisting of C$_{1-5}$ alkyl, C$_{1-4}$ haloalkyl, C$_{3-6}$ cycloalkyl, monovalent of C$_{2-5}$ alkylene carbonate, —COO(C$_{1-4}$ alkyl), halogen, cyano, thiazolyl, and (1,3-dioxolan-2-yl)methyl.

2. The compound or a pharmaceutically acceptable salt thereof according to claim 1, wherein, A is unsubstituted or substituted with one to three substituents each independently selected from the group consisting of C$_{1-4}$ alkyl; C$_{1-4}$ alkoxy; C$_{1-4}$ haloalkyl; halogen; phenyl unsubstituted or substituted with halogen, or C$_{1-4}$ haloalkyl; pyrazolyl unsubstituted or substituted with C$_{1-5}$ alkyl, thiazolyl, or C$_{1-4}$ haloalkyl; thiophenyl unsubstituted or substituted with C$_{1-5}$ alkyl, or —COO(C$_{1-4}$ alkyl); pyrrolyl unsubstituted or substituted with C$_{1-5}$ alkyl and/or —COO(C$_{1-4}$ alkyl); di(C$_{1-4}$ alkyl) amino; morpholino; piperidinyl; furanyl; and pyrrolidinyl.

3. The compound or a pharmaceutically acceptable salt thereof according to claim 1, wherein L is —CH$_2$CH$_2$—, —CH=CH—, —CH=CF—, —CH=C(CH$_3$)—, or —C≡C—.

4. The compound or a pharmaceutically acceptable salt thereof according to claim 1, wherein the compound represented by Chemical Formula 1 is represented by the following Chemical Formulas 1-1 to 1-5:

[Chemical Formula 1-1]

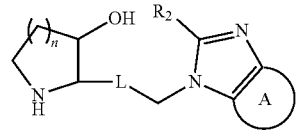

[Chemical Formula 1-2]

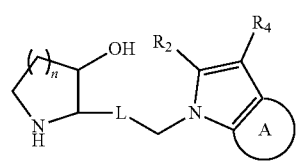

[Chemical Formula 1-3]

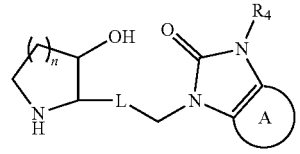

[Chemical Formula 1-4]

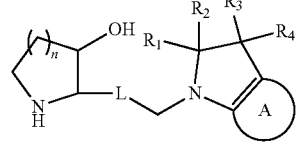

[Chemical Formula 1-5]

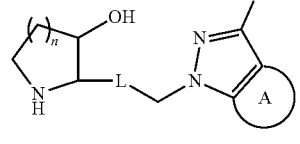

in Chemical Formulas 1-1 to 1-5, n, L, R$_1$ to R$_4$ and A are as defined in claim 1.

5. The compound or a pharmaceutically acceptable salt thereof according to claim 1, wherein R$_1$ to R$_4$ are each independently hydrogen, methyl, hydroxymethyl, hydroxy, amino, carboxy, —COOCH$_3$, —CONH$_2$, —CONHCH$_3$, or —CON(CH$_3$)$_2$; or R$_1$ and R$_3$, together with each other, link X$_1$ and X$_2$ via a double bond.

6. The compound or a pharmaceutically acceptable salt thereof according to claim 1, wherein A is benzene, pyridine, pyrimidine, or pyrimidinedione ring, and A is unsubstituted or substituted with one to three substituents each independently selected from the group consisting of methyl, isobutyl, methoxy, trifluoromethyl, fluoro, chloro, bromo, phenyl, phenyl substituted with fluoro, phenyl substituted with chloro, phenyl substituted with trifluoromethyl, thiophenyl, thiophenyl substituted with methyl, thiophenyl substituted with —COOCH$_3$, pyrazolyl substituted with difluoromethyl, pyrazolyl substituted with methyl, pyrazolyl substituted with thiazolyl, pyrrolyl substituted with methyl and —COOCH$_2$CH$_3$, furanyl, dimethylamino, diethylamino, methylethylamino, morpholino, piperidinyl, and pyrrolidinyl.

7. The compound or a pharmaceutically acceptable salt thereof according to claim 1, wherein A is benzene, and A is unsubstituted or substituted with one to three substituents each independently selected from the group consisting of C$_{1-4}$ alkyl; C$_{1-4}$ alkoxy; halogen; and phenyl unsubstituted or substituted with halogen or C$_{1-4}$ haloalkyl.

8. The compound or a pharmaceutically acceptable salt thereof according to claim 1, wherein A is pyridine, and A is unsubstituted or substituted with one or two substituents each independently selected from the group consisting of $C_{1-4}$ alkyl; $C_{1-4}$ alkoxy; halogen; and phenyl substituted with halogen.

9. The compound or a pharmaceutically acceptable salt thereof according to claim 1, wherein A is pyrimidine, and A is substituted with a substituent selected from the group consisting of halogen; di($C_{1-4}$ alkyl)amino; morpholino; piperidinyl; and pyrrolidinyl.

10. The compound or a pharmaceutically acceptable salt thereof according to claim 1, wherein A is pyrimidinedione, and A is unsubstituted or substituted with one or two $C_{1-4}$ alkyl.

11. A compound or a pharmaceutically acceptable salt thereof, wherein the compound is selected from the group consisting of:
1) (2R,3S)-2-(3-(6-chloro-1H-benzo[d]imidazol-1-yl)propyl)piperidin-3-ol,
2) (2R,3S)-2-(3-(4-bromo-1H-benzo[d]imidazol-1-yl)propyl)piperidin-3-ol,
3) (2R,3S)-2-(3-(5-bromo-1H-benzo[d]imidazol-1-yl)propyl)piperidin-3-ol,
4) (2R,3S)-2-(3-(6-bromo-1H-benzo[d]imidazol-1-yl)propyl)piperidin-3-ol,
5) (2R,3S)-2-(3-(7-bromo-1H-benzo[d]imidazol-1-yl)propyl)piperidin-3-ol,
6) (2R,3S)-2-(3-(4-fluoro-1H-benzo[d]imidazol-1-yl)propyl)piperidin-3-ol,
7) (2R,3S)-2-(3-(5-fluoro-1H-benzo[d]imidazol-1-yl)propyl)piperidin-3-ol,
8) (2R,3S)-2-(3-(6-fluoro-1H-benzo[d]imidazol-1-yl)propyl)piperidin-3-ol,
9) (2R,3S)-2-(3-(7-fluoro-1H-benzo[d]imidazol-1-yl)propyl)piperidin-3-ol,
10) (2R,3S)-2-(3-(4-chloro-1H-benzo[d]imidazol-1-yl)propyl)piperidin-3-ol,
11) (2R,3S)-2-(3-(5-chloro-1H-benzo[d]imidazol-1-yl)propyl)piperidin-3-ol,
12) (2R,3S)-2-(3-(7-chloro-1H-benzo[d]imidazol-1-yl)propyl)piperidin-3-ol,
13) (2R,3S)-2-(3-(6-methyl-1H-benzo[d]imidazol-1-yl)propyl)piperidin-3-ol,
14) (2R,3S)-2-(3-(5-methyl-1H-benzo[d]imidazol-1-yl)propyl)piperidin-3-ol,
15) (2R,3S)-2-(3-(6-(trifluoromethyl)-1H-benzo[d]imidazol-1-yl)propyl)piperidin-3-ol,
16) (2R,3S)-2-(3-(7-(trifluoromethyl)-1H-benzo[d]imidazol-1-yl)propyl)piperidin-3-ol,
17) (2R,3S)-2-(3-(7-(trifluoromethoxy)-1H-benzo[d]imidazol-1-yl)propyl)piperidin-3-ol,
18) (2R,3S)-2-(3-(4-(pyrrolidin-1-yl)-1H-benzo[d]imidazol-1-yl)propyl)piperidin-3-ol,
19) (2R,3S)-2-(3-(4-(piperidin-1-yl)-1H-benzo[d]imidazol-1-yl)propyl)piperidin-3-ol,
20) (2R,3S)-2-(3-(4-(3-fluorophenyl)-1H-benzo[d]imidazol-1-yl)propyl)piperidin-3-ol,
21) (2R,3S)-2-(3-(4-(3-chlorophenyl)-1H-benzo[d]imidazol-1-yl)propyl)piperidin-3-ol,
22) (2R,3S)-2-(3-(5-(3-fluorophenyl)-1H-benzo[d]imidazol-1-yl)propyl)piperidin-3-ol,
23) (2R,3S)-2-(3-(6-(2-fluorophenyl)-1H-benzo[d]imidazol-1-yl)propyl)piperidin-3-ol,
24) (2R,3S)-2-(3-(6-(3-fluorophenyl)-1H-benzo[d]imidazol-1-yl)propyl)piperidin-3-ol,
25) (2R,3S)-2-(3-(6-(4-fluorophenyl)-1H-benzo[d]imidazol-1-yl)propyl)piperidin-3-ol,
26) (2R,3S)-2-(3-(7-(2-fluorophenyl)-1H-benzo[d]imidazol-1-yl)propyl)piperidin-3-ol,
27) (2R,3S)-2-(3-(7-(3-fluorophenyl)-1H-benzo[d]imidazol-1-yl)propyl)piperidin-3-ol,
28) (2R,3S)-2-(3-(7-(4-fluorophenyl)-1H-benzo[d]imidazol-1-yl)propyl)piperidin-3-ol,
29) (2R,3S)-2-(3-(5-(1H-pyrazol-4-yl)-1H-benzo[d]imidazol-1-yl)propyl)piperidin-3-ol,
30) (2R,3S)-2-(3-(6-(1H-pyrazol-4-yl)-1H-benzo[d]imidazol-1-yl)propyl)piperidin-3-ol,
31) (2R,3S)-2-(3-(7-(1H-pyrazol-4-yl)-1H-benzo[d]imidazol-1-yl)propyl)piperidin-3-ol,
32) (2R,3S)-2-(3-(6-chloro-5-fluoro-1H-benzo[d]imidazol-1-yl)propyl)piperidin-3-ol,
33) (2R,3S)-2-(3-(6-bromo-5-fluoro-1H-benzo[d]imidazol-1-yl)propyl)piperidin-3-ol,
34) (2R,3S)-2-(3-(5-chloro-6-fluoro-1H-benzo[d]imidazol-1-yl)propyl)piperidin-3-ol,
35) (2R,3S)-2-(3-(5-bromo-6-fluoro-1H-benzo[d]imidazol-1-yl)propyl)piperidin-3-ol,
36) (2R,3S)-2-(3-(6-bromo-5-chloro-1H-benzo[d]imidazol-1-yl)propyl)piperidin-3-ol,
37) (2R,3S)-2-(3-(6-chloro-5-methoxy-1H-benzo[d]imidazol-1-yl)propyl)piperidin-3-ol,
38) (2R,3S)-2-(3-(6-fluoro-5-methoxy-1H-benzo[d]imidazol-1-yl)propyl)piperidin-3-ol,
39) (2R,3S)-2-(3-(5-fluoro-6-methyl-1H-benzo[d]imidazol-1-yl)propyl)piperidin-3-ol,
40) (2R,3S)-2-(3-(4,5-dichloro-1H-benzo[d]imidazol-1-yl)propyl)piperidin-3-ol,
41) (2S,3S)-2-(3-(4,5-dichloro-1H-benzo[d]imidazol-1-yl)propyl)piperidin-3-ol,
42) (2S,3R)-2-(3-(4,5-dichloro-1H-benzo[d]imidazol-1-yl)propyl)piperidin-3-ol,
43) (2R,3R)-2-(3-(4,5-dichloro-1H-benzo[d]imidazol-1-yl)propyl)piperidin-3-ol,
44) (2R,3S)-2-(3-(4-chloro-5-methyl-1H-benzo[d]imidazol-1-yl)propyl)piperidin-3-ol,
45) (2R,3S)-2-(3-(5-bromo-4-methyl-1H-benzo[d]imidazol-1-yl)propyl)piperidin-3-ol,
46) (2R,3S)-2-(3-(5-chloro-4-methyl-1H-benzo[d]imidazol-1-yl)propyl)piperidin-3-ol,
47) (2R,3S)-2-(3-(5-bromo-4-fluoro-1H-benzo[d]imidazol-1-yl)propyl)piperidin-3-ol,
48) (2R,3S)-2-(3-(6-bromo-7-fluoro-1H-benzo[d]imidazol-1-yl)propyl)piperidin-3-ol,
49) (2R,3S)-2-(3-(4,5-difluoro-1H-benzo[d]imidazol-1-yl)propyl)piperidin-3-ol,
50) (2R,3S)-2-(3-(6,7-difluoro-1H-benzo[d]imidazol-1-yl)propyl)piperidin-3-ol,
51) (2R,3S)-2-(3-(4,5-dimethyl-1H-benzo[d]imidazol-1-yl)propyl)piperidin-3-ol,
52) (2R,3S)-2-(3-(5,6-difluoro-1H-benzo[d]imidazol-1-yl)propyl)piperidin-3-ol,
53) (2R,3S)-2-(3-(5,6-dichloro-1H-benzo[d]imidazol-1-yl)propyl)piperidin-3-ol,
54) (2R,3S)-2-(3-(5,6-dibromo-1H-benzo[d]imidazol-1-yl)propyl)piperidin-3-ol,
55) (2R,3S)-2-(3-(5,6-dimethyl-1H-benzo[d]imidazol-1-yl)propyl)piperidin-3-ol,
56) (2R,3S)-2-(3-(6,7-dichloro-1H-benzo[d]imidazol-1-yl)propyl)piperidin-3-ol,
57) (2R,3S)-2-(3-(4,6-difluoro-1H-benzo[d]imidazol-1-yl)propyl)piperidin-3-ol,
58) (2R,3S)-2-(3-(5,7-difluoro-1H-benzo[d]imidazol-1-yl)propyl)piperidin-3-ol,
59) (2R,3S)-2-(3-(4-chloro-5-methoxy-1H-benzo[d]imidazol-1-yl)propyl)piperidin-3-ol, 60) (2R,3S)-2-(3-(7-chloro-6-methoxy-1H-benzo[d]imidazol-1-yl)propyl)piperidin-3-ol,
61) (2R,3S)-2-(3-(6-chloro-4-methyl-1H-benzo[d]imidazol-1-yl)propyl)piperidin-3-ol,
62) (2R,3S)-2-(3-(4-chloro-5-fluoro-1H-benzo[d]imidazol-1-yl)propyl)piperidin-3-ol,
63) (2R,3S)-2-(3-(6-bromo-4-methyl-1H-benzo[d]imidazol-1-yl)propyl)piperidin-3-ol,
64) (2R,3S)-2-(3-(5-fluoro-4-methyl-1H-benzo[d]imidazol-1-yl)propyl)piperidin-3-ol,
65) (2R,3S)-2-(3-(6-fluoro-7-methyl-1H-benzo[d]imidazol-1-yl)propyl)piperidin-3-ol,
66) (2R,3S)-2-(3-(4-chloro-5-(trifluoromethyl)-1H-benzo[d]imidazol-1-yl)propyl)piperidin-3-ol,
67) (2R,3S)-2-(3-(7-chloro-6-(trifluoromethyl)-1H-benzo[d]imidazol-1-yl)propyl)piperidin-3-ol,
68) methyl 7-bromo-1-(3-((2R,3S)-3-hydroxypiperidin-2-yl)propyl)-1H-benzo[d]imidazole-5-carboxylate,
69) (2R,3S)-2-(3-(7-bromo-5-chloro-1H-benzo[d]imidazol-1-yl)propyl)piperidin-3-ol,
70) (2R,3S)-2-(3-(5-bromo-7-chloro-1H-benzo[d]imidazol-1-yl)propyl)piperidin-3-ol,
71) (2R,3S)-2-(3-(7-bromo-5-(trifluoromethyl)-1H-benzo[d]imidazol-1-yl)propyl)piperidin-3-ol,
72) (2R,3S)-2-(3-(6-bromo-4-fluoro-1H-benzo[d]imidazol-1-yl)propyl)piperidin-3-ol,
73) (2R,3S)-2-(3-(5-bromo-7-fluoro-1H-benzo[d]imidazol-1-yl)propyl)piperidin-3-ol,
74) (2R,3S)-2-(3-(7-chloro-4-fluoro-1H-benzo[d]imidazol-1-yl)propyl)piperidin-3-ol,
75) (2R,3S)-2-(3-(5-bromo-4-nitro-1H-benzo[d]imidazol-1-yl)propyl)piperidin-3-ol,
76) (2R,3S)-2-(3-(6-bromo-7-nitro-1H-benzo[d]imidazol-1-yl)propyl)piperidin-3-ol,
77) (2R,3S)-2-(3-(4-chloro-5-nitro-1H-benzo[d]imidazol-1-yl)propyl)piperidin-3-ol,
78) (2R,3S)-2-(3-(7-chloro-5-(trifluoromethyl)-1H-benzo[d]imidazol-1-yl)propyl)piperidin-3-ol,
79) (2R,3S)-2-(3-(5-chloro-7-fluoro-1H-benzo[d]imidazol-1-yl)propyl)piperidin-3-ol,
80) (2R,3S)-2-(3-(5,7-dichloro-1H-benzo[d]imidazol-1-yl)propyl)piperidin-3-ol,
81) (2R,3S)-2-(3-(5-chloro-7-(1H-pyrazol-4-yl)-1H-benzo[d]imidazol-1-yl)propyl)piperidin-3-ol,
82) (2R,3S)-2-(3-(7-(1H-pyrazol-4-yl)-5-(trifluoromethyl)-1H-benzo[d]imidazol-1-yl)propyl)piperidin-3-ol,
83) (2R,3S)-2-(3-(5-chloro-7-(3-fluorophenyl)-1H-benzo[d]imidazol-1-yl)propyl)piperidin-3-ol,
84) (2R,3S)-2-(3-(7-(3-fluorophenyl)-5-(trifluoromethyl)-1H-benzo[d]imidazol-1-yl)propyl)piperidin-3-ol,
85) (2R,3S)-2-(3-(5-chloro-7-(2-methylthiazol-5-yl)-1H-benzo[d]imidazol-1-yl)propyl)piperidin-3-ol,
86) (2R,3S)-2-(3-(5-chloro-7-(pyridin-3-yl)-1H-benzo[d]imidazol-1-yl)propyl)piperidin-3-ol,
87) (2R,3S)-2-(3-(5-chloro-7-(5-fluoropyridin-3-yl)-1H-benzo[d]imidazol-1-yl)propyl)piperidin-3-ol,
88) 5-(5-chloro-1-(3-((2R,3S)-3-hydroxypiperidin-2-yl)propyl)-1H-benzo[d]imidazol-7-yl)-1-methylpyridin-2(1H)-one,
89) (2R,3S)-2-(3-(5-chloro-7-(1-(difluoromethyl)-1H-pyrazol-4-yl)-1H-benzo[d]imidazol-1-yl)propyl)piperidin-3-ol,
90) (2R,3S)-2-(3-(5-chloro-7-(isoxazol-3-yl)-1H-benzo[d]imidazol-1-yl)propyl)piperidin-3-ol,
91) (2R,3S)-2-(3-(5-chloro-7-(thiophen-3-yl)-1H-benzo[d]imidazol-1-yl)propyl)piperidin-3-ol,
92) (2R,3S)-2-(3-(5-chloro-7-(2-methylthiophen-3-yl)-1H-benzo[d]imidazol-1-yl)propyl)piperidin-3-ol,
93) (2R,3S)-2-(3-(5-chloro-7-(3,5-dimethylisoxazol-4-yl)-1H-benzo[d]imidazol-1-yl)propyl)piperidin-3-ol,
94) (2R,3S)-2-(3-(5-chloro-7-(3,6-dihydro-2H-pyran-4-yl)-1H-benzo[d]imidazol-1-yl)propyl)piperidin-3-ol,
95) (2R,3S)-2-(3-(7-(1-((1,3-dioxolan-2-yl)methyl)-1H-pyrazol-4-yl)-5-chloro-1H-benzo[d]imidazol-1-yl)propyl)piperidin-3-ol,
96) (2R,3S)-2-(3-(5-chloro-7-(1-methyl-1H-imidazol-5-yl)-1H-benzo[d]imidazol-1-yl)propyl)piperidin-3-ol,
97) (2R,3S)-2-(3-(5-chloro-7-(1-methyl-1H-pyrazol-4-yl)-1H-benzo[d]imidazol-1-yl)propyl)piperidin-3-ol,
98) (2R,3S)-2-(3-(7-(pyrrolidin-1-yl)-1H-benzo[d]imidazol-1-yl)propyl)piperidin-3-ol,
99) (2R,3S)-2-(3-(5-chloro-7-(pyrrolidin-1-yl)-1H-benzo[d]imidazol-1-yl)propyl)piperidin-3-ol,
100) (2R,3S)-2-(3-(5-chloro-7-(2-cyclopropylthiazol-5-yl)-1H-benzo[d]imidazol-1-yl)propyl)piperidin-3-ol,
101) (2R,3S)-2-(3-(5-chloro-7-(1-(thiazol-2-yl)-1H-pyrazol-4-yl)-1H-benzo[d]imidazol-1-yl)propyl)piperidin-3-ol,
102) (2R,3S)-2-(3-(5-chloro-7-(1-(oxetan-3-yl)-1H-pyrazol-4-yl)-1H-benzo[d]imidazol-1-yl)propyl)piperidin-3-ol,
103) (2R,3S)-2-(3-(5-chloro-7-(2-(tetrahydro-2H-pyran-4-yl)thiazol-4-yl)-1H-benzo[d]imidazol-1-yl)propyl)piperidin-3-ol,
104) (2R,3S)-2-(3-(5-chloro-7-(furan-3-yl)-1H-benzo[d]imidazol-1-yl)propyl)piperidin-3-ol,
105) 4-(5-chloro-1-(3-((2R,3S)-3-hydroxypiperidin-2-yl)propyl)-1H-benzo[d]imidazol-7-yl)thiazole-2-carbonitrile,
106) (2R,3S)-2-(3-(7-(1-(tert-butyl)-1H-pyrazol-4-yl)-5-chloro-1H-benzo[d]imidazol-1-yl)propyl)piperidin-3-ol,
107) (2R,3S)-2-(3-(5-chloro-7-(1-isopentyl-1H-pyrazol-4-yl)-1H-benzo[d]imidazol-1-yl)propyl)piperidin-3-ol,
108) (2R,3S)-2-(3-(5-chloro-7-(1-isopropyl-1H-pyrazol-4-yl)-1H-benzo[d]imidazol-1-yl)propyl)piperidin-3-ol,
109) (2R,3S)-2-(3-(5-chloro-7-(4-methylthiophen-3-yl)-1H-benzo[d]imidazol-1-yl)propyl)piperidin-3-ol,
110) ethyl 3-(5-chloro-1-(3-((2R,3S)-3-hydroxypiperidin-2-yl)propyl)-1H-benzo[d]imidazol-7-yl)furan-2-carboxylate,
111) methyl 4-(5-chloro-1-(3-((2R,3S)-3-hydroxypiperidin-2-yl)propyl)-1H-benzo[d]imidazol-7-yl)thiophene-2-carboxylate,
112) (2R,3S)-2-(3-(5-chloro-7-(1-(2-fluoroethyl)-1H-pyrazol-4-yl)-1H-benzo[d]imidazol-1-yl)propyl)piperidin-3-ol,
113) (2R,3S)-2-(3-(7-(1-butyl-1H-pyrazol-4-yl)-5-chloro-1H-benzo[d]imidazol-1-yl)propyl)piperidin-3-ol,
114) (2R,3S)-2-(3-(5-chloro-7-(2,5-dimethylthiophen-3-yl)-1H-benzo[d]imidazol-1-yl)propyl)piperidin-3-ol,
115) (2R,3S)-2-(3-(5-chloro-7-(1-isobutyl-1H-pyrazol-4-yl)-1H-benzo[d]imidazol-1-yl)propyl)piperidin-3-ol,
116) ethyl 4-(5-chloro-1-(3-((2R,3S)-3-hydroxypiperidin-2-yl)propyl)-1H-benzo[d]imidazol-7-yl)-1-methyl-1H-pyrrole-2-carboxylate,
117) (2R,3S)-2-(3-(5-chloro-1H-imidazo[4,5-b]pyridin-1-yl)propyl)piperidin-3-ol,
118) (2R,3S)-2-(3-(5-chloro-3H-imidazo[4,5-b]pyridin-3-yl)propyl)piperidin-3-ol, 119) (2R,3S)-2-(3-(5-bromo-1H-imidazo[4,5-b]pyridin-1-yl)propyl)piperidin-3-ol,
120) (2R,3S)-2-(3-(6-bromo-1H-imidazo[4,5-b]pyridin-1-yl)propyl)piperidin-3-ol,
121) (2R,3S)-2-(3-(5-methyl-1H-imidazo[4,5-b]pyridin-1-yl)propyl)piperidin-3-ol,
122) (2R,3S)-2-(3-(6-chloro-1H-imidazo[4,5-c]pyridin-1-yl)propyl)piperidin-3-ol,
123) (2R,3S)-2-(3-(6-chloro-3H-imidazo[4,5-c]pyridin-3-yl)propyl)piperidin-3-ol,
124) (2R,3S)-2-(3-(6-bromo-1H-imidazo[4,5-c]pyridin-1-yl)propyl)piperidin-3-ol,
125) (2R,3S)-2-(3-(6-bromo-3H-imidazo[4,5-c]pyridin-3-yl)propyl)piperidin-3-ol,
126) (2R,3S)-2-(3-(7-chloro-1H-imidazo[4,5-b]pyridin-1-yl)propyl)piperidin-3-ol,
127) (2R,3S)-2-(3-(5,6-dichloro-1H-imidazo[4,5-b]pyridin-1-yl)propyl)piperidin-3-ol,
128) (2R,3S)-2-(3-(7-bromo-1H-imidazo[4,5-c]pyridin-1-yl)propyl)piperidin-3-ol,
129) (2R,3S)-2-(3-(5-(trifluoromethyl)-3H-imidazo[4,5-b]pyridin-3-yl)propyl)piperidin-3-ol,
130) (2R,3S)-2-(3-(6,7-dichloro-3H-imidazo[4,5-b]pyridin-3-yl)propyl)piperidin-3-ol,
131) (2R,3S)-2-(3-(6-chloro-7-methyl-3H-imidazo[4,5-b]pyridin-3-yl)propyl)piperidin-3-ol,
132) (2R,3S)-2-(3-(6-bromo-7-methyl-3H-imidazo[4,5-b]pyridin-3-yl)propyl)piperidin-3-ol,
133) (2R,3S)-2-(3-(6-bromo-7-chloro-3H-imidazo[4,5-b]pyridin-3-yl)propyl)piperidin-3-ol,
134) (2R,3S)-2-(3-(7-chloro-6-(3-chlorophenyl)-3H-imidazo[4,5-b]pyridin-3-yl)propyl)piperidin-3-ol,
135) (2R,3S)-2-(3-(2-chloro-7H-purin-7-yl)propyl)piperidin-3-ol,
136) (2R,3S)-2-(3-(2-chloro-9H-purin-9-yl)propyl)piperidin-3-ol,
137) (2R,3S)-2-(3-(6-(dimethylamino)-9H-purin-9-yl)propyl)piperidin-3-ol,
138) (2R,3S)-2-(3-(6-(diethylamino)-9H-purin-9-yl)propyl)piperidin-3-ol,
139) (2R,3S)-2-(3-(6-(ethyl(methyl)amino)-9H-purin-9-yl)propyl)piperidin-3-ol,
140) (2R,3S)-2-(3-(6-morpholino-9H-purin-9-yl)propyl)piperidin-3-ol,
141) (2R,3S)-2-(3-(6-(piperidin-1-yl)-9H-purin-9-yl)propyl)piperidin-3-ol,
142) (2R,3S)-2-(3-(6-(pyrrolidin-1-yl)-9H-purin-9-yl)propyl)piperidin-3-ol,
143) 1-(3-((2R,3S)-3-hydroxypiperidin-2-yl)propyl)-1H-benzo[d]imidazol-2-ol,
144) 5,6-dichloro-1-(3-((2R,3S)-3-hydroxypiperidin-2-yl)propyl)-1H-benzo[d]imidazol-2-ol,
145) (2R,3S)-2-(3-(2-(hydroxymethyl)-1H-benzo[d]imidazol-1-yl)propyl)piperidin-3-ol,
146) (2R,3S)-2-(3-(2-(hydroxymethyl)-4,5-dimethyl-1H-benzo[d]imidazol-1-yl)propyl)piperidin-3-ol,
147) (2R,3S)-2-(3-(5,6-dichloro-2-(hydroxymethyl)-1H-benzo[d]imidazol-1-yl)propyl)piperidin-3-ol,
148) (2R,3S)-2-(3-(2-amino-5,6-dichloro-1H-benzo[d]imidazol-1-yl)propyl)piperidin-3-ol,
149) methyl 7-bromo-1-(3-((2R,3S)-3-hydroxypiperidin-2-yl)propyl)-1H-indole-3-carboxylate,
150) methyl 5-bromo-1-(3-((2R,3S)-3-hydroxypiperidin-2-yl)propyl)-1H-indole-3-carboxylate,
151) methyl 6-bromo-1-(3-((2R,3S)-3-hydroxypiperidin-2-yl)propyl)-1H-indole-3-carboxylate,
152) methyl 4-chloro-1-(3-((2R,3S)-3-hydroxypiperidin-2-yl)propyl)-1H-indole-3-carboxylate,
153) methyl 6-chloro-1-(3-((2R,3S)-3-hydroxypiperidin-2-yl)propyl)-1H-indole-3-carboxylate,
154) methyl 7-chloro-1-(3-((2R,3S)-3-hydroxypiperidin-2-yl)propyl)-1H-indole-3-carboxylate,
155) (2R,3S)-2-(3-(5-chloro-3-cyclopropyl-1H-indazol-1-yl)propyl)piperidin-3-ol,
156) (2R,3S)-2-(3-(5-chloro-3-(trifluoromethyl)-1H-indazol-1-yl)propyl)piperidin-3-ol,
157) (2R,3S)-2-(3-(5-chloro-3-(1-(difluoromethyl)-1H-pyrazol-4-yl)-1H-indazol-1-yl)propyl)piperidin-3-ol,
158) (2R,3S)-2-(3-(6-chloro-3-(1-(difluoromethyl)-1H-pyrazol-4-yl)-1H-indazol-1-yl)propyl)piperidin-3-ol,
159) 1-(3-((2R,3S)-3-hydroxypiperidin-2-yl)propyl)-3-methyl-1H-benzo[d]imidazol-2(3H)-one,
160) 5-bromo-1-(3-((2R,3S)-3-hydroxypiperidin-2-yl)propyl)-1H-benzo[d]imidazol-2(3H)-one,
161) 6-bromo-1-(3-((2R,3S)-3-hydroxypiperidin-2-yl)propyl)-1H-benzo[d]imidazol-2(3H)-one,
162) 7-(3-((2R,3S)-3-hydroxypiperidin-2-yl)propyl)-1,3-dimethyl-1H-purine-2,6(3H,7H)-dione,
163) 7-(3-((2R,3S)-3-hydroxypiperidin-2-yl)propyl)-3-methyl-1H-purine-2,6(3H,7H)-dione,
164) 9-(3-((2R,3S)-3-hydroxypiperidin-2-yl)propyl)-1-methyl-1H-purine-2,6(3H,9H)-dione,
165) 7-(3-((2R,3S)-3-hydroxypiperidin-2-yl)propyl)-3-isobutyl-1-methyl-1H-purine-2,6(3H,7H)-dione,
166) (2R,3S)-2-((E)-3-(5,6-dichloro-1H-benzo[d]imidazol-1-yl)prop-1-enyl)piperidin-3-ol,
167) (2R,3S)-2-((E)-3-(5-fluoro-4-methyl-1H-benzo[d]imidazol-1-yl)prop-1-enyl)piperidin-3-ol,
168) (2R,3S)-2-((E)-3-(5-bromo-4-methyl-1H-benzo[d]imidazol-1-yl)prop-1-enyl)piperidin-3-ol,
169) (2R,3S)-2-((E)-3-(5,6-dimethyl-1H-benzo[d]imidazol-1-yl)prop-1-enyl)piperidin-3-ol,
170) (2R,3S)-2-((E)-3-(5,6-dibromo-1H-benzo[d]imidazol-1-yl)prop-1-enyl)piperidin-3-ol,
171) (2R,3S)-2-((E)-3-(5,6-difluoro-1H-benzo[d]imidazol-1-yl)prop-1-enyl)piperidin-3-ol,
172) (2R,3S)-2-((E)-3-(4,5-dimethyl-1H-benzo[d]imidazol-1-yl)prop-1-enyl)piperidin-3-ol,
173) (2R,3S)-2-((E)-3-(5-chloro-4-methyl-1H-benzo[d]imidazol-1-yl)prop-1-enyl)piperidin-3-ol,
174) (2R,3S)-2-((E)-3-(4,5-dichloro-1H-benzo[d]imidazol-1-yl)prop-1-en-1-yl)piperidin-3-ol,
175) (2R,3S)-2-((E)-3-(4-chloro-5-methyl-1H-benzo[d]imidazol-1-yl)prop-1-en-1-yl)piperidin-3-ol,
176) (2R,3S)-2-((E)-3-(5-bromo-4-nitro-1H-benzo[d]imidazol-1-yl)prop-1-en-1-yl)piperidin-3-ol,
177) (2R,3S)-2-((E)-3-(6-bromo-7-nitro-1H-benzo[d]imidazol-1-yl)prop-1-en-1-yl)piperidin-3-ol,
178) (2R,3S)-2-((E)-3-(4-chloro-5-nitro-1H-benzo[d]imidazol-1-yl)prop-1-en-1-yl)piperidin-3-ol,
179) (2R,3S)-2-((E)-3-(4,6-difluoro-1H-benzo[d]imidazol-1-yl)prop-1-en-1-yl)piperidin-3-ol,
180) (2R,3S)-2-((E)-3-(6-chloro-4-methyl-1H-benzo[d]imidazol-1-yl)prop-1-en-1-yl)piperidin-3-ol,
181) (2R,3S)-2-((E)-3-(7-chloro-5-(trifluoromethyl)-1H-benzo[d]imidazol-1-yl)prop-1-en-1-yl)piperidin-3-ol,
182) (2R,3S)-2-((E)-3-(5,7-dichloro-1H-benzo[d]imidazol-1-yl)prop-1-en-1-yl)piperidin-3-ol,
183) (2R,3S)-2-((E)-3-(5-chloro-7-fluoro-1H-benzo[d]imidazol-1-yl)prop-1-en-1-yl)piperidin-3-ol,
184) (2R,3S)-2-((E)-3-(5-bromo-1H-imidazo[4,5-b]pyridin-1-yl)prop-1-enyl)piperidin-3-ol, 185) (2R,3S)-2-((E)-3-(7-chloro-6-(3-chlorophenyl)-3H-imidazo[4,5-b]pyridin-3-yl)prop-1-enyl)piperidin-3-ol,
186) (2R,3S)-2-((E)-3-(6-bromo-7-methyl-3H-imidazo[4,5-b]pyridin-3-yl)prop-1-enyl)piperidin-3-ol,
187) (2R,3S)-2-((E)-3-(6-bromo-7-chloro-3H-imidazo[4,5-b]pyridin-3-yl)prop-1-enyl)piperidin-3-ol,
188) (2R,3S)-2-((E)-3-(6-chloro-7-methyl-3H-imidazo[4,5-b]pyridin-3-yl)prop-1-enyl)piperidin-3-ol,
189) (2R,3S)-2-((E)-3-(6,7-dichloro-3H-imidazo[4,5-b]pyridin-3-yl)prop-1-enyl)piperidin-3-ol,
190) (2R,3S)-2-((E)-3-(6-(3-chlorophenyl)-1H-benzo[d]imidazol-1-yl)prop-1-enyl)piperidin-3-ol,
191) (2R,3S)-2-((E)-3-(6-(3-fluorophenyl)-1H-benzo[d]imidazol-1-yl)prop-1-enyl)piperidin-3-ol,
192) (2R,3S)-2-((E)-3-(6-(3-(trifluoromethyl)phenyl)-1H-benzo[d]imidazol-1-yl)prop-1-enyl)piperidin-3-ol,
193) (2R,3S)-2-((E)-3-(5-bromo-6,7-difluoro-2-methyl-1H-benzo[d]imidazol-1-yl)prop-1-enyl)piperidin-3-ol,
194) (2R,3S)-2-((E)-3-(indolin-1-yl)prop-1-enyl)piperidin-3-ol,
195) (2R,3S)-2-((E)-3-(5-chloroindolin-1-yl)prop-1-enyl)piperidin-3-ol,
196) (2R,3S)-2-((E)-3-(1H-pyrrolo[2,3-b]pyridin-1-yl)prop-1-enyl)piperidin-3-ol,
197) (2R,3S)-2-((E)-3-(6-chloro-1H-indol-1-yl)prop-1-enyl)piperidin-3-ol,
198) (2R,3S)-2-((E)-3-(6-chloro-1H-indazol-1-yl)prop-1-enyl)piperidin-3-ol,
199) (2R,3S)-2-((E)-3-(4-chloro-7H-pyrrolo[2,3-d]pyrimidin-7-yl)prop-1-enyl)piperidin-3-ol,
200) (2R,3S)-2-((E)-3-(5-chloro-1H-pyrazolo[3,4-b]pyridin-1-yl)prop-1-enyl)piperidin-3-ol,
201) (2R,3S)-2-((E)-3-(3,5-dimethyl-1H-indazol-1-yl)prop-1-enyl)piperidin-3-ol,
202) methyl 7-bromo-1-((E)-3-((2R,3S)-3-hydroxypiperidin-2-yl)allyl)-1H-indole-3-carboxylate,
203) 7-bromo-1-((E)-3-((2R,3S)-3-hydroxypiperidin-2-yl)allyl)-1H-indole-3-carboxylic acid,
204) 5-bromo-1-((E)-3-((2R,3S)-3-hydroxypiperidin-2-yl)allyl)-1H-indole-3-carboxylic acid,
205) 4-chloro-1-((E)-3-((2R,3S)-3-hydroxypiperidin-2-yl)allyl)-1H-indole-3-carboxylic acid,
206) 6-chloro-1-((E)-3-((2R,3S)-3-hydroxypiperidin-2-yl)allyl)-1H-indole-3-carboxylic acid,
207) 7-chloro-1-((E)-3-((2R,3S)-3-hydroxypiperidin-2-yl)allyl)-1H-indole-3-carboxylic acid,
208) 6-fluoro-1-((E)-3-((2R,3S)-3-hydroxypiperidin-2-yl)allyl)-1H-indole-3-carboxylic acid,
209) 1-((E)-3-((2R,3S)-3-hydroxypiperidin-2-yl)allyl)-1H-indole-3-carboxylic acid,
210) methyl 4-chloro-1-((E)-3-((2R,3S)-3-hydroxypiperidin-2-yl)allyl)-1H-indole-3-carboxylate,
211) methyl 6-chloro-1-((E)-3-((2R,3S)-3-hydroxypiperidin-2-yl)allyl)-1H-indole-3-carboxylate,
212) methyl 7-chloro-1-((E)-3-((2R,3S)-3-hydroxypiperidin-2-yl)allyl)-1H-indole-3-carboxylate,
213) methyl 5-bromo-1-((E)-3-((2R,3S)-3-hydroxypiperidin-2-yl)allyl)-1H-indole-3-carboxylate,
214) methyl 6-bromo-1-((E)-3-((2R,3S)-3-hydroxypiperidin-2-yl)allyl)-1H-indole-3-carboxylate,
215) 5-bromo-1-((E)-3-((2R,3S)-3-hydroxypiperidin-2-yl)allyl)-N-methyl-1H-indole-3-carboxamide,
216) 5-bromo-1-((E)-3-((2R,3S)-3-hydroxypiperidin-2-yl)allyl)-N,N-dimethyl-1H-indole-3-carboxamide,
217) (2R,3S)-2-((Z)-3-(5-chloro-4-methyl-1H-benzo[d]imidazol-1-yl)-2-fluoroprop-1-enyl)piperidin-3-ol,
218) (2R,3S)-2-((Z)-3-(5-bromo-4-methyl-1H-benzo[d]imidazol-1-yl)-2-fluoroprop-1-enyl)piperidin-3-ol,
219) (2R,3S)-2-((Z)-3-(5,6-dichloro-1H-benzo[d]imidazol-1-yl)-2-fluoroprop-1-enyl)piperidin-3-ol,
220) (2R,3S)-2-((Z)-3-(5,6-dichloro-2-(hydroxymethyl)-1H-benzo[d]imidazol-1-yl)-2-fluoroprop-1-enyl)piperidin-3-ol,
221) (2R,3S)-2-((E)-3-(5-chloro-4-methyl-1H-benzo[d]imidazol-1-yl)-2-methylprop-1-enyl)piperidin-3-ol,
222) (2R,3S)-2-((E)-3-(5-bromo-4-methyl-1H-benzo[d]imidazol-1-yl)-2-methylprop-1-enyl)piperidin-3-ol,
223) (2R,3S)-2-((E)-3-(5,6-dichloro-1H-benzo[d]imidazol-1-yl)-2-methylprop-1-enyl)piperidin-3-ol,
224) (2R,3S)-2-((E)-3-(5,6-dichloro-2-(hydroxymethyl)-1H-benzo[d]imidazol-1-yl)-2-methylprop-1-enyl)piperidin-3-ol,
225) (2R,3S)-2-(3-(5,6-dichloro-1H-benzo[d]imidazol-1-yl)prop-1-ynyl)piperidin-3-ol,
226) (2R,3S)-2-(3-(5-bromo-4-methyl-1H-benzo[d]imidazol-1-yl)prop-1-ynyl)piperidin-3-ol,
227) (2R,3S)-2-(3-(5-chloro-4-methyl-1H-benzo[d]imidazol-1-yl)prop-1-ynyl)piperidin-3-ol,
228) (2R,3S)-2-(3-(5,6-dibromo-1H-benzo[d]imidazol-1-yl)prop-1-ynyl)piperidin-3-ol,
229) (2R,3S)-2-(3-(5-fluoro-4-methyl-1H-benzo[d]imidazol-1-yl)prop-1-ynyl)piperidin-3-ol, and
230) (2R,3S)-2-((E)-3-(5,6-dichloro-1H-benzo[d]imidazol-1-yl)prop-1-enyl)pyrrolidin-3-ol.

12. A pharmaceutical composition comprising the compound according to claim 1 or a pharmaceutically acceptable salt thereof as an active ingredient and a pharmaceutically acceptable carrier.

13. A method for preparing a compound represented by the following Chemical Formula 1 comprising the steps of:
reacting a compound represented by the following Chemical Formula 1-A with a compound represented by the following Chemical Formula 1-B in the presence of a base to prepare a compound represented by the following Chemical Formula 1-C; and
reacting a compound represented by the Chemical Formula 1-C in the presence of an acid to prepare a compound represented by the following Chemical Formula 1:

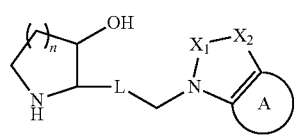

[Chemical Formula 1]

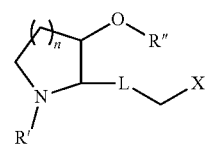

[Chemical Formula 1-A]

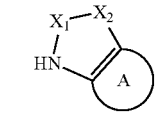

[Chemical Formula 1-B]

-continued

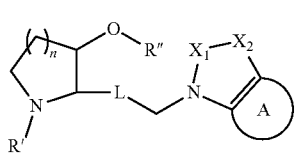
[Chemical Formula 1-C]

in Chemical Formulas 1, 1-A, 1-B, and 1-C,
n, L, $X_1$, $X_2$ and A are as defined in claim 1,
X is halogen, and
R' and R" are each independently a protecting group.

14. A method for preparing a compound represented by the following Chemical Formula 1-1 comprising the steps of:
reacting a compound represented by the following Chemical Formula 2-A with a compound represented by the following Chemical Formula 2-B in the presence of a base to prepare a compound represented by the following Chemical Formula 2-C;
reacting an amine group and a nitro group of the compound represented by the Chemical Formula 2-C to form a ring, thereby preparing a compound represented by the following Chemical Formula 2-D; and
reacting a compound represented by the Chemical Formula 2-D in the presence of an acid to prepare a compound represented by the following Chemical Formula 1-1:

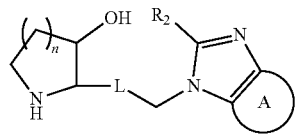
[Chemical Formula 1-1]

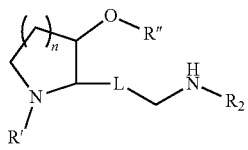
[Chemical Formula 2-A]

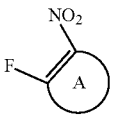
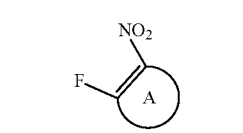
[Chemical Formula 2-B]

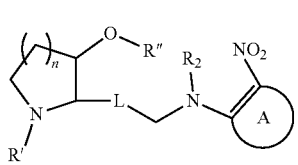
[Chemical Formula 2-C]

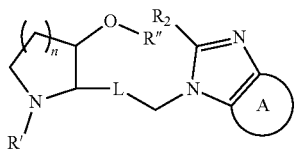
[Chemical Formula 2-D]

in Chemical Formulas 1-1, 2-A, 2-B, 2-C, and 2-D,
n, L, $R_2$ and A are as defined in claim 1, and
R' and R" are each independently a protecting group.

15. A method for preparing a compound represented by the following Chemical Formula 3 comprising the steps of:
reacting the compound represented by the following Chemical Formula 3-A with (carbethoxymethylene) triphenylphosphorane to prepare a compound represented by the following Chemical Formula 3-B;
hydrogenating the compound represented by the following Chemical Formula 3-B to prepare a compound represented by the following Chemical Formula 3-C;
hydrolyzing the compound represented by the Chemical Formula 3-C to prepare a compound represented by the following Chemical Formula 3-D;
subjecting the compound represented by the Chemical Formula 3-D to a carbonyl reduction reaction to prepare a compound represented by the following Chemical Formula 3-E;
brominating the compound represented by the Chemical Formula 3-E to prepare a compound represented by the following Chemical Formula 3-F;
subjecting the compound represented by the Chemical Formula 3-F to an azide reaction to prepare a compound represented by the following Chemical Formula 3-G; and
aminating the compound represented by the Chemical Formula 3-G to prepare a compound represented by the following Chemical Formula 3:

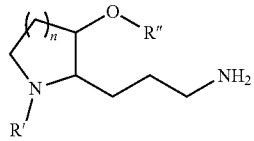
[Chemical Formula 3]

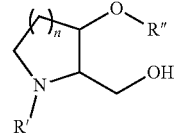
[Chemical Formula 3-A]

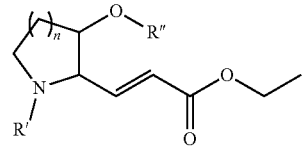
[Chemical Formula 3-B]

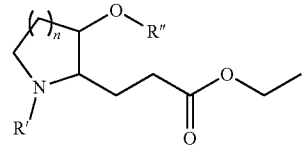
[Chemical Formula 3-C]

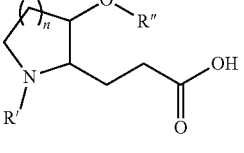
[Chemical Formula 3-D]

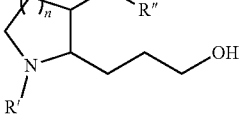
[Chemical Formula 3-E]

-continued

[Chemical Formula 3-F]

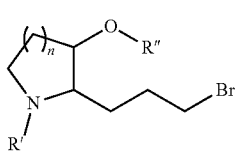

[Chemical Formula 3-G]

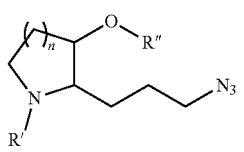

in Chemical Formulas 3, 3-A, 3-B, 3-C, 3-D, 3-E, 3-F, and 3-G, n is 1 or 2, and

R' and R" are each independently a protecting group.

16. A method of treating inflammatory diseases, autoimmune diseases or fibrosis comprising administering to a subject in need thereof an effective amount of the compound according to claim 1 or a pharmaceutically acceptable salt thereof.

* * * * *